(12) United States Patent
Pendri et al.

(10) Patent No.: US 8,633,200 B2
(45) Date of Patent: Jan. 21, 2014

(54) INHIBITORS OF HUMAN IMMUNODEFICIENCY VIRUS REPLICATION

(75) Inventors: Annapurna Pendri, South Glastonbury, CT (US); Guo Li, Wallingford, CT (US); Samuel Gerritz, Guilford, CT (US); David R. Langley, Meriden, CT (US); George L. Trainor, Wilmington, DE (US); Nicholas A. Meanwell, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/224,802

(22) Filed: Sep. 2, 2011

(65) Prior Publication Data
US 2012/0225888 A1 Sep. 6, 2012

Related U.S. Application Data

(60) Provisional application No. 61/380,759, filed on Sep. 8, 2010.

(51) Int. Cl.
*A01N 43/90* (2006.01)
*A61K 31/519* (2006.01)
*C07D 487/00* (2006.01)

(52) U.S. Cl.
USPC .................................. 514/259.3; 544/281

(58) Field of Classification Search
None
See application file for complete search history.

(56) References Cited

U.S. PATENT DOCUMENTS

| | | |
|---|---|---|
| 2008/0221159 A1 | 9/2008 | Tsantrizos et al. |
| 2010/0292227 A1 | 11/2010 | Yoakim et al. |
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0118249 A1 | 5/2011 | Tsantrizos et al. |
| 2011/0207626 A1 | 8/2011 | Inazawa et al. |
| 2012/0129840 A1 | 5/2012 | Chalton et al. |
| 2012/0316161 A1 | 12/2012 | Carlens et al. |

OTHER PUBLICATIONS

Borisy, et. al., Proceedings of the National Academy of Sciences of the United States of America, 100(13) 7977-7982.*
Borisy, et. al., Proceedings of the National Academy of Sciences of the United States of America, (2003) 100(13) 7977-7982.*

* cited by examiner

*Primary Examiner* — Jeffrey Murray
(74) *Attorney, Agent, or Firm* — James Epperson

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

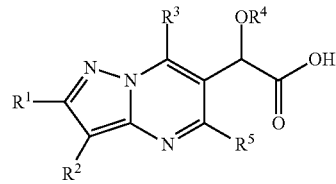

13 Claims, No Drawings

INHIBITORS OF HUMAN IMMUNODEFICIENCY VIRUS REPLICATION

CROSS REFERENCE TO RELATED APPLICATIONS

This patent application claims the benefit of U.S. provisional patent application No. 61/380,759 filed Sep. 8, 2010.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33 million people worldwide are infected with the virus (UNAIDS: Report on the Global HIV/AIDS Epidemic, December 1998). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, and WO2009062308.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

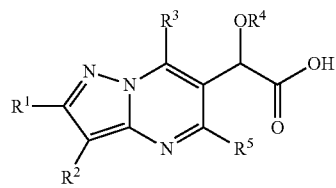

where:
$R^1$ is H, alkyl, cycloalkyl, or $Ar^1$;
$R^2$ is H, alkyl, cycloalkyl, or $Ar^1$;
$R^3$ is alkyl or $Ar^2$;
$R^4$ is alkyl or haloalkyl;
$R^5$ is alkyl;
$Ar^1$ is phenyl, pyridinyl, tetralinyl, indazolyl, or chromanyl, and is substituted with 0-3 substituents selected from halo, alkyl, haloalkyl, alkoxy, haloalkoxy, phenyl, benzyl, phenoxy, benzyloxy, halobenzyloxy, (alkoxy)benzyloxy, phenoxyalkyl, CONH(phenyl), CONH(benzyl), and $Ar^3$;
$Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;
or $Ar^2$ is

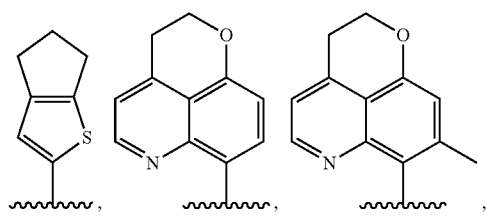

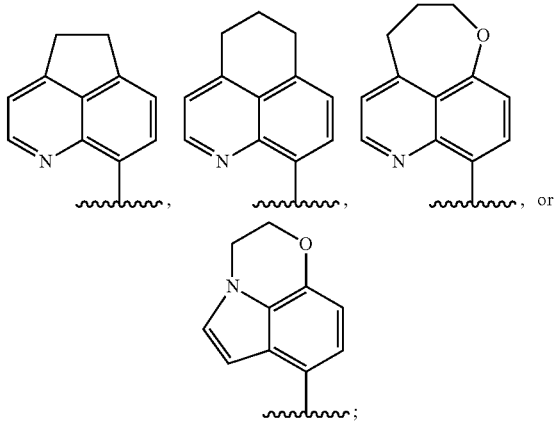

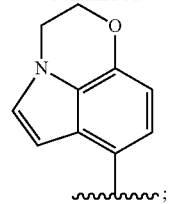

Ar³ is phenyl, pyridinyl, pyrazolyl, quinolinyl, chromanyl, or indazolyl, and is substituted with 0-3 substituents selected from the group consisting of halo, alkyl, haloalkyl, alkoxy, haloalkoxy, phenyl, and methylpiperazinyl;

or a pharmaceutically acceptable salt thereof.

Another aspect of the invention is a compound of formula I where:

$R^1$ is H, alkyl, cycloalkyl, or $Ar^1$;

$R^2$ is H, alkyl, cycloalkyl, or $Ar^1$;

$R^3$ is alkyl or $Ar^2$;

$R^4$ is alkyl or haloalkyl;

$R^5$ is alkyl;

$Ar^1$ is phenyl, pyridinyl, or chromanyl, and is substituted with 0-3 substituents selected from halo, alkyl, haloalkyl, alkoxy, haloalkoxy, phenyl, benzyl, phenoxy, and phenoxyalkyl; and $Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;

or $Ar^2$ is

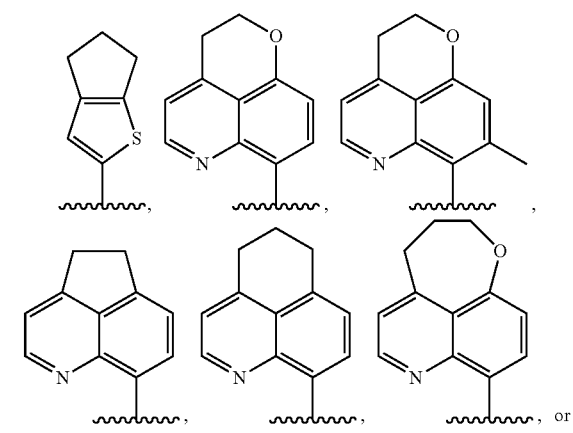

or a pharmaceutically acceptable salt thereof.

Another aspect of the invention is a compound of formula I where $R^1$ is $Ar^1$; $R^2$ is H; $R^3$ is $Ar^2$; $R^4$ is alkyl; $R^5$ is methyl; $Ar^1$ is phenyl, pyridinyl, or chromanyl, and is substituted with 0-3 substituents selected from halo, alkyl, haloalkyl, alkoxy, haloalkoxy, phenyl, benzyl, phenoxy, and phenoxyalkyl; and $Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido; or a pharmaceutically acceptable salt thereof.

Another aspect of the invention is a compound of formula I where $R^1$ is $Ar^1$; $R^2$ is H; $R^3$ is $Ar^2$; $R^4$ is alkyl; $R^5$ is methyl; $Ar^1$ is phenyl substituted with 0-1 alkyl substituents; and $Ar^2$ is phenyl, pyridinyl, indanyl, naphthyl, benzofuranyl, dihydrobenzofuranyl, benzodioxyl, chromanyl, benzodioxanyl, or indolyl, and is substituted with 0-3 substituents selected from halo, cyano, alkyl, haloalkyl, hydroxy, alkoxy, haloalkoxy, phenoxy, benzyloxy, and acetamido; or a pharmaceutically acceptable salt thereof.

Another aspect of the invention is a compound of formula I where $R^1$ is H and $R^2$ is $Ar^1$.

Another aspect of the invention is a compound of formula I where $R^1$ is $Ar^1$ and $R^2$ is H.

Another aspect of the invention is a compound of formula I where $R^3$ is $Ar^2$.

Another aspect of the invention is a compound of formula I where $Ar^2$ is phenyl, pyridinyl, indanyl, naphthyl, benzofuranyl, dihydrobenzofuranyl, benzodioxyl, chromanyl, benzodioxanyl, or indolyl, and is substituted with 0-3 substituents selected from halo, cyano, alkyl, haloalkyl, hydroxy, alkoxy, haloalkoxy, phenoxy, benzyloxy, and acetamido.

Another aspect of the invention is a compound of formula I where $R^4$ is alkyl.

Another aspect of the invention is a compound of formula I where $R^5$ is methyl.

Another aspect of the invention is a compound of formula I where $Ar^1$ is phenyl substituted with 0-1 alkyl substituents.

Another aspect of the invention is a compound of formula I where $R^1$ is $Ar^1$; $R^2$ is H; $R^3$ is $Ar^2$; $R^4$ is alkyl; $R^5$ is methyl; $Ar^1$ is phenyl or pyridinyl, and is substituted with 1 $Ar^3$ substituent and 0-2 substituents selected from halo, alkyl, haloalkyl, alkoxy, and haloalkoxy; and $Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido; or a pharmaceutically acceptable salt thereof.

Another aspect of the invention is a compound of formula I where $R^1$ is $Ar^1$; $R^2$ is H; and $Ar^1$ is phenyl or pyridinyl, and is substituted with 1 $Ar^3$ substituent and 0-2 substituents selected from halo, alkyl, haloalkyl, alkoxy, and haloalkoxy.

Another aspect of the invention is a compound of formula I where $Ar^2$ is phenyl, pyridinyl, indanyl, naphthyl, benzofuranyl, dihydrobenzofuranyl, benzodioxyl, chromanyl, benzodioxanyl, or indolyl, and is substituted with 0-3 substituents selected from halo, cyano, alkyl, haloalkyl, hydroxy, alkoxy, haloalkoxy, phenoxy, benzyloxy, and acetamido.

Another aspect of the invention is a compound of formula I where $Ar^3$ is phenyl, pyridinyl, pyrazolyl, quinolinyl, chromanyl, or indazolyl, and is substituted with 0-3 substituents selected from the group consisting of halo, alkyl, haloalkyl, alkoxy, haloalkoxy, phenyl, and methylpiperazinyl.

Another aspect of the invention is a compound of formula I where $Ar^3$ is phenyl, pyridinyl, pyrazolyl, quinolinyl, chromanyl, or indazolyl, and is substituted with 1-3 substituents selected from the group consisting of halo, alkyl, haloalkyl, alkoxy, haloalkoxy, phenyl, and methylpiperazinyl.

Another aspect of the invention is a compound of formula I where $Ar^3$ is phenyl, pyridinyl, or pyrazolyl, and is substituted with 1-3 substituents selected from the group consisting of halo, alkyl, haloalkyl, alkoxy, haloalkoxy, phenyl, and methylpiperazinyl.

Another aspect of the invention is a compound of formula I where $Ar^3$ is phenyl, pyridinyl, or pyrazolyl, and is substituted with 1-3 substituents selected from the group consisting of halo, alkyl, haloalkyl, alkoxy, and haloalkoxy.

For a compound of Formula I, the scope of any instance of a variable substituent, including $R^1$, $R^2$, $R^3$, $R^4$, $R^5$, $Ar^1$, $Ar^2$, and $Ar^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. "Tetralin" means tetrahydronaphthalene. Terms with a hydrocarbon moiety (e.g. alkoxy) include straight and branched isomers for the hydrocarbon portion. Parenthetic and multi-parenthetic terms are intended to clarify bonding relationships to those skilled in the art. For example, a term such as ((R)alkyl) means an alkyl substituent further substituted with the substituent R.

"Chroman" means

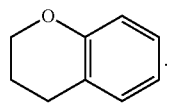

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication

A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where (Fa)=1/[1+($ED_{50}$/drug conc.)$^m$] (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the EC$_{50}$ values. Results are shown in Table 1. Activity equal to A refers to a compound having an EC$_{50}$≤100 nM, while B and C denote compounds having an EC$_{50}$ between 100 nM and 1 uM (B) or >1 uM (C).

TABLE 1

| Example | Structure | Activity EC$_{50}$ μM |
|---|---|---|
| 1 | 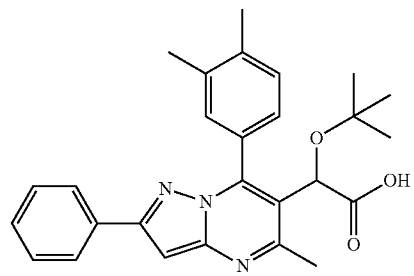 [SMILES: Cc1ccc(-c2c(C(OC(C)(C)C)C(=O)O)c(C)nc3cc(-c4ccccc4)nn23)cc1C] | C |
| 2 | 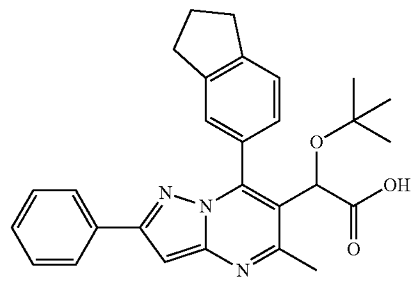 [SMILES: Cc1nc2cc(-c3ccccc3)nn2c(-c2ccc3c(c2)CCC3)c1C(OC(C)(C)C)C(=O)O] | C |
| 3 | 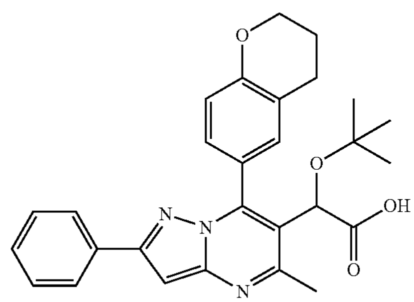 [SMILES: Cc1nc2cc(-c3ccccc3)nn2c(-c2ccc3c(c2)CCCO3)c1C(OC(C)(C)C)C(=O)O] | B |
| 4 | 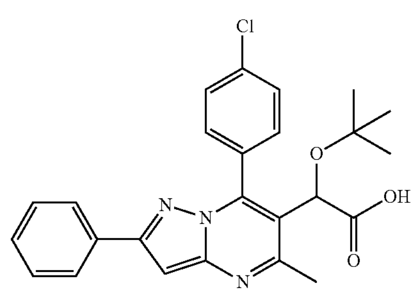 [SMILES: Cc1nc2cc(-c3ccccc3)nn2c(-c2ccc(Cl)cc2)c1C(OC(C)(C)C)C(=O)O] | C |
| 5 | 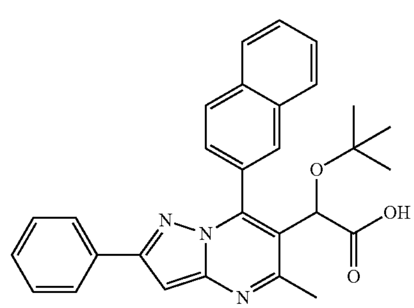 [SMILES: Cc1nc2cc(-c3ccccc3)nn2c(-c2ccc3ccccc3c2)c1C(OC(C)(C)C)C(=O)O] | C |

TABLE 1-continued

| Example | Structure | Activity | EC$_{50}$ μM |
|---|---|---|---|
| 6 | 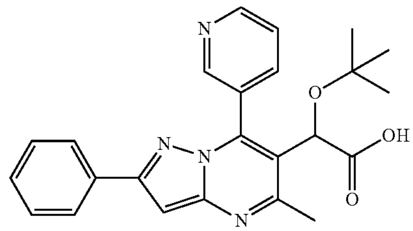 [SMILES: Cc1nc2cc(-c3ccccc3)nn2c(-c2cccnc2)c1C(OC(C)(C)C)C(=O)O] | C | |
| 7 | 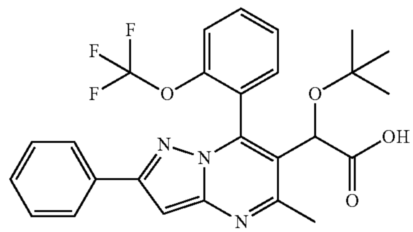 [SMILES: Cc1nc2cc(-c3ccccc3)nn2c(-c2ccccc2OC(F)(F)F)c1C(OC(C)(C)C)C(=O)O] | C | |
| 8 | 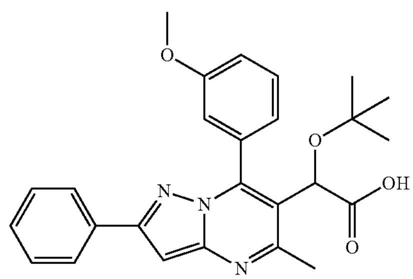 [SMILES: COc1cccc(-c2c(C(OC(C)(C)C)C(=O)O)c(C)nc3cc(-c4ccccc4)nn23)c1] | C | |
| 9 | 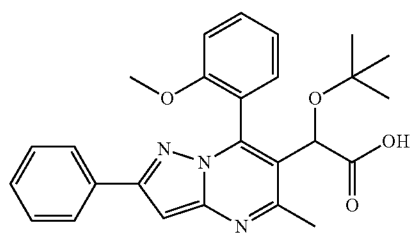 [SMILES: COc1ccccc1-c1c(C(OC(C)(C)C)C(=O)O)c(C)nc2cc(-c3ccccc3)nn12] | C | |
| 10 | 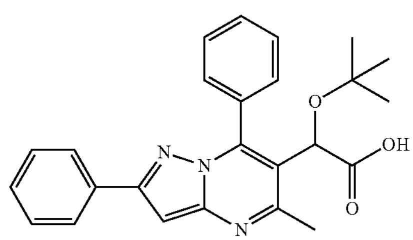 [SMILES: Cc1nc2cc(-c3ccccc3)nn2c(-c2ccccc2)c1C(OC(C)(C)C)C(=O)O] | C | |
| 11 | 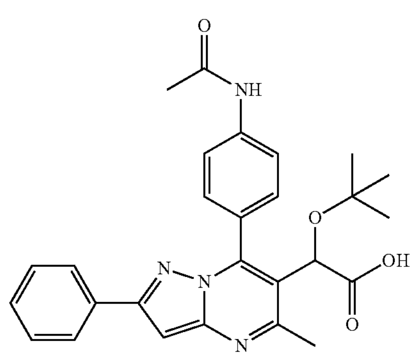 [SMILES: CC(=O)Nc1ccc(-c2c(C(OC(C)(C)C)C(=O)O)c(C)nc3cc(-c4ccccc4)nn23)cc1] | C | |

TABLE 1-continued

| Example | Structure | Activity | EC$_{50}$ μM |
|---------|-----------|----------|--------------|
| 12 | 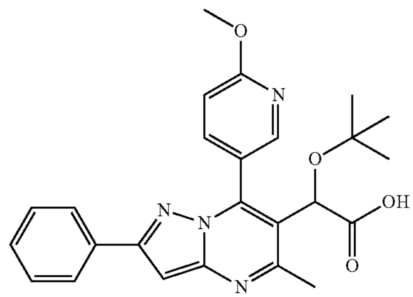 [SMILES: COc1ccc(-c2c(C(OC(C)(C)C)C(=O)O)c(C)nc3cc(-c4ccccc4)nn23)cn1] | C | |
| 13 | 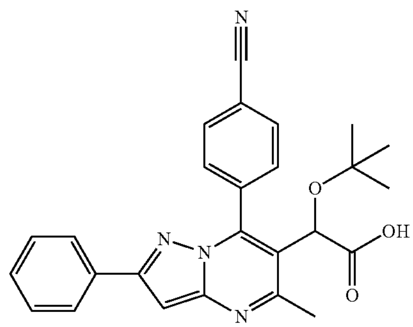 [SMILES: Cc1nc2cc(-c3ccccc3)nn2c(-c2ccc(C#N)cc2)c1C(OC(C)(C)C)C(=O)O] | C | |
| 14 | 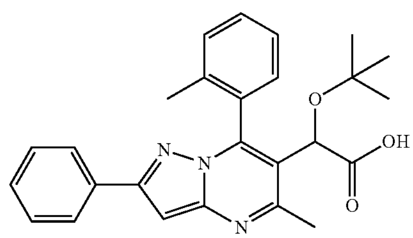 [SMILES: Cc1ccccc1-c1c(C(OC(C)(C)C)C(=O)O)c(C)nc2cc(-c3ccccc3)nn12] | C | |
| 15 | 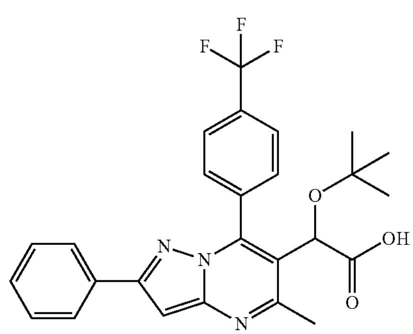 [SMILES: Cc1nc2cc(-c3ccccc3)nn2c(-c2ccc(C(F)(F)F)cc2)c1C(OC(C)(C)C)C(=O)O] | C | |
| 16 | 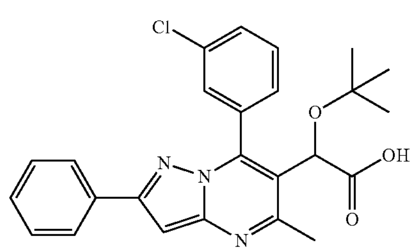 [SMILES: Cc1nc2cc(-c3ccccc3)nn2c(-c2cccc(Cl)c2)c1C(OC(C)(C)C)C(=O)O] | C | |

TABLE 1-continued

| Example | Structure | Activity | EC$_{50}$ μM |
|---|---|---|---|
| 17 | 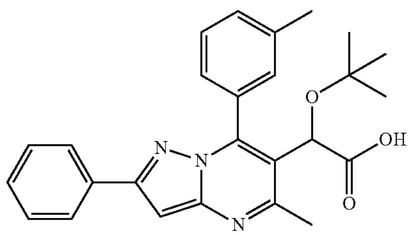 [SMILES: Cc1cccc(-c2c(C(OC(C)(C)C)C(=O)O)c(C)nc3cc(-c4ccccc4)nn23)c1] | C | |
| 18 | 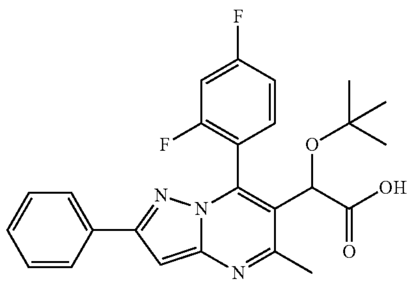 [SMILES: Cc1nc2cc(-c3ccccc3)nn2c(-c2ccc(F)cc2F)c1C(OC(C)(C)C)C(=O)O] | C | |
| 19 | 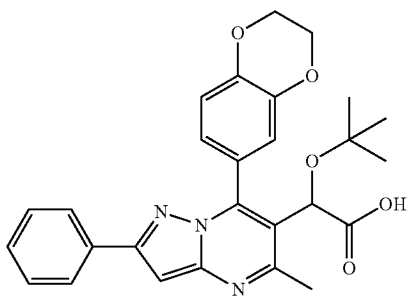 [SMILES: Cc1nc2cc(-c3ccccc3)nn2c(-c2ccc3c(c2)OCCO3)c1C(OC(C)(C)C)C(=O)O] | C | |
| 20 | 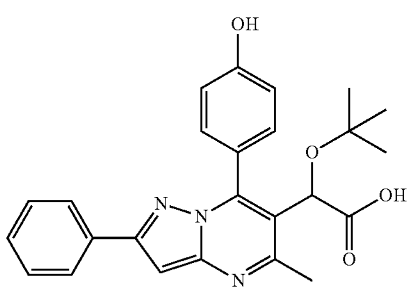 [SMILES: Cc1nc2cc(-c3ccccc3)nn2c(-c2ccc(O)cc2)c1C(OC(C)(C)C)C(=O)O] | C | |
| 21 | 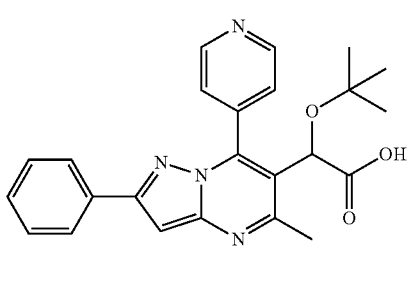 [SMILES: Cc1nc2cc(-c3ccccc3)nn2c(-c2ccncc2)c1C(OC(C)(C)C)C(=O)O] | C | |

TABLE 1-continued

| Example | Structure | Activity | EC$_{50}$ μM |
|---------|-----------|----------|--------------|
| 22 | 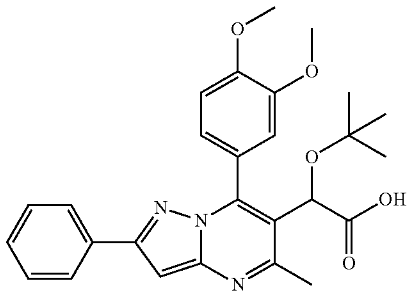 [SMILES: COc1ccc(-c2c(C(OC(C)(C)C)C(=O)O)c(C)nc3cc(-c4ccccc4)nn23)cc1OC] | C | |
| 23 | 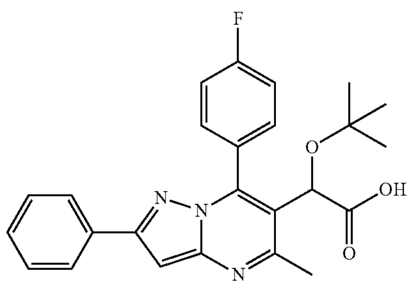 [SMILES: Cc1nc2cc(-c3ccccc3)nn2c(-c2ccc(F)cc2)c1C(OC(C)(C)C)C(=O)O] | C | |
| 24 | 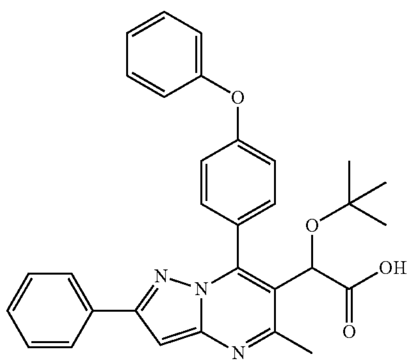 [SMILES: Cc1nc2cc(-c3ccccc3)nn2c(-c2ccc(Oc3ccccc3)cc2)c1C(OC(C)(C)C)C(=O)O] | C | |
| 25 | 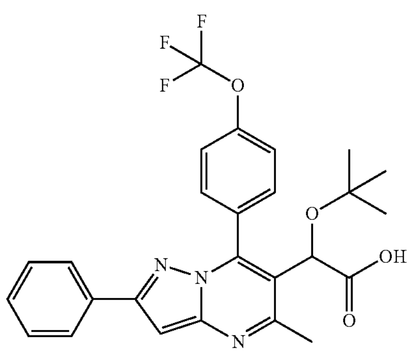 [SMILES: Cc1nc2cc(-c3ccccc3)nn2c(-c2ccc(OC(F)(F)F)cc2)c1C(OC(C)(C)C)C(=O)O] | C | |
| 26 | 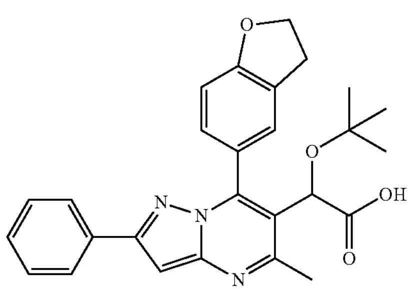 [SMILES: Cc1nc2cc(-c3ccccc3)nn2c(-c2ccc3c(c2)CCO3)c1C(OC(C)(C)C)C(=O)O] | B | |

TABLE 1-continued

| Example | Structure | Activity | EC$_{50}$ μM |
|---------|-----------|----------|--------------|
| 27 | 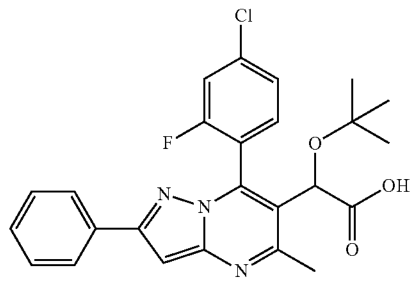 | C | |
| 28 | 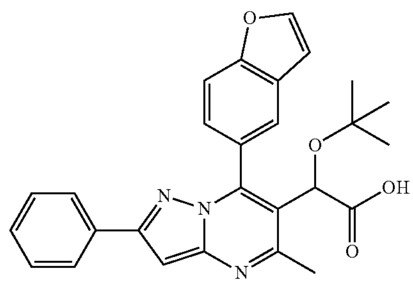 [SMILES: Cc1nc2cc(-c3ccccc3)nn2c(-c2ccc3occc3c2)c1C(OC(C)(C)C)C(=O)O] | C | |
| 29 | 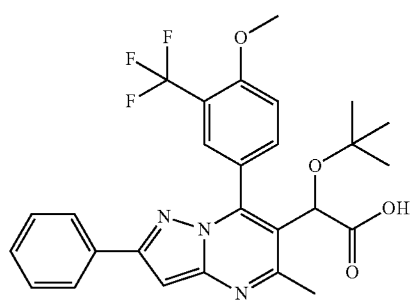 [SMILES: COc1ccc(-c2c(C(OC(C)(C)C)C(=O)O)c(C)nc3cc(-c4ccccc4)nn23)cc1C(F)(F)F] | C | |
| 30 | 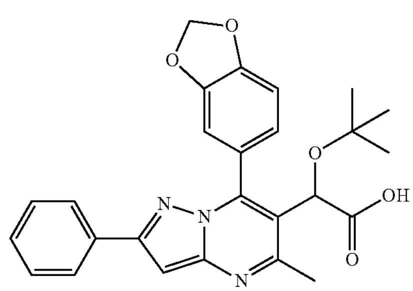 [SMILES: Cc1nc2cc(-c3ccccc3)nn2c(-c2ccc3c(c2)OCO3)c1C(OC(C)(C)C)C(=O)O] | C | |
| 31 | 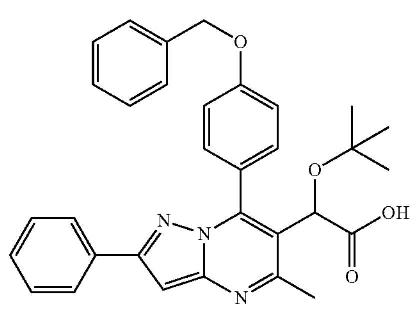 [SMILES: Cc1nc2cc(-c3ccccc3)nn2c(-c2ccc(OCc3ccccc3)cc2)c1C(OC(C)(C)C)C(=O)O] | C | |

TABLE 1-continued

| Example | Structure | Activity | EC$_{50}$ μM |
|---------|-----------|----------|--------------|
| 32 | 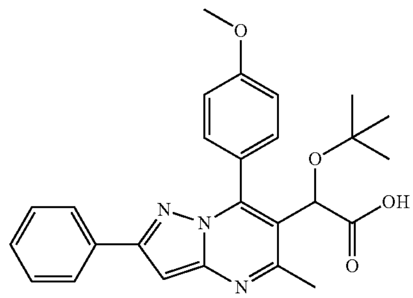 | C | |
| 33 | 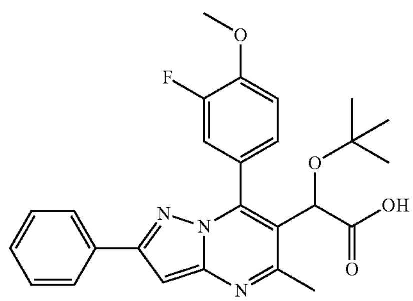 [SMILES: COc1ccc(-c2c(C(OC(C)(C)C)C(=O)O)c(C)nc3cc(-c4ccccc4)nn23)cc1F] | C | |
| 34 | 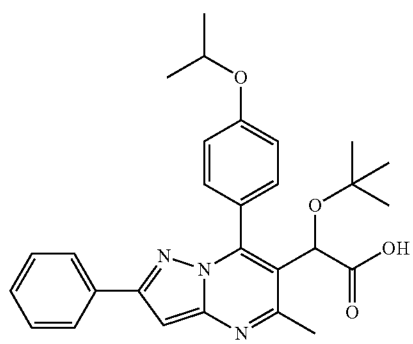 [SMILES: Cc1nc2cc(-c3ccccc3)nn2c(-c2ccc(OC(C)C)cc2)c1C(OC(C)(C)C)C(=O)O] | C | |
| 35 | 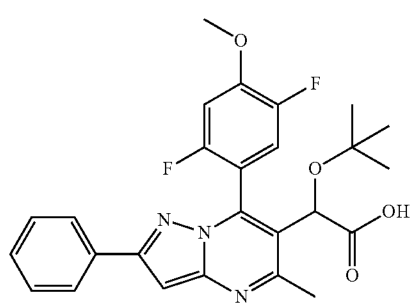 [SMILES: COc1cc(F)c(-c2c(C(OC(C)(C)C)C(=O)O)c(C)nc3cc(-c4ccccc4)nn23)cc1F] | C | |
| 36 | 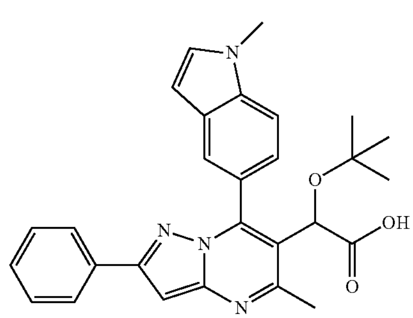 [SMILES: Cc1nc2cc(-c3ccccc3)nn2c(-c2ccc3c(ccn3C)c2)c1C(OC(C)(C)C)C(=O)O] | B | |

TABLE 1-continued

| Example | Structure | Activity | EC$_{50}$ μM |
|---|---|---|---|
| 37 | 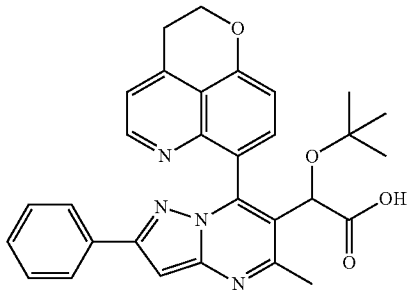 [SMILES: Cc1nc2cc(-c3ccccc3)nn2c(-c2ccc3c4c(ccnc24)CCO3)c1C(OC(C)(C)C)C(=O)O] | C | |
| 38 | 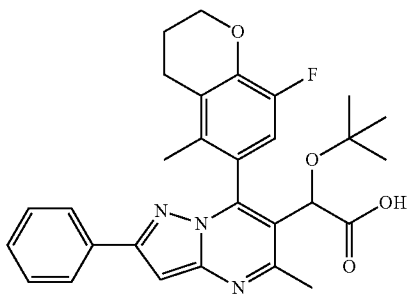 [SMILES: Cc1nc2cc(-c3ccccc3)nn2c(-c2cc(F)c3c(c2C)CCCO3)c1C(OC(C)(C)C)C(=O)O] | B | |
| 39 | 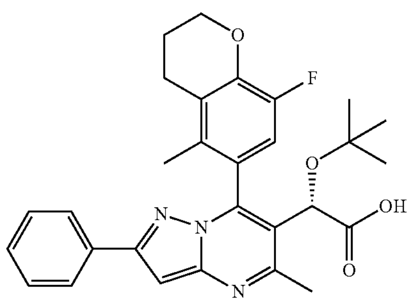 [SMILES: Cc1nc2cc(-c3ccccc3)nn2c(-c2cc(F)c3c(c2C)CCCO3)c1[C@H](OC(C)(C)C)C(=O)O] | A | |
| 40 | 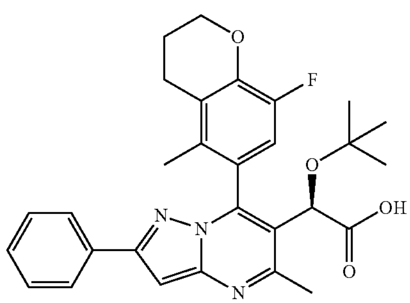 | C | |
| 41 | 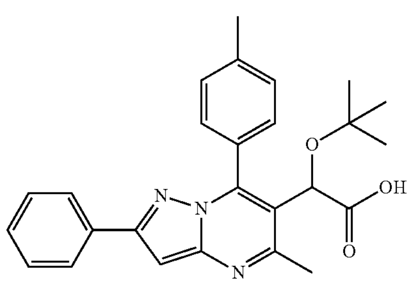 [SMILES: Cc1ccc(-c2c(C(OC(C)(C)C)C(=O)O)c(C)nc3cc(-c4ccccc4)nn23)cc1] | B | 0.6 |

TABLE 1-continued

| Example | Structure | Activity | EC$_{50}$ μM |
|---|---|---|---|
| 42 | 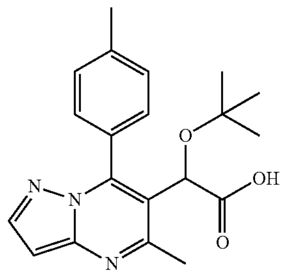 [SMILES: Cc1ccc(-c2c(C(OC(C)(C)C)C(=O)O)c(C)nc3ccnn23)cc1] | C | 4.5 |
| 43 | 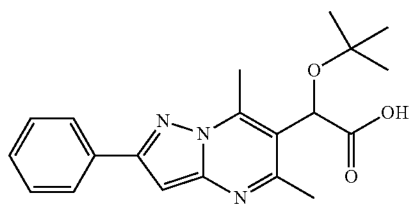 [SMILES: Cc1nc2cc(-c3ccccc3)nn2c(C)c1C(OC(C)(C)C)C(=O)O] | C | 40 |
| 44 | 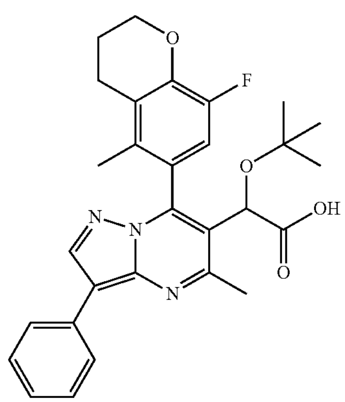 [SMILES: Cc1nc2c(-c3ccccc3)cnn2c(-c2cc(F)c3c(c2C)CCCO3)c1C(OC(C)(C)C)C(=O)O] | C | 3 |
| 45 | 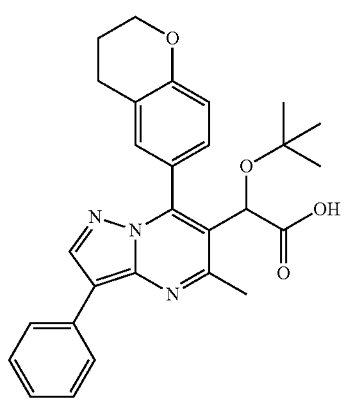 [SMILES: Cc1nc2c(-c3ccccc3)cnn2c(-c2ccc3c(c2)CCCO3)c1C(OC(C)(C)C)C(=O)O] | B | 0.24 |
| 46 | 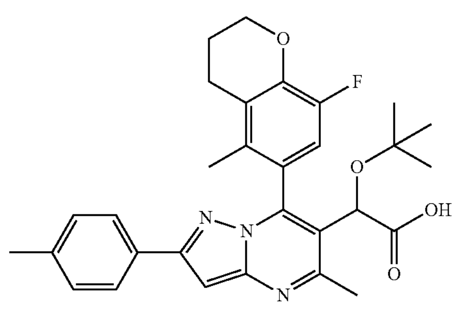 [SMILES: Cc1ccc(-c2cc3nc(C)c(C(OC(C)(C)C)C(=O)O)c(-c4cc(F)c5c(c4C)CCCO5)n3n2)cc1] | A | 0.09 |

TABLE 1-continued

| Example | Structure | Activity | EC$_{50}$ μM |
|---|---|---|---|
| 47 | 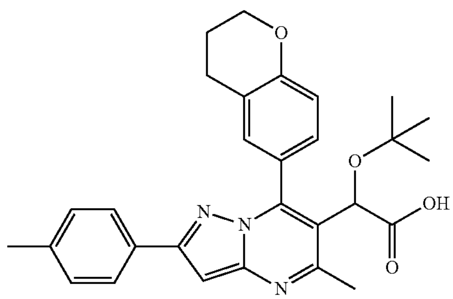 [SMILES: Cc1ccc(-c2cc3nc(C)c(C(OC(C)(C)C)C(=O)O)c(-c4ccc5c(c4)CCCO5)n3n2)cc1] | A | 0.08 |
| 48 | 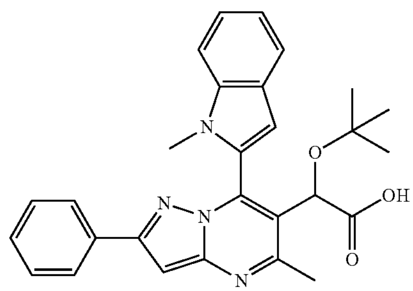 [SMILES: Cc1nc2cc(-c3ccccc3)nn2c(-c2cc3ccccc3n2C)c1C(OC(C)(C)C)C(=O)O] | C | |
| 49 | 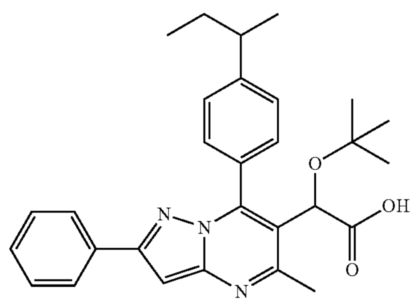 [SMILES: CCC(C)c1ccc(-c2c(C(OC(C)(C)C)C(=O)O)c(C)nc3cc(-c4ccccc4)nn23)cc1] | C | |
| 50 | 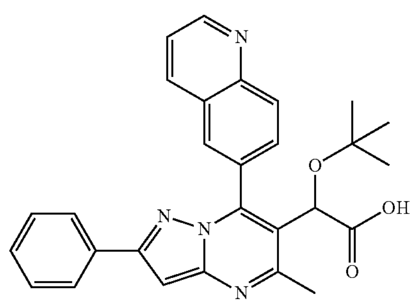 [SMILES: Cc1nc2cc(-c3ccccc3)nn2c(-c2ccc3ncccc3c2)c1C(OC(C)(C)C)C(=O)O] | C | 2.4 |
| 51 | 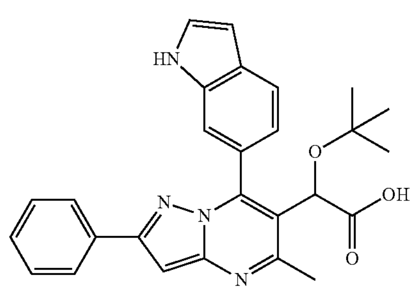 [SMILES: Cc1nc2cc(-c3ccccc3)nn2c(-c2ccc3cc[nH]c3c2)c1C(OC(C)(C)C)C(=O)O] | C | |

TABLE 1-continued

| Example | Structure | Activity | EC$_{50}$ μM |
|---|---|---|---|
| 52 | 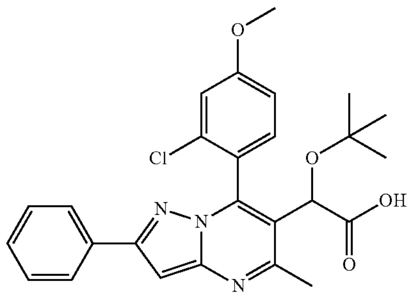 [SMILES: COc1ccc(-c2c(C(OC(C)(C)C)C(=O)O)c(C)nc3cc(-c4ccccc4)nn23)c(Cl)c1] | C | |
| 53 | 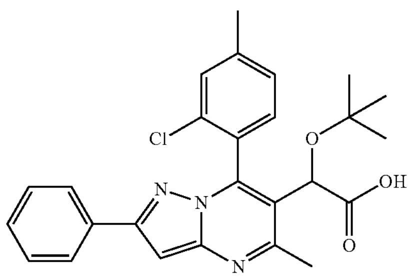 [SMILES: Cc1ccc(-c2c(C(OC(C)(C)C)C(=O)O)c(C)nc3cc(-c4ccccc4)nn23)c(Cl)c1] | B | |
| 54 | 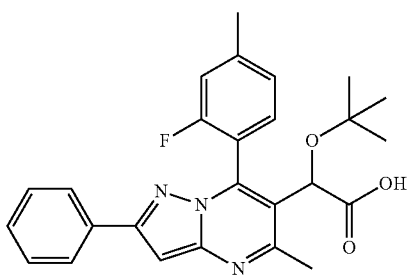 [SMILES: Cc1ccc(-c2c(C(OC(C)(C)C)C(=O)O)c(C)nc3cc(-c4ccccc4)nn23)c(F)c1] | B | |
| 55 | 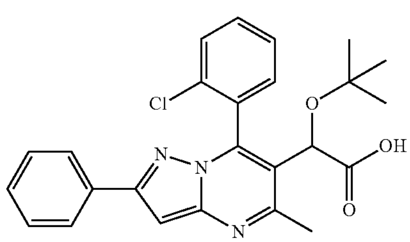 [SMILES: Cc1nc2cc(-c3ccccc3)nn2c(-c2ccccc2Cl)c1C(OC(C)(C)C)C(=O)O] | C | |
| 56 | 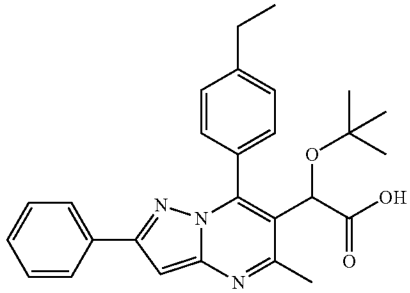 [SMILES: CCc1ccc(-c2c(C(OC(C)(C)C)C(=O)O)c(C)nc3cc(-c4ccccc4)nn23)cc1] | C | |

TABLE 1-continued

| Example | Structure | Activity | EC$_{50}$ µM |
|---|---|---|---|
| 57 | 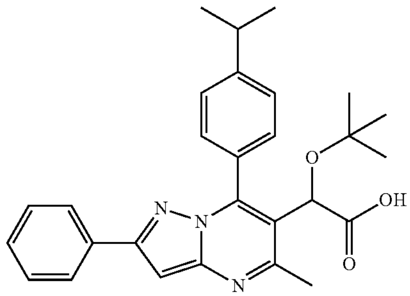 [SMILES: Cc1nc2cc(-c3ccccc3)nn2c(-c2ccc(C(C)C)cc2)c1C(OC(C)(C)C)C(=O)O] | C | 1.7 |
| 58 | 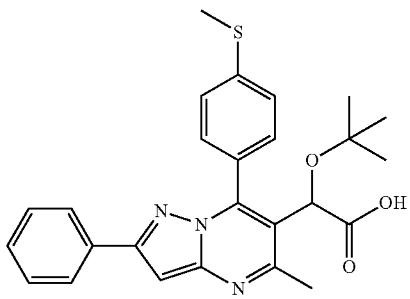 | C | 3.1 |
| 59 | 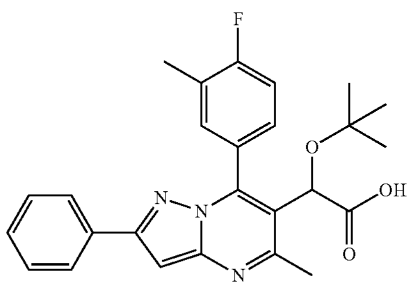 [SMILES: Cc1cc(-c2c(C(OC(C)(C)C)C(=O)O)c(C)nc3cc(-c4ccccc4)nn23)ccc1F] | C | |
| 60 | 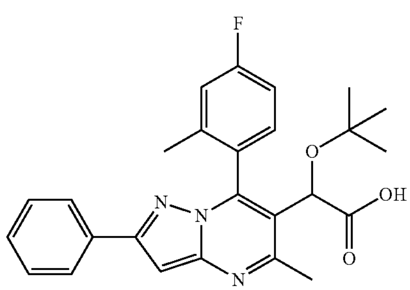 [SMILES: Cc1cc(F)ccc1-c1c(C(OC(C)(C)C)C(=O)O)c(C)nc2cc(-c3ccccc3)nn12] | C | |
| 61 | 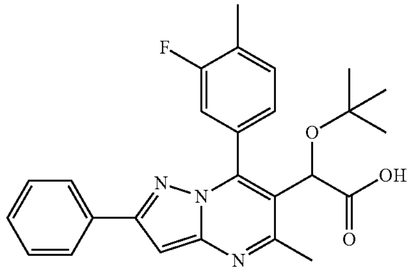 | C | |

TABLE 1-continued

| Example | Structure | Activity | EC₅₀ μM |
|---------|-----------|----------|---------|
| 62 | 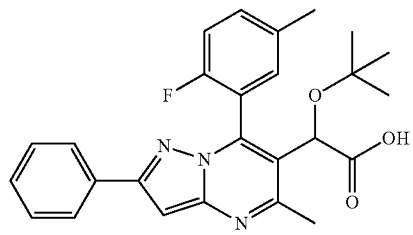 [SMILES: Cc1ccc(F)c(-c2c(C(OC(C)(C)C)C(=O)O)c(C)nc3cc(-c4ccccc4)nn23)c1] | C | 5 |
| 63 | 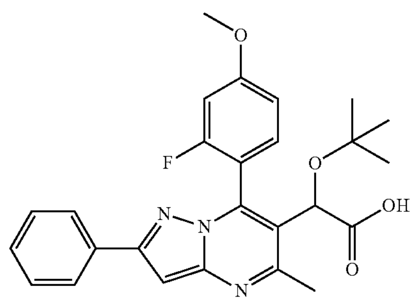 [SMILES: COc1ccc(-c2c(C(OC(C)(C)C)C(=O)O)c(C)nc3cc(-c4ccccc4)nn23)c(F)c1] | C | |
| 64 | 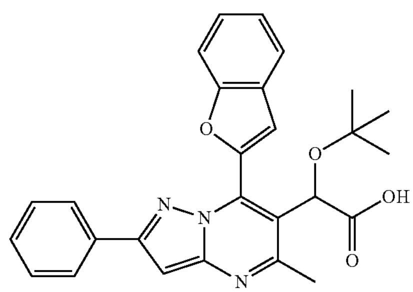 [SMILES: Cc1nc2cc(-c3ccccc3)nn2c(-c2cc3ccccc3o2)c1C(OC(C)(C)C)C(=O)O] | C | |
| 65 | 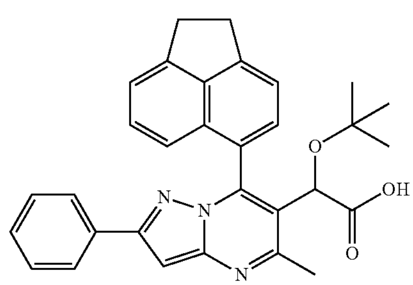 [SMILES: Cc1nc2cc(-c3ccccc3)nn2c(-c2ccc3c4c(cccc24)CC3)c1C(OC(C)(C)C)C(=O)O] | C | |
| 66 | 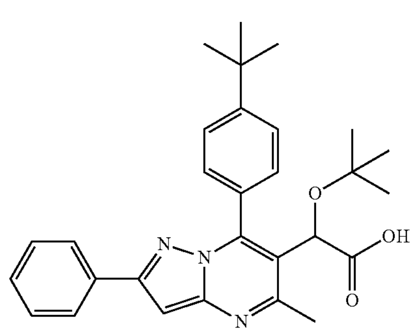 [SMILES: Cc1nc2cc(-c3ccccc3)nn2c(-c2ccc(C(C)(C)C)cc2)c1C(OC(C)(C)C)C(=O)O] | C | |

TABLE 1-continued
| Example | Structure | Activity | EC$_{50}$ μM |
|---|---|---|---|
| 67 | 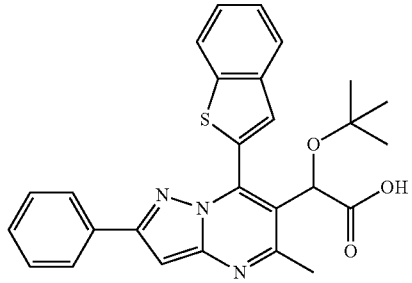 [SMILES: Cc1nc2cc(-c3ccccc3)nn2c(-c2cc3ccccc3s2)c1C(OC(C)(C)C)C(=O)O] | C | |
| 68 | 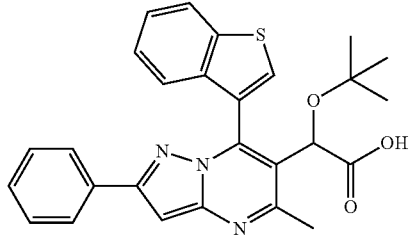 [SMILES: Cc1nc2cc(-c3ccccc3)nn2c(-c2csc3ccccc23)c1C(OC(C)(C)C)C(=O)O] | C | |
| 69 | 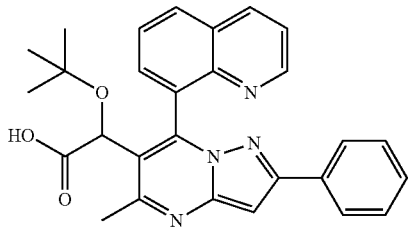 [SMILES: Cc1nc2cc(-c3ccccc3)nn2c(-c2cccc3cccnc23)c1C(OC(C)(C)C)C(=O)O] | C | |
| 70 | 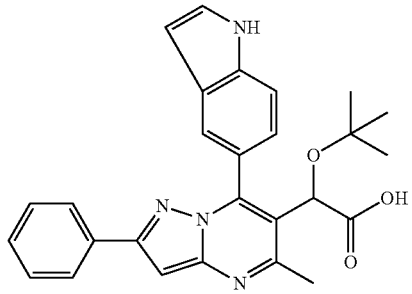 [SMILES: Cc1nc2cc(-c3ccccc3)nn2c(-c2ccc3[nH]ccc3c2)c1C(OC(C)(C)C)C(=O)O] | C | |
| 71 | 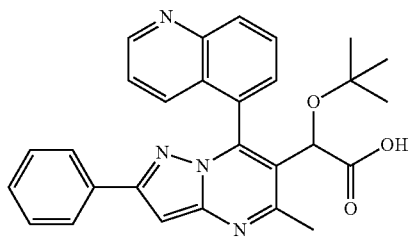 [SMILES: Cc1nc2cc(-c3ccccc3)nn2c(-c2cccc3ncccc23)c1C(OC(C)(C)C)C(=O)O] | C | |
| 72 | 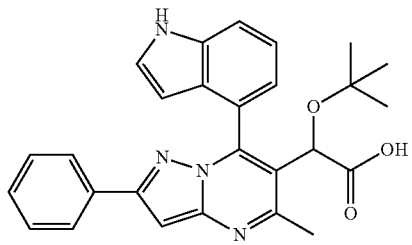 [SMILES: Cc1nc2cc(-c3ccccc3)nn2c(-c2cccc3[nH]ccc23)c1C(OC(C)(C)C)C(=O)O] | C | |

TABLE 1-continued

| Example | Structure | Activity | EC$_{50}$ μM |
|---------|-----------|----------|--------------|
| 73 | 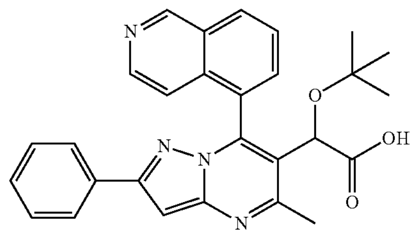 [SMILES: Cc1nc2cc(-c3ccccc3)nn2c(-c2cccc3cnccc23)c1C(OC(C)(C)C)C(=O)O] | C | |
| 74 | 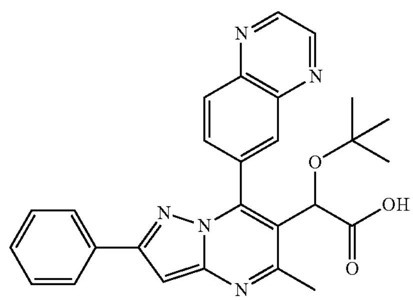 [SMILES: Cc1nc2cc(-c3ccccc3)nn2c(-c2ccc3nccnc3c2)c1C(OC(C)(C)C)C(=O)O] | C | |
| 75 | 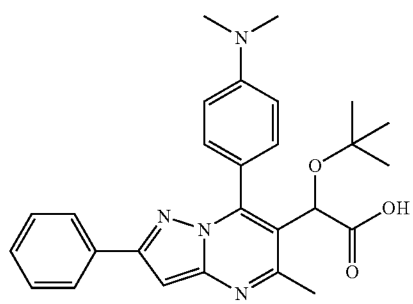 [SMILES: Cc1nc2cc(-c3ccccc3)nn2c(-c2ccc(N(C)C)cc2)c1C(OC(C)(C)C)C(=O)O] | C | |
| 76 | 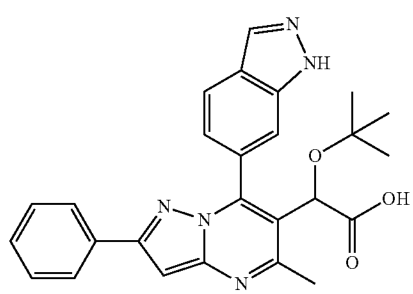 [SMILES: Cc1nc2cc(-c3ccccc3)nn2c(-c2ccc3cn[nH]c3c2)c1C(OC(C)(C)C)C(=O)O] | C | |
| 77 | 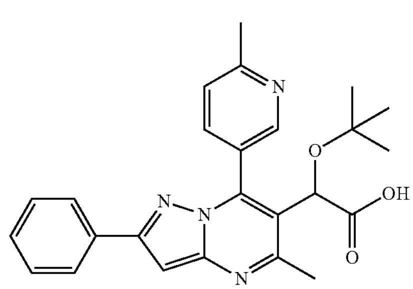 [SMILES: Cc1ccc(-c2c(C(OC(C)(C)C)C(=O)O)c(C)nc3cc(-c4ccccc4)nn23)cn1] | C | |

TABLE 1-continued

| Example | Structure | Activity | EC$_{50}$ μM |
|---------|-----------|----------|--------------|
| 78 | 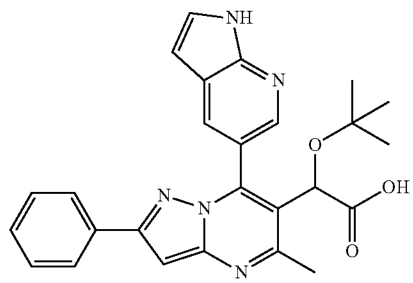 [SMILES: Cc1nc2cc(-c3ccccc3)nn2c(-c2cnc3[nH]ccc3c2)c1C(OC(C)(C)C)C(=O)O] | C | |
| 79 | 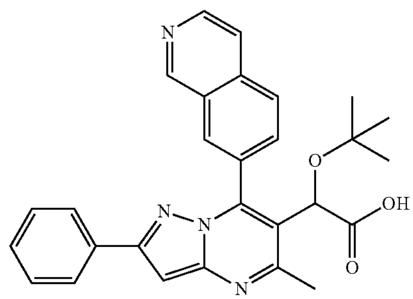 [SMILES: Cc1nc2cc(-c3ccccc3)nn2c(-c2ccc3ccncc3c2)c1C(OC(C)(C)C)C(=O)O] | C | |
| 80 | 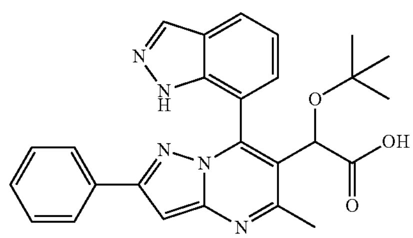 [SMILES: Cc1nc2cc(-c3ccccc3)nn2c(-c2cccc3cn[nH]c23)c1C(OC(C)(C)C)C(=O)O] | C | |
| 81 | 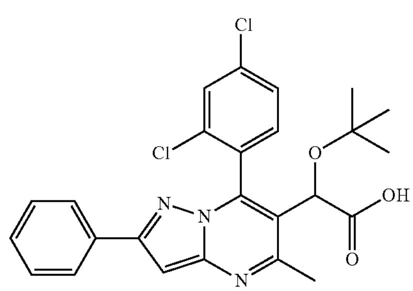 [SMILES: Cc1nc2cc(-c3ccccc3)nn2c(-c2ccc(Cl)cc2Cl)c1C(OC(C)(C)C)C(=O)O] | C | |
| 82 | 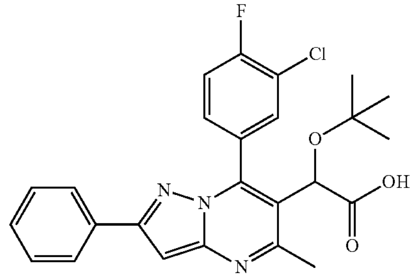 | C | |

TABLE 1-continued

| Example | Structure | Activity | EC$_{50}$ μM |
|---|---|---|---|
| 83 | 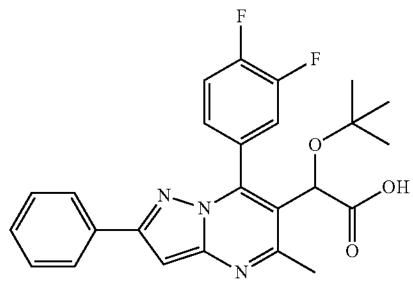 | C | |
| 84 | 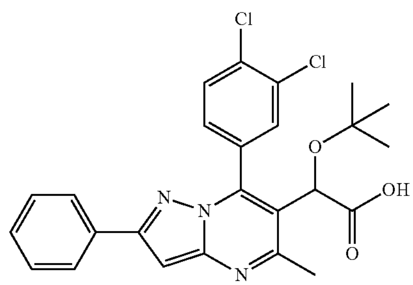 | C | |
| 85 | 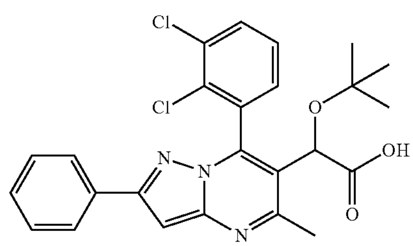 [SMILES: Cc1nc2cc(-c3ccccc3)nn2c(-c2cccc(Cl)c2Cl)c1C(OC(C)(C)C)C(=O)O] | C | |
| 86 | 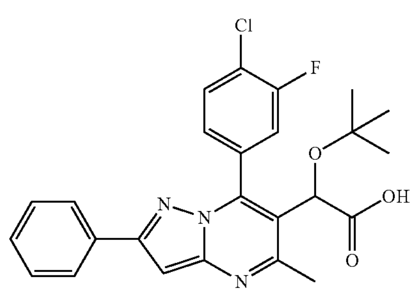 [SMILES: Cc1nc2cc(-c3ccccc3)nn2c(-c2ccc(Cl)c(F)c2)c1C(OC(C)(C)C)C(=O)O] | C | |
| 87 | 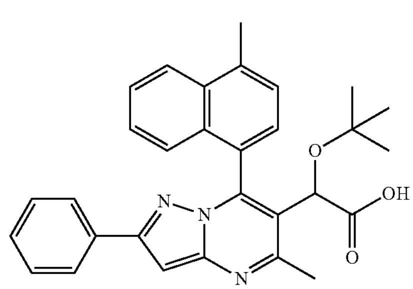 [SMILES: Cc1nc2cc(-c3ccccc3)nn2c(-c2ccc(C)c3ccccc23)c1C(OC(C)(C)C)C(=O)O] | C | |

TABLE 1-continued

| Example | Structure | Activity | EC$_{50}$ μM |
|---------|-----------|----------|--------------|
| 88 | 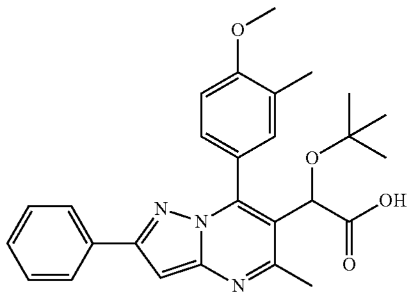 [SMILES: COc1ccc(-c2c(C(OC(C)(C)C)C(=O)O)c(C)nc3cc(-c4ccccc4)nn23)cc1C] | C | |
| 89 | 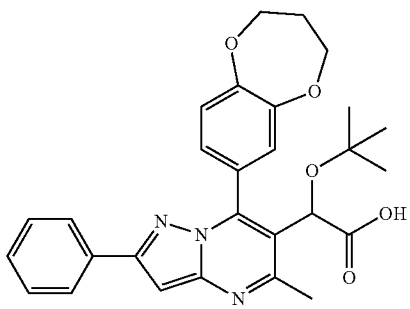 [SMILES: Cc1nc2cc(-c3ccccc3)nn2c(-c2ccc3c(c2)OCCCO3)c1C(OC(C)(C)C)C(=O)O] | C | |
| 90 | 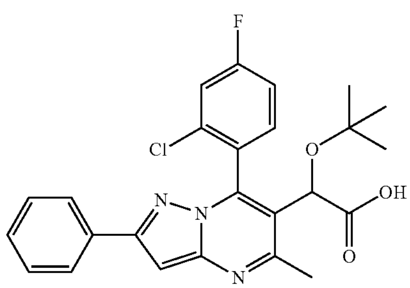 [SMILES: Cc1nc2cc(-c3ccccc3)nn2c(-c2ccc(F)cc2Cl)c1C(OC(C)(C)C)C(=O)O] | C | |
| 91 | 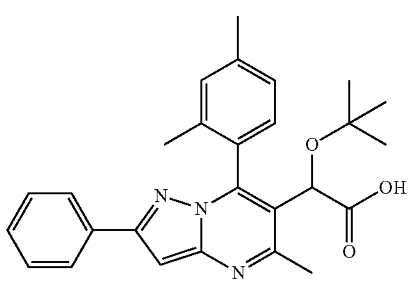 [SMILES: Cc1ccc(-c2c(C(OC(C)(C)C)C(=O)O)c(C)nc3cc(-c4ccccc4)nn23)c(C)c1] | C | |
| 92 | 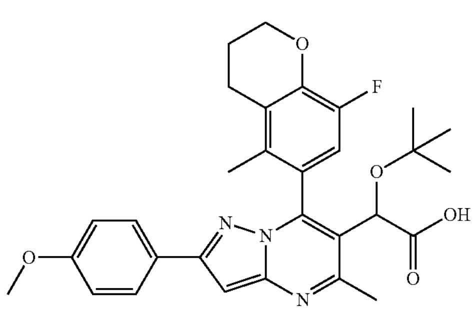 | B | |

TABLE 1-continued

| Example | Structure | Activity | EC$_{50}$ μM |
|---|---|---|---|
| 93 | 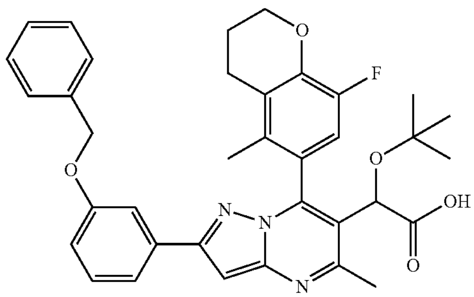 | A | 0.10 |
| 94 | 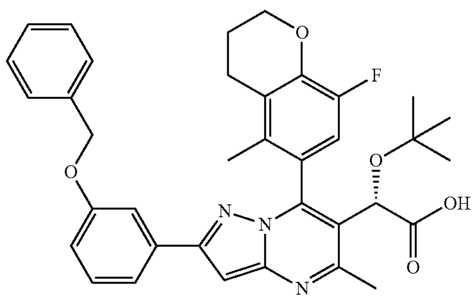 | A | |
| 95 | 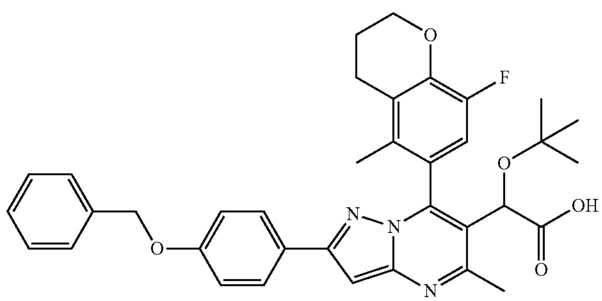 [SMILES: Cc1nc2cc(-c3ccc(OCc4ccccc4)cc3)nn2c(-c2cc(F)c3c(c2C)CCCO3)c1C(OC(C)(C)C)C(=O)O] | A | |
| 96 | 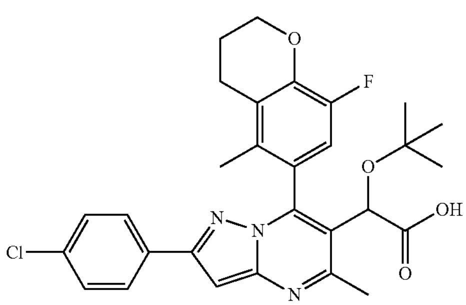 [SMILES: Cc1nc2cc(-c3ccc(Cl)cc3)nn2c(-c2cc(F)c3c(c2C)CCCO3)c1C(OC(C)(C)C)C(=O)O] | B | |
| 97 | 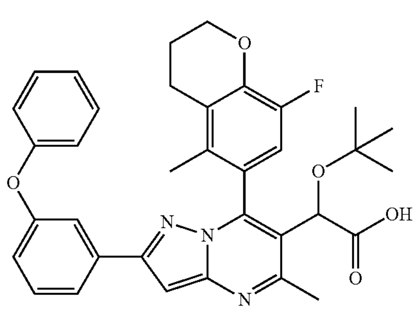 [SMILES: Cc1nc2cc(-c3cccc(Oc4ccccc4)c3)nn2c(-c2cc(F)c3c(c2C)CCCO3)c1C(OC(C)(C)C)C(=O)O] | A | 0.06 |

TABLE 1-continued

| Example | Structure | Activity | EC$_{50}$ μM |
|---------|-----------|----------|--------------|
| 98 | 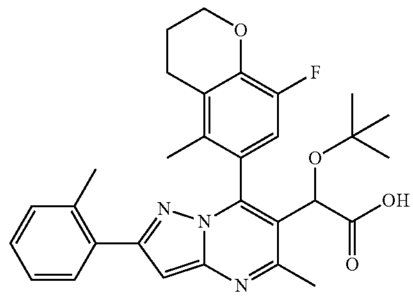 [SMILES: Cc1ccccc1-c1cc2nc(C)c(C(OC(C)(C)C)C(=O)O)c(-c3cc(F)c4c(c3C)CCCO4)n2n1] | C | |
| 99 | 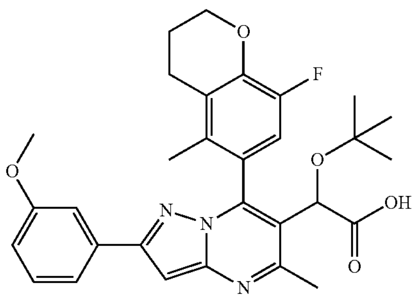 [SMILES: COc1cccc(-c2cc3nc(C)c(C(OC(C)(C)C)C(=O)O)c(-c4cc(F)c5c(c4C)CCCO5)n3n2)c1] | B | 0.35 |
| 100 | 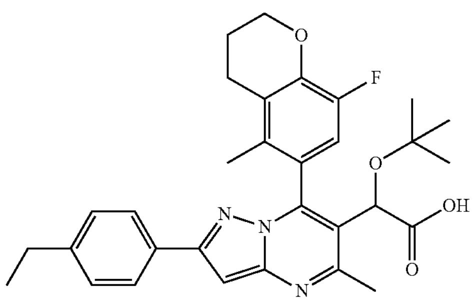 | B | |
| 101 | 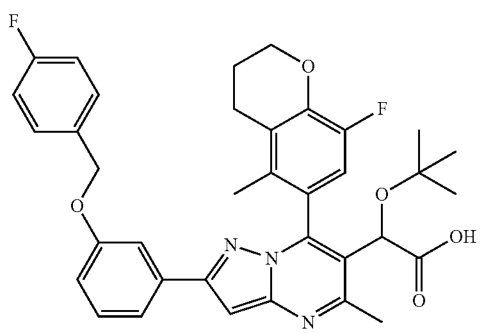 [SMILES: Cc1nc2cc(-c3cccc(OCc4ccc(F)cc4)c3)nn2c(-c2cc(F)c3c(c2C)CCCO3)c1C(OC(C)(C)C)C(=O)O] | A | |
| 102 | 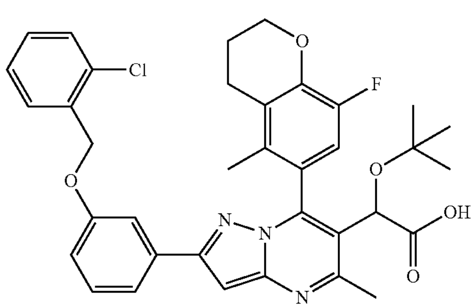 [SMILES: Cc1nc2cc(-c3cccc(OCc4ccccc4Cl)c3)nn2c(-c2cc(F)c3c(c2C)CCCO3)c1C(OC(C)(C)C)C(=O)O] | A | |

TABLE 1-continued

| Example | Structure | Activity | EC$_{50}$ μM |
|---|---|---|---|
| 103 | 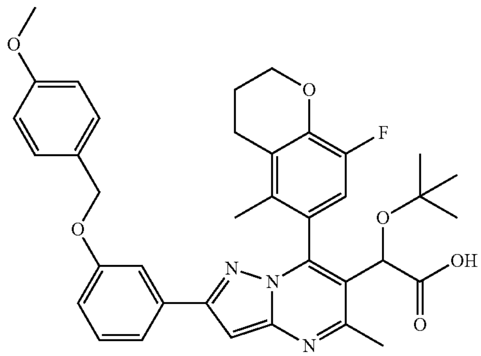 [SMILES: COc1ccc(COc2cccc(-c3cc4nc(C)c(C(OC(C)(C)C)C(=O)O)c(-c5cc(F)c6c(c5C)CCCO6)n4n3)c2)cc1] | A | |
| 104 | 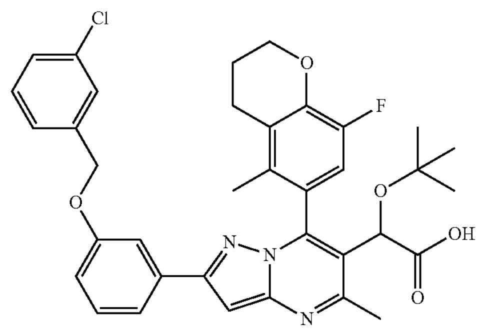 [SMILES: Cc1nc2cc(-c3cccc(OCc4cccc(Cl)c4)c3)nn2c(-c2cc(F)c3c(c2C)CCCO3)c1C(OC(C)(C)C)C(=O)O] | A | |
| 105 | 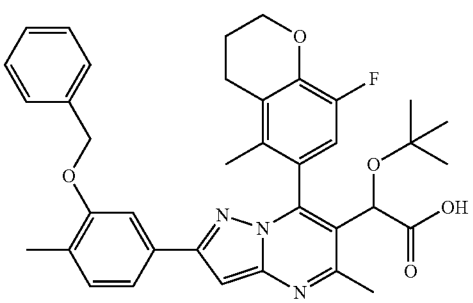 [SMILES: Cc1ccc(-c2cc3nc(C)c(C(OC(C)(C)C)C(=O)O)c(-c4cc(F)c5c(c4C)CCCO5)n3n2)cc1OCc1ccccc1] | A | |
| 106 | 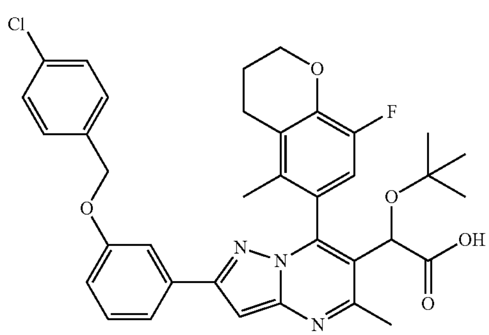 [SMILES: Cc1nc2cc(-c3cccc(OCc4ccc(Cl)cc4)c3)nn2c(-c2cc(F)c3c(c2C)CCCO3)c1C(OC(C)(C)C)C(=O)O] | A | 0.04 |
| 107 | 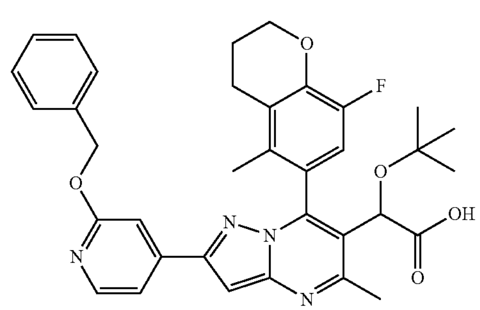 | A | 0.008 |

TABLE 1-continued

| Example | Structure | Activity | EC$_{50}$ μM |
|---|---|---|---|
| 108 | 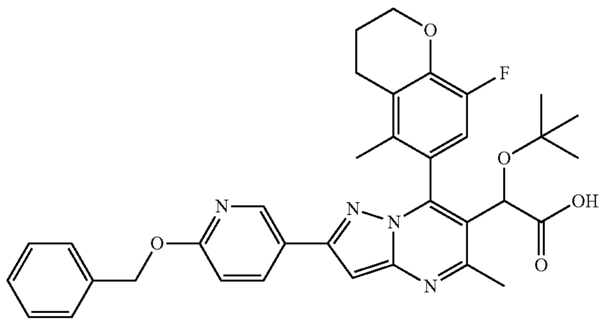 [SMILES: Cc1nc2cc(-c3ccc(OCc4ccccc4)nc3)nn2c(-c2cc(F)c3c(c2C)CCCO3)c1C(OC(C)(C)C)C(=O)O] | A | |
| 109 | 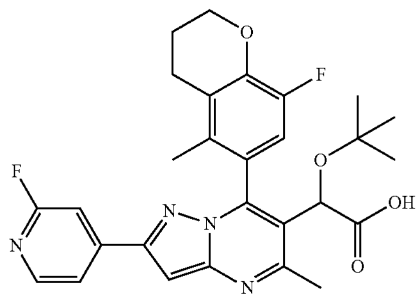 | B | 0.27 |
| 110 | 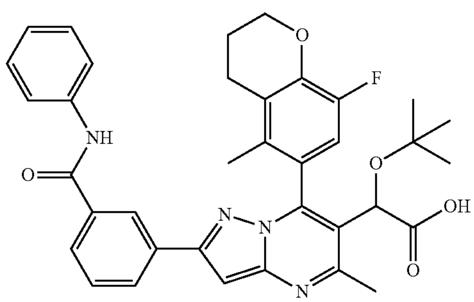 [SMILES: Cc1nc2cc(-c3cccc(C(=O)Nc4ccccc4)c3)nn2c(-c2cc(F)c3c(c2C)CCCO3)c1C(OC(C)(C)C)C(=O)O] | B | |
| 111 | 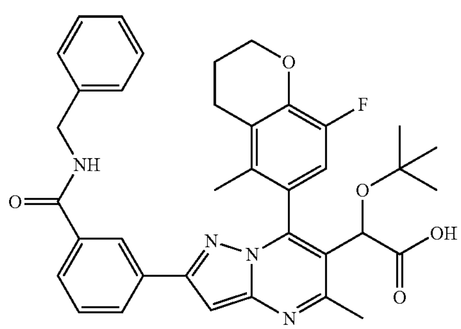 [SMILES: Cc1nc2cc(-c3cccc(C(=O)NCc4ccccc4)c3)nn2c(-c2cc(F)c3c(c2C)CCCO3)c1C(OC(C)(C)C)C(=O)O] | B | |
| 112 | 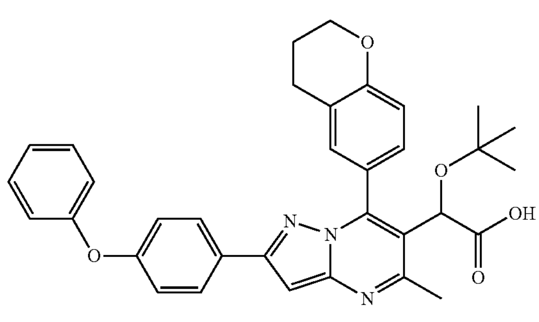 [SMILES: Cc1nc2cc(-c3ccc(Oc4ccccc4)cc3)nn2c(-c2ccc3c(c2)CCCO3)c1C(OC(C)(C)C)C(=O)O] | B | |

TABLE 1-continued

| Example | Structure | Activity | EC$_{50}$ μM |
|---------|-----------|----------|--------------|
| 113 | 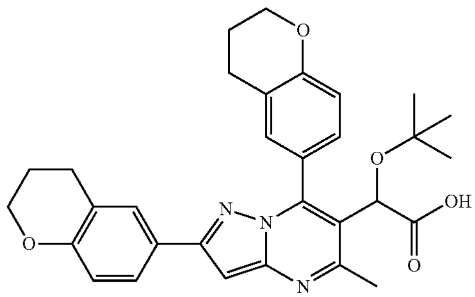 [SMILES: Cc1nc2cc(-c3ccc4c(c3)CCCO4)nn2c(-c2ccc3c(c2)CCCO3)c1C(OC(C)(C)C)C(=O)O] | B | 0.11 |
| 114 | 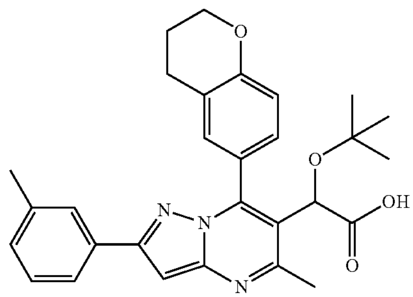 [SMILES: Cc1cccc(-c2cc3nc(C)c(C(OC(C)(C)C)C(=O)O)c(-c4ccc5c(c4)CCCO5)n3n2)c1] | B | |
| 115 | 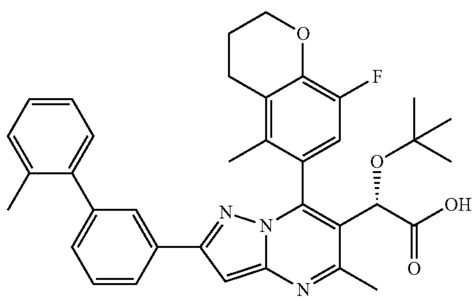 | A | 0.02 |
| 116 | 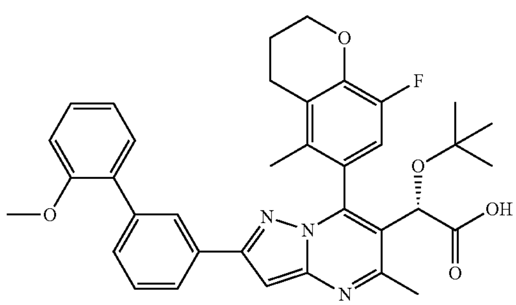 [SMILES: COc1ccccc1-c1cccc(-c2cc3nc(C)c([C@H](OC(C)(C)C)C(=O)O)c(-c4cc(F)c5c(c4C)CCCO5)n3n2)c1] | A | |
| 117 | 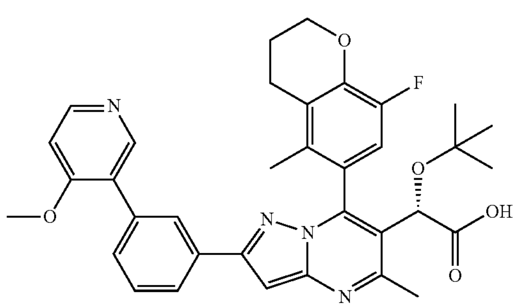 [SMILES: COc1ccncc1-c1cccc(-c2cc3nc(C)c([C@H](OC(C)(C)C)C(=O)O)c(-c4cc(F)c5c(c4C)CCCO5)n3n2)c1] | A | |

TABLE 1-continued
| Example | Structure | Activity | EC$_{50}$ μM |
|---|---|---|---|
| 118 | 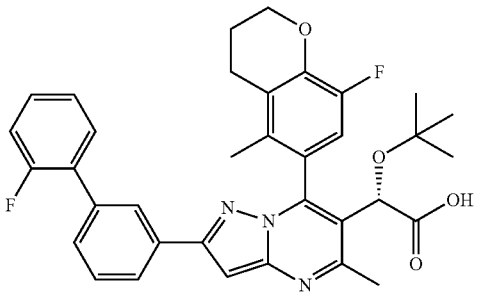 [SMILES: Cc1nc2cc(-c3cccc(-c4ccccc4F)c3)nn2c(-c2cc(F)c3c(c2C)CCCO3)c1[C@H](OC(C)(C)C)C(=O)O] | A | |
| 119 | 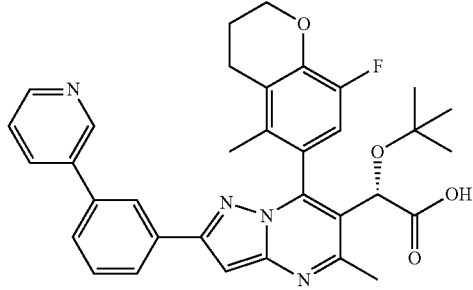 [SMILES: Cc1nc2cc(-c3cccc(-c4cccnc4)c3)nn2c(-c2cc(F)c3c(c2C)CCCO3)c1[C@H](OC(C)(C)C)C(=O)O] | A | |
| 120 | 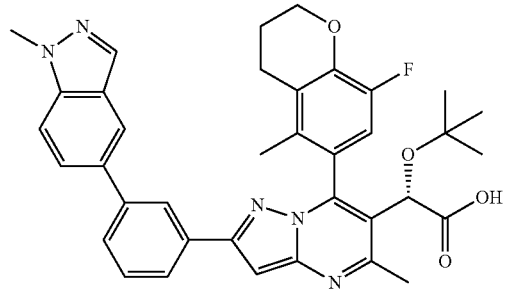 [SMILES: Cc1nc2cc(-c3cccc(-c4ccc5c(cnn5C)c4)c3)nn2c(-c2cc(F)c3c(c2C)CCCO3)c1[C@H](OC(C)(C)C)C(=O)O] | A | 0.002 |
| 121 | 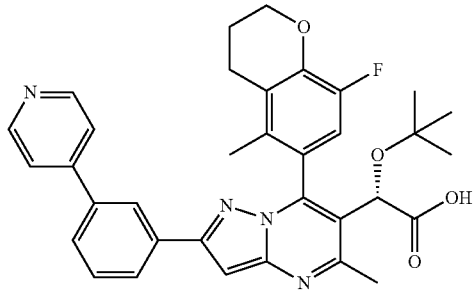 [SMILES: Cc1nc2cc(-c3cccc(-c4ccncc4)c3)nn2c(-c2cc(F)c3c(c2C)CCCO3)c1[C@H](OC(C)(C)C)C(=O)O] | A | |
| 122 | 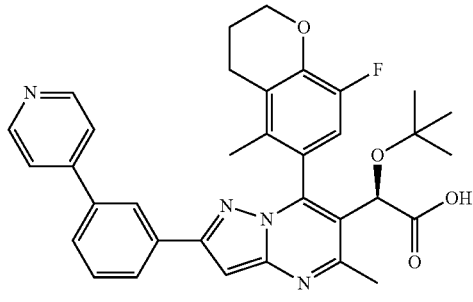 [SMILES: Cc1nc2cc(-c3cccc(-c4ccncc4)c3)nn2c(-c2cc(F)c3c(c2C)CCCO3)c1[C@@H](OC(C)(C)C)C(=O)O] | C | |

TABLE 1-continued
| Example | Structure | Activity | EC$_{50}$ µM |
|---|---|---|---|
| 123 | 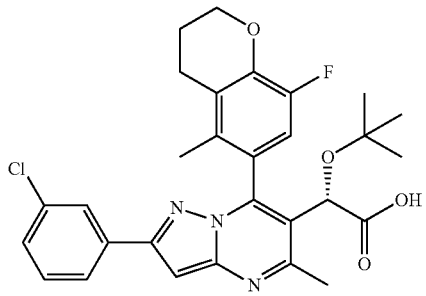 [SMILES: Cc1nc2cc(-c3cccc(Cl)c3)nn2c(-c2cc(F)c3c(c2C)CCCO3)c1[C@H](OC(C)(C)C)C(=O)O] | A | |
| 124 | 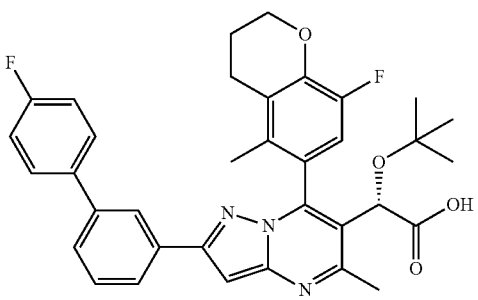 [SMILES: Cc1nc2cc(-c3cccc(-c4ccc(F)cc4)c3)nn2c(-c2cc(F)c3c(c2C)CCCO3)c1[C@H](OC(C)(C)C)C(=O)O] | A | |
| 125 | 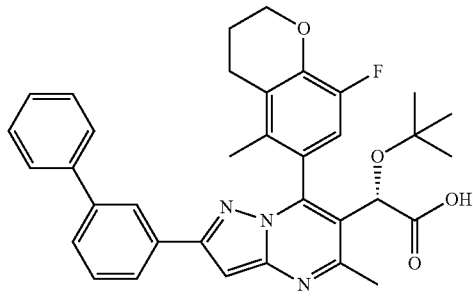 | A | |
| 126 | 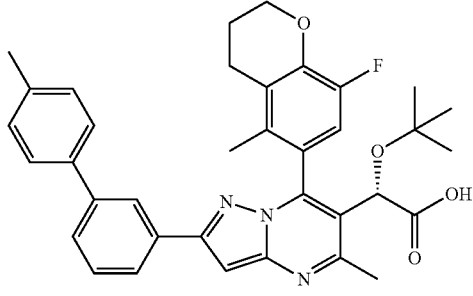 [SMILES: Cc1ccc(-c2cccc(-c3cc4nc(C)c([C@H](OC(C)(C)C)C(=O)O)c(-c5cc(F)c6c(c5C)CCCO6)n4n3)c2)cc1] | A | |
| 127 | 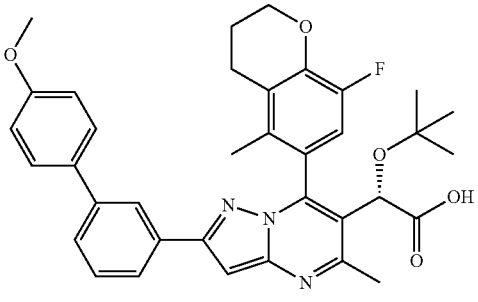 [SMILES: COc1ccc(-c2cccc(-c3cc4nc(C)c([C@H](OC(C)(C)C)C(=O)O)c(-c5cc(F)c6c(c5C)CCCO6)n4n3)c2)cc1] | A | |

TABLE 1-continued

| Example | Structure | Activity | EC$_{50}$ μM |
|---|---|---|---|
| 128 | 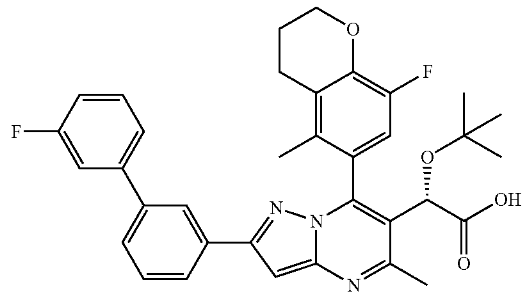 [SMILES: Cc1nc2cc(-c3cccc(-c4cccc(F)c4)c3)nn2c(-c2cc(F)c3c(c2C)CCCO3)c1[C@H](OC(C)(C)C)C(=O)O] | A | |
| 129 | 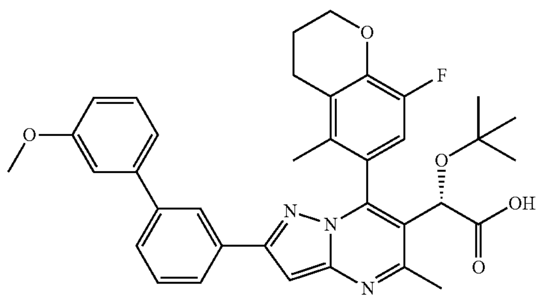 [SMILES: COc1cccc(-c2cccc(-c3cc4nc(C)c([C@H](OC(C)(C)C)C(=O)O)c(-c5cc(F)c6c(c5C)CCCO6)n4n3)c2)c1] | A | |
| 130 | 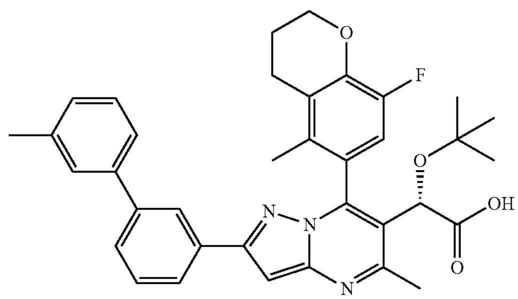 [SMILES: Cc1cccc(-c2cccc(-c3cc4nc(C)c([C@H](OC(C)(C)C)C(=O)O)c(-c5cc(F)c6c(c5C)CCCO6)n4n3)c2)c1] | A | |
| 131 | 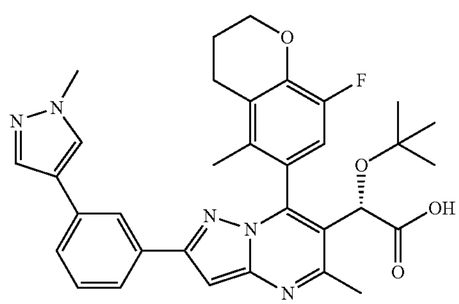 [SMILES: Cc1nc2cc(-c3cccc(-c4cnn(C)c4)c3)nn2c(-c2cc(F)c3c(c2C)CCCO3)c1[C@H](OC(C)(C)C)C(=O)O] | A | |
| 132 | 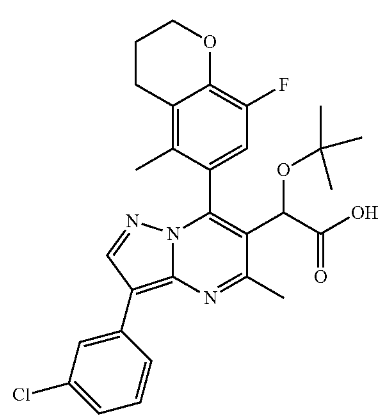 [SMILES: Cc1nc2c(-c3cccc(Cl)c3)cnn2c(-c2cc(F)c3c(c2C)CCCO3)c1C(OC(C)(C)C)C(=O)O] | B | |

TABLE 1-continued

| Example | Structure | Activity | EC$_{50}$ μM |
|---|---|---|---|
| 133 | 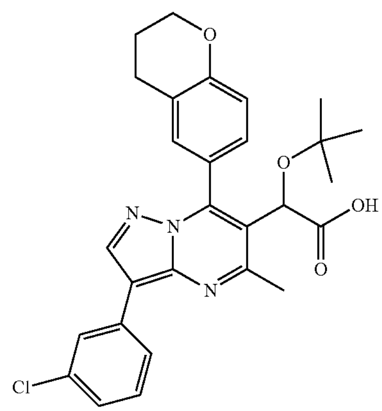 [SMILES: Cc1nc2c(-c3cccc(Cl)c3)cnn2c(-c2ccc3c(c2)CCCO3)c1C(OC(C)(C)C)C(=O)O] | B | |
| 134 | 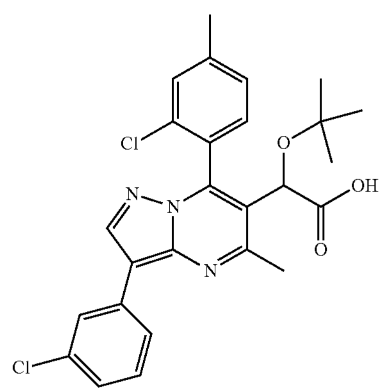 [SMILES: Cc1ccc(-c2c(C(OC(C)(C)C)C(=O)O)c(C)nc3c(-c4cccc(Cl)c4)cnn23)c(Cl)c1] | C | |
| 135 | 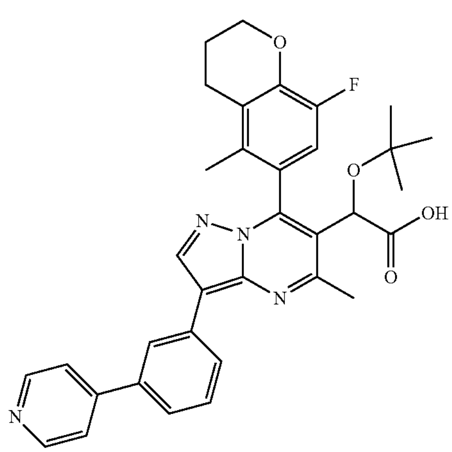 [SMILES: Cc1nc2c(-c3cccc(-c4ccncc4)c3)cnn2c(-c2cc(F)c3c(c2C)CCCO3)c1C(OC(C)(C)C)C(=O)O] | B | |

TABLE 1-continued

| Example | Structure | Activity | EC$_{50}$ μM |
|---------|-----------|----------|--------------|
| 136 | 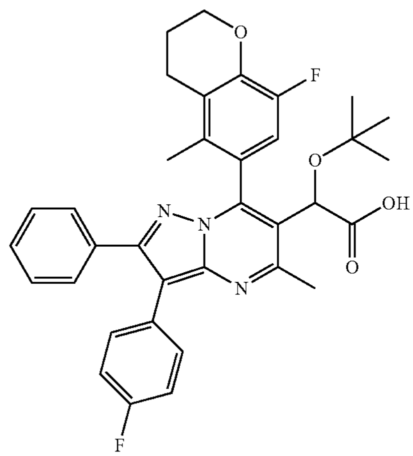 [SMILES: Cc1nc2c(-c3ccc(F)cc3)c(-c3ccccc3)nn2c(-c2cc(F)c3c(c2C)CCCO3)c1C(OC(C)(C)C)C(=O)O] | C | 1.6 |
| 137 | 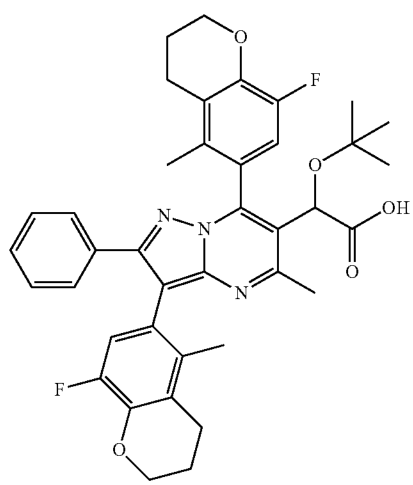 [SMILES: Cc1nc2c(-c3cc(F)c4c(c3C)CCCO4)c(-c3ccccc3)nn2c(-c2cc(F)c3c(c2C)CCCO3)c1C(OC(C)(C)C)C(=O)O] | C | |
| 138 | 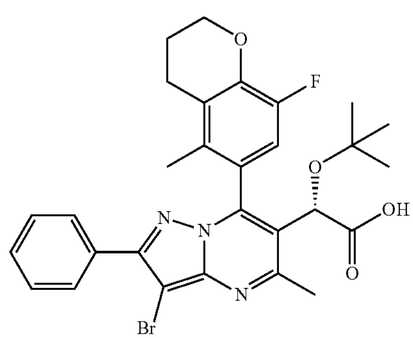 [SMILES: Cc1nc2c(Br)c(-c3ccccc3)nn2c(-c2cc(F)c3c(c2C)CCCO3)c1[C@H](OC(C)(C)C)C(=O)O] | B | |

TABLE 1-continued

| Example | Structure | Activity | EC$_{50}$ μM |
|---------|-----------|----------|--------------|
| 139 | 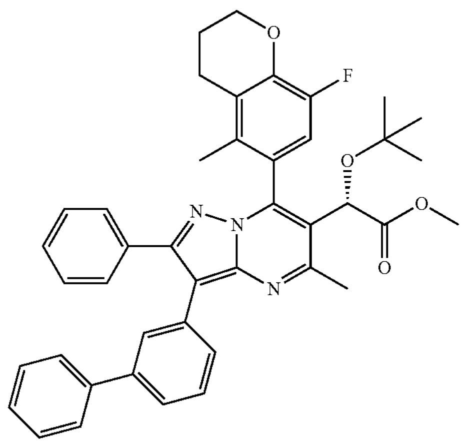 [SMILES: COC(=O)[C@@H](OC(C)(C)C)c1c(C)nc2c(-c3cccc(-c4ccccc4)c3)c(-c3ccccc3)nn2c1-c1cc(F)c2c(c1C)CCCO2] | C | |
| 140 | 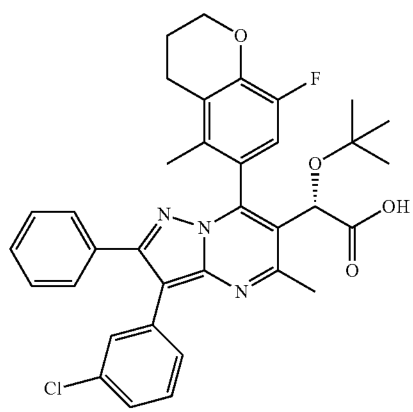 [SMILES: Cc1nc2c(-c3cccc(Cl)c3)c(-c3ccccc3)nn2c(-c2cc(F)c3c(c2C)CCCO3)c1[C@H](OC(C)(C)C)C(=O)O] | B | 1 |
| 141 | 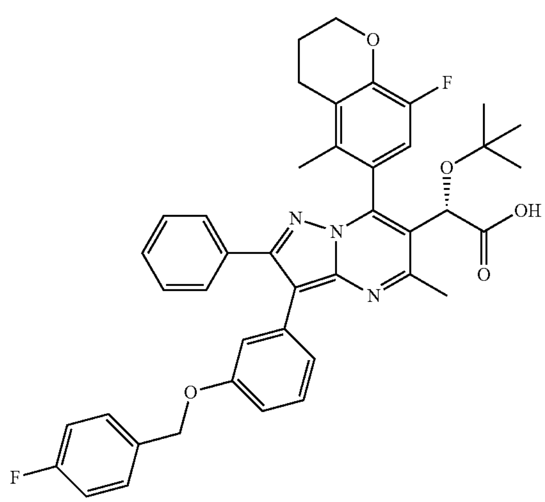 [SMILES: Cc1nc2c(-c3cccc(OCc4ccc(F)cc4)c3)c(-c3ccccc3)nn2c(-c2cc(F)c3c(c2C)CCCO3)c1[C@H](OC(C)(C)C)C(=O)O] | C | 3.3 |

TABLE 1-continued

| Example | Structure | Activity | EC$_{50}$ μM |
|---|---|---|---|
| 142 | 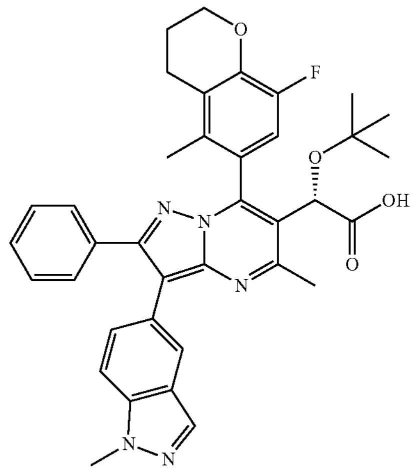 [SMILES: Cc1nc2c(-c3ccc4c(cnn4C)c3)c(-c3ccccc3)nn2c(-c2cc(F)c3c(c2C)CCCO3)c1[C@H](OC(C)(C)C)C(=O)O] | B | |
| 143 | 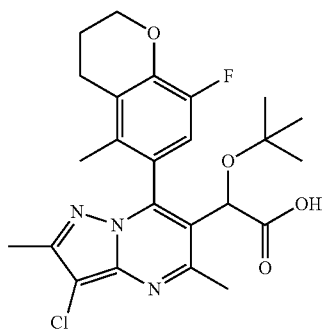 [SMILES: Cc1nc2c(Cl)c(C)nn2c(-c2cc(F)c3c(c2C)CCCO3)c1C(OC(C)(C)C)C(=O)O] | B | |
| 144 | 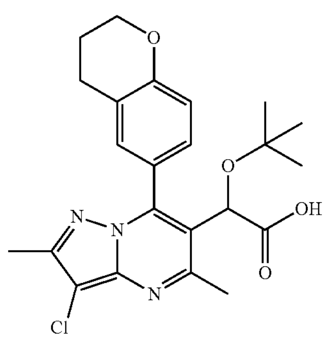 [SMILES: Cc1nc2c(Cl)c(C)nn2c(-c2ccc3c(c2)CCCO3)c1C(OC(C)(C)C)C(=O)O] | B | |
| 145 | 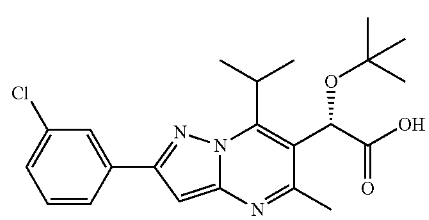 [SMILES: Cc1nc2cc(-c3cccc(Cl)c3)nn2c(C(C)C)c1[C@H](OC(C)(C)C)C(=O)O] | C | |
| 146 | 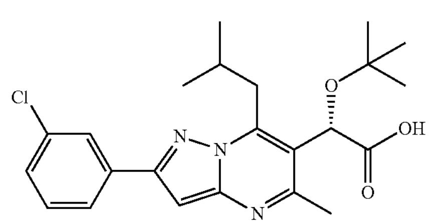 [SMILES: Cc1nc2cc(-c3cccc(Cl)c3)nn2c(CC(C)C)c1[C@H](OC(C)(C)C)C(=O)O] | C | |

TABLE 1-continued

| Example | Structure | Activity | EC$_{50}$ μM |
|---|---|---|---|
| 147 | 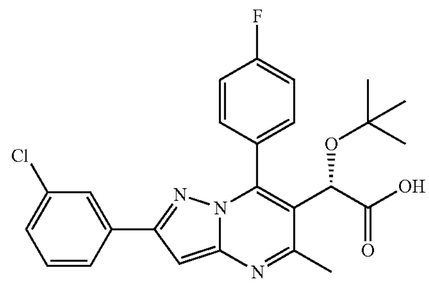 [SMILES: Cc1nc2cc(-c3cccc(Cl)c3)nn2c(-c2ccc(F)cc2)c1[C@H](OC(C)(C)C)C(=O)O] | C | |
| 148 | 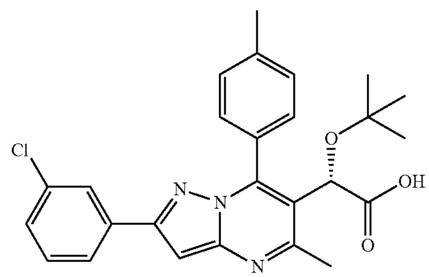 [SMILES: Cc1ccc(-c2c([C@H](OC(C)(C)C)C(=O)O)c(C)nc3cc(-c4cccc(Cl)c4)nn23)cc1] | B | 0.88 |
| 149 | 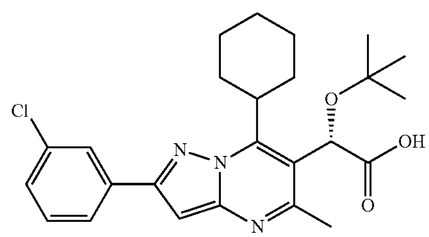 [SMILES: Cc1nc2cc(-c3cccc(Cl)c3)nn2c(C2CCCCC2)c1[C@H](OC(C)(C)C)C(=O)O] | C | |
| 150 | 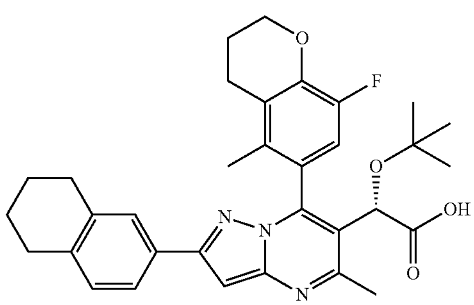 [SMILES: Cc1nc2cc(-c3ccc4c(c3)CCCC4)nn2c(-c2cc(F)c3c(c2C)CCCO3)c1[C@H](OC(C)(C)C)C(=O)O] | A | |
| 151 | 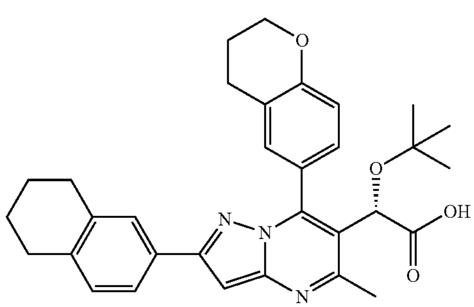 [SMILES: Cc1nc2cc(-c3ccc4c(c3)CCCC4)nn2c(-c2ccc3c(c2)CCCO3)c1[C@H](OC(C)(C)C)C(=O)O] | A | |

TABLE 1-continued

| Example | Structure | Activity | EC$_{50}$ μM |
|---------|-----------|----------|--------------|
| 152 | 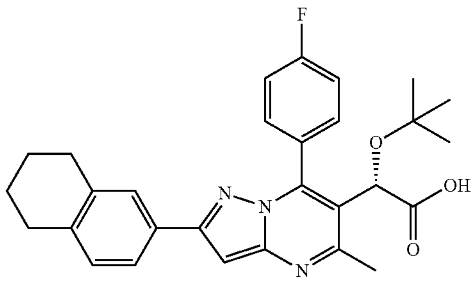 | C | |
| 153 | 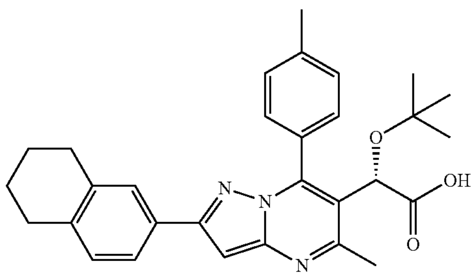 [SMILES: Cc1ccc(-c2c([C@H](OC(C)(C)C)C(=O)O)c(C)nc3cc(-c4ccc5c(c4)CCCC5)nn23)cc1] | B | |
| 154 | 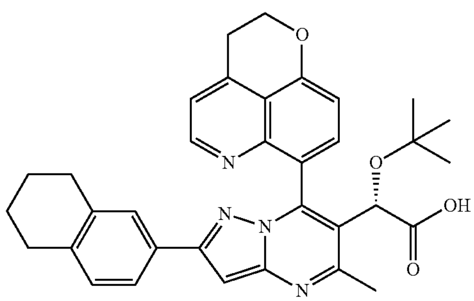 [SMILES: Cc1nc2cc(-c3ccc4c(c3)CCCC4)nn2c(-c2ccc3c4c(ccnc24)CCO3)c1[C@H](OC(C)(C)C)C(=O)O] | C | |
| 155 | 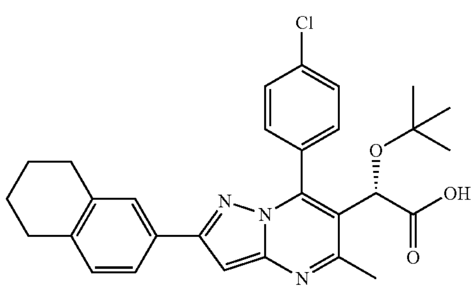 | B | |
| 156 | 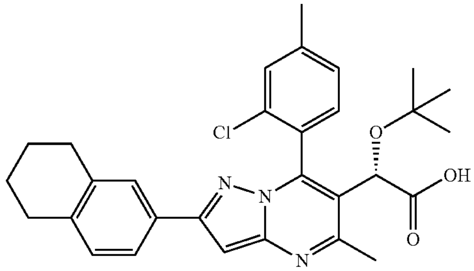 | C | |

TABLE 1-continued

| Example | Structure | Activity | EC$_{50}$ μM |
|---|---|---|---|
| 157 | 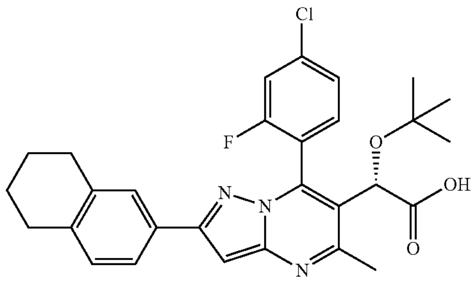 [SMILES: Cc1nc2cc(-c3ccc4c(c3)CCCC4)nn2c(-c2ccc(Cl)cc2F)c1[C@H](OC(C)(C)C)C(=O)O] | B | |
| 158 | 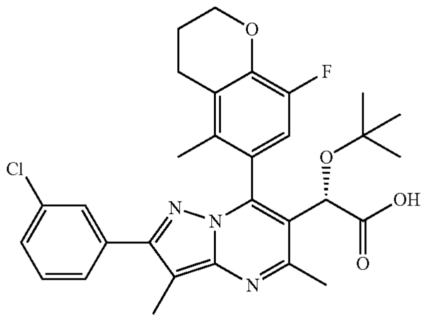 [SMILES: Cc1nc2c(C)c(-c3cccc(Cl)c3)nn2c(-c2cc(F)c3c(c2C)CCCO3)c1[C@H](OC(C)(C)C)C(=O)O] | B | |
| 159 | 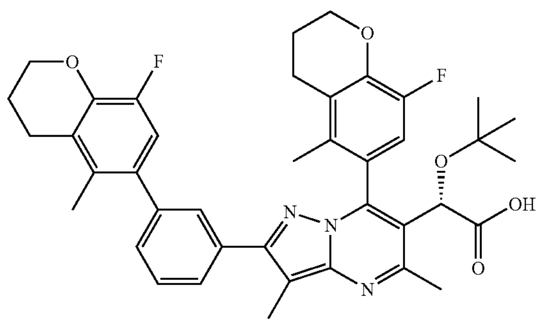 [SMILES: Cc1nc2c(C)c(-c3cccc(-c4cc(F)c5c(c4C)CCCO5)c3)nn2c(-c2cc(F)c3c(c2C)CCCO3)c1[C@H](OC(C)(C)C)C(=O)O] | A | |
| 160 | 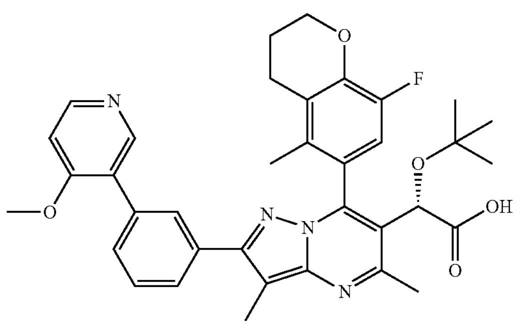 [SMILES: COc1ccncc1-c1cccc(-c2nn3c(-c4cc(F)c5c(c4C)CCCO5)c([C@H](OC(C)(C)C)C(=O)O)c(C)nc3c2C)c1] | A | 0.01 |
| 161 | 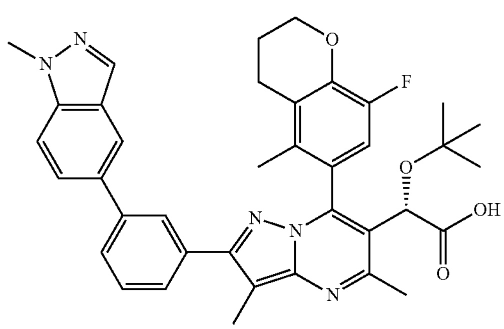 [SMILES: Cc1nc2c(C)c(-c3cccc(-c4ccc5c(cnn5C)c4)c3)nn2c(-c2cc(F)c3c(c2C)CCCO3)c1[C@H](OC(C)(C)C)C(=O)O] | A | |

TABLE 1-continued

| Example | Structure | Activity | EC$_{50}$ μM |
|---|---|---|---|
| 162 | 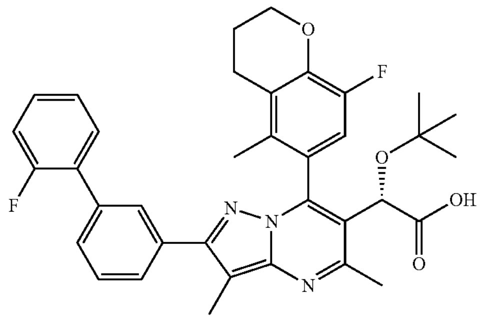 [SMILES: Cc1nc2c(C)c(-c3cccc(-c4ccccc4F)c3)nn2c(-c2cc(F)c3c(c2C)CCCO3)c1[C@H](OC(C)(C)C)C(=O)O] | A | |
| 163 | 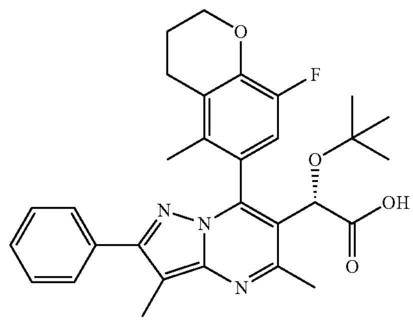 [SMILES: Cc1nc2c(C)c(-c3ccccc3)nn2c(-c2cc(F)c3c(c2C)CCCO3)c1[C@H](OC(C)(C)C)C(=O)O] | A | 0.20 |
| 164 | 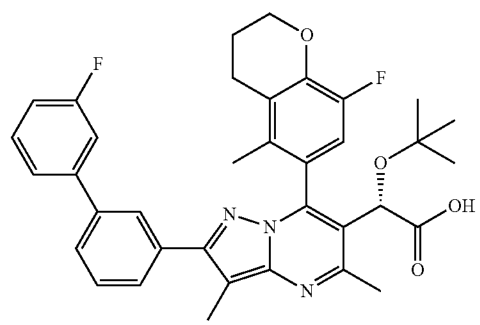 [SMILES: Cc1nc2c(C)c(-c3cccc(-c4cccc(F)c4)c3)nn2c(-c2cc(F)c3c(c2C)CCCO3)c1[C@H](OC(C)(C)C)C(=O)O] | A | |
| 165 | 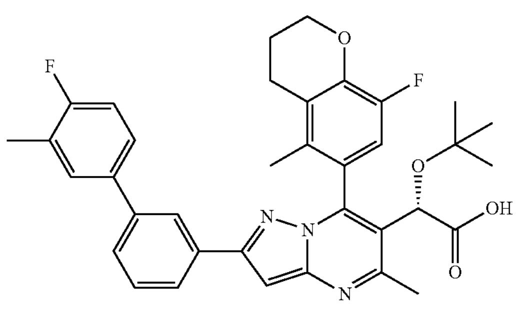 | A | |
| 166 | 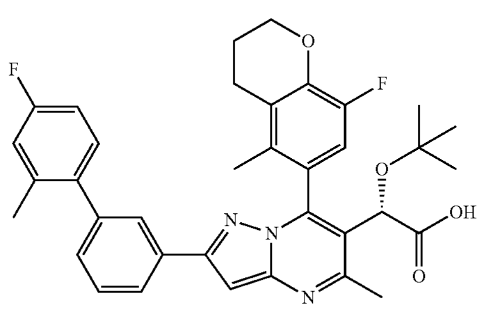 [SMILES: Cc1cc(F)ccc1-c1cccc(-c2cc3nc(C)c([C@H](OC(C)(C)C)C(=O)O)c(-c4cc(F)c5c(c4C)CCCO5)n3n2)c1] | A | |

TABLE 1-continued

| Example | Structure | Activity | EC₅₀ μM |
|---|---|---|---|
| 167 | 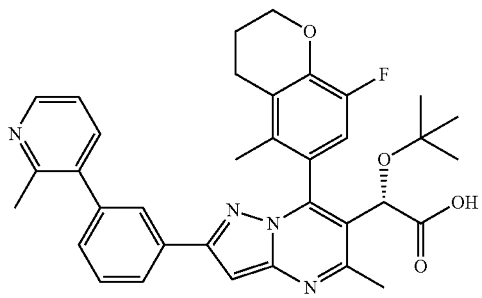 | A | |
| 168 | 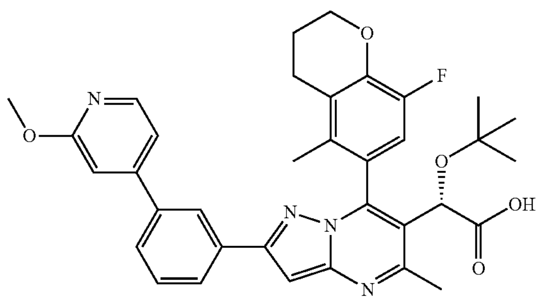 [SMILES: COc1cc(-c2cccc(-c3cc4nc(C)c([C@H](OC(C)(C)C)C(=O)O)c(-c5cc(F)c6c(c5C)CCCO6)n4n3)c2)ccn1] | A | |
| 169 | 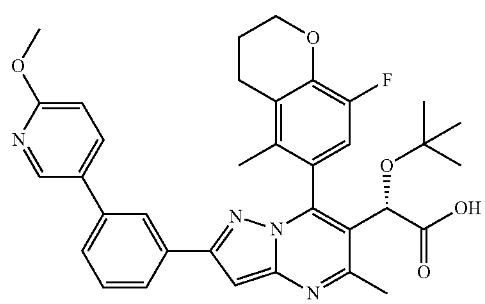 | A | |
| 170 | 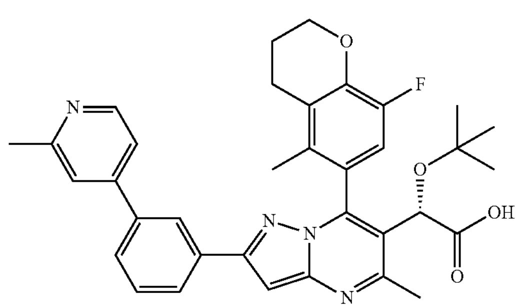 [SMILES: Cc1cc(-c2cccc(-c3cc4nc(C)c([C@H](OC(C)(C)C)C(=O)O)c(-c5cc(F)c6c(c5C)CCCO6)n4n3)c2)ccn1] | A | |
| 171 | 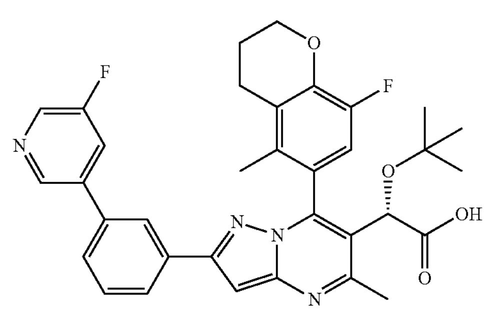 [SMILES: Cc1nc2cc(-c3cccc(-c4cncc(F)c4)c3)nn2c(-c2cc(F)c3c(c2C)CCCO3)c1[C@H](OC(C)(C)C)C(=O)O] | A | |

TABLE 1-continued

| Example | Structure | Activity EC$_{50}$ μM |
|---|---|---|
| 172 | 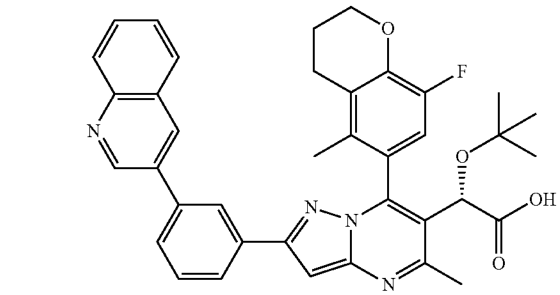 [SMILES: Cc1nc2cc(-c3cccc(-c4cnc5ccccc5c4)c3)nn2c(-c2cc(F)c3c(c2C)CCCO3)c1[C@H](OC(C)(C)C)C(=O)O] | A |
| 173 | 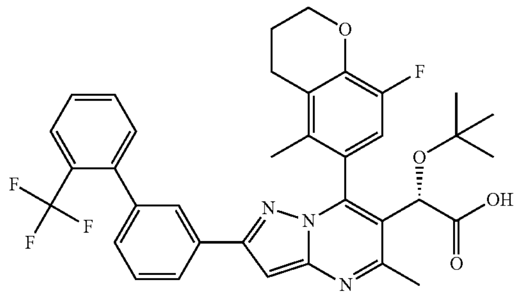 [SMILES: Cc1nc2cc(-c3cccc(-c4ccccc4C(F)(F)F)c3)nn2c(-c2cc(F)c3c(c2C)CCCO3)c1[C@H](OC(C)(C)C)C(=O)O] | A |
| 174 | 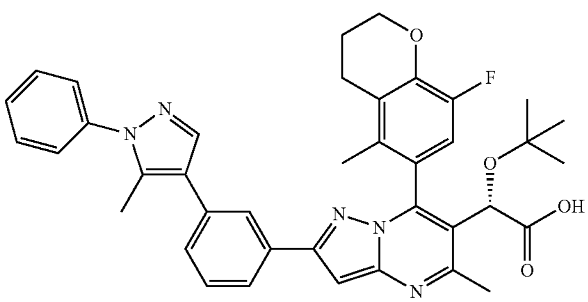 [SMILES: Cc1nc2cc(-c3cccc(-c4cnn(-c5ccccc5)c4C)c3)nn2c(-c2cc(F)c3c(c2C)CCCO3)c1[C@H](OC(C)(C)C)C(=O)O] | A |
| 175 | 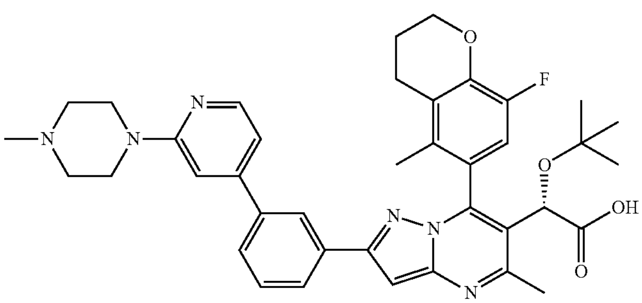 [SMILES: Cc1nc2cc(-c3cccc(-c4ccnc(N5CCN(C)CC5)c4)c3)nn2c(-c2cc(F)c3c(c2C)CCCO3)c1[C@H](OC(C)(C)C)C(=O)O] | A |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "cc" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1.

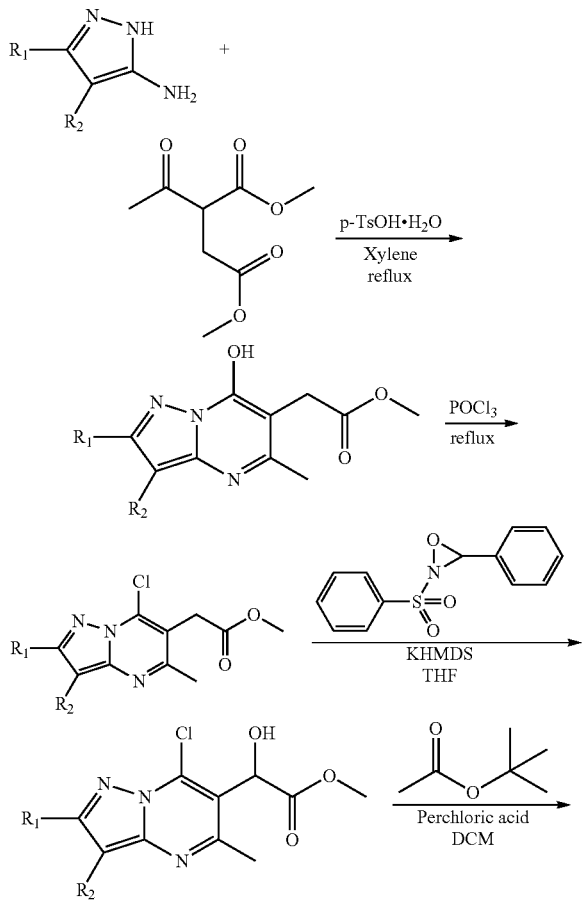

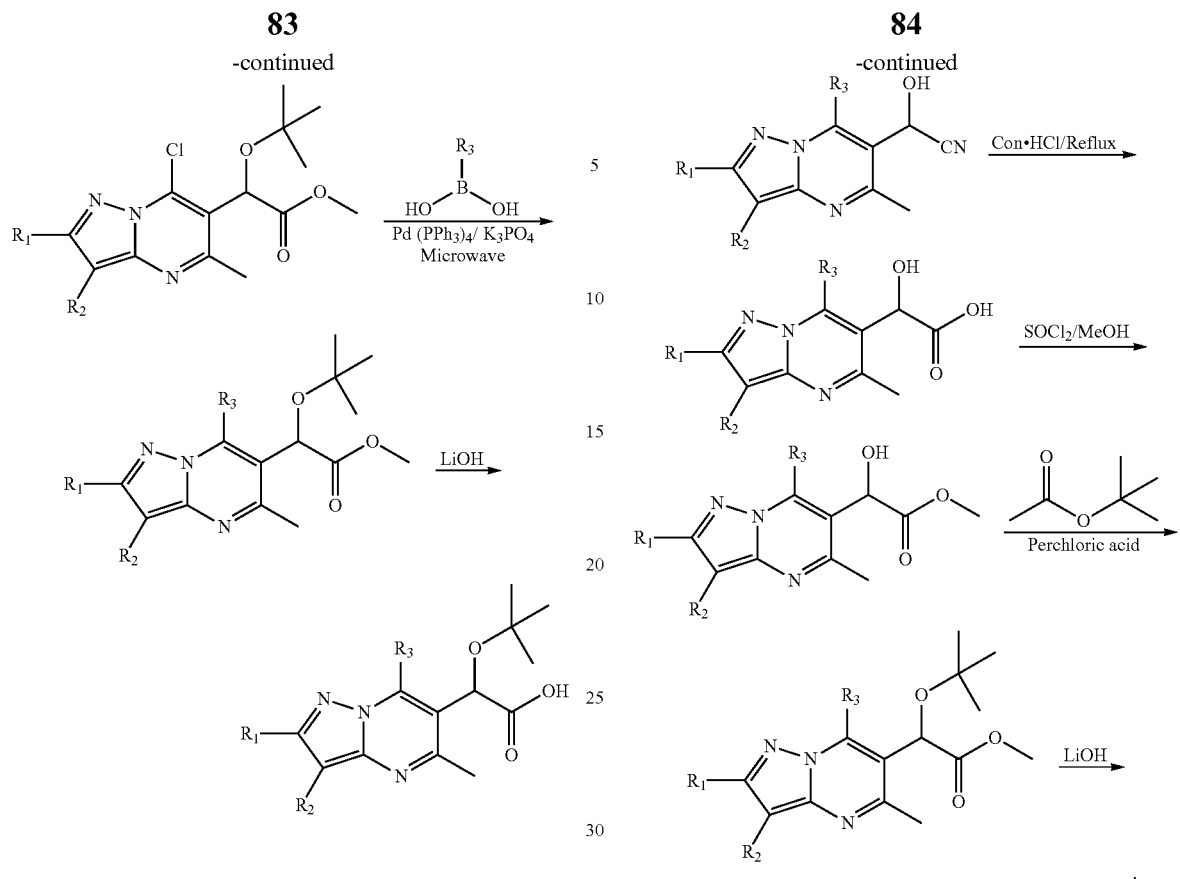

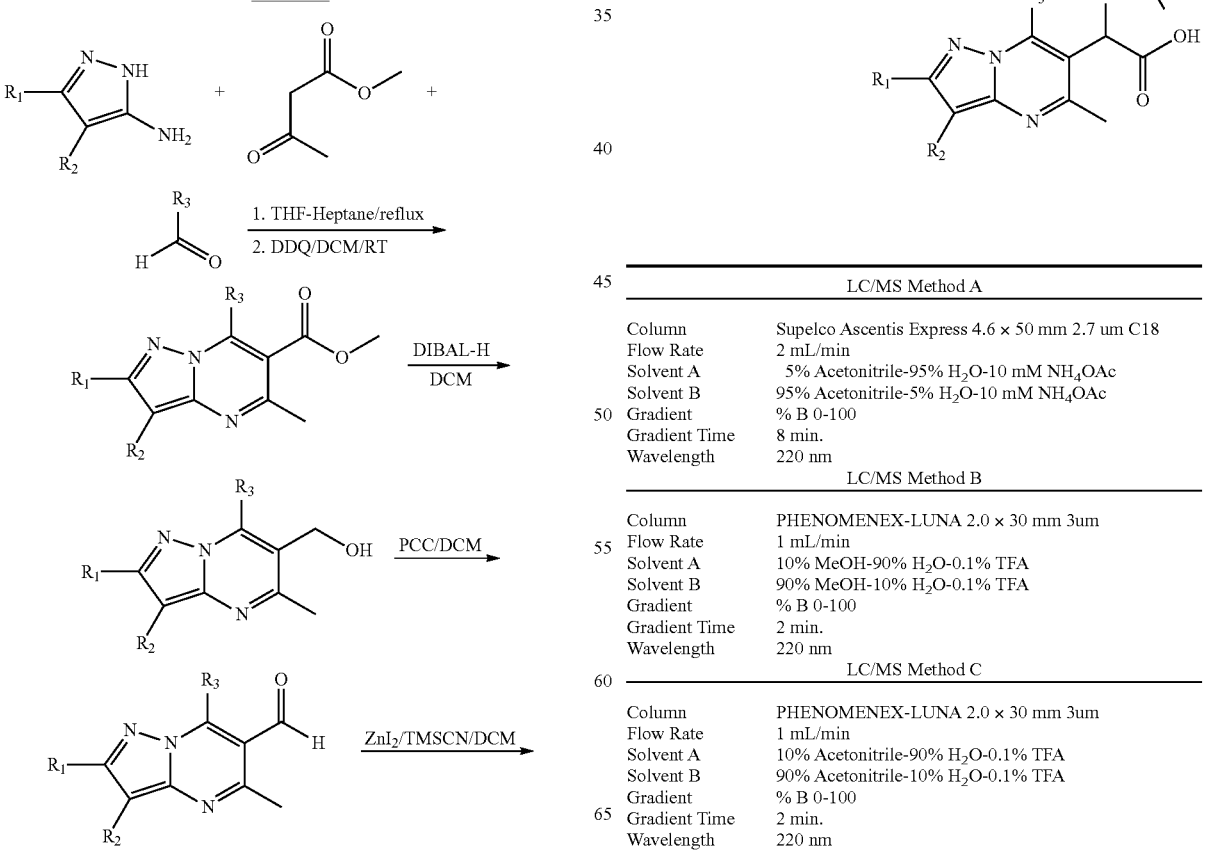

| LC/MS Method A | |
|---|---|
| Column | Supelco Ascentis Express 4.6 × 50 mm 2.7 um C18 |
| Flow Rate | 2 mL/min |
| Solvent A | 5% Acetonitrile-95% $H_2O$-10 mM $NH_4OAc$ |
| Solvent B | 95% Acetonitrile-5% $H_2O$-10 mM $NH_4OAc$ |
| Gradient | % B 0-100 |
| Gradient Time | 8 min. |
| Wavelength | 220 nm |
| LC/MS Method B | |
| Column | PHENOMENEX-LUNA 2.0 × 30 mm 3um |
| Flow Rate | 1 mL/min |
| Solvent A | 10% MeOH-90% $H_2O$-0.1% TFA |
| Solvent B | 90% MeOH-10% $H_2O$-0.1% TFA |
| Gradient | % B 0-100 |
| Gradient Time | 2 min. |
| Wavelength | 220 nm |
| LC/MS Method C | |
| Column | PHENOMENEX-LUNA 2.0 × 30 mm 3um |
| Flow Rate | 1 mL/min |
| Solvent A | 10% Acetonitrile-90% $H_2O$-0.1% TFA |
| Solvent B | 90% Acetonitrile-10% $H_2O$-0.1% TFA |
| Gradient | % B 0-100 |
| Gradient Time | 2 min. |
| Wavelength | 220 nm |

-continued

LC/MS Method D

| Column | Waters Xbridge 4.6 × 100 mm 3.5 um C18 |
|---|---|
| Flow Rate | 1 mL/min |
| Solvent A | $H_2O$-10 mM $NH_4OAc$ |
| Solvent B | Acetonitrile-10 mM $NH_4OAc$ |
| Gradient | % B 30-95 |
| Gradient Time | 11 min. |
| Wavelength | 220 nm |

LC/MS Method E

| Column | Waters Sunfire 4.6 × 100 mm 3.5 um C18 |
|---|---|
| Flow Rate | 1 mL/min |
| Solvent A | $H_2O$-0.1% TFA |
| Solvent B | Acetonitrile-0.1% TFA |
| Gradient | % B 30-95 |
| Gradient Time | 6 min. |
| Wavelength | 220 nm |

DESCRIPTION OF SPECIFIC EMBODIMENTS

Scheme 3.

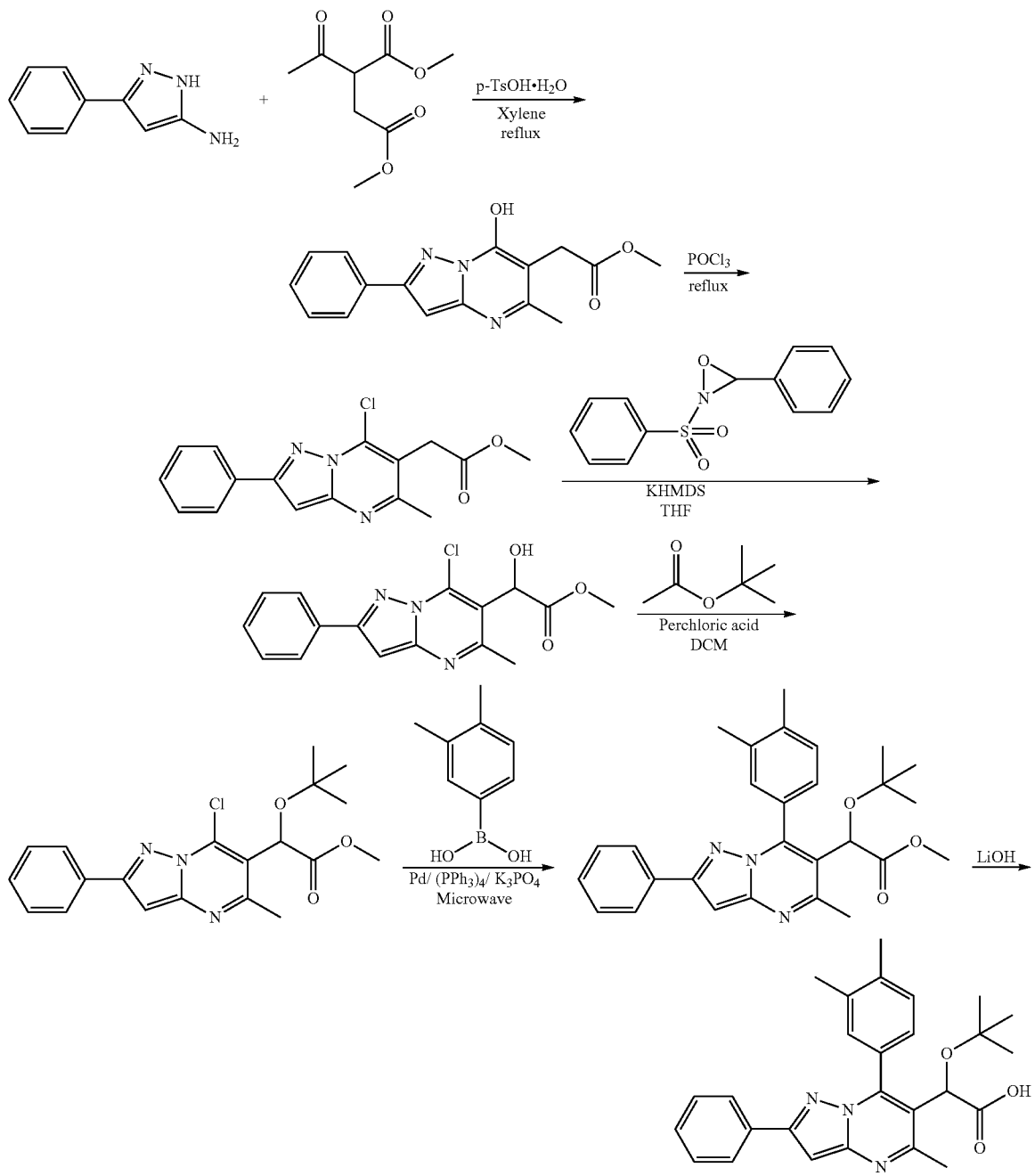

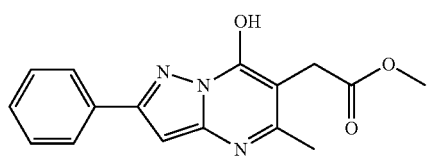

Methyl 2-(5-methyl-7-oxo-2-phenyl-4,7-dihydropyrazolo[1,5-a]pyrimidin-6-yl)acetate To a solution of 3-phenyl-1H-pyrazol-5-amine (4 g, 25.1 mmol) and dimethyl 2-acetylsuccinate (12 mL, 74.0 mmol) in xylene (120 mL) was added p-toluenesulfonic acid monohydrate (50 mg, 0.263 mmol). The reaction mixture was heated at reflux under a Dean-Stark trap for 20 h. The solid was filtered and washed with hexanes to afford the title compound (6.4 g, 86%). $^1$H-NMR (400 MHz, MeOD) δ ppm 2.37 (3H, s), 3.66 (2H, s), 3.72 (3H, s), 6.46 (1H, s), 7.34-7.53 (3H, m), 7.87-8.06 (2H, m).

| Methyl 2-(5-methyl-7-oxo-2-phenyl-4,7-dihydropyrazolo[1,5-a]pyrimidin-6-yl)acetate | |
|---|---|
| MS (M + H)$^+$ Calcd. | 298 |
| MS (M + H)$^+$ Observ. | 298 |
| Retention Time | 1.15 min |
| | LC Condition |
| Solvent A | 10% Acetonitrile: 90% Water: 0.1% TFA |
| Solvent B | 90% Acetonitrile: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile: Water: TFA |
| Column | Phenomenex Luna C18, 30 × 2, 3 u |

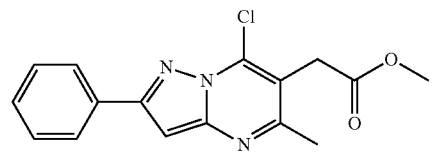 [SMILES: COC(=O)Cc1c(C)nc2cc(-c3ccccc3)nn2c1Cl]

Methyl 2-(7-chloro-5-methyl-2-phenylpyrazolo[1,5-a]pyrimidin-6-yl)acetate

To methyl 2-(5-methyl-7-oxo-2-phenyl-4,7-dihydropyrazolo[1,5-a]pyrimidin-6-yl)acetate (3 g, 10.09 mmol) was added POCl$_3$ (25 mL, 268 mmol). The reaction mixture was heated at reflux for 1 h. After cooling, the reaction mixture was added drop-wise to ice-water. A brown solid precipitated. The solid was filtered and washed with water, then dissolved in ethyl acetate. The organic solution was washed with saturated NaHCO$_3$ and dried over sodium sulfate. The solvent was evaporated to give the title compound (2.77 g, 84%). $^1$H-NMR (400 MHz, DMSO-d$_6$) δ ppm 2.58 (3H, s), 3.71 (3H, s), 4.04 (2H, s), 7.29 (1H, s), 7.43-7.58 (3H, m), 8.07 (2H, d, J=7.0 Hz).

| Methyl 2-(7-chloro-5-methyl-2-phenylpyrazolo[1,5-a]pyrimidin-6-yl)acetate | |
|---|---|
| MS (M + H)$^+$ Calcd. | 316 |
| MS (M + H)$^+$ Observ. | 316 |
| Retention Time | 2.09 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

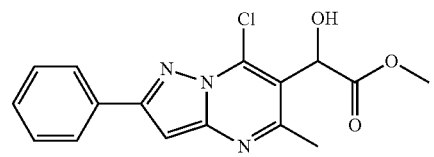 [SMILES: COC(=O)C(O)c1c(C)nc2cc(-c3ccccc3)nn2c1Cl]

Methyl 2-(7-chloro-5-methyl-2-phenylpyrazolo[1,5-a]pyrimidin-6-yl)-2-hydroxyacetate To a stirred solution of KHMDS (0.5 M in toluene, 9.50 mL, 4.75 mmol) in THF (24 mL) at −78° C. was added a solution of methyl 2-(7-chloro-5-methyl-2-phenylpyrazolo[1,5-a]pyrimidin-6-yl)acetate (1 g, 3.17 mmol) in THF (24 mL) dropwise over 40 min. The mixture was stirred at −78° C. for 30 min. A solution of 3-phenyl-2-(phenylsulfonyl)-1,2-oxaziridine (1.241 g, 4.75 mmol) in THF (24 mL) was added over 20 min and the reaction mixture was stirred for additional 30 min at −78° C. The reaction mixture was quenched with saturated NH$_4$Cl aqueous solution (4 mL). The reaction mixture was allowed to warm to room temperature and then diluted with ethyl acetate (100 mL). The organic phase was washed with water and brine and dried with sodium sulfate. The solvent was evaporated. Purification by silica gel chromatography provided the title compound (535 mg, 50.9%). $^1$H-NMR (500 MHz, CDCl$_3$) δ ppm 2.62 (3H, s), 3.83 (3H, s), 5.29 (1H, s), 5.76 (1H, s), 6.94 (1H, s), 7.38-7.50 (3H, m), 8.00-8.02 (2H, m).

| Methyl 2-(7-chloro-5-methyl-2-phenylpyrazolo[1,5-a]pyrimidin-6-yl)-2-hydroxyacetate | |
|---|---|
| MS (M + H)$^+$ Calcd. | 332 |
| MS (M + H)$^+$ Observ. | 332 |
| Retention Time | 2.03 min |
| | LC Condition |

Methyl 2-(7-chloro-5-methyl-2-phenylpyrazolo[1,5-a]pyrimidin-6-yl)-2-hydroxyacetate

| Solvent A | 10% methanol:90% Water:0.1% TFA |
|---|---|
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

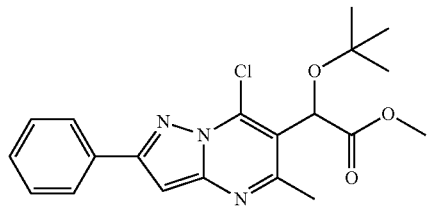 [SMILES: COC(=O)C(OC(C)(C)C)c1c(C)nc2cc(-c3ccccc3)nn2c1Cl]

Methyl 2-tert-butoxy-2-(7-chloro-5-methyl-2-phenylpyrazolo[1,5-a]pyrimidin-6-yl)acetate To a suspension of methyl 2-(7-chloro-5-methyl-2-phenylpyrazolo[1,5-a]pyrimidin-6-yl)-2-hydroxyacetate (100 mg, 0.301 mmol) in tert-butyl acetate (2 mL) at room temperature was added $CH_2Cl_2$ (2 mL) followed by perchloric acid (0.027 mL, 0.452 mmol). The reaction mixture was stirred for 2 h at room temperature. The reaction mixture was quenched with water and diluted with ethyl acetate. The organic phase was washed with saturated $NaHCO_3$ and dried over sodium sulfate. The solvent was evaporated. Purification by silica gel chromatography provided the title compound (71 mg, 60.7%). $^1$H-NMR (500 MHz, $CDCl_3$) δ ppm 1.27 (9H, s), 2.66 (3H, s), 3.73 (3H, s), 5.66 (1H, s), 6.93 (1H, s), 7.34-7.52 (3H, m), 8.01 (2H, d, J=7.3 Hz).

| Methyl 2-tert-butoxy-2-(7-chloro-5-methyl-2-phenylpyrazolo[1,5-a]pyrimidin-6-yl)acetate | |
|---|---|
| MS (M + H)$^+$ Calcd. | 388 |
| MS (M + H)$^+$ Observ. | 388 |
| Retention Time | 2.42 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

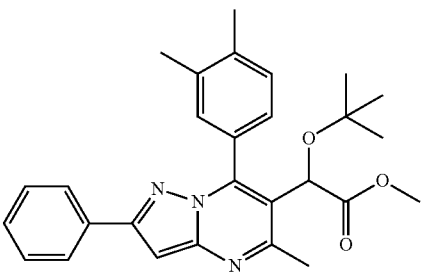 [SMILES: COC(=O)C(OC(C)(C)C)c1c(C)nc2cc(-c3ccccc3)nn2c1-c1ccc(C)c(C)c1]

Methyl 2-tert-butoxy-2-(7-(3,4-dimethylphenyl)-5-methyl-2-phenylpyrazolo[1,5-a]pyrimidin-6-yl)acetate, TFA salt To a 0.5-2 mL microwave tube was added methyl 2-tert-butoxy-2-(7-chloro-5-methyl-2-phenylpyrazolo[1,5-a]pyrimidin-6-yl)acetate (20 mg, 0.052 mmol), tetrakis(triphenylphosphine)palladium(0) (8.94 mg, 7.73 μmol), 3,4-dimethylphenylboronic acid (11.60 mg, 0.077 mmol), DMF (1.5 mL), followed by 2M $K_3PO_4$ solution (100 μl). The reaction mixture was heated in a microwave reactor at 130° C. for 15 min. The reaction mixture was filtered and the filtrate purified by preparative HPLC to afford (16 mg, 54.3%) of the title compound as TFA salt. Preparative HPLC condition: Phenomenex Luna C18 30×100 mm S10, 50 to 100% B over 22 minute gradient, 8 minute hold time, A=10% methanol 90% water 0.1% TFA, B=90% methanol 10% water 0.1% TFA. Flow rate: 40 ml/min.

$^1$H-NMR (300 MHz, $CDCl_3$, 60° C.) δ ppm 0.97 (9H, s), 2.34 (3H, s), 2.39 (3H, s), 2.74 (3H, s), 3.78 (3H, s), 5.14 (1H, s), 7.00 (1H, s), 7.27-7.48 (6H, m), 7.82 (2H, dd, J=7.9, 1.6 Hz).

| Methyl 2-tert-butoxy-2-(7-(3,4-dimethylphenyl)-5-methyl-2-phenylpyrazolo[1,5-a]pyrimidin-6-yl)acetate, TFA salt. | |
|---|---|
| MS (M + H)$^+$ Calcd. | 458 |
| MS (M + H)$^+$ Observ. | 458 |
| Retention Time | 2.52 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 1

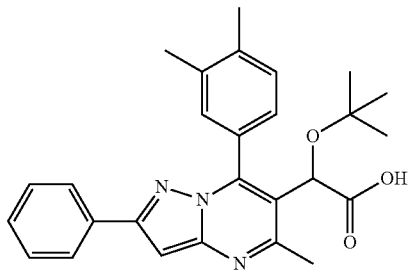 [SMILES: Cc1ccc(-c2c(C(OC(C)(C)C)C(=O)O)c(C)nc3cc(-c4ccccc4)nn23)cc1C]

2-tert-Butoxy-2-(7-(3,4-dimethylphenyl)-5-methyl-2-phenylpyrazolo[1,5-a]pyrimidin-6-yl)acetic acid, TFA salt To a solution of methyl 2-tert-butoxy-2-(7-(3,4-dimethylphenyl)-5-methyl-2-phenylpyrazolo[1,5-a]pyrimidin-6-yl)acetate, TFA salt (15 mg, 0.026 mmol) in dioxane (0.5 mL) was added 1.5 N LiOH aqueous solution (0.5 mL, 0.750 mmol). The reaction mixture was stirred at 50° C. for 2 h. The reaction mixture was filtered and the filtrate was purified by preparative HPLC to afford (10 mg, 67.7%) of the title compound as TFA salt. Preparative HPLC condition: Phenomenex Luna C18 30×100 mm S10, 50 to 100% B over 22 minute gradient, 6 minute hold time, A=10% methanol 90% water 0.1% TFA, B=90% methanol 10% water 0.1% TFA. Flow rate: 40 ml/min. $^1$H-NMR (400 MHz, MeOD) δ ppm 0.97 (9H, s), 2.40 (3H, s), 2.45 (3H, s), 2.68 (3H, s), 5.18 (1H, s), 6.93 (1H, s), 7.32-7.57 (6H, m), 7.80-7.94 (2H, m).

| 2-tert-Butoxy-2-(7-(3,4-dimethylphenyl)-5-methyl-2-phenylpyrazolo[1,5-a]pyrimidin-6-yl)acetic acid, TFA salt. | |
|---|---|
| MS (M + H)$^+$ Calcd. | 444 |
| MS (M + H)$^+$ Observ. | 444 |
| Retention Time | 2.440 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

Compounds in the Table 2 (Examples 2-38) were synthesized using the procedure described above using the appropriate boronic acids.

TABLE 2

| Example | Structure | RT (min) | HPLC method | MW | Observed mass |
|---|---|---|---|---|---|
| 2 | 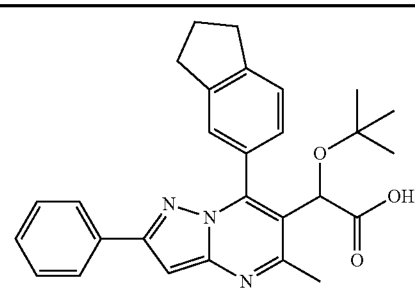 | 5.42 | A | 455.5 | 456 |
| 3 | 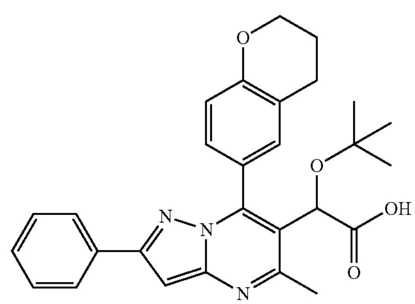 [SMILES: Cc1nc2cc(-c3ccccc3)nn2c(-c2ccc3c(c2)CCCO3)c1C(OC(C)(C)C)C(=O)O] | 4.80 | A | 471.5 | 472 |
| 4 | 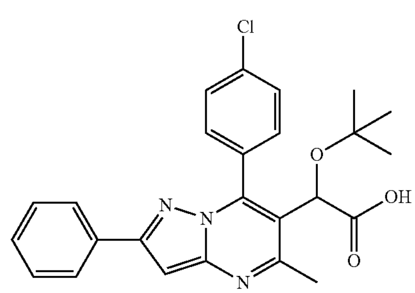 [SMILES: Cc1nc2cc(-c3ccccc3)nn2c(-c2ccc(Cl)cc2)c1C(OC(C)(C)C)C(=O)O] | 5.16 | A | 449.9 | 450 |

TABLE 2-continued
| Example | Structure | RT (min) | HPLC method | MW | Observed mass |
|---|---|---|---|---|---|
| 5 | 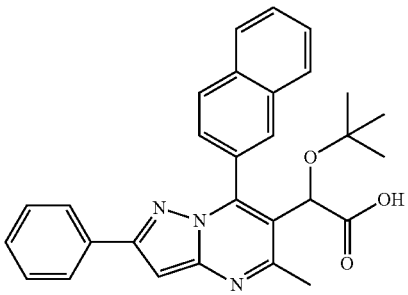 [SMILES: Cc1nc2cc(-c3ccccc3)nn2c(-c2ccc3ccccc3c2)c1C(OC(C)(C)C)C(=O)O] | 5.31 | A | 465.5 | 466 |
| 6 | 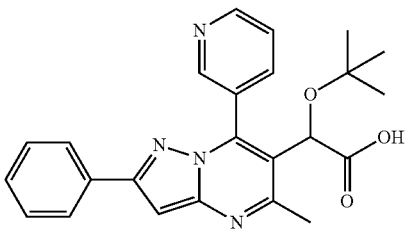 [SMILES: Cc1nc2cc(-c3ccccc3)nn2c(-c2cccnc2)c1C(OC(C)(C)C)C(=O)O] | 3.81 | A | 416.4 | 417 |
| 7 | 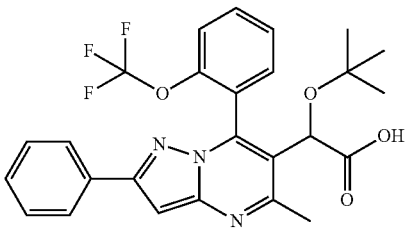 [SMILES: Cc1nc2cc(-c3ccccc3)nn2c(-c2ccccc2OC(F)(F)F)c1C(OC(C)(C)C)C(=O)O] | 4.86 | A | 499.4 | 500 |
| 8 | 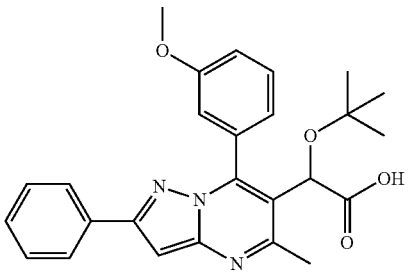 [SMILES: COc1cccc(-c2c(C(OC(C)(C)C)C(=O)O)c(C)nc3cc(-c4ccccc4)nn23)c1] | 4.66 | A | 445.5 | 446 |
| 9 | 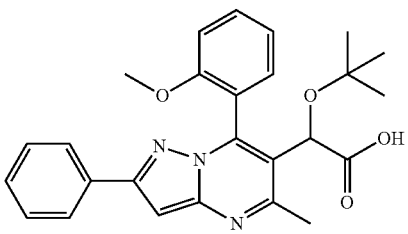 [SMILES: COc1ccccc1-c1c(C(OC(C)(C)C)C(=O)O)c(C)nc2cc(-c3ccccc3)nn12] | 4.30 | A | 445.5 | 446 |
| 10 | 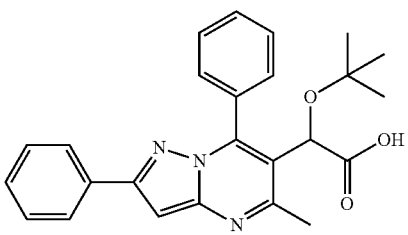 [SMILES: Cc1nc2cc(-c3ccccc3)nn2c(-c2ccccc2)c1C(OC(C)(C)C)C(=O)O] | 4.72 | A | 415.4 | 416 |

TABLE 2-continued
| Example | Structure | RT (min) | HPLC method | MW | Observed mass |
|---|---|---|---|---|---|
| 11 | 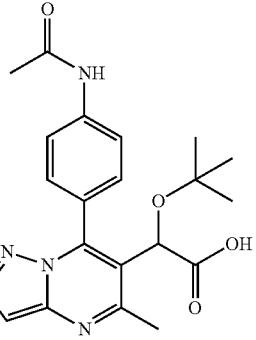 | 3.74 | A | 472.5 | 473 |
| 12 | 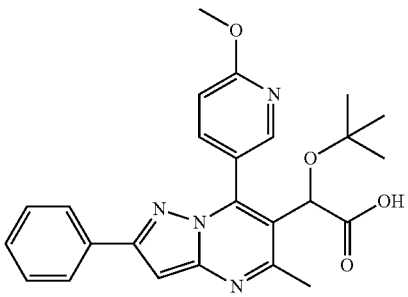 [SMILES: COc1ccc(-c2c(C(OC(C)(C)C)C(=O)O)c(C)nc3cc(-c4ccccc4)nn23)cn1] | 4.46 | A | 446.5 | 447 |
| 13 | 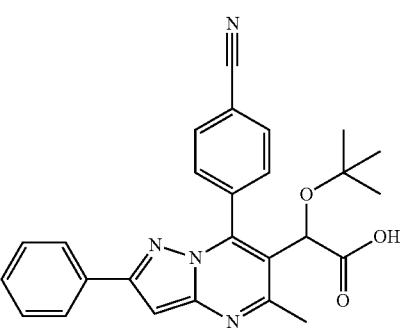 [SMILES: Cc1nc2cc(-c3ccccc3)nn2c(-c2ccc(C#N)cc2)c1C(OC(C)(C)C)C(=O)O] | 4.66 | A | 440.4 | 441 |
| 14 | 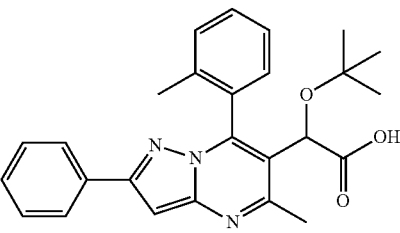 [SMILES: Cc1ccccc1-c1c(C(OC(C)(C)C)C(=O)O)c(C)nc2cc(-c3ccccc3)nn12] | 4.76 | A | 429.5 | 430 |
| 15 | 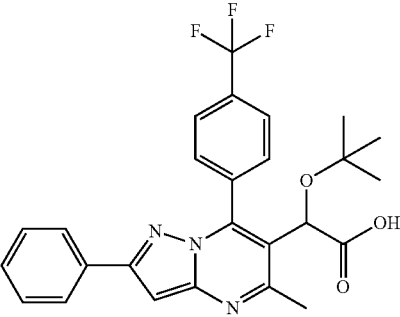 [SMILES: Cc1nc2cc(-c3ccccc3)nn2c(-c2ccc(C(F)(F)F)cc2)c1C(OC(C)(C)C)C(=O)O] | 5.26 | A | 483.4 | 484 |

TABLE 2-continued

| Example | Structure | RT (min) | HPLC method | MW | Observed mass |
|---|---|---|---|---|---|
| 16 | 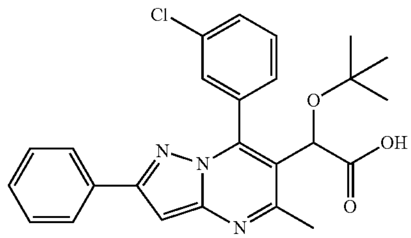 [SMILES: Cc1nc2cc(-c3ccccc3)nn2c(-c2cccc(Cl)c2)c1C(OC(C)(C)C)C(=O)O] | 5.13 | A | 449.9 | 450 |
| 17 | 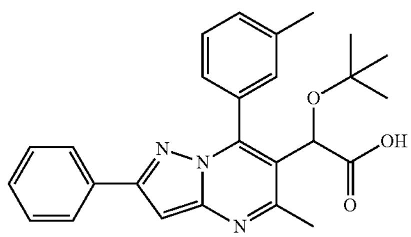 | 5.01 | A | 429.5 | 430 |
| 18 | 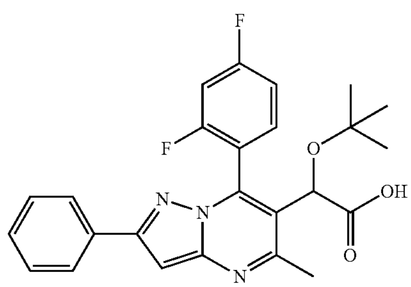 [SMILES: Cc1nc2cc(-c3ccccc3)nn2c(-c2ccc(F)cc2F)c1C(OC(C)(C)C)C(=O)O] | 4.85 | A | 451.4 | 452 |
| 19 | 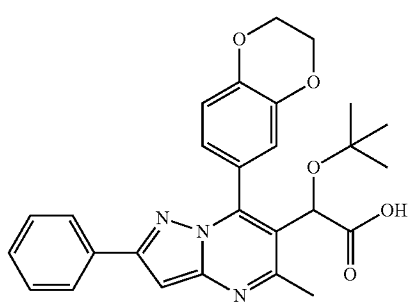 [SMILES: Cc1nc2cc(-c3ccccc3)nn2c(-c2ccc3c(c2)OCCO3)c1C(OC(C)(C)C)C(=O)O] | 4.44 | A | 473.5 | 474 |
| 20 | 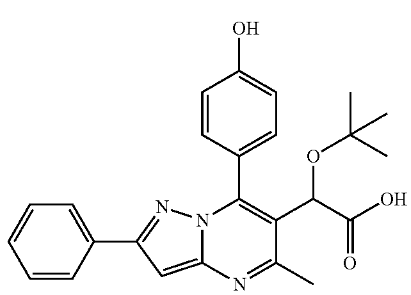 [SMILES: Cc1nc2cc(-c3ccccc3)nn2c(-c2ccc(O)cc2)c1C(OC(C)(C)C)C(=O)O] | 4.13 | A | 431.4 | 432 |

TABLE 2-continued

| Example | Structure | RT (min) | HPLC method | MW | Observed mass |
|---------|-----------|----------|-------------|------|---------------|
| 21 | 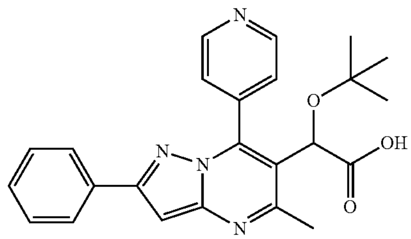 [SMILES: Cc1nc2cc(-c3ccccc3)nn2c(-c2ccncc2)c1C(OC(C)(C)C)C(=O)O] | 3.77 | A | 416.5 | 417 |
| 22 | 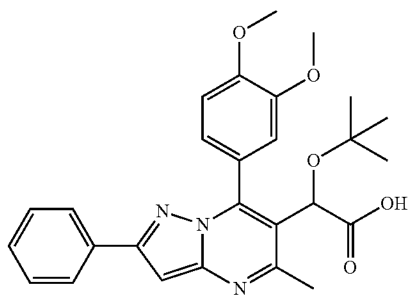 [SMILES: COc1ccc(-c2c(C(OC(C)(C)C)C(=O)O)c(C)nc3cc(-c4ccccc4)nn23)cc1OC] | 4.14 | A | 475.5 | 476 |
| 23 | 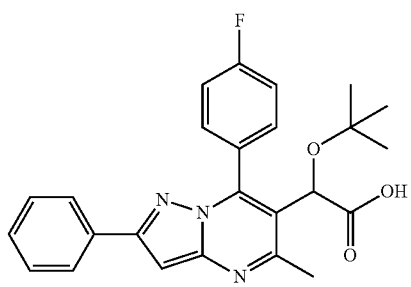 [SMILES: Cc1nc2cc(-c3ccccc3)nn2c(-c2ccc(F)cc2)c1C(OC(C)(C)C)C(=O)O] | 5.17 | A | 433.5 | 434 |
| 24 | 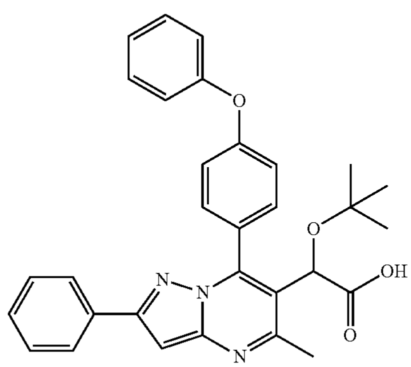 [SMILES: Cc1nc2cc(-c3ccccc3)nn2c(-c2ccc(Oc3ccccc3)cc2)c1C(OC(C)(C)C)C(=O)O] | 6.05 | A | 507.6 | 508 |
| 25 | 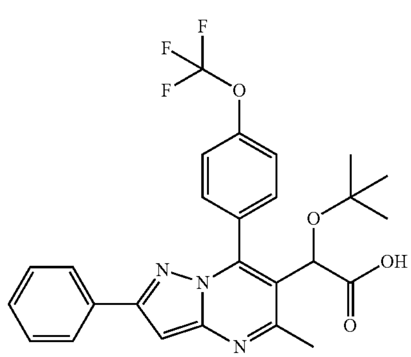 [SMILES: Cc1nc2cc(-c3ccccc3)nn2c(-c2ccc(OC(F)(F)F)cc2)c1C(OC(C)(C)C)C(=O)O] | 5.95 | A | 499.5 | 500 |

TABLE 2-continued

| Example | Structure | RT (min) | HPLC method | MW | Observed mass |
|---|---|---|---|---|---|
| 26 | 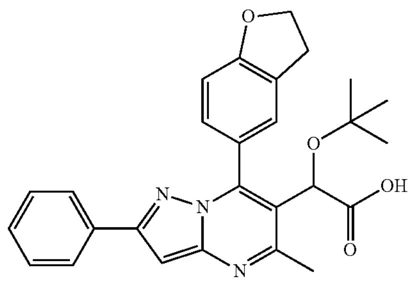 [SMILES: Cc1nc2cc(-c3ccccc3)nn2c(-c2ccc3c(c2)CCO3)c1C(OC(C)(C)C)C(=O)O] | 4.97 | A | 457.5 | 458 |
| 27 | 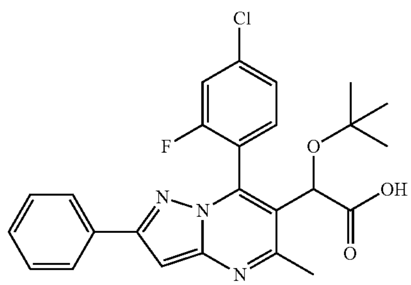 [SMILES: Cc1nc2cc(-c3ccccc3)nn2c(-c2ccc(Cl)cc2F)c1C(OC(C)(C)C)C(=O)O] | 5.57 | A | 467.9 | 468 |
| 28 | 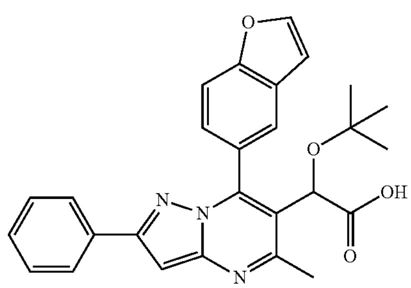 [SMILES: Cc1nc2cc(-c3ccccc3)nn2c(-c2ccc3occc3c2)c1C(OC(C)(C)C)C(=O)O] | 4.95 | A | 455.5 | 456 |
| 29 | 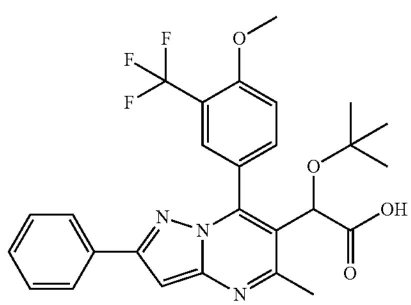 [SMILES: COc1ccc(-c2c(C(OC(C)(C)C)C(=O)O)c(C)nc3cc(-c4ccccc4)nn23)cc1C(F)(F)F] | 5.62 | A | 513.5 | 514 |
| 30 | 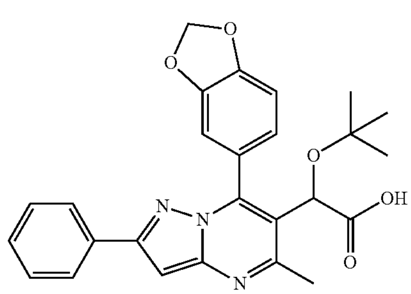 [SMILES: Cc1nc2cc(-c3ccccc3)nn2c(-c2ccc3c(c2)OCO3)c1C(OC(C)(C)C)C(=O)O] | 4.85 | A | 459.5 | 460 |

TABLE 2-continued

| Example | Structure | RT (min) | HPLC method | MW | Observed mass |
|---------|-----------|----------|-------------|-----|---------------|
| 31 | 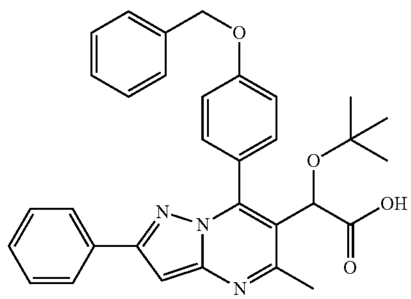 [SMILES: Cc1nc2cc(-c3ccccc3)nn2c(-c2ccc(OCc3ccccc3)cc2)c1C(OC(C)(C)C)C(=O)O] | 6.27 | A | 521.6 | 522 |
| 32 | 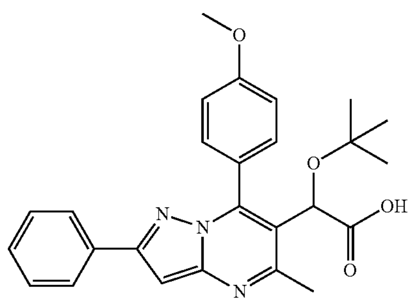 | 4.86 | A | 445.5 | 446 |
| 33 | 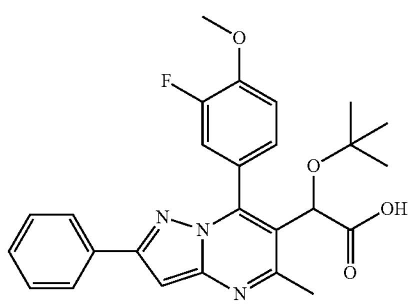 [SMILES: COc1ccc(-c2c(C(OC(C)(C)C)C(=O)O)c(C)nc3cc(-c4ccccc4)nn23)cc1F] | 5.07 | A | 463.5 | 464 |
| 34 | 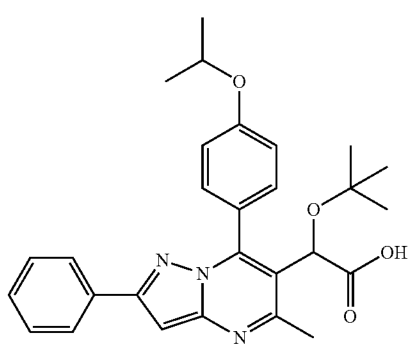 [SMILES: Cc1nc2cc(-c3ccccc3)nn2c(-c2ccc(OC(C)C)cc2)c1C(OC(C)(C)C)C(=O)O] | 5.80 | A | 473.6 | 474 |
| 35 | 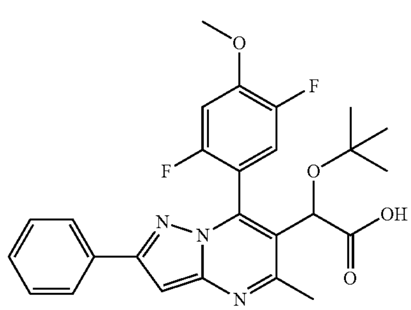 | 4.67 | A | 481.5 | 482 |

TABLE 2-continued
| Example | Structure | RT (min) | HPLC method | MW | Observed mass |
|---|---|---|---|---|---|
| 36 | 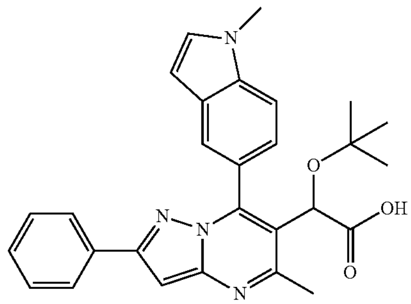 [SMILES: Cc1nc2cc(-c3ccccc3)nn2c(-c2ccc3c(ccn3C)c2)c1C(OC(C)(C)C)C(=O)O] | 2.31 | B | 468.5 | 469 |
| 37 | 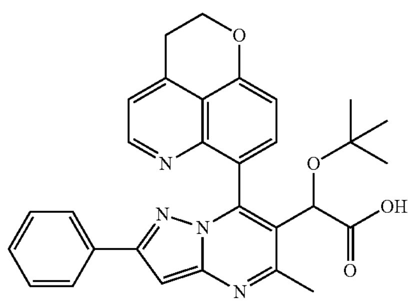 [SMILES: Cc1nc2cc(-c3ccccc3)nn2c(-c2ccc3c4c(ccnc24)CCO3)c1C(OC(C)(C)C)C(=O)O] | 1.475 | C | 508.6 | 509 |
| 38 | 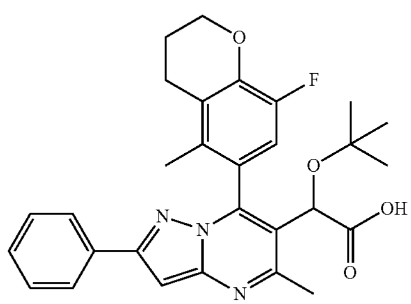 [SMILES: Cc1nc2cc(-c3ccccc3)nn2c(-c2cc(F)c3c(c2C)CCCO3)c1C(OC(C)(C)C)C(=O)O] | 1.970 | C | 503.6 | 504 |
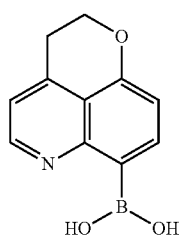 [SMILES: OB(O)c1ccc2c3c(ccnc13)CCO2]
2,3-dihydropyrano[4,3,2-de]quinolin-7-ylboronic acid
The title compound was prepared from the known procedure as described in Reference: WO 2009/062285.
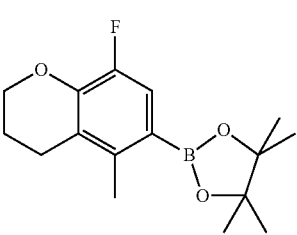 [SMILES: Cc1c(B2OC(C)(C)C(C)(C)O2)cc(F)c2c1CCCO2]
2-(8-fluoro-5-methylchroman-6-yl)-4,4,5,5-tetramethyl-1,3,2 dioxaborolane
The title compound was prepared from the known procedure as described in the reference WO 2009/062285.

Example 39

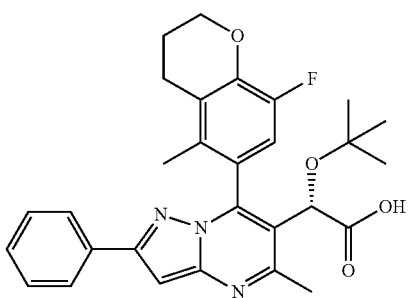

(2S)-2-tert-butoxy-2-(7-(8-fluoro-5-methylchroman-6-yl)-5-methyl-2-phenylpyrazolo[1,5-a]pyrimidin-6-yl)acetic acid The title compound was synthesized using a two step method starting from the racemic ester precursor for Example 39. The racemic ester was separated into two enantiomers using a chiral column and (2S)-methyl 2-tert-butoxy-2-(7-(8-fluoro-5-methylchroman-6-yl)-5-methyl-2-phenylpyrazolo[1,5-a]pyrimidin-6-yl)acetate was isolated. Chiral separation method: Chiralpak AD-H preparative column, 20×250 mm, 5 μm. Mobile Phase: 15% MeOH in $CO_2$ @ 150 Bar. Temp: 35° C. Flow rate: 45.0 mL/min. for 14 min. UV was monitored @ 254 nm. Hydrolysis of (2S)-methyl 2-tert-butoxy-2-(7-(8-fluoro-5-methylchroman-6-yl)-5-methyl-2-phenylpyrazolo[1,5-a]pyrimidin-6-yl)acetate as described in Example 1 provided the title compound with 100% enantiomeric excess. Retention time: 4.38 min. Chiral SFC method: Chiralpak AD-H analytical column, 4.6×250 mm, 5 μm. Mobile Phase: 15% MeOH in $CO_2$. Temp: 35° C. Flow rate: 2.0 mL/min. for 14 min. UV monitored @ 254 nm.

Example 40

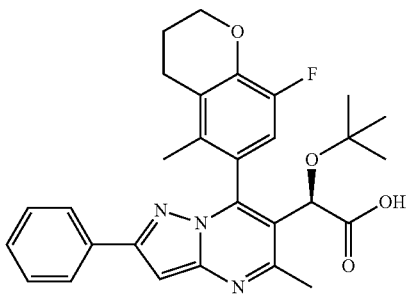

(2R)-2-tert-butoxy-2-(7-(8-fluoro-5-methylchroman-6-yl)-5-methyl-2-phenylpyrazolo[1,5-a]pyrimidin-6-yl)acetic acid The title compound was synthesized using a two step method starting from the racemic ester precursor for Example 39. The racemic ester was separated into two enantiomers using a chiral column and (2R)-methyl 2-tert-butoxy-2-(7-(8-fluoro-5-methylchroman-6-yl)-5-methyl-2-phenylpyrazolo[1,5-a]pyrimidin-6-yl)acetate was isolated. Chiral separation method: Chiralpak AD-H preparative column, 20×250 mm, 5 μm to give two enantiomers. Mobile Phase: 15% MeOH in $CO_2$ @ 150 Bar. Temp: 35° C. Flow rate: 45.0 mL/min. for 14 min. UV was monitored @ 254 nm. Hydrolysis of (2R)-methyl 2-tert-butoxy-2-(7-(8-fluoro-5-methylchroman-6-yl)-5-methyl-2-phenylpyrazolo[1,5-a]pyrimidin-6-yl)acetate as described in Example 1 provided the title compound with 100% enantiomeric excess. Retention time: 9.94 min. Chiral SFC method: Chiralpak AD-H analytical column, 4.6×250 mm, 5 μm. Mobile Phase: 15% MeOH in $CO_2$. Temp: 35° C. Flow rate: 2.0 mL/min. for 14 min. UV monitored @ 254 nm.

Scheme 4.

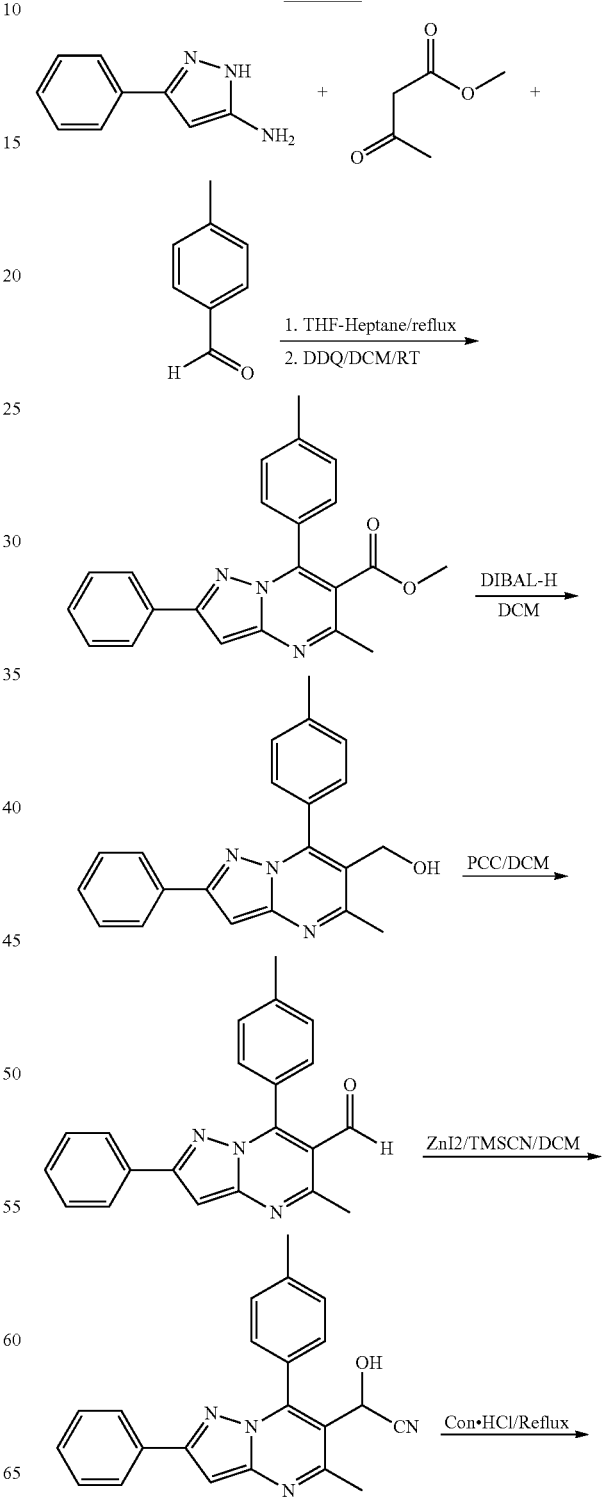

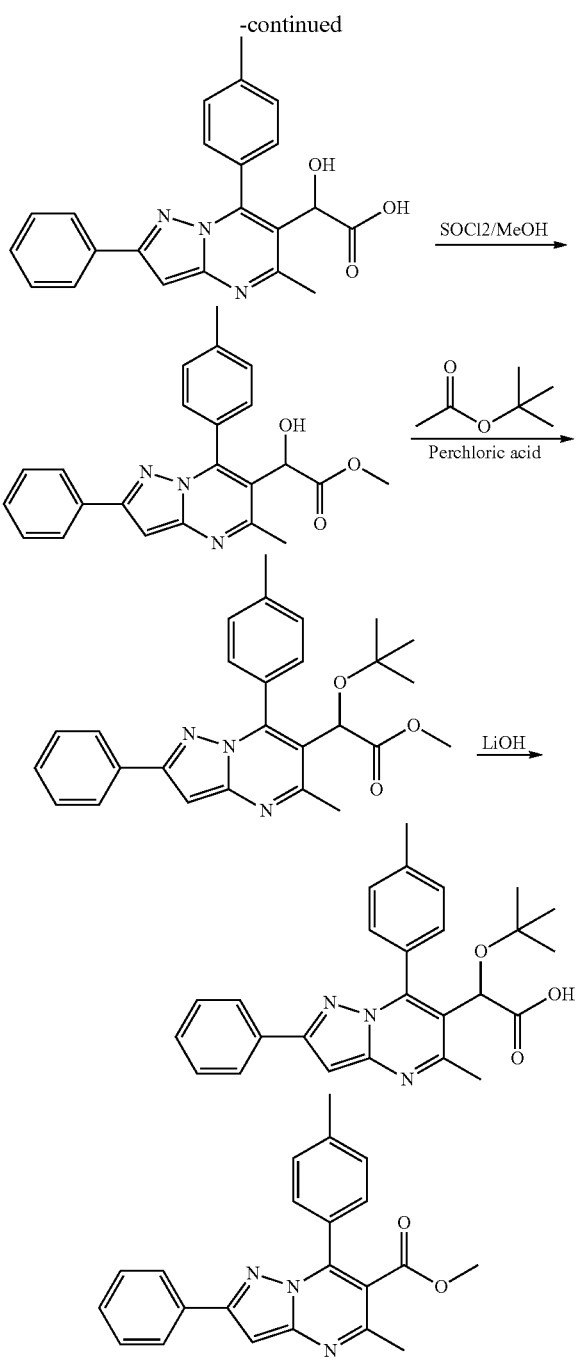

Methyl 5-methyl-2-phenyl-7-p-tolylpyrazolo[1,5-a]pyrimidine-6-carboxylate

To a stirred solution of 4-methylbenzaldehyde (1.2 g, 9.99 mmol), 3-phenyl-1H-pyrazol-5-amine (1.6 g, 9.99 mmol), and methyl 3-oxobutanoate (1.3 g, 10.99 mmol) in THF (80 mL) and heptane (20 mL) was added piperidine (30 mL, 0.303 mmol). The reaction mixture was heated at reflux for 20 h. The solvent was evaporated and the crude material was dissolved in CH$_2$Cl$_2$. DDQ (2041 mg, 8.99 mmol) was added and the mixture was stirred at room temperature for 1 h. The solvent was evaporated. Purification by silica gel chromatography provided the title compound (2.3 g, 64.4%). $^1$H-NMR (500 MHz, CDCl$_3$) δ ppm 2.47 (3H, s), 2.65 (3H, s), 3.64 (3H, s), 6.93 (1H, s), 7.31-7.47 (5H, m), 7.63 (2H, d, J=7.9 Hz), 7.86-7.99 (2H, m).

| Methyl 5-methyl-2-phenyl-7-p-tolylpyrazolo[1,5-a]pyrimidine-6-carboxylate. | |
|---|---|
| MS (M + H)$^+$ Calcd. | 358 |
| MS (M + H)$^+$ Observ. | 358 |
| Retention Time | 2.32 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

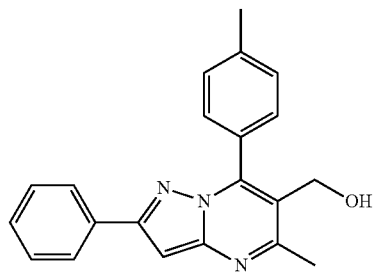 [SMILES: Cc1ccc(-c2c(CO)c(C)nc3cc(-c4ccccc4)nn23)cc1]

(5-Methyl-2-phenyl-7-p-tolylpyrazolo[1,5-a]pyrimidin-6-yl)methanol

To a stirred solution of methyl 5-methyl-2-phenyl-7-p-tolylpyrazolo[1,5-a]pyrimidine-6-carboxylate (800 mg, 2.238 mmol) in CH$_2$Cl$_2$ (50 mL) was added DIBAL-H, 1M in THF (6.72 mL, 6.72 mmol) dropwise. The reaction mixture was stirred at room temperature for 1 h before being quenched with saturated NH$_4$Cl solution. The aqueous layer was extracted with CH$_2$Cl$_2$ and the combined organic layer was dried over anhydrous Na$_2$SO$_4$, filtered and concentrated. The residue was purified by silica gel chromatography to give the title compound (344 mg, 46.7%). $^1$H-NMR (500 MHz, CDCl$_3$) δ ppm 1.61 (1H, t, J=5.0 Hz), 2.49 (3H, s), 2.78 (3H, s), 4.59 (2H, d, J=5.0 Hz), 6.88 (1H, s), 7.29-7.42 (5H, m), 7.56 (2H, d, J=8.2 Hz), 7.81-7.96 (2H, m).

| (5-Methyl-2-phenyl-7-p-tolylpyrazolo[1,5-a]pyrimidin-6-yl)methanol. | |
|---|---|
| MS (M + H)$^+$ Calcd. | 330 |
| MS (M + H)$^+$ Observ. | 330 |
| Retention Time | 1.65 min |
| | LC Condition |
| Solvent A | 10% Acetonitrile: 90% Water: 0.1% TFA |
| Solvent B | 90% Acetonitrile: 10% Water: 0.1% TFA |
| Start % B | 0 |
| Final % B | 100 |
| Gradient Time | 2 min |
| Flow Rate | 1 mL/min |
| Wavelength | 220 |

5-Methyl-2-phenyl-7-p-tolylpyrazolo[1,5-a]pyrimi-dine-6-carbaldehyde

| (5-Methyl-2-phenyl-7-p-tolylpyrazolo[1,5-a]pyrimidin-6-yl)methanol. | |
|---|---|
| Solvent Pair | Acetonitrile: Water: TFA |
| Column | Phenomenex Luna C18, 30 × 2, 3 u |

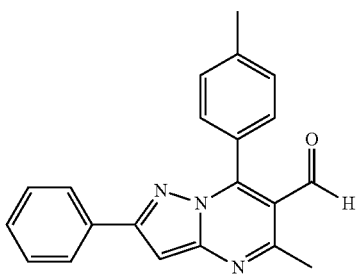 [SMILES: Cc1ccc(-c2c(C=O)c(C)nc3cc(-c4ccccc4)nn23)cc1]

5-Methyl-2-phenyl-7-p-tolylpyrazolo[1,5-a]pyrimi-dine-6-carbaldehyde

To a stirred solution of (5-methyl-2-phenyl-7-p-tolylpyrazolo[1,5-a]pyrimidin-6-yl)methanol (100 mg, 0.304 mmol) in CH$_2$Cl$_2$ (8 mL) was added PCC (98 mg, 0.455 mmol). The reaction mixture was stirred at room temperature for 16 h. The solvent was evaporated and the residue was purified by silica gel chromatography to give the title compound (82 mg, 83%). $^1$H-NMR (500 MHz, CDCl$_3$) δ ppm 2.52 (3H, s), 2.89 (3H, s), 6.98 (1H, s), 7.33-7.50 (5H, m), 7.60 (2H, d, J=7.9 Hz), 7.91 (2H, dd, J=8.1, 1.4 Hz), 9.80 (1H, s).

| 5-Methyl-2-phenyl-7-p-tolylpyrazolo[1,5-a]pyrimidine-6-carbaldehyde. | |
|---|---|
| MS (M + H)$^+$ Calcd. | 328 |
| MS (M + H)$^+$ Observ. | 328 |
| Retention Time | 2.00 min |
| | LC Condition |
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna C18, 30 × 2, 3u |

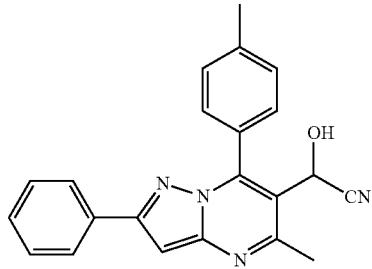 [SMILES: Cc1ccc(-c2c(C(O)C#N)c(C)nc3cc(-c4ccccc4)nn23)cc1]

2-Hydroxy-2-(5-methyl-2-phenyl-7-p-tolylpyrazolo [1,5-a]pyrimidin-6-yl)acetonitrile To a solution of 5-methyl-2-phenyl-7-p-tolylpyrazolo[1,5-a]pyrimidine-6-carbaldehyde (30 mg, 0.092 mmol) in CH$_2$Cl$_2$ (2 mL) at 0° C. was added zinc iodide (14.63 mg, 0.046 mmol) followed by TMS-CN (0.049 mL, 0.367 mmol). The reaction mixture was stirred at room temperature for 4 h and diluted with CH$_2$Cl$_2$ (100 ml), washed with water, and dried over Na$_2$SO$_4$. The solvent was evaporated and the residue was purified by preparative HPLC to give the title compound (15 mg, 46.2%) as TFA salt. Preparative HPLC condition: Phenomenex Luna C18 30×100 mm S10, 40 to 100% B over 22 minute gradient, 7 minute hold time, A=10% methanol 90% water 0.1% TFA, B=90% methanol 10% water 0.1% TFA. Flow rate: 40 ml/min. $^1$H-NMR (500 MHz, CDCl$_3$) δ ppm 2.46 (3H, s), 2.89 (3H, s), 5.39 (1H, s), 6.85 (1H, s), 7.16-7.25 (3H, m), 7.30-7.44 (4H, m), 7.63-7.76 (2H, m).

| 2-Hydroxy-2-(5-methyl-2-phenyl-7-p-tolylpyrazolo[1,5-a]pyrimidin-6-yl)acetic acid. | |
|---|---|
| MS (M + H)$^+$ Calcd. | 355 |
| MS (M + H)$^+$ Observ. | 355 |
| Retention Time | 1.80 min |
| | LC Condition |
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna C18, 30 × 2, 3u |

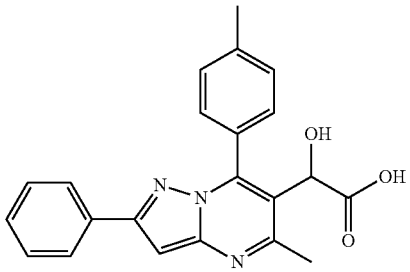 [SMILES: Cc1ccc(-c2c(C(O)C(=O)O)c(C)nc3cc(-c4ccccc4)nn23)cc1]

2-Hydroxy-2-(5-methyl-2-phenyl-7-p-tolylpyrazolo [1,5-a]pyrimidin-6-yl)acetic acid A solution of 2-hydroxy-2-(5-methyl-2-phenyl-7-p-tolylpyrazolo[1,5-a]pyrimidin-6-yl)acetonitrile (28 mg, 0.079 mmol) in conc. HCl (400 μL, 4.87 mmol) was heated at 90° C. for 3 h. The solvent was evaporated and the residue was purified by preparative HPLC to afford (14 mg, 47.5%) of the title compound. $^1$H-NMR (400 MHz, MeOD) δ ppm 2.51 (3H, s), 2.67 (3H, s), 5.19 (1H, s), 6.95 (1H, s), 7.29-7.51 (5H, m), 7.57 (2H, d, J=8.3 Hz), 7.80-7.93 (2H, m).

| 2-Hydroxy-2-(5-methyl-2-phenyl-7-p-tolylpyrazolo[1,5-a]pyrimidin-6-yl)acetic acid. | |
| --- | --- |
| MS (M + H)+ Calcd. | 374 |
| MS (M + H)+ Observ. | 374 |
| Retention Time | 1.48 min |
| | LC Condition |
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna C18, 30 × 2, 3u |

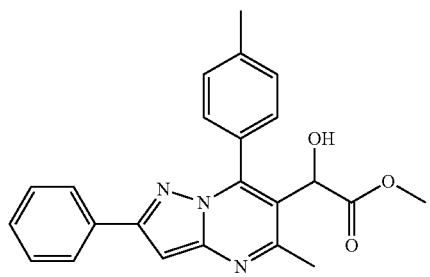 [SMILES: COC(=O)C(O)c1c(C)nc2cc(-c3ccccc3)nn2c1-c1ccc(C)cc1]

Methyl 2-hydroxy-2-(5-methyl-2-phenyl-7-p-tolylpyrazolo[1,5-a]pyrimidin-6-yl)acetate To a solution of 2-hydroxy-2-(5-methyl-2-phenyl-7-p-tolylpyrazolo[1,5-a]pyrimidin-6-yl)acetic acid (6 mg, 0.016 mmol) in methanol (2 mL) was added thionyl chroride (0.0023 mL, 0.032 mmol). The reaction mixture was stirred at 40° C. for 16 hrs. The solvent was evaporated to give the title compound. The crude product was used directly for next step.

| Methyl 2-hydroxy-2-(5-methyl-2-phenyl-7-p-tolylpyrazolo[1,5-a]pyrimidin-6-yl)acetate. | |
| --- | --- |
| MS (M + H)+ Calcd. | 388 |
| MS (M + H)+ Observ. | 388 |
| Retention Time | 2.15 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

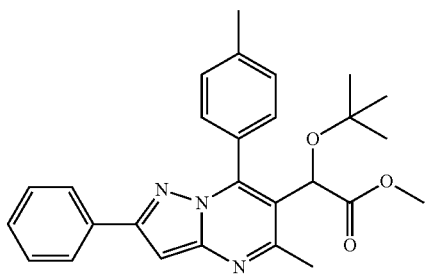 [SMILES: COC(=O)C(OC(C)(C)C)c1c(C)nc2cc(-c3ccccc3)nn2c1-c1ccc(C)cc1]

Methyl 2-tert-butoxy-2-(5-methyl-2-phenyl-7-p-tolylpyrazolo[1,5-a]pyrimidin-6-yl)acetate To a solution of methyl 2-hydroxy-2-(5-methyl-2-phenyl-7-p-tolylpyrazolo[1,5-a]pyrimidin-6-yl)acetate (6.20 mg, 0.016 mmol) in tert-butyl acetate (0.3 mL) at room temperature was added perchloric acid (0.008 mL, 0.128 mmol). The reaction mixture was stirred for 2 h at room temperature. The reaction mixture was quenched with water and diluted with ethyl acetate. The organic phase was washed with saturated NaHCO₃ and dried over sodium sulfate. The solvent was evaporated to give the title compound. The crude product was used directly for next step.

| Methyl 2-tert-butoxy-2-(5-methyl-2-phenyl-7-p-tolylpyrazolo[1,5-a]pyrimidin-6-yl)acetate. | |
| --- | --- |
| MS (M + H)+ Calcd. | 444 |
| MS (M + H)+ Observ. | 444 |
| Retention Time | 2.25 min |
| | LC Condition |
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna C18, 30 × 2, 3u |

Example 41

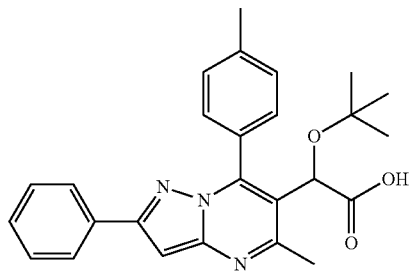

2-tert-Butoxy-2-(5-methyl-2-phenyl-7-p-tolylpyrazolo[1,5-a]pyrimidin-6-yl)acetic acid, TFA salt To a solution of methyl 2-tert-butoxy-2-(5-methyl-2-phenyl-7-p-tolylpyrazolo[1,5-a]pyrimidin-6-yl)acetate (7.10 mg, 0.016 mmol) in dioxane (0.5 mL) was added 1.5 N LiOH aqueous solution (0.5 mL, 0.750 mmol). The reaction mixture was stirred at 50° C. for 2 h. The reaction mixture was filtered and the filtrate was purified by preparative HPLC to afford (4 mg, 43.7% for 3 steps) of the title compound as TFA salt. Preparative HPLC condition: Waters Sunfire C18 30×100 mm 5 u, 50 to 100% B over 22 minute gradient, 6 minute hold time, A=10% methanol 90% water 0.1% TFA, B=90% methanol 10% water 0.1% TFA. Flow rate: 40 ml/min. $^1$H-NMR (400 MHz, MeOD) δ ppm 0.97 (9H, s), 2.53 (3H, s), 2.69 (3H, s), 5.19 (1H, s), 6.94 (1H, s), 7.28-7.43 (3H, m), 7.49 (2H, d, J=8.0 Hz), 7.67 (2H, dd, J=7.8, 2.8 Hz), 7.82-7.91 (2H, m).

| 2-tert-Butoxy-2-(5-methyl-2-phenyl-7-p-tolylpyrazolo[1,5-a]pyrimidin-6-yl)acetic acid, TFA salt. | |
| --- | --- |
| MS (M + H)$^+$ Calcd. | 430 |
| MS (M + H)$^+$ Observ. | 430 |
| Retention Time | 2.31 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Scheme 5.

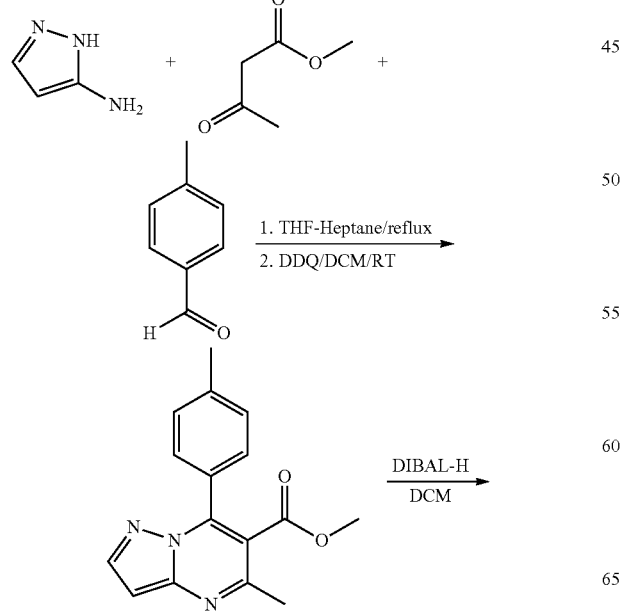

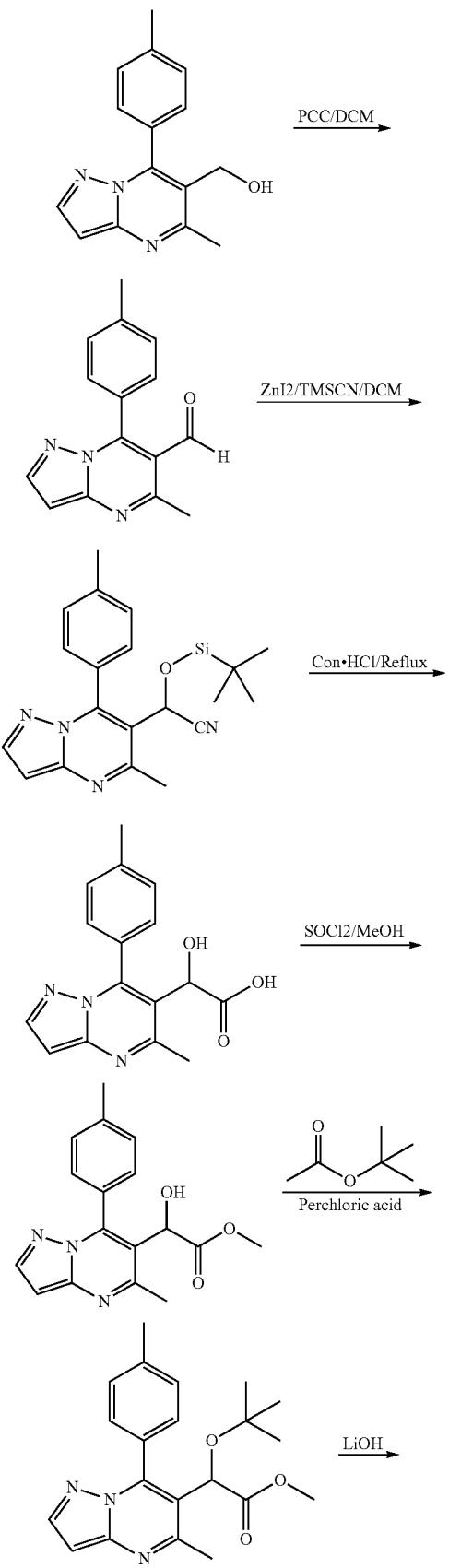

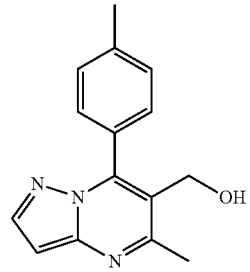 [SMILES: Cc1ccc(-c2c(CO)c(C)nc3ccnn23)cc1]

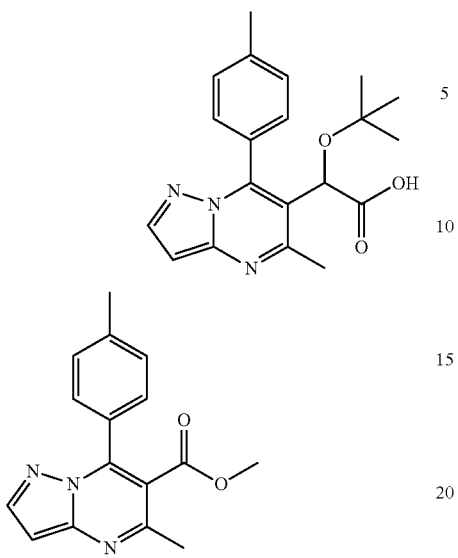

Methyl 5-methyl-7-p-tolylpyrazolo[1,5-a]pyrimidine-6-carboxylate

To a stirred solution of 4-methylbenzaldehyde (723 mg, 6.02 mmol), 1H-pyrazol-5-amine (500 mg, 6.02 mmol), and methyl 3-oxobutanoate (769 mg, 6.62 mmol) in THF (80 mL) and heptane (20 mL) was added piperidine (10 mL, 0.101 mmol). The reaction mixture was heated at reflux for 20 h. The solvent was evaporated and the crude material was dissolved in $CH_2Cl_2$. DDQ (1229 mg, 5.42 mmol) was added and the mixture was stirred at room temperature for 1 h. The solvent was evaporated. Purification by silica gel chromatography provided the title compound (1120 mg, 66.2%). $^1$H-NMR (500 MHz, CD Cl$_3$) δ ppm 2.44 (3H, s), 2.65 (3H, s), 3.63 (3H, s), 6.65 (1H, d, J=2.4 Hz), 7.34 (2H, d, J=8.1 Hz), 7.52 (2H, d, J=8.1 Hz), 8.10 (1H, d, J=2.4 Hz).

| Methyl 5-methyl-7-p-tolylpyrazolo[1,5-a]pyrimidine-6-carboxylate | |
|---|---|
| MS (M + H)$^+$ Calcd. | 282 |
| MS (M + H)$^+$ Observ. | 282 |
| Retention Time | 1.51 min |
| | LC Condition |
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna C18, 30 × 2, 3u |

(5-Methyl-7-p-tolylpyrazolo[1,5-a]pyrimidin-6-yl) methanol

To a stirred solution of methyl 5-methyl-7-p-tolylpyrazolo[1,5-a]pyrimidine-6-carboxylate (950 mg, 3.38 mmol) in $CH_2Cl_2$ (50 mL) was added DIBAL-H, 1M in THF (16.9 mL, 16.9 mmol) dropwise. The reaction mixture was stirred at room temperature for 1 h before being quenched with saturated NH$_4$Cl solution. The aqueous layer was extracted with $CH_2Cl_2$ and the combined organic layer was dried over anhydrous Na$_2$SO$_4$, filtered and concentrated. The residue was purified by silica gel chromatography to give the title compound (482 mg, 56.3%). $^1$H-NMR (500 MHz, CDCl$_3$) δ ppm 1.64 (1H, t, J=4.9 Hz), 2.45 (3H, s), 2.78 (3H, s), 4.58 (2H, d, J=4.9 Hz), 6.60 (1H, d, J=2.4 Hz), 7.34-7.40 (2H, m), 7.42-7.49 (2H, m), 8.00 (1H, d, J=2.4 Hz).

| (5-Methyl-7-p-tolylpyrazolo[1,5-a]pyrimidin-6-yl)methanol. | |
|---|---|
| MS (M + H)$^+$ Calcd. | 254 |
| MS (M + H)$^+$ Observ. | 254 |
| Retention Time | 1.67 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

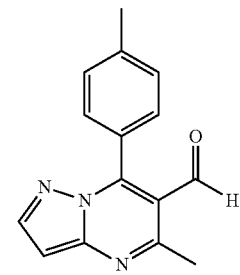 [SMILES: Cc1ccc(-c2c(C=O)c(C)nc3ccnn23)cc1]

5-Methyl-7-p-tolylpyrazolo[1,5-a]pyrimidine-6-carbaldehyde

To a stirred solution of (5-methyl-7-p-tolylpyrazolo[1,5-a]pyrimidin-6-yl)methanol (300 mg, 1.18 mmol) in $CH_2Cl_2$ (24 mL) was added PCC (383 mg, 1.78 mmol). The reaction mixture was stirred at room temperature for 16 h. The solvent was evaporated and the residue was purified by silica gel chromatography to give the title compound (212 mg, 71.2%).

¹H-NMR (500 MHz, CDCl₃) δ ppm 2.48 (3H, s), 2.89 (3H, s), 6.69 (1H, d, J=2.4 Hz), 7.43 (2H, d, J=7.9 Hz), 7.51 (2H, d, J=7.9 Hz), 8.18 (1H, d, J=2.4 Hz), 9.82 (1H, s).

| 5-Methyl-7-p-tolylpyrazolo[1,5-a]pyrimidine-6-carbaldehyde. | |
|---|---|
| MS (M + H)⁺ Calcd. | 252 |
| MS (M + H)⁺ Observ. | 252 |
| Retention Time | 1.98 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

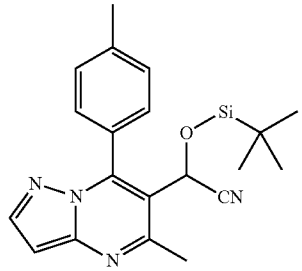

2-(5-Methyl-7-p-tolylpyrazolo[1,5-a]pyrimidin-6-yl)-2-(trimethylsilyloxy)acetonitrile To a solution of 5-methyl-7-p-tolylpyrazolo[1,5-a]pyrimidine-6-carbaldehyde (200 mg, 0.796 mmol) in CH₂Cl₂ (30 mL) at 0° C. was added zinc iodide (127 mg, 0.398 mmol) followed by TMS-CN (0.427 mL, 3.18 mmol). The mixture was stirred at 0° C. for 1.5 h and at room temp for 2 h. The reaction mixture was diluted with CH₂Cl₂ (100 mL), washed with water, and dried over Na₂SO₄. The solvent was evaporated to give the title compound (234 mg, 84%) without further purification.

| 2-(5-Methyl-7-p-tolylpyrazolo[1,5-a]pyrimidin-6-yl)-2-(trimethylsilyloxy)acetonitrile. | |
|---|---|
| MS (M + H)⁺ Calcd. | 362 |
| MS (M + H)⁺ Observ. | 362 |
| Retention Time | 2.17 min |
| | LC Condition |
| Solvent A | 5% methanol:95% Water:10 mM Ammonium Acetate |
| Solvent B | 95% methanol:5% Water:10 mM Ammonium Acetate |
| Start % B | 0 |
| Final % B | 100 |
| Gradient Time | 2 min |
| Flow Rate | 1 mL/min |
| Wavelength | 220 |
| Solvent Pair | methanol:Water:Ammonium Acetate |
| Column | Phenomenex Luna 2.0 × 30 mm 3 um |

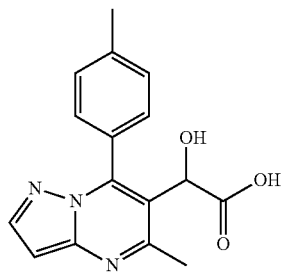 [SMILES: Cc1ccc(-c2c(C(O)C(=O)O)c(C)nc3ccnn23)cc1]

2-hydroxy-2-(5-methyl-7-p-tolylpyrazolo[1,5-a]pyrimidin-6-yl)acetic acid, TFA salt A mixture of 2-(5-methyl-7-p-tolylpyrazolo[1,5-a]pyrimidin-6-yl)-2-(trimethylsilyloxy)acetonitrile (238 mg, 0.679 mmol) and conc. HCl (400 μL, 4.87 mmol) was heated in a sealed tube at 110° C. for 3 h. The solvent was evaporated and the residue was purified by preparative HPLC to afford (134 mg, 47.5%) of the title compound as TFA salt. ¹H-NMR (400 MHz, MeOD) δ ppm 2.48 (3H, s), 2.67 (3H, s), 5.15 (1H, s), 6.62 (1H, d, J=2.4 Hz), 7.38-7.52 (4H, m), 8.02 (1H, d, J=2.4 Hz).

| 2-hydroxy-2-(5-methyl-7-p-tolylpyrazolo[1,5-a]pyrimidin-6-yl)acetic acid, TFA salt. | |
|---|---|
| MS (M + H)⁺ Calcd. | 298 |
| MS (M + H)⁺ Observ. | 298 |
| Retention Time | 1.46 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

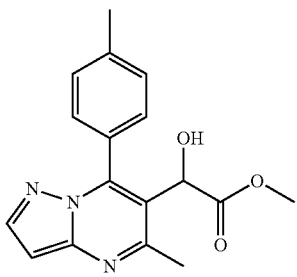 [SMILES: COC(=O)C(O)c1c(C)nc2ccnn2c1-c1ccc(C)cc1]

Methyl 2-hydroxy-2-(5-methyl-7-p-tolylpyrazolo[1,5-a]pyrimidin-6-yl)acetate, HCl salt To a solution of 2-hydroxy-2-(5-methyl-7-p-tolylpyrazolo[1,5-a]pyrimidin-6-yl)acetic acid, TFA salt (60 mg, 0.146 mmol) in MeOH (2 mL) was added thionyl chroride (0.021 mL, 0.292 mmol). The reaction mixture was stirred at 40° C. for 6 h. The solvent was evaporated to give the title compound (50 mg, 99%). $^1$H-NMR (500 MHz, CDCl$_3$) δ ppm 2.45 (3H, s), 2.58 (3H, s), 3.77 (3H, s), 5.20 (1H, s), 6.62 (1H, d, J=2.4 Hz), 7.33-7.50 (4H, m), 8.02 (1H, d, J=2.4 Hz).

| Methyl 2-hydroxy-2-(5-methyl-7-p-tolylpyrazolo[1,5-a]pyrimidin-6-yl)acetate, HCl salt. | |
|---|---|
| MS (M + H)$^+$ Calcd. | 312 |
| MS (M + H)$^+$ Observ. | 312 |
| Retention Time | 1.71 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

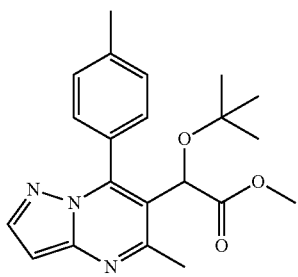 [SMILES: COC(=O)C(OC(C)(C)C)c1c(C)nc2ccnn2c1-c1ccc(C)cc1]

Methyl 2-tert-butoxy-2-(5-methyl-7-p-tolylpyrazolo[1,5-a]pyrimidin-6-yl)acetate

To a suspension of methyl 2-hydroxy-2-(5-methyl-7-p-tolylpyrazolo[1,5-a]pyrimidin-6-yl)acetate (40 mg, 0.128 mmol) in tert-butyl acetate (1 mL) at room temperature was added perchloric acid (0.015 mL, 0.257 mmol). The reaction mixture was stirred for 2 h at room temperature before being quenched with water and diluted with ethyl acetate. The organic phase was washed with saturated NaHCO$_3$ and dried over sodium sulfate. The solvent was evaporated. Purification by silica gel chromatography provided the title compound (26 mg, 55.1%). $^1$H-NMR (500 MHz, CDCl$_3$) δ ppm 0.96 (9H, m), 2.46 (3H, s), 2.66 (3H, s), 3.78 (3H, s), 5.10 (1H, s), 6.59 (1H, d, J=2.4 Hz), 7.37-7.40 (2H, m), 7.43-7.55 (2H, m), 7.99 (1H, d, J=2.4 Hz).

| Methyl 2-tert-butoxy-2-(5-methyl-7-p-tolylpyrazolo[1,5-a]pyrimidin-6-yl)acetate. | |
|---|---|
| MS (M + H)$^+$ Calcd. | 368 |
| MS (M + H)$^+$ Observ. | 368 |
| Retention Time | 2.21 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 42

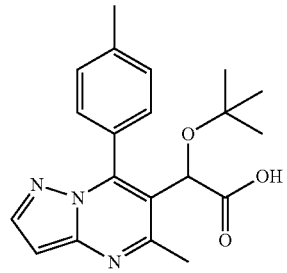 [SMILES: Cc1ccc(-c2c(C(OC(C)(C)C)C(=O)O)c(C)nc3ccnn23)cc1]

2-tert-Butoxy-2-(5-methyl-7-p-tolylpyrazolo[1,5-a]pyrimidin-6-yl)acetic acid, TFA salt To a solution of methyl 2-tert-butoxy-2-(5-methyl-7-p-tolylpyrazolo[1,5-c]pyrimidin-6-yl)acetate (19 mg, 0.052 mmol) in dioxane (0.5 mL) was added 1.5 N LiOH aqueous solution (0.5 mL, 0.750 mmol). The reaction mixture was stirred at 50° C. for 2 h. The reaction mixture was filtered and the filtrate was purified by preparative HPLC to afford (22 mg, 91%) of the title compound as TFA salt. Preparative HPLC condition: Phenomenex Luna C18 30×100 mm S10, 30 to 100% B over 15 minute gradient, 6 minute hold time, A=10% methanol 90% water 0.1% TFA, B=90% methanol 10% water 0.1% TFA. Flow rate: 35 mL/min. $^1$H-NMR (500 MHz, MeOD) δ ppm 0.98 (9H, s), 2.52 (3H, s), 2.70 (3H, s), 5.16 (1H, s), 6.63 (1H, d, J=2.4 Hz), 7.42-7.66 (4H, m), 8.03 (1H, d, J=2.4 Hz).

| 2-tert-Butoxy-2-(5-methyl-7-p-tolylpyrazolo[1,5-a]pyrimidin-6-yl)acetic acid, TFA salt. | |
|---|---|
| MS (M + H)$^+$ Calcd. | 354 |
| MS (M + H)$^+$ Observ. | 354 |
| Retention Time | 1.46 min |

123
-continued 2-tert-Butoxy-2-(5-methyl-7-p-tolylpyrazolo[1,5-a]pyrimidin-6-yl)acetic acid, TFA salt.

| LC Condition | |
|---|---|
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna 2.0 × 30 mm 3 um |

Scheme 6

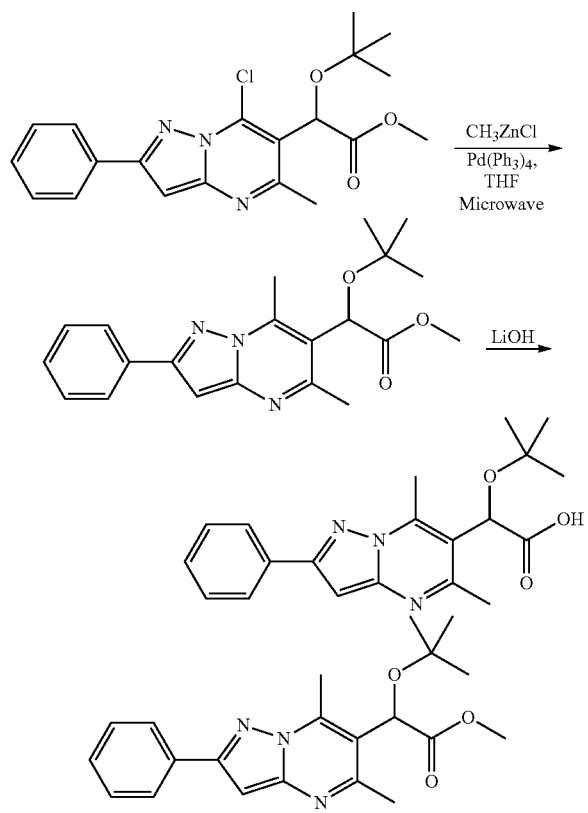

Methyl 2-tert-butoxy-2-(5,7-dimethyl-2-phenylpyrazolo[1,5-a]pyrimidin-6-yl)acetate, TFA salt To a 0.5-2 mL microwave tube was added methyl 2-tert-butoxy-2-(7-chloro-5-methyl-2-phenylpyrazolo[1,5-a]pyrimidin-6-yl)acetate (20 mg, 0.052 mmol), Pd(Ph₃P)₄ (20 mg, 0.017 mmol) followed by methylzinc(II) chloride (0.5 mL, 1.000 mmol) and THF (0.8 mL). The reaction mixture was heated in a microwave reactor at 130° C. for 15 min. The reaction mixture was quenched with water. The aqueous layer was extracted with ethyl acetate and the combined organic layer was dried over anhydrous $Na_2SO_4$, filtered and concentrated. The residue was purified by Preparative HPLC to give the title compound (15 mg, 60.4%) as TFA salt. Preparative HPLC condition: Waters Sunfire C18 30×100 mm 5 u, 50 to 100% B over 20 min gradient, 6 min hold time, A=10% methanol 90% water 0.1% TFA, B=90% methanol 10% water 0.1% TFA. Flow rate: 35 mL/min. ¹H-NMR (400 MHz, CDCl₃) δ ppm 1.28 (9H, s), 2.85 (3H, s), 3.10 (3H, s), 3.75 (3H, s), 5.41 (1H, s), 7.06 (1H, s), 7.38-7.56 (3H, m), 8.02-8.04 (2H, m).

| Methyl 2-tert-butoxy-2-(5,7-dimethyl-2-phenylpyrazolo[1,5-a]pyrimidin-6-yl)acetate, TFA salt. | |
|---|---|
| MS (M + H)⁺ Calcd. | 368 |
| MS (M + H)⁺ Observ. | 368 |
| Retention Time | 2.23 min |
| LC Condition | |
| Solvent A | 5% MeOH: 95% Water: 10 mM Ammonium Acetate |
| Solvent B | 95% MeOH: 5% Water: 10 mM Ammonium Acetate |
| Start % B | 0 |
| Final % B | 100 |
| Gradient Time | 2 min |
| Flow Rate | 1 mL/min |
| Wavelength | 220 |
| Solvent Pair | MeOH: Water: Ammonium Acetate |
| Column | Phenomenex Luna 2 × 30 mm 3 um |

Example 43

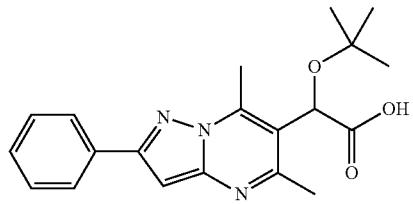 [SMILES: Cc1nc2cc(-c3ccccc3)nn2c(C)c1C(OC(C)(C)C)C(=O)O]

2-tert-Butoxy-2-(5,7-dimethyl-2-phenylpyrazolo[1,5-a]pyrimidin-6-yl)acetic acid, TFA salt To a solution of methyl 2-tert-butoxy-2-(5,7-dimethyl-2-phenylpyrazolo[1,5-a]pyrimidin-6-yl)acetate, TFA (15 mg, 0.031 mmol) in dioxane (0.5 mL) was added 1.5 N LiOH aqueous solution (0.5 mL, 0.750 mmol). The reaction mixture was stirred at room temperature for 4 h. The reaction mixture was filtered and the filtrate was purified by preparative HPLC to afford (13 mg, 89%) of the title compound as the TFA salt. Preparative HPLC condition: Waters Sunfire C18 30×100 mm 5 u, 50 to 100% B over 20 min gradient, 6 min hold time, A=10% methanol 90% water 0.1% TFA, B=90% methanol 10% water 0.1% TFA. Flow rate: 40 mL/min. ¹H-NMR (500 MHz, CDCl₃) δ ppm 1.27 (9H, s), 2.85 (3H, s), 3.10 (3H, s), 5.41 (1H, s), 7.07 (1H, s), 7.34-7.55 (3H, m), 7.89-8.06 (2H, m), 9.92 (1H, br. s.).

| 2-tert-Butoxy-2-(5,7-dimethyl-2-phenylpyrazolo[1,5-a]pyrimidin-6-yl)acetic acid, TFA salt. | |
|---|---|
| MS (M + H)⁺ Calcd. | 354 |
| MS (M + H)⁺ Observ. | 354 |
| Retention Time | 2.31 min |
| LC Condition | |

-continued

| 2-tert-Butoxy-2-(5,7-dimethyl-2-phenylpyrazolo [1,5-a]pyrimidin-6-yl)acetic acid, TFA salt. | |
|---|---|
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

Scheme 7

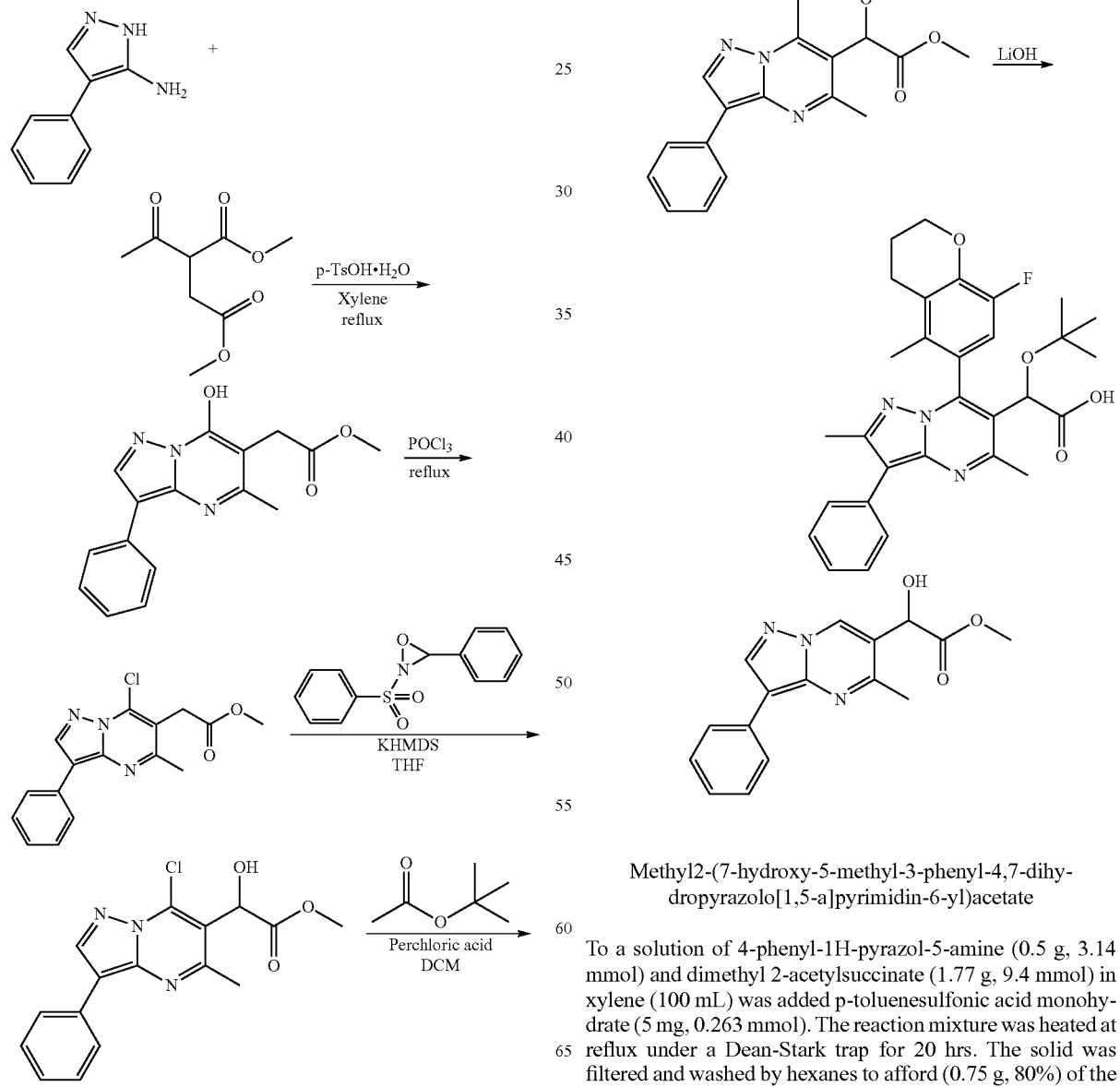

Methyl 2-(7-hydroxy-5-methyl-3-phenyl-4,7-dihydropyrazolo[1,5-a]pyrimidin-6-yl)acetate To a solution of 4-phenyl-1H-pyrazol-5-amine (0.5 g, 3.14 mmol) and dimethyl 2-acetylsuccinate (1.77 g, 9.4 mmol) in xylene (100 mL) was added p-toluenesulfonic acid monohydrate (5 mg, 0.263 mmol). The reaction mixture was heated at reflux under a Dean-Stark trap for 20 hrs. The solid was filtered and washed by hexanes to afford (0.75 g, 80%) of the title compound. $^1$H-NMR (500 MHz, DMSO-$d_6$) δ ppm 2.38

(3H, s), 3.39 (2H, s), 3.59 (3H, s), 7.33 (1H, S), 7.47 (2H, m), 7.57 (2H, m) 8.13 (1H, S), 11.87 (1H, s).

| Methyl 2-(7-hydroxy-5-methyl-3-phenyl-4,7-dihydropyrazolo[1,5-a]pyrimidin-6-yl)acetate | |
|---|---|
| MS (M + H)$^+$ Calcd. | 298 |
| MS (M + H)$^+$ Observ. | 298 |
| Retention Time | 1.64 min |
| | LC Condition |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

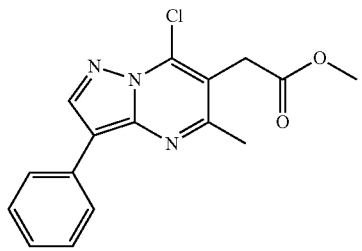 [SMILES: COC(=O)Cc1c(C)nc2c(-c3ccccc3)cnn2c1Cl]

Methyl 2-(7-chloro-5-methyl-3-phenylpyrazolo[1,5-a]pyrimidin-6-yl)acetate

To methyl 2-(7-hydroxy-5-methyl-3-phenyl-4,7-dihydropyrazolo[1,5-a]pyrimidin-6-yl)acetate (0.5 g, 1.68 mmol) was added POCl$_3$ (1 mL). The reaction mixture was heated at reflux for 1 h. After cooling, the reaction mixture was added drop-wise to ice-water. A brown solid precipitated. The solid were filtered and washed with water, then dissolved in ethyl acetate. The organic solution was washed with saturated NaHCO$_3$ and dried over sodium sulfate. The solvent was evaporated to give the title compound (0.48 g, 90%). $^1$H-NMR (500 MHz, MeOD) δ ppm 2.66 (3H, s), 3.77 (3H, s), 4.04 (2H, s), 7.26 (1H, s), 7.42 (2H, s), 8.09 (2H, s), 8.57 (1H, s).

| Methyl 2-(7-chloro-5-methyl-3-phenylpyrazolo[1,5-a]pyrimidin-6-yl)acetate | |
|---|---|
| MS (M + H)$^+$ Calcd. | 316 |
| MS (M + H)$^+$ Observ. | 316 |
| Retention Time | 1.71 min |
| | LC Condition |
| Solvent A | 10% Acetonitrile:90% Water:0.1% TFA |
| Solvent B | 90% Acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Acetonitrile:Water:TFA |
| Column | Phenomenex Luna 2.0 × 30 mm 3 um |

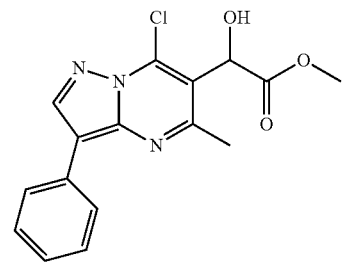 [SMILES: COC(=O)C(O)c1c(C)nc2c(-c3ccccc3)cnn2c1Cl]

Methyl 2-(7-chloro-5-methyl-3-phenylpyrazolo[1,5-a]pyrimidin-6-yl)-2-hydroxyacetate To a stirred solution of KHMDS (0.5 M in toluene, 4.6 mL, 4.75 mmol) in THF (12 mL) at −78° C. was added a solution of methyl 2-(7-chloro-5-methyl-3-phenylpyrazolo[1,5-a]pyrimidin-6-yl)acetate (0.48 g, 1.5 mmol) in THF (12 mL) over 20 mins. The reaction mixture was stirred at −78° C. for 30 min. A solution of 3-phenyl-2-(phenylsulfonyl)-1,2-oxaziridine (0.6 g, 2.3 mmol) in THF (12 mL) was added over 10 min and the resulted reaction mixture was stirred for an additional 30 min at −78° C. The reaction mixture was quenched with saturated NH$_4$Cl aqueous solution (2 mL). The mixture was allowed to warm up to room temperature and diluted with EtOAc (100 mL). The organic phase was washed with water and brine and dried with sodium sulfate. The solvent was evaporated. Purification by silica gel chromatography provided the title compound (250 mg, 51%). $^1$H-NMR (500 MHz, DMSO-d6) δ ppm 2.65 (3H, s), 3.7 (3H, s), 5.79 (1H, s), 6.62 (1H, s), 7.35-7.59 (3H, m), 8.95 (1H, s).

| Methyl 2-(7-chloro-5-methyl-3-phenylpyrazolo[1,5-a]pyrimidin-6-yl)-2-hydroxyacetate | |
|---|---|
| MS (M + H)$^+$ Calcd. | 332 |
| MS (M + H)$^+$ Observ. | 332 |
| Retention Time | 2.05 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

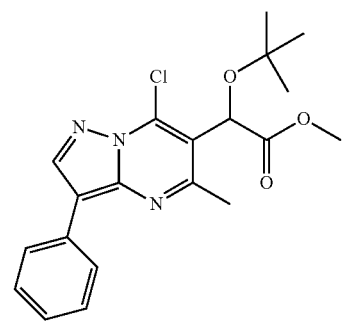 [SMILES: COC(=O)C(OC(C)(C)C)c1c(C)nc2c(-c3ccccc3)cnn2c1Cl]

Methyl 2-tert-butoxy-2-(7-chloro-5-methyl-3-phenylpyrazolo[1,5-a]pyrimidin-6-yl)acetate To a suspension of methyl 2-(7-chloro-5-methyl-2-phenylpyrazolo[1,5-c]pyrimidin-6-yl)-2-hydroxyacetate (250 mg, 0.75 mmol) in tert-butyl acetate (8 mL) at room temperature was added $CH_2Cl_2$ (15 mL) followed by perchloric acid (114 mg, 1.13 mmol). The reaction mixture was stirred for 2 h at room temperature. The reaction mixture was diluted with ethyl acetate (15 mL). The organic phase was washed with saturated $NaHCO_3$ (2×10 mL), followed by water (1×10 mL) and dried over sodium sulfate. The solvent was evaporated. Purification by silica gel chromatography provided the title compound (110 mg, 38%). $^1$H-NMR (500 MHz, DMSO-$d_6$) δ ppm 1.23 (9H, s), 3.33 (3H, s), 3.69 (3H, s), 5.72 (1H, s), 7.29 (1H, s), 7.47 (2H, s), 8.14 (2H, s), 8.85 (1H, s).

| Methyl 2-tert-butoxy-2-(7-chloro-5-methyl-32-phenylpyrazolo[1,5-a]pyrimidin-6-yl)acetate | |
|---|---|
| MS (M + H)$^+$ Calcd. | 388 |
| MS (M + H)$^+$ Observ. | 388 |
| Retention Time | 2.42 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

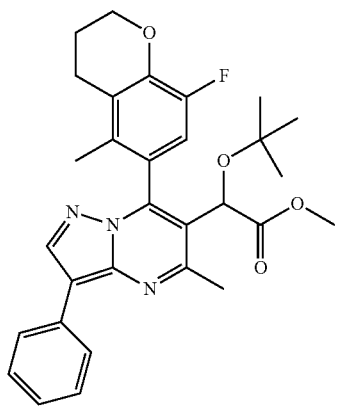 [SMILES: COC(=O)C(OC(C)(C)C)c1c(C)nc2c(-c3ccccc3)cnn2c1-c1cc(F)c2c(c1C)CCCO2]

Methyl 2-tert-butoxy-2-(7-(8-fluoro-5-methylchroman-6-yl)-5-methyl-3-phenylpyrazolo[1,5-a]pyrimidin-6-yl)acetate, TFA salt To a 2-5 mL microwave tube was added methyl 2-tert-butoxy-2-(7-chloro-5-methyl-2-phenylpyrazolo[1,5-a]pyrimidin-6-yl)acetate (20 mg, 0.052 mmol), tetrakis(triphenylphosphine) palladium(0) (8.94 mg, 7.73 mmol), 8-fluoro-5-methylchroman-6-ylboronic acid (16 mg, 0.077 mmol), dioxane (1.5 mL), followed by 2M $K_3PO_4$ solution (77 uL). The reaction mixture was heated in a microwave reactor at 130° C. for 30 min. The reaction mixture was filtered and the filtrate was purified by preparative HPLC to afford (13 mg, 38%) of the title compound as the TFA salt. Preparative HPLC condition: Phenomenex Luna C18 30×100 mm S10, 30 to 100% B over 17 min gradient, 5 min hold time, A=10% methanol 90% water 0.1% TFA, B=90% methanol 10% water 0.1% TFA. Flow rate: 40 mL/min. $^1$H-NMR (500 MHz, MeOD) δ ppm 1.18 (9H, s), 1.86 (3H, m), 2.2 (2H, m), 2.81 (3H, s), 2.74 (2H, s), 3.68 (3H, s), 4.30 (2H, m), 5.09 (1H, s), 6.90 (1H, s), 7.21-7.42 (4H, m), 8.11 (1H, s), 8.38 (1H, s).

| Methyl 2-tert-butoxy-2-(7-(8-fluoro-5-methylchroman-6-yl)-5-methyl-3-phenylpyrazolo[1,5-a]pyrimidin-6-yl)acetate, TFA salt. | |
|---|---|
| MS (M + H)$^+$ Calcd. | 518 |
| MS (M + H)$^+$ Observ. | 518 |
| Retention Time | 2.51 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 44

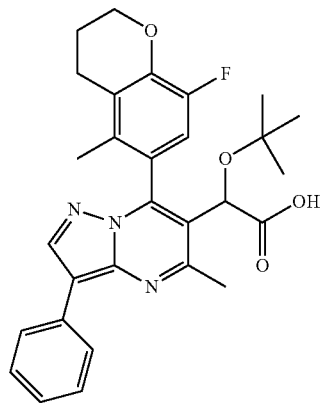 [SMILES: Cc1nc2c(-c3ccccc3)cnn2c(-c2cc(F)c3c(c2C)CCCO3)c1C(OC(C)(C)C)C(=O)O]

2-tert-Butoxy-2-(7-(8-fluoro-5-methylchroman-6-yl)-5-methyl-3-phenylpyrazolo[1,5-a]pyrimidin-6-yl)acetic acid, TFA salt To a solution of methyl 2-tert-butoxy-2-(7-(8-fluoro-5-methylchroman-6-yl)-5-methyl-3-phenylpyrazolo[1,5-a]pyrimidin-6-yl)acetate, TFA salt (9 mg, 0.017 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (5 mg, 43%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (500 MHz, MeOD) δ ppm 1.19 (9H, s), 1.57 (1H, s), 1.86 (3H, s), 2.14 (2H, br. s.), 2.78 (2H, s), 2.84 (3H, s), 4.30 (1H, s), 5.04 (1H, s), 6.92 (1H, s), 7.26 (1H, s), 7.42 (1H, s), 8.04-8.13 (1H, m), 8.37 (1H, s).

| 2-tert-Butoxy-2-(7-(8-fluoro-5-methylchroman-6-yl)-5-methyl-3-phenylpyrazolo[1,5-a]pyrimidin-6-yl)acetic acid, TFA salt. | |
| --- | --- |
| MS (M + H)+ Calcd. | 504 |
| MS (M + H)+ Observ. | 504 |
| Retention Time | 2.42 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Scheme 8.

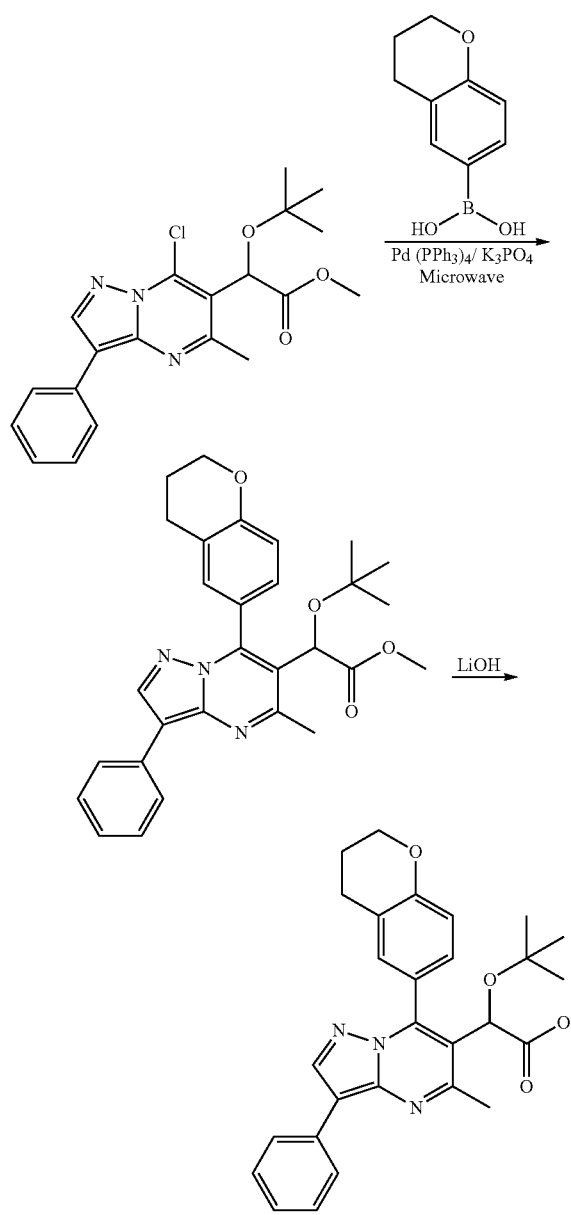

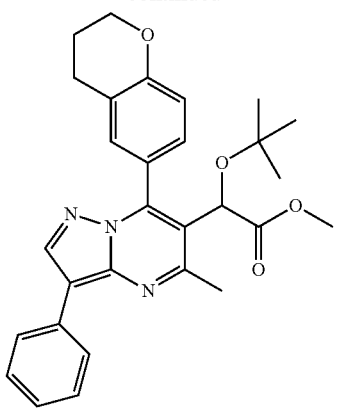

Methyl 2-tert-butoxy-2-(7-(chroman-6-yl)-5-methyl-3-phenylpyrazolo[1,5-a]pyrimidin-6-yl)acetate, TFA salt To a 2-5 mL microwave tube was added methyl 2-tert-butoxy-2-(7-chloro-5-methyl-3-phenylpyrazolo[1,5-a]pyrimidin-6-yl)acetate (20 mg, 0.052 mmol), tetrakis(triphenylphosphine)palladium(0) (6 mg, 0.005 mmol), 2-(chroman-6-yl)-4,4,5,5-tetramethyl-1,3,2-dioxaborolane (20 mg, 0.077 mmol), dioxane (1.5 mL), followed by 2M $K_3PO_4$ solution (77 uL). The reaction mixture was heated in a microwave reactor at 130° C. for 30 min. The reaction was filtered and the filtrate was purified by preparative HPLC to afford (13 mg, 52%) of the title compound as the TFA salt. Preparative HPLC condition: Phenomenex Luna C18 30×100 mm S10, 30 to 100% B over 17 mingradient, 5 min hold time, A=10% methanol 90% water 0.1% TFA, B=90% methanol 10% water 0.1% TFA. Flow rate: 40 mL/min. $^1$H-NMR (500 MHz, MeOD) δ ppm 0.99 (9H, s), 2.2 (2H, m), 2.74 (2H, s), 2.81 (3H, s), 3.8 (3H, s), 4.26 (2H, m), 5.24 (1H, s), 6.97 (1H, s), 7.22 (1H, s), 7.32-7.42 (3H, m), 8.10 (2H, s), 8.37 (1H, s).

| Methyl 2-tert-butoxy-2-(7-chroman-6-yl)-5-methyl-3-phenylpyrazolo[1,5-a]pyrimidin-6-yl)acetate, TFA salt. | |
| --- | --- |
| MS (M + H)+ Calcd. | 486 |
| MS (M + H)+ Observ. | 486 |
| Retention Time | 2.49 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

Example 45

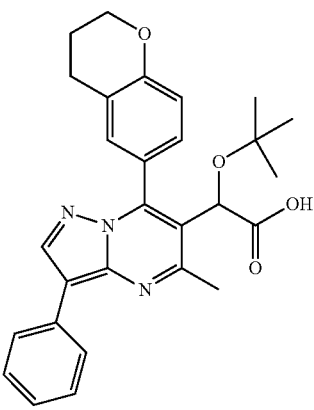

2-tert-Butoxy-2-(7-(chroman-6-yl)-5-methyl-3-phenylpyrazolo[1,5-a]pyrimidin-6-yl)acetic acid, TFA salt To a solution of methyl 2-tert-butoxy-2-(7-chroman-6-yl)-5-methyl-3-phenylpyrazolo[1,5-a]pyrimidin-6-yl)acetate, TFA salt (13 mg, 0.027 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (12 mg, 76%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (500 MHz, MeOD) δ ppm 0.99 (9H, br. s.), 2.07 (2H, br. s.), 2.74 (3H, br. s.), 2.82-2.96 (2H, m), 4.29 (2H, br. s.), 5.21 (1H, s), 6.98 (1H, s), 7.24 (1H, s), 7.41 (4H, s), 8.11 (2H, s), 8.38 (1H, s).

| 2-tert-Butoxy-2-(7-(chroman-6-yl)-5-methyl-3-phenylpyrazolo[1,5-a]pyrimidin-6-yl)acetic acid, TFA salt. | |
|---|---|
| MS (M + H)$^+$ Calcd. | 472 |
| MS (M + H)$^+$ Observ. | 472 |
| Retention Time | 2.39 min |
| LC Condition | |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

Scheme 9.

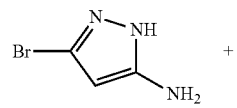

+

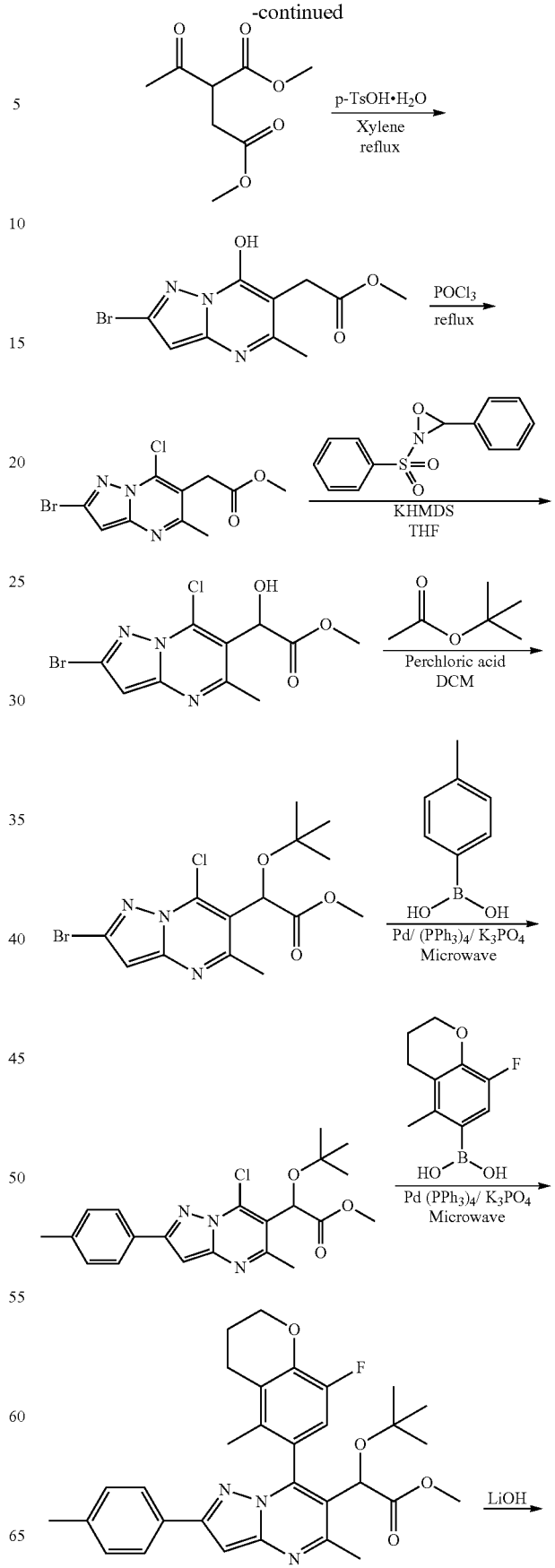

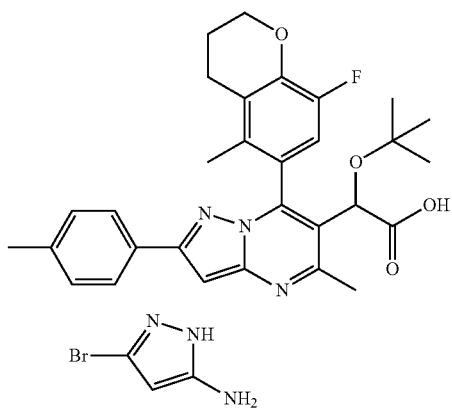

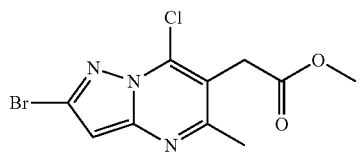

Methyl 2-(2-bromo-7-chloro-5-methylpyrazolo[1,5-a]pyrimidin-6-yl)acetate

To methyl 2-(2-bromo-5-methyl-7-oxo-4,7-dihydropyrazolo [1,5-a]pyrimidin-6-yl)acetate (180 mg, 0.600 mmol) was added POCl₃ (1 mL, 10.73 mmol). The reaction mixture was heated at reflux for 1 h. After cooling, the reaction mixture was added drop-wise to ice-water. A brown solid precipitated. The solid was filtered and washed with water to give the title compound (158 mg, 83%). $^1$H NMR (500 MHz, DMSO-$d_6$) δ ppm 2.56 (3H, s), 3.69 (3H, s), 4.01 (2H, s), 6.99 (1H, s).

3-Bromo-1H-pyrazol-5-amine was prepared as described in reference: *Journal of Medicinal Chemistry*, 2010, 53, 3, 1245.

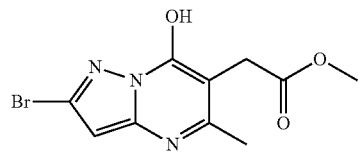 [SMILES: COC(=O)Cc1c(C)nc2cc(Br)nn2c1O]

Methyl 2-(2-bromo-7-hydroxy-5-methylpyrazolo[1, 5-a]pyrimidin-6-yl)acetate

To a solution of 3-bromo-1H-pyrazol-5-amine (0.2 g, 1.235 mmol) and dimethyl 2-acetylsuccinate (0.697 g, 3.70 mmol) in xylene (10 mL) was added p-toluenesulfonic acid monohydrate (2 mg, 10.51 mmol). The reaction mixture was heated at reflux under a Dean-Stark trap for 8 h. The solid was filtered and washed with hexanes to afford the title compound (0.201 g, 54.2%). $^1$H NMR (400 MHz, MeOD) δ ppm 2.37 (3H, s), 3.65 (2H, s), 3.71 (3H, s), 6.20 (1H, s).

| Methyl 2-(2-bromo-7-hydroxy-5-methylpyrazolo [1,5-a]pyrimidin-6-yl)acetate. | |
|---|---|
| MS (M + H)⁺ Calcd. | 300 |
| MS (M + H)⁺ Observ. | 300 |
| Retention Time | 1.32 min |
| LC Condition | |
| Solvent A | 10% MeOH: 90% Water: 0.1% TFA |
| Solvent B | 90% MeOH: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | MeOH: Water: TFA |
| Column | Phenomenex Luna C18, 30 × 2, 3 u |

| Methyl 2-(2-bromo-7-chloro-5-methylpyrazolo[1,5-a]pyrimidin-6-yl)acetate | |
|---|---|
| MS (M + H)⁺ Calcd. | 318 |
| MS (M + H)⁺ Observ. | 318 |
| Retention Time | 1.78 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

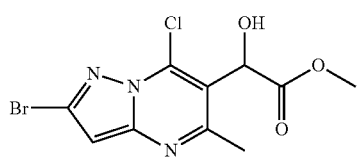 [SMILES: COC(=O)C(O)c1c(C)nc2cc(Br)nn2c1Cl]

Methyl 2-(2-bromo-7-chloro-5-methylpyrazolo[1,5-a]pyrimidin-6-yl)-2-hydroxyacetate To a stirred solution of KHMDS (0.5 M in toluene, 2.83 mL, 1.413 mmol) in THF (6 mL) at −78° C. was added a solution of methyl 2-(2-bromo-7-chloro-5-methylpyrazolo[1,5-a]pyrimidin-6-yl)acetate (300 mg, 0.942 mmol) in THF (6 mL) dropwise over 20 min. The mixture was stirred at −78° C. for 30 min. A solution of 3-phenyl-2-(phenylsulfonyl)-1,2-oxaziridine (369 mg, 1.413 mmol) in THF (6 mL) was added over 15 min and the reaction mixture was stirred for additional 60 min at −78° C. The reaction mixture was quenched with saturated NH₄Cl aqueous solution (4 mL). The reaction mixture was allowed to warm to room temperature and then diluted with ethyl acetate (100 mL). The organic phase was washed with water and brine and dried with sodium sulfate. The solvent was evaporated. Purification by silica gel chromatography provided the title compound (85 mg, 27%). $^1$H NMR (400 MHz, CHLOROFORM-d) δ ppm 2.63 (3H, s), 3.84 (3H, s), 5.74 (1H, s), 6.71 (1H, s).

| Methyl 2-(2-bromo-7-chloro-5-methylpyrazolo[1,5-a]pyrimidin-6-yl)-2-hydroxyacetate | |
|---|---|
| MS (M + H)⁺ Calcd. | 334 |
| MS (M + H)⁺ Observ. | 334 |
| Retention Time | 1.692 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

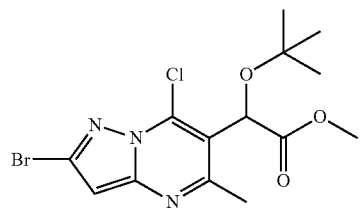 [SMILES: COC(=O)C(OC(C)(C)C)c1c(C)nc2cc(Br)nn2c1Cl]

Methyl 2-(2-bromo-7-chloro-5-methylpyrazolo[1,5-a]pyrimidin-6-yl)-2-tert-butoxyacetate To a suspension of methyl 2-(2-bromo-7-chloro-5-methylpyrazolo[1,5-a]pyrimidin-6-yl)-2-hydroxyacetate (80 mg, 0.239 mmol) in tert-butyl acetate (2 mL) at room temperature was added CH₂Cl₂ (2 mL) followed by perchloric acid (0.022 mL, 0.359 mmol). The reaction mixture was stirred for 4 h at room temperature. The reaction mixture was quenched with water and diluted with ethyl acetate. The organic phase was washed with saturated NaHCO₃ and dried over sodium sulfate. The solvent was evaporated. Purification by silica gel chromatography provided the title compound (56 mg, 59.9%). ¹H NMR (500 MHz, MeOD) δ ppm 1.27 (9H, s), 2.62 (3H, s), 3.74 (3H, s), 5.75 (1H, s), 6.75 (1H, s).

| Methyl 2-(2-bromo-7-chloro-5-methylpyrazolo[1,5-a]pyrimidin-6-yl)-2-tert-butoxyacetate | |
|---|---|
| MS (M + H)⁺ Calcd. | 390 |
| MS (M + H)⁺ Observ. | 390 |
| Retention Time | 2.217 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

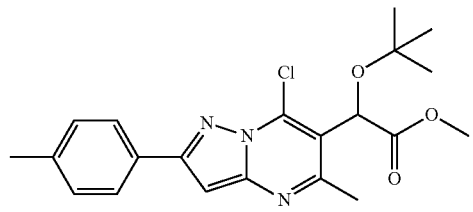

Methyl 2-tert-butoxy-2-(7-chloro-5-methyl-2-p-tolylpyrazolo[1,5-a]pyrimidin-6-yl)acetate, TFA salt To a 2-5 mL microwave tube was added methyl 2-(2-bromo-7-chloro-5-methylpyrazolo[1,5-a]pyrimidin-6-yl)-2-tert-butoxyacetate (28 mg, 0.072 mmol), tetrakis(triphenylphosphine)palladium(0) (12.42 mg, 10.75 µmol), p-tolylboronic acid (10.72 mg, 0.079 mmol), DMF (3 mL), followed by 2M K₂CO₃ solution (100 µl). The reaction mixture was heated in a microwave reactor at 70° C. for 60 min. The reaction mixture was filtered and the filtrate purified by preparative HPLC to afford (16 mg, 43.3%) of the title compound as TFA salt. Preparative HPLC condition: Waters Atlantis OBD 30×100 mm 5 u, 50 to 100% B over 20 minute gradient, 6 minute hold time, A=10% methanol 90% water 0.1% TFA, B=90% methanol 10% water 0.1% TFA. Flow rate: 35 ml/min. ¹H NMR (500 MHz, MeOD) δ ppm 1.29 (9H, s), 2.40 (3H, s), 2.62 (3H, s), 3.75 (3H, s), 5.79 (1H, s), 6.98 (1H, s), 7.30 (2H, d, J=7.9 Hz), 7.92 (2H, d, J=7.9 Hz).

| Methyl 2-tert-butoxy-2-(7-chloro-5-methyl-2-p-tolylpyrazolo[1,5-a]pyrimidin-6-yl)acetate, TFA salt | |
|---|---|
| MS (M + H)⁺ Calcd. | 402 |
| MS (M + H)⁺ Observ. | 402 |
| Retention Time | 2.44 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

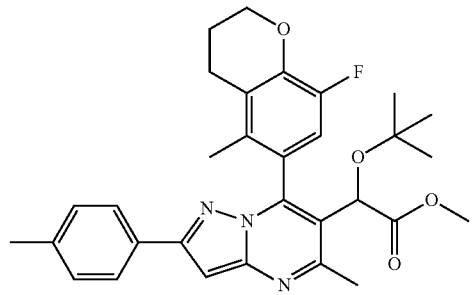

Methyl 2-tert-butoxy-2-(7-(8-fluoro-5-methylchroman-6-yl)-5-methyl-2-p-tolylpyrazolo[1,5-a]pyrimidin-6-yl)acetate, TFA salt To a 0.5-2 mL microwave tube was added methyl 2-tert-butoxy-2-(7-chloro-5-methyl-2-p-tolylpyrazolo[1,5-a]pyrimidin-6-yl)acetate, TFA (8 mg, 0.016 mmol), tetrakis(triphenylphosphine)palladium(0) (2.69 mg, 2.326 µmol), 2-(8- fluoro-5-methylchroman-6-yl)-4,4,5,5-tetramethyl-1,3,2-dioxaborolane (9.06 mg, 0.031 mmol), DMF (0.7 mL), followed by 2M K$_3$PO$_4$ solution (50 µl). The reaction mixture was heated in a microwave reactor at 130° C. for 15 min. The reaction mixture was filtered and the filtrate purified by preparative HPLC to afford the title compound as TFA salt (5 mg, 49.9%). Preparative HPLC condition: Waters Atlantis OBD 30×100 mm 5 u, 50 to 100% B over 20 minute gradient, 6 minute hold time, A=10% methanol 90% water 0.1% TFA, B=90% methanol 10% water 0.1% TFA. Flow rate: 35 ml/min. $^1$H NMR (400 MHz, CHLOROFORM-d) δ ppm 1.19 (9H, s), 1.86 (3H, s), 2.16-2.23 (2H, m), 2.38 (3H, s), 2.76-2.81 (2H, m), 2.86 (3H, s), 3.68 (3H, s), 4.33-4.40 (2H, m), 5.06 (1H, s), 6.89 (1H, d, J=10.5 Hz), 7.01 (1H, s), 7.21 (2H, d, J=8.0 Hz), 7.72 (2H, d, J=8.0 Hz).

| Methyl 2-tert-butoxy-2-(7-(8-fluoro-5-methylchroman-6-yl)-5-methyl-2-p-tolylpyrazolo[1,5-a]pyrimidin-6-yl)acetate, TFA salt. | |
|---|---|
| MS (M + H)$^+$ Calcd. | 532 |
| MS (M + H)$^+$ Observ. | 532 |
| Retention Time | 2.51 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

Example 46

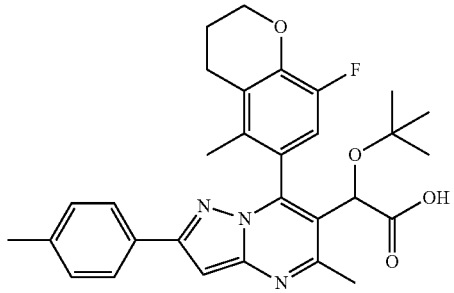 [SMILES: Cc1ccc(-c2cc3nc(C)c(C(OC(C)(C)C)C(=O)O)c(-c4cc(F)c5c(c4C)CCCO5)n3n2)cc1]

2-tert-Butoxy-2-(7-(8-fluoro-5-methylchroman-6-yl)-5-methyl-2-p-tolylpyrazolo[1,5-a]pyrimidin-6-yl)acetic acid, TFA salt To a solution of methyl 2-tert-butoxy-2-(7-(8-fluoro-5-methylchroman-6-yl)-5-methyl-2-p-tolylpyrazolo[1,5-a]pyrimidin-6-yl)acetate, TFA salt (5 mg, 7.74 µmol) in dioxane (0.5 mL) was added 1N LiOH aqueous solution (0.5 mL, 0.5 mmol). The reaction mixture was stirred at 50° C. for 1 h. The reaction mixture was filtered and the filtrate purified by preparative HPLC to afford (4 mg, 82%) of the title compound as TFA salt. Preparative HPLC condition: Waters Atlantis OBD 30×100 mm 5 u, 50 to 100% B over 22 minute gradient, 6 minute hold time, A=10% methanol 90% water 0.1% TFA, B=90% methanol 10% water 0.1% TFA. Flow rate: 40 ml/min. $^1$H NMR (500 MHz, MeOD) δ ppm 1.17 (9H, s), 1.87 (3H, s), 2.10-2.22 (2H, m), 2.35 (3H, s), 2.76 (3H, s), 2.78-2.86 (2H, m), 4.24-4.40 (2H, m), 5.01 (1H, s), 6.88 (1H, s), 6.94 (1H, d, J=10.7 Hz), 7.21 (2H, d, J=7.9 Hz), 7.71 (2H, d, J=8.2 Hz).

| 2-tert-Butoxy-2-(7-(8-fluoro-5-methylchroman-6-yl)-5-methyl-2-p-tolylpyrazolo[1,5-a]pyrimidin-6-yl)acetic acid, TFA salt | |
|---|---|
| MS (M + H)$^+$ Calcd. | 518 |
| MS (M + H)$^+$ Observ. | 518 |
| Retention Time | 2.428 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

Compounds shown in the Table 3 were synthesized using the method described for example 46 with appropriate boronic acids.

TABLE 3

| Example | Structure | RT (min) | HPLC method | MW | Observed mass |
|---|---|---|---|---|---|
| 47 | 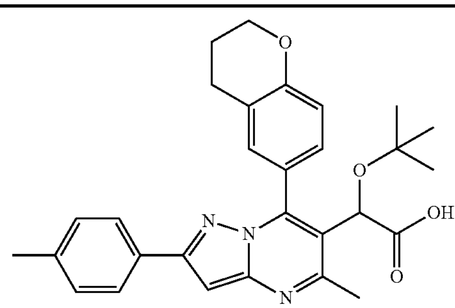 | 2.423 | A | 485.6 | 486 |

Compounds in the Table 4 (Examples 48-91) were synthesized using the procedure described for Example 1 using the appropriate boronic acids.

TABLE 4

| Example | Structure | RT (min) | HPLC method | MW | Observed mass |
|---|---|---|---|---|---|
| 48 | 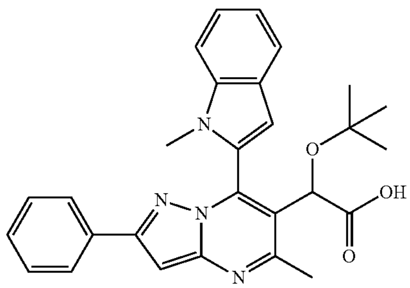 [SMILES: Cc1nc2cc(-c3ccccc3)nn2c(-c2cc3ccccc3n2C)c1C(OC(C)(C)C)C(=O)O] | 7.24 | D | 468.6 | 469 |
| 49 | 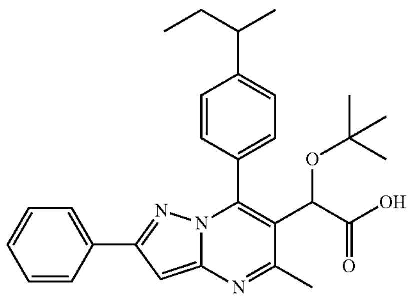 [SMILES: CCC(C)c1ccc(-c2c(C(OC(C)(C)C)C(=O)O)c(C)nc3cc(-c4ccccc4)nn23)cc1] | 8.87 | D | 471.6 | 472 |
| 50 | 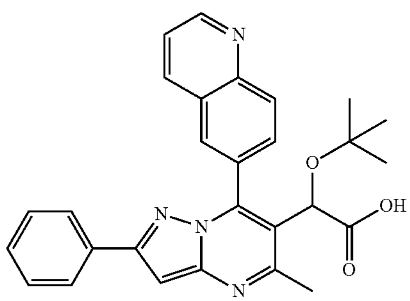 [SMILES: Cc1nc2cc(-c3ccccc3)nn2c(-c2ccc3ncccc3c2)c1C(OC(C)(C)C)C(=O)O] | 5.11 | D | 466.5 | 467 |
| 51 | 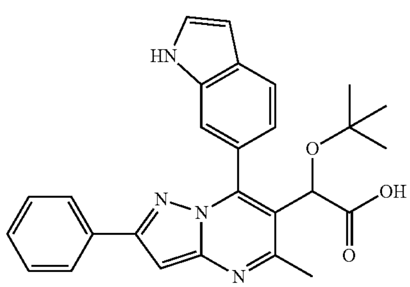 [SMILES: Cc1nc2cc(-c3ccccc3)nn2c(-c2ccc3cc[nH]c3c2)c1C(OC(C)(C)C)C(=O)O] | 6.76 | D | 454.5 | 455 |
| 52 | 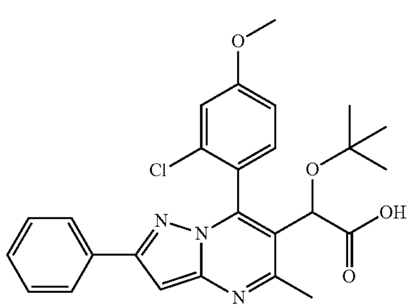 [SMILES: COc1ccc(-c2c(C(OC(C)(C)C)C(=O)O)c(C)nc3cc(-c4ccccc4)nn23)c(Cl)c1] | 7.00 | D | 480.0 | 480 |

TABLE 4-continued

| Example | Structure | RT (min) | HPLC method | MW | Observed mass |
|---|---|---|---|---|---|
| 53 | 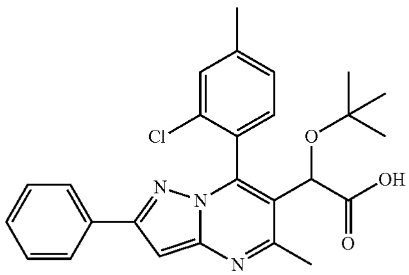 [SMILES: Cc1ccc(-c2c(C(OC(C)(C)C)C(=O)O)c(C)nc3cc(-c4ccccc4)nn23)c(Cl)c1] | 7.35 | D | 464.0 | 464 |
| 54 | 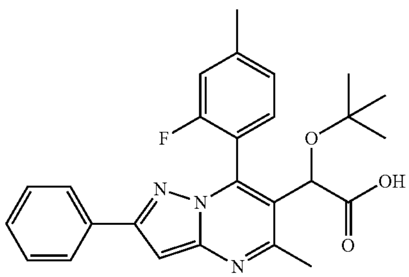 | 6.59 | D | 447.5 | 448 |
| 55 | 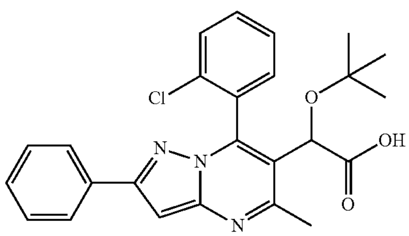 [SMILES: Cc1nc2cc(-c3ccccc3)nn2c(-c2ccccc2Cl)c1C(OC(C)(C)C)C(=O)O] | 5.77 | E | 449.94 | 450 |
| 56 | 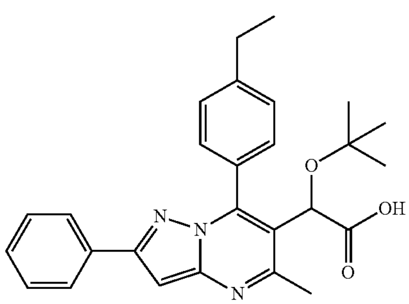 [SMILES: CCc1ccc(-c2c(C(OC(C)(C)C)C(=O)O)c(C)nc3cc(-c4ccccc4)nn23)cc1] | 6.21 | E | 443.5 | 444 |
| 57 | 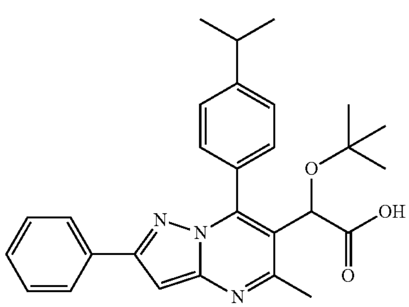 [SMILES: Cc1nc2cc(-c3ccccc3)nn2c(-c2ccc(C(C)C)cc2)c1C(OC(C)(C)C)C(=O)O] | 6.53 | E | 457.6 | 458 |

TABLE 4-continued

| Example | Structure | RT (min) | HPLC method | MW | Observed mass |
|---|---|---|---|---|---|
| 58 | 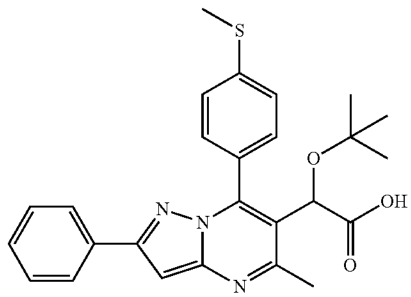 | 5.82 | E | 461.6 | 462 |
| 59 | 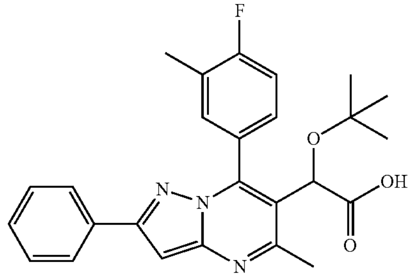 [SMILES: Cc1cc(-c2c(C(OC(C)(C)C)C(=O)O)c(C)nc3cc(-c4ccccc4)nn23)ccc1F] | 5.88 | E | 447.5 | 448 |
| 60 | 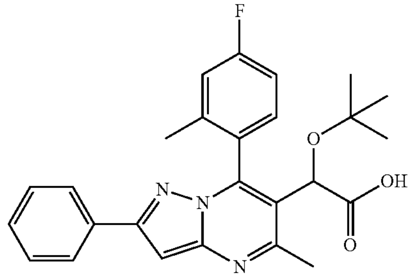 [SMILES: Cc1cc(F)ccc1-c1c(C(OC(C)(C)C)C(=O)O)c(C)nc2cc(-c3ccccc3)nn12] | 5.75 | E | 447.5 | 448 |
| 61 | 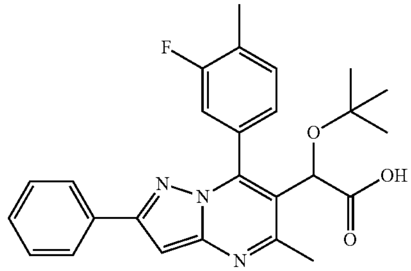 | 5.88 | E | 447.5 | 448 |
| 62 | 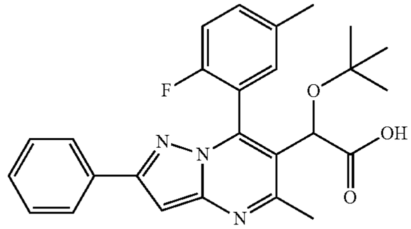 [SMILES: Cc1ccc(F)c(-c2c(C(OC(C)(C)C)C(=O)O)c(C)nc3cc(-c4ccccc4)nn23)c1] | 5.66 | E | 447.5 | 448 |

TABLE 4-continued

| Example | Structure | RT (min) | HPLC method | MW | Observed mass |
|---|---|---|---|---|---|
| 63 | 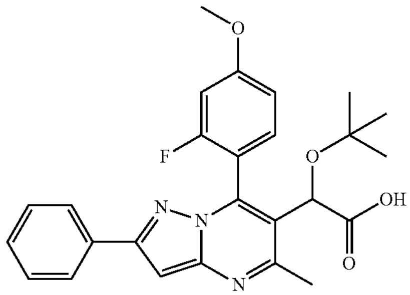 [SMILES: COc1ccc(-c2c(C(OC(C)(C)C)C(=O)O)c(C)nc3cc(-c4ccccc4)nn23)c(F)c1] | 5.41 | E | 463.5 | 464 |
| 64 | 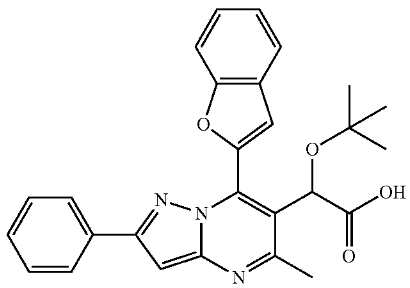 [SMILES: Cc1nc2cc(-c3ccccc3)nn2c(-c2cc3ccccc3o2)c1C(OC(C)(C)C)C(=O)O] | 7.09 | D | 456.2 | 456 |
| 65 | 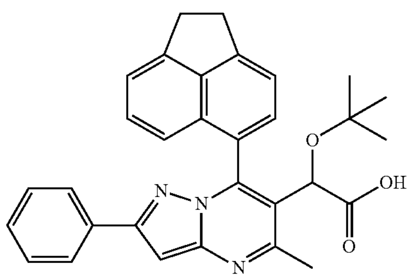 [SMILES: Cc1nc2cc(-c3ccccc3)nn2c(-c2ccc3c4c(cccc24)CC3)c1C(OC(C)(C)C)C(=O)O] | 7.75 | D | 492.11 | 492 |
| 66 | 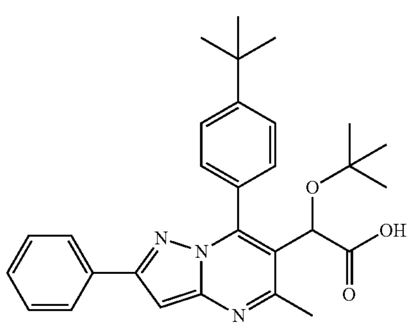 [SMILES: Cc1nc2cc(-c3ccccc3)nn2c(-c2ccc(C(C)(C)C)cc2)c1C(OC(C)(C)C)C(=O)O] | 8.72 | D | 472.11 | 472 |
| 67 | 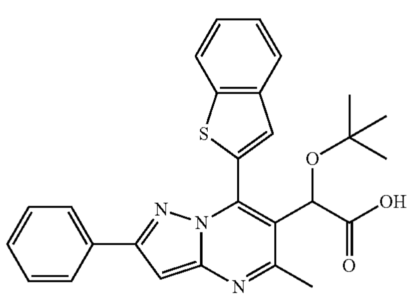 | 7.79 | D | 472.06 | 472 |

TABLE 4-continued

| Example | Structure | RT (min) | HPLC method | MW | Observed mass |
|---|---|---|---|---|---|
| 68 | 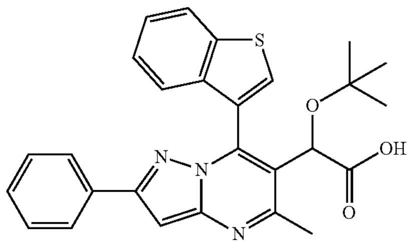 [SMILES: Cc1nc2cc(-c3ccccc3)nn2c(-c2csc3ccccc23)c1C(OC(C)(C)C)C(=O)O] | 7.23 | D | 472.06 | 472 |
| 69 | 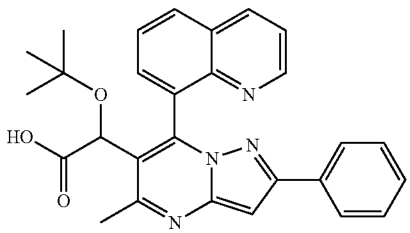 [SMILES: Cc1nc2cc(-c3ccccc3)nn2c(-c2cccc3cccnc23)c1C(OC(C)(C)C)C(=O)O] | 4.51 | D | 467.08 | 467 |
| 70 | 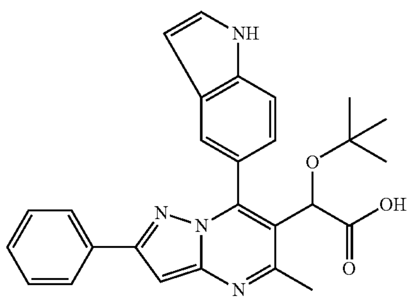 [SMILES: Cc1nc2cc(-c3ccccc3)nn2c(-c2ccc3[nH]ccc3c2)c1C(OC(C)(C)C)C(=O)O] | 5.78 | D | 455.07 | 455 |
| 71 | 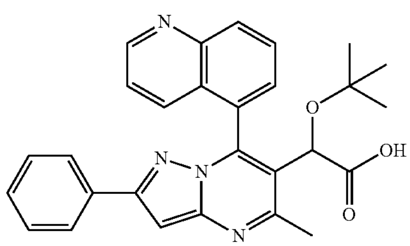 [SMILES: Cc1nc2cc(-c3ccccc3)nn2c(-c2cccc3ncccc23)c1C(OC(C)(C)C)C(=O)O] | 5.06 | D | 467.08 | 467 |
| 72 | 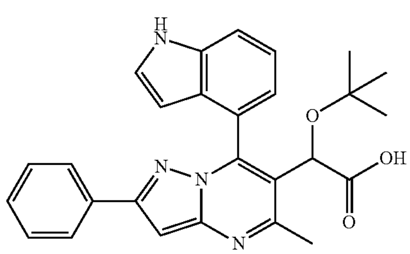 [SMILES: Cc1nc2cc(-c3ccccc3)nn2c(-c2cccc3[nH]ccc23)c1C(OC(C)(C)C)C(=O)O] | 4.62 | D | 455.07 | 455 |
| 73 | 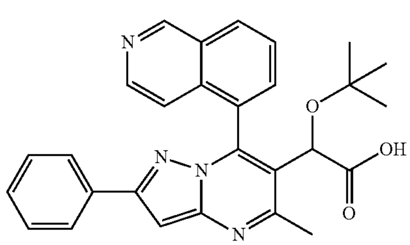 [SMILES: Cc1nc2cc(-c3ccccc3)nn2c(-c2cccc3cnccc23)c1C(OC(C)(C)C)C(=O)O] | 5.03 | D | 467.08 | 467 |

TABLE 4-continued

| Example | Structure | RT (min) | HPLC method | MW | Observed mass |
|---|---|---|---|---|---|
| 74 | 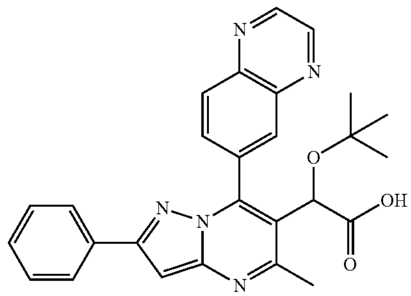 [SMILES: Cc1nc2cc(-c3ccccc3)nn2c(-c2ccc3nccnc3c2)c1C(OC(C)(C)C)C(=O)O] | 5.1 | D | 468.02 | 468 |
| 75 | 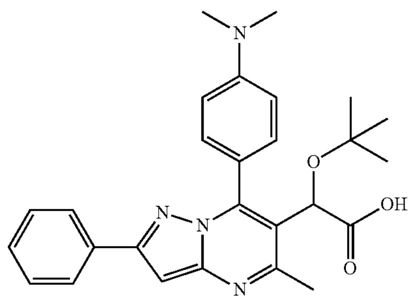 [SMILES: Cc1nc2cc(-c3ccccc3)nn2c(-c2ccc(N(C)C)cc2)c1C(OC(C)(C)C)C(=O)O] | 7.04 | D | 459.12 | 459 |
| 76 | 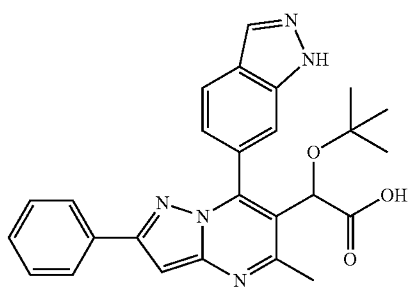 [SMILES: Cc1nc2cc(-c3ccccc3)nn2c(-c2ccc3cn[nH]c3c2)c1C(OC(C)(C)C)C(=O)O] | 5.61 | D | 456.02 | 456 |
| 77 | 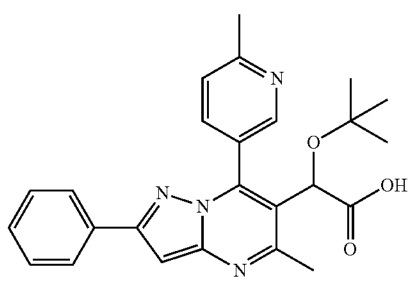 [SMILES: Cc1ccc(-c2c(C(OC(C)(C)C)C(=O)O)c(C)nc3cc(-c4ccccc4)nn23)cn1] | 4.99 | D | 431.07 | 431 |
| 78 | 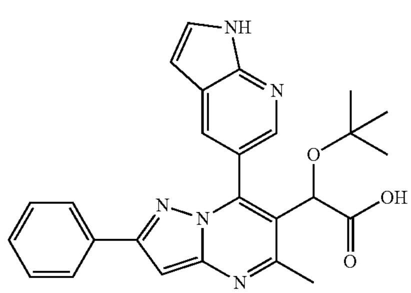 [SMILES: Cc1nc2cc(-c3ccccc3)nn2c(-c2cnc3[nH]ccc3c2)c1C(OC(C)(C)C)C(=O)O] | 5.03 | D | 456.02 | 456 |

TABLE 4-continued

| Example | Structure | RT (min) | HPLC method | MW | Observed mass |
|---|---|---|---|---|---|
| 79 | 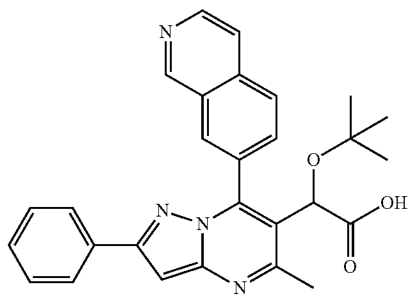 [SMILES: Cc1nc2cc(-c3ccccc3)nn2c(-c2ccc3ccncc3c2)c1C(OC(C)(C)C)C(=O)O] | 5.73 | D | 467.08 | 467 |
| 80 | 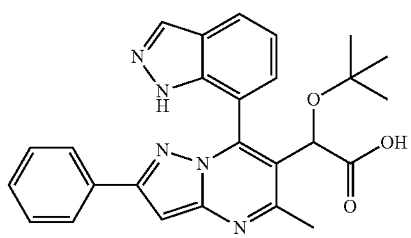 [SMILES: Cc1nc2cc(-c3ccccc3)nn2c(-c2cccc3cn[nH]c23)c1C(OC(C)(C)C)C(=O)O] | 3.21 | D | 456.02 | 456 |
| 81 | 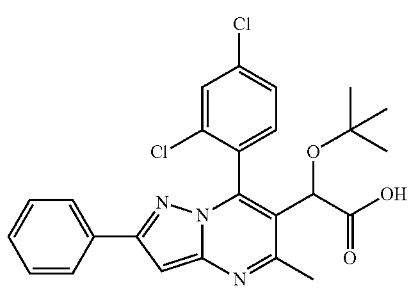 [SMILES: Cc1nc2cc(-c3ccccc3)nn2c(-c2ccc(Cl)cc2Cl)c1C(OC(C)(C)C)C(=O)O] | 6.1 | E | 484.3 | 484 |
| 82 | 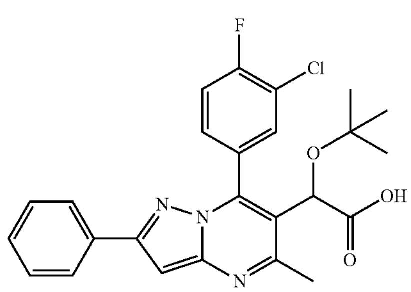 [SMILES: Cc1nc2cc(-c3ccccc3)nn2c(-c2ccc(F)c(Cl)c2)c1C(OC(C)(C)C)C(=O)O] | 6 | E | 467.9 | 468 |
| 83 | 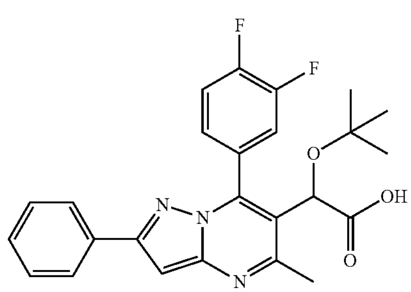 [SMILES: Cc1nc2cc(-c3ccccc3)nn2c(-c2ccc(F)c(F)c2)c1C(OC(C)(C)C)C(=O)O] | 5.7 | E | 451.5 | 452 |

TABLE 4-continued

| Example | Structure | RT (min) | HPLC method | MW | Observed mass |
|---------|-----------|----------|-------------|------|---------------|
| 84 | 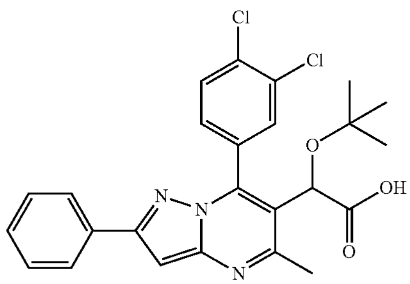 | 6.4 | E | 484.4 | 484 |
| 85 | 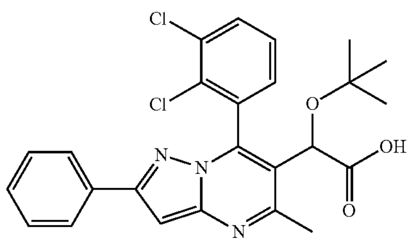 [SMILES: Cc1nc2cc(-c3ccccc3)nn2c(-c2cccc(Cl)c2Cl)c1C(OC(C)(C)C)C(=O)O] | 6.3 | E | 484.4 | 484 |
| 86 | 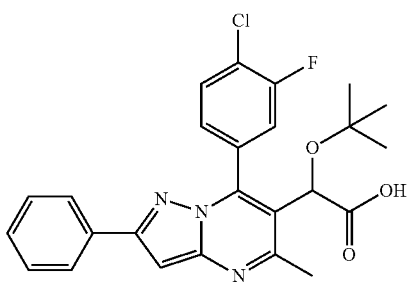 [SMILES: Cc1nc2cc(-c3ccccc3)nn2c(-c2ccc(Cl)c(F)c2)c1C(OC(C)(C)C)C(=O)O] | 6 | E | 467.9 | 468 |
| 87 | 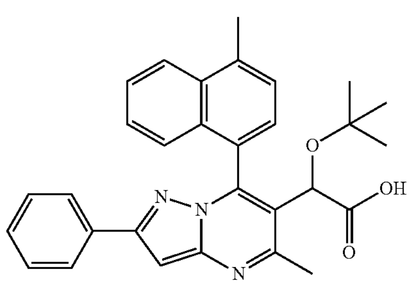 [SMILES: Cc1nc2cc(-c3ccccc3)nn2c(-c2ccc(C)c3ccccc23)c1C(OC(C)(C)C)C(=O)O] | 6 | E | 479.5 | 480 |
| 88 | 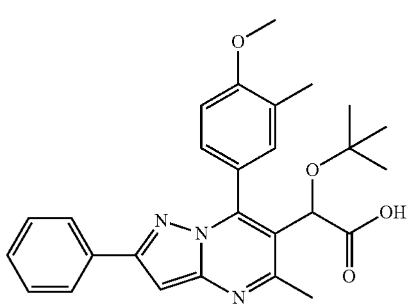 [SMILES: COc1ccc(-c2c(C(OC(C)(C)C)C(=O)O)c(C)nc3cc(-c4ccccc4)nn23)cc1C] | 5.8 | E | 459.5 | 460 |

TABLE 4-continued

| Example | Structure | RT (min) | HPLC method | MW | Observed mass |
|---|---|---|---|---|---|
| 89 | 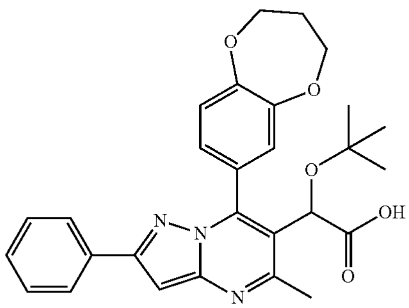 [SMILES: Cc1nc2cc(-c3ccccc3)nn2c(-c2ccc3c(c2)OCCCO3)c1C(OC(C)(C)C)C(=O)O] | 5.4 | E | 487.5 | 488 |
| 90 | 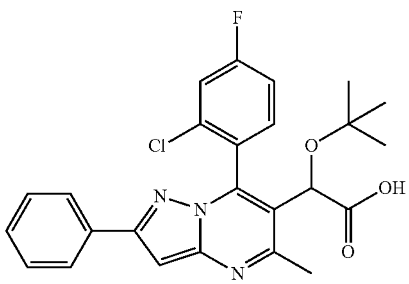 | 5.6 | E | 467.9 | 468 |
| 91 | 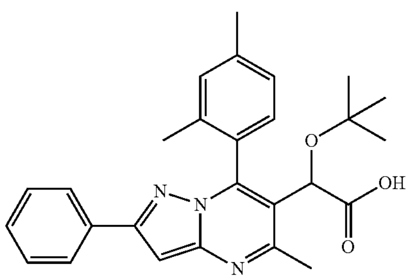 [SMILES: Cc1ccc(-c2c(C(OC(C)(C)C)C(=O)O)c(C)nc3cc(-c4ccccc4)nn23)c(C)c1] | 6 | E | 443.5 | 444 |

Examples 92-114 were synthesized using the procedure described for Example 46.

Example 92

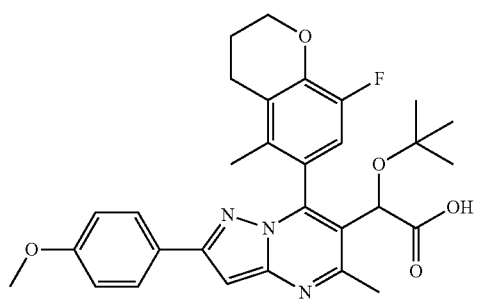

2-tert-Butoxy-2-(7-(8-fluoro-5-methylchroman-6-yl)-2-(4-methoxyphenyl)-5-methylpyrazolo[1,5-a]pyrimidin-6-yl)acetic acid, TFA salt

| | |
|---|---|
| MS (M + H)+ Calcd. | 534 |
| MS (M + H)+ Observ. | 534 |

2-tert-Butoxy-2-(7-(8-fluoro-5-methylchroman-6-yl)-2-(4-methoxyphenyl)-5-methylpyrazolo[1,5-a]pyrimidin-6-yl)acetic acid, TFA salt

| | |
|---|---|
| Retention Time | 2.318 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.77 (d, J=8.8 Hz, 2H), 7.05-6.76 (m, 4H), 5.11 (s, 1H), 4.34 (t, J=4.5 Hz, 2H), 3.84 (s, 3H), 2.91-2.66 (m, 5H), 2.17 (dd, J=6.1, 4.4 Hz, 2H), 1.91 (s, 3H), 1.22 (s, 9H).

Example 93

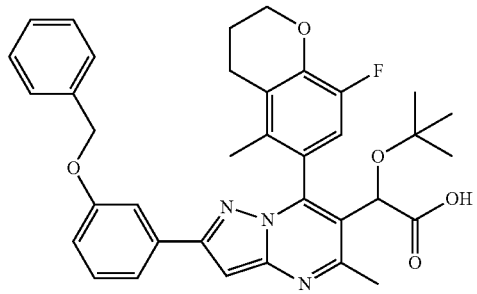

| 2-(2-(3-(Benzyloxy)phenyl)-7-(8-fluoro-5-methylchroman-6-yl)-5-methylpyrazolo[1,5-a]pyrimidin-6-yl)-2-tert-butoxyacetic acid, TFA salt | |
|---|---|
| MS (M + H)+ Calcd. | 610 |
| MS (M + H)+ Observ. | 610 |
| Retention Time | 2.468 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.48-7.27 (m, 8H), 6.96 (dd, J=8.2, 1.8 Hz, 1H), 6.93-6.88 (m, 2H), 5.08 (s, 3H), 4.46-4.12 (m, 2H), 2.92-2.73 (m, 5H), 2.26-2.08 (m, 2H), 1.91 (s, 3H), 1.20 (s, 9H).

Example 94

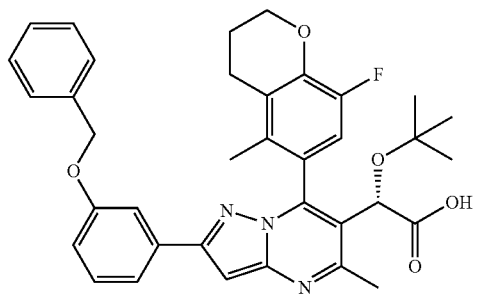 [SMILES: Cc1nc2cc(-c3cccc(OCc4ccccc4)c3)nn2c(-c2cc(F)c3c(c2C)CCCO3)c1C(OC(C)(C)C)C(=O)O]

(2S)-2-(2-(3-(Benzyloxy)phenyl)-7-(8-fluoro-5-methylchroman-6-yl)-5-methyl-pyrazolo[1,5-a]pyrimidin-6-yl)-2-tert-butoxyacetic acid The title compound was separated from the racemic compound Example 93 using a chiral column and (2S)-2-(2-(3-(benzyloxy)phenyl)-7-(8-fluoro-5-methylchroman-6-yl)-5-methyl-pyrazolo[1,5-a]pyrimidin-6-yl)-2-tert-butoxyacetic acid was isolated. Chiral separation method: Chiralpak AD-H preparative column, 20×250 mm, 5 µm. Mobile Phase: 30% MeOH in $CO_2$ @ 110 Bar. Temp: 35° C. Flow rate: 45.0 mL/min. for 15 min. UV was monitored @ 266 nm. Retention time: 4.82 min.

Example 95

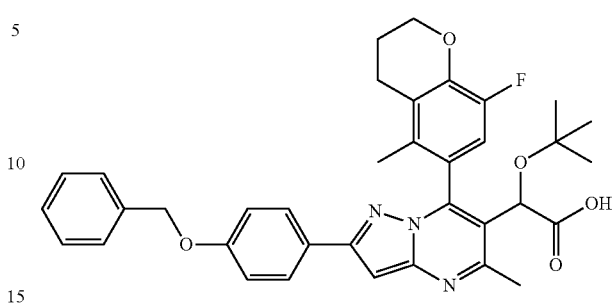

| 2-(2-(4-(Benzyloxy)phenyl)-7-(8-fluoro-5-methylchroman-6-yl)-5-methylpyrazolo[1,5-a]pyrimidin-6-yl)-2-tert-butoxyacetic acid, TFA salt | |
|---|---|
| MS (M + H)+ Calcd. | 610 |
| MS (M + H)+ Observ. | 610 |
| Retention Time | 2.467 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.76 (d, J=8.8 Hz, 2H), 7.47-7.32 (m, 5H), 7.04-6.95 (m, 3H), 6.91 (d, J=10.5 Hz, 1H), 5.11 (d, J=2.0 Hz, 3H), 4.44-4.25 (m, 2H), 2.92-2.59 (m, 5H), 2.28-2.10 (m, 2H), 1.89 (s, 3H), 1.22 (s, 9H).

Example 96

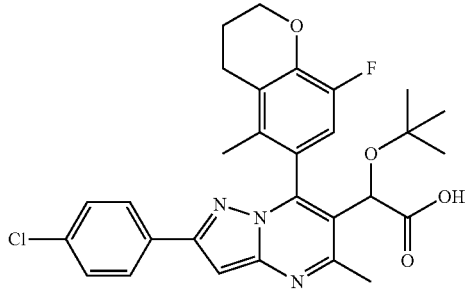 [SMILES: Cc1nc2cc(-c3ccc(Cl)cc3)nn2c(-c2cc(F)c3c(c2C)CCCO3)c1C(OC(C)(C)C)C(=O)O]

| 2-tert-Butoxy-2-(2-(4-chlorophenyl)-7-(8-fluoro-5-methylchroman-6-yl)-5-methylpyrazolo[1,5-a]pyrimidin-6-yl)acetic acid, TFA salt | |
|---|---|
| MS (M + H)+ Calcd. | 538 |
| MS (M + H)+ Observ. | 538 |
| Retention Time | 2.53 min |
| | LC Condition |
| Solvent A | 10% methanol:90% Water:0.1% TFA |
| Solvent B | 90% methanol:10% Water:0.1% TFA |

-continued

| 2-tert-Butoxy-2-(2-(4-chlorophenyl)-7-(8-fluoro-5-methylchroman-6-yl)-5-methylpyrazolo[1,5-a]pyrimidin-6-yl)acetic acid, TFA salt | |
|---|---|
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.87-7.71 (m, 2H), 7.45-7.33 (m, 2H), 7.02-6.82 (m, 2H), 5.12 (s, 1H), 4.48-4.23 (m, 2H), 2.82-2.75 (m, 5H), 2.18 (dd, J=6.0, 3.8 Hz, 2H), 1.93 (s, 3H), 1.23 (s, 9H).

Example 97

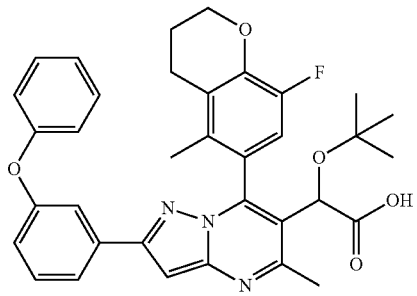 [SMILES: Cc1nc2cc(-c3cccc(Oc4ccccc4)c3)nn2c(-c2cc(F)c3c(c2C)CCCO3)c1C(OC(C)(C)C)C(=O)O]

| 2-tert-Butoxy-2-(7-(8-fluoro-5-methylchroman-6-yl)-5-methyl-2-(3-phenoxyphenyl)pyrazolo[1,5-a]pyrimidin-6-yl)acetic acid, TFA salt | |
|---|---|
| MS (M + H)$^+$ Calcd. | 596 |
| MS (M + H)$^+$ Observ. | 596 |
| Retention Time | 2.505 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.62-7.49 (m, 2H), 7.41-7.31 (m, 3H), 7.17-6.95 (m, 5H), 6.90 (d, J=10.8 Hz, 1H), 5.12 (s, 1H), 4.50-4.22 (m, 2H), 2.89-2.66 (m, 5H), 2.17 (dd, J=6.0, 4.0 Hz, 2H), 1.90 (s, 3H), 1.28-1.09 (m, 9H).

Example 98

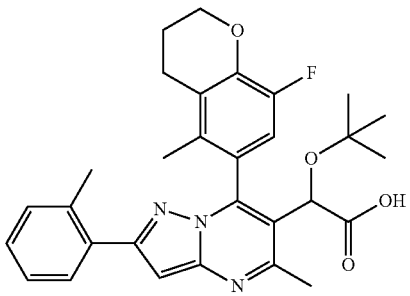 [SMILES: Cc1ccccc1-c1cc2nc(C)c(C(OC(C)(C)C)C(=O)O)c(-c3cc(F)c4c(c3C)CCCO4)n2n1]

| 2-tert-Butoxy-2-(7-(8-fluoro-5-methylchroman-6-yl)-5-methyl-2-o-tolylpyrazolo[1,5-a]pyrimidin-6-yl)acetic acid, TFA salt | |
|---|---|
| MS (M + H)$^+$ Calcd. | 518 |
| MS (M + H)$^+$ Observ. | 518 |
| Retention Time | 2.377 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.50-7.43 (m, 2H), 7.22-7.17 (m, 2H), 6.90 (d, J=10.7 Hz, 1H), 6.83 (s, 1H), 5.12 (s, 1H), 4.31-4.25 (m, 2H), 2.82-2.66 (m, 5H), 2.36 (s, 3H), 1.95 (s, 3H), 1.23 (s, 9H).

Example 99

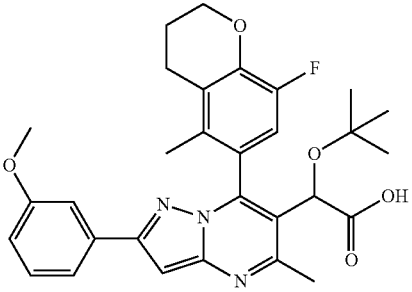 [SMILES: COc1cccc(-c2cc3nc(C)c(C(OC(C)(C)C)C(=O)O)c(-c4cc(F)c5c(c4C)CCCO5)n3n2)c1]

| 2-tert-Butoxy-2-(7-(8-fluoro-5-methylchroman-6-yl)-2-(3-methoxyphenyl)-5-methylpyrazolo[1,5-a]pyrimidin-6-yl)acetic acid | |
|---|---|
| MS (M + H)$^+$ Calcd. | 534 |
| MS (M + H)$^+$ Observ. | 534 |
| Retention Time | 2.330 min |
| | LC Condition |
| Solvent A | 10% methanol:90% Water:0.1% TFA |
| Solvent B | 90% methanol:10% Water:0.1% TFA |
| Start % B | 0 |

-continued 2-tert-Butoxy-2-(7-(8-fluoro-5-methylchroman-6-yl)-2-(3-methoxyphenyl)-5-methylpyrazolo[1,5-a]pyrimidin-6-yl)acetic acid

| | |
|---|---|
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.55-7.29 (m, 4H), 6.98-6.84 (m, 2H), 5.27 (s, 1H), 4.45-4.25 (m, 2H), 3.86 (s, 3H), 2.86-2.62 (m, 5H), 2.31-2.09 (m, 2H), 1.85 (s, 3H), 1.10 (s, 9H).

Example 100

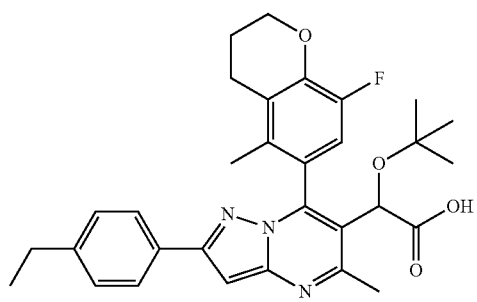 [SMILES: CCc1ccc(-c2cc3nc(C)c(C(OC(C)(C)C)C(=O)O)c(-c4cc(F)c5c(c4C)CCCO5)n3n2)cc1]

2-tert-Butoxy-2-(2-(4-ethylphenyl)-7-(8-fluoro-5-methylchroman-6-yl)-5-methylpyrazolo[1,5-a]pyrimidin-6-yl)acetic acid, TFA salt

| | |
|---|---|
| MS (M + H)$^+$ Calcd. | 532 |
| MS (M + H)$^+$ Observ. | 532 |
| Retention Time | 2.448 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.73 (d, J=7.9 Hz, 2H), 7.25-7.18 (m, 2H), 6.99-6.80 (m, 2H), 5.09 (s, 1H), 4.34-4.31 (m, 2H), 2.75-2.63 (m, 7H), 1.92 (s, 3H), 1.24-1.21 (m, 12H).

Example 101

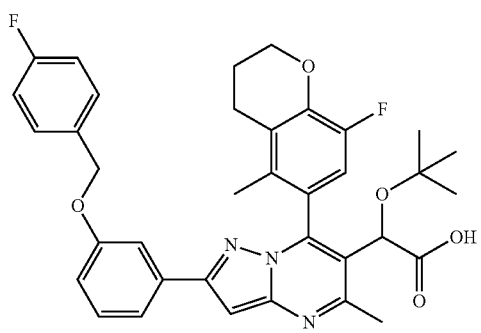 [SMILES: Cc1nc2cc(-c3cccc(OCc4ccc(F)cc4)c3)nn2c(-c2cc(F)c3c(c2C)CCCO3)c1C(OC(C)(C)C)C(=O)O]

2-tert-Butoxy-2-(7-(8-fluoro-5-methylchroman-6-yl)-2-(3-(4-fluorobenzyloxy)phenyl)-5-methylpyrazolo[1,5-a]pyrimidin-6-yl)acetic acid, TFA salt

| | |
|---|---|
| MS (M + H)$^+$ Calcd. | 628 |
| MS (M + H)$^+$ Observ. | 628 |
| Retention Time | 2.453 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.46-7.37 (m, 4H), 7.30 (t, J=8.2 Hz, 1H), 7.11-7.02 (m, 2H), 6.97-6.87 (m, 3H), 5.08 (s, 1H), 5.04 (s, 2H), 4.37-4.28 (m, 2H), 2.78-2.68 (m, 5H), 2.21-2.11 (m, J=4.6 Hz, 2H), 1.92 (s, 3H), 1.20 (s, 9H).

Example 102

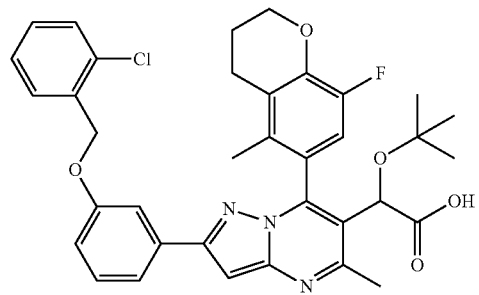

2-tert-Butoxy-2-(2-(3-(2-chlorobenzyloxy)phenyl)-7-(8-fluoro-5-methylchroman-6-yl)-5-methylpyrazolo[1,5-a]pyrimidin-6-yl)acetic acid, TFA salt

| | |
|---|---|
| MS (M + H)$^+$ Calcd. | 644 |
| MS (M + H)$^+$ Observ. | 644 |

-continued

| 2-tert-Butoxy-2-(2-(3-(2-chlorobenzyloxy)phenyl)-7-(8-fluoro-5-methylchroman-6-yl)-5-methylpyrazolo[1,5-a]pyrimidin-6-yl)acetic acid, TFA salt | |
|---|---|
| Retention Time | 2.562 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.54 (dd, J=7.0, 2.1 Hz, 1H), 7.48-7.27 (m, 6H), 7.02-6.79 (m, 3H), 5.20 (s, 2H), 5.09 (s, 1H), 4.33 (dt, J=6.6, 3.5 Hz, 2H), 2.84-2.65 (m, 5H), 2.15 (d, J=5.8 Hz, 2H), 1.89 (s, 3H), 1.21 (s, 9H).

Example 103

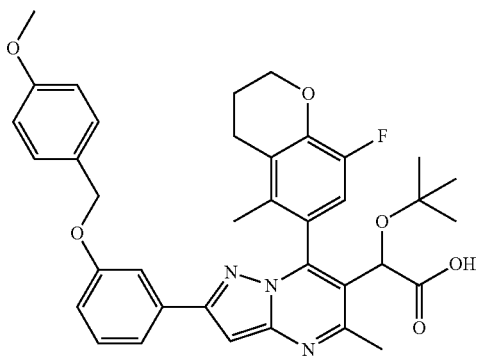 [SMILES: COc1ccc(COc2cccc(-c3cc4nc(C)c(C(OC(C)(C)C)C(=O)O)c(-c5cc(F)c6c(c5C)CCCO6)n4n3)c2)cc1]

| 2-tert-Butoxy-2-(7-(8-fluoro-5-methylchroman-6-yl)-2-(3-(4-methoxybenzyloxy)phenyl)-5-methylpyrazolo[1,5-a]pyrimidin-6-yl)acetic acid, TFA salt | |
|---|---|
| MS (M + H)$^+$ Calcd. | 640 |
| MS (M + H)$^+$ Observ. | 640 |
| Retention Time | 2.452 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.50-7.29 (m, 5H), 6.99-6.85 (m, 5H), 5.10 (s, 1H), 5.02 (s, 2H), 4.41-4.27 (m, 2H), 3.83 (s, 3H), 2.87-2.63 (m, 5H), 2.17 (d, J=5.8 Hz, 2H), 1.95 (s, 3H), 1.23 (s, 9H).

Example 104

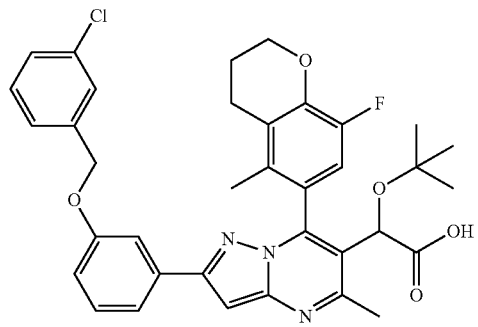 [SMILES: Cc1nc2cc(-c3cccc(OCc4cccc(Cl)c4)c3)nn2c(-c2cc(F)c3c(c2C)CCCO3)c1C(OC(C)(C)C)C(=O)O]

| 2-tert-Butoxy-2-(2-(3-(3-chlorobenzyloxy)phenyl)-7-(8-fluoro-5-methylchroman-6-yl)-5-methylpyrazolo[1,5-a]pyrimidin-6-yl)acetic acid, TFA salt | |
|---|---|
| MS (M + H)$^+$ Calcd. | 644 |
| MS (M + H)$^+$ Observ. | 644 |
| Retention Time | 2.550 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.50-7.41 (m, 3H), 7.38-7.29 (m, 4H), 7.01-6.86 (m, 3H), 5.10 (s, 1H), 5.07 (s, 2H), 4.48-4.24 (m, 2H), 2.81-2.64 (m, 5H), 2.27-2.07 (m, 2H), 1.92 (s, 3H), 1.22 (s, 9H).

Example 105

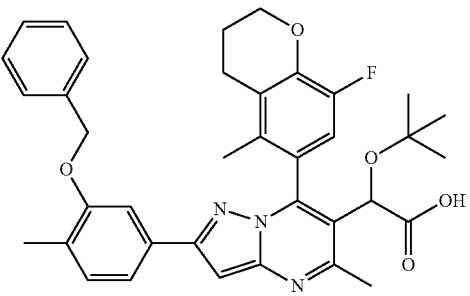

| 2-(2-(3-(Benzyloxy)-4-methylphenyl)-7-(8-fluoro-5-methylchroman-6-yl)-5-methylpyrazolo[1,5-a]pyrimidin-6-yl)-2-tert-butoxyacetic acid | |
|---|---|
| MS (M + H)+ Calcd. | 624 |
| MS (M + H)+ Observ. | 624 |
| Retention Time | 3.15 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, METHANOL-$d_4$) δ 7.46-7.40 (m, 3H), 7.39-7.26 (m, 4H), 7.16 (dd, J=7.6, 0.6 Hz, 1H), 6.95 (d, J=10.7 Hz, 1H), 6.85 (s, 1H), 4.94 (s, 1H), 4.35-4.24 (m, 2H), 3.00 (s, 3H), 2.87 (d, J=0.9 Hz, 2H), 2.75-2.74 (m, 2H), 2.26 (s, 3H), 2.20-2.10 (m, 2H), 1.92 (s, 3H), 1.17 (s, 9H).

Example 106

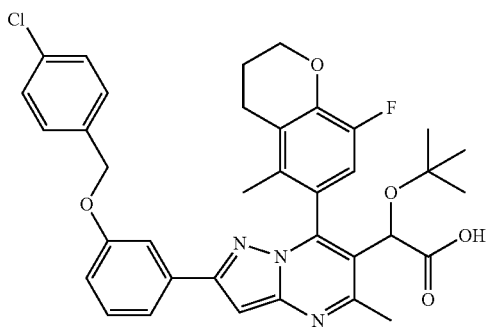 [SMILES: Cc1nc2cc(-c3cccc(OCc4ccc(Cl)cc4)c3)nn2c(-c2cc(F)c3c(c2C)CCCO3)c1C(OC(C)(C)C)C(=O)O]

| 2-tert-Butoxy-2-(2-(3-(4-chlorobenzyloxy)phenyl)-7-(8-fluoro-5-methylchroman-6-yl)-5-methylpyrazolo[1,5-a]pyrimidin-6-yl)acetic acid, TFA salt | |
|---|---|
| MS (M + H)+ Calcd. | 644 |
| MS (M + H)+ Observ. | 644 |
| Retention Time | 2.552 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.48-7.29 (m, 7H), 7.05-6.87 (m, 3H), 5.11 (s, 1H), 5.07 (s, 2H), 4.41-4.29 (m, 2H), 2.86-2.70 (m, 5H), 2.23-2.10 (m, 2H), 1.91 (s, 3H), 1.23 (s, 9H).

Example 107

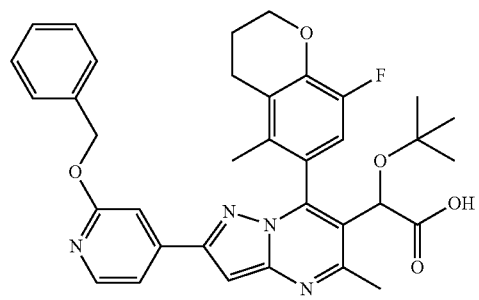

| 2-(2-(2-(Benzyloxy)pyridin-4-yl)-7-(8-fluoro-5-methylchroman-6-yl)-5-methylpyrazolo[1,5-a]pyrimidin-6-yl)-2-tert-butoxyacetic acid, TFA salt | |
|---|---|
| MS (M + H)+ Calcd. | 611 |
| MS (M + H)+ Observ. | 611 |
| Retention Time | 2.428 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 8.28 (d, J=5.5 Hz, 1H), 7.56-7.30 (m, 7H), 7.00 (s, 1H), 6.88 (d, J=10.4 Hz, 1H), 5.40 (s, 2H), 5.10 (s, 1H), 4.47-4.20 (m, 2H), 2.82-2.66 (m, 5H), 2.17 (dd, J=11.0, 6.4 Hz, 2H), 1.90 (s, 3H), 1.21 (s, 9H).

Example 108

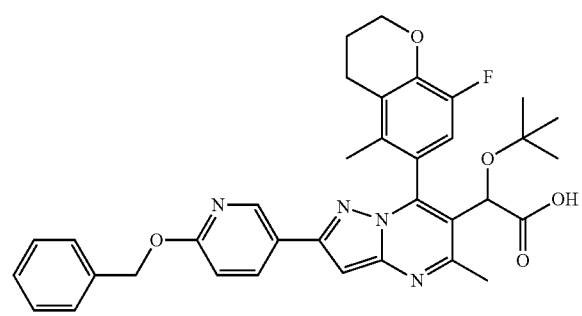 [SMILES: Cc1nc2cc(-c3ccc(OCc4ccccc4)nc3)nn2c(-c2cc(F)c3c(c2C)CCCO3)c1C(OC(C)(C)C)C(=O)O]

| 2-(2-(6-(Benzyloxy)pyridin-3-yl)-7-(8-fluoro-5-methylchroman-6-yl)-5-methylpyrazolo[1,5-a]pyrimidin-6-yl)-2-tert-butoxyacetic acid, TFA salt | |
|---|---|
| MS (M + H)+ Calcd. | 611 |
| MS (M + H)+ Observ. | 611 |
| Retention Time | 2.422 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 8.65 (d, J=2.1 Hz, 1H), 8.04 (dd, J=8.5, 2.4 Hz, 1H), 7.53-7.28 (m, 5H), 6.98-6.74 (m, 3H), 5.40 (s, 2H), 5.10 (s, 1H), 4.47-4.10 (m, 2H), 2.89-2.66 (m, 5H), 2.16 (d, J=6.4 Hz, 2H), 1.92 (s, 3H), 1.22 (s, 9H).

Example 109

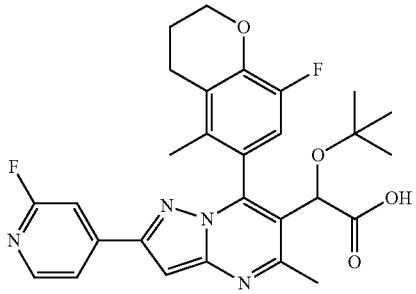

| 2-tert-Butoxy-2-(7-(8-fluoro-5-methylchroman-6-yl)-2-(2-fluoropyridin-4-yl)-5-methylpyrazolo[1,5-a]pyrimidin-6-yl)acetic acid, TFA salt | |
|---|---|
| MS (M + H)+ Calcd. | 523 |
| MS (M + H)+ Observ. | 523 |
| Retention Time | 2.250 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 8.28 (d, J=5.3 Hz, 1H), 7.65 (d, J=5.3 Hz, 1H), 7.41 (s, 1H), 7.06 (s, 1H), 6.91 (d, J=10.8 Hz, 1H), 5.13 (s, 1H), 4.51-4.23 (m, 2H), 2.80-2.78 (m, 5H), 2.32-2.07 (m, 2H), 2.00-1.79 (m, 3H), 1.24 (s, 9H).

Example 110

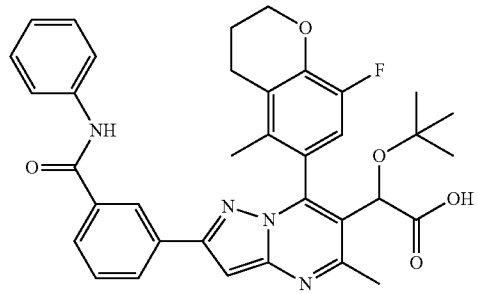 [SMILES: Cc1nc2cc(-c3cccc(C(=O)Nc4ccccc4)c3)nn2c(-c2cc(F)c3c(c2C)CCCO3)c1C(OC(C)(C)C)C(=O)O]

| 2-tert-Butoxy-2-(7-(8-fluoro-5-methylchroman-6-yl)-5-methyl-2-(3-(phenylcarbamoyl)phenyl)pyrazolo[1,5-a]pyrimidin-6-yl)acetic acid, TFA salt | |
|---|---|
| MS (M + H)+ Calcd. | 623 |
| MS (M + H)+ Observ. | 623 |
| Retention Time | 2.303 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 8.36-8.13 (m, 2H), 8.07-7.83 (m, 2H), 7.75-7.48 (m, 3H), 7.40 (t, J=7.9 Hz, 2H), 7.23-7.14 (m, 1H), 7.09 (s, 1H), 6.93 (d, J=10.3 Hz, 1H), 5.12 (s, 1H), 4.45-4.25 (m, 2H), 2.97-2.67 (m, 5H), 2.27-2.08 (m, 2H), 1.94 (s, 3H), 1.23 (s, 9H).

Example 111

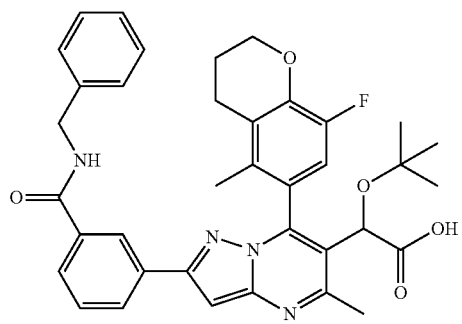 [SMILES: Cc1nc2cc(-c3cccc(C(=O)NCc4ccccc4)c3)nn2c(-c2cc(F)c3c(c2C)CCCO3)c1C(OC(C)(C)C)C(=O)O]

2-(2-(3-(Benzylcarbamoyl)phenyl)-7-(8-fluoro-5-methylchroman-6-yl)-5-methylpyrazolo[1,5-a]pyrimidin-6-yl)-2-tert-butoxyacetic acid, TFA salt

| | |
|---|---|
| MS (M + H)+ Calcd. | 637 |
| MS (M + H)+ Observ. | 637 |
| Retention Time | 2.277 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 8.15 (s, 1H), 8.05-7.90 (m, 1H), 7.78 (d, J=7.9 Hz, 1H), 7.48 (t, J=7.8 Hz, 1H), 7.40-7.28 (m, 5H), 7.01 (s, 1H), 6.88 (d, J=10.4 Hz, 1H), 6.69 (t, J=5.3 Hz, 1H), 5.08 (s, 1H), 4.77-4.56 (m, 2H), 4.40-4.23 (m, 2H), 2.87-2.57 (m, 5H), 2.25-2.03 (m, 2H), 1.88 (s, 3H), 1.20 (s, 9H).

Example 112

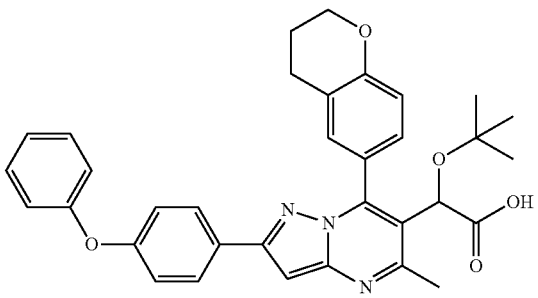 [SMILES: Cc1nc2cc(-c3ccc(Oc4ccccc4)cc3)nn2c(-c2ccc3c(c2)CCCO3)c1C(OC(C)(C)C)C(=O)O]

2-tert-Butoxy-2-(7-(chroman-6-yl)-5-methyl-2-(4-phenoxyphenyl)pyrazolo[1,5-a]pyrimidin-6-yl)acetic acid, TFA salt

| | |
|---|---|
| MS (M + H)+ Calcd. | 564 |
| MS (M + H)+ Observ. | 564 |
| Retention Time | 2.505 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.85 (d, J=8.9 Hz, 2H), 7.57-7.51 (m, 2H), 7.36-7.33 (m, 2H), 7.14-7.11 (m, 1H), 7.05-6.79 (m, 6H), 5.33 (s, 1H), 4.45-4.18 (m, 2H), 2.85 (t, J=6.0 Hz, 2H), 2.73 (s, 3H), 2.23-1.95 (m, 2H), 1.11-0.87 (m, 9H).

Example 113

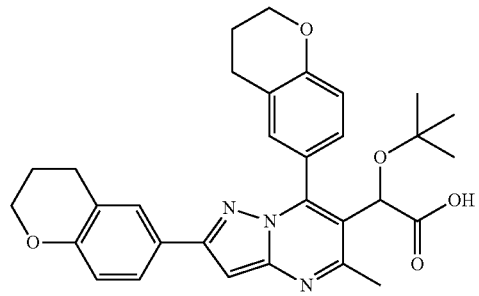

2-tert-Butoxy-2-(2,7-di(chroman-6-yl)-5-methylpyrazolo[1,5-a]pyrimidin-6-yl)acetic acid, TFA salt

| | |
|---|---|
| MS (M + H)+ Calcd. | 528 |
| MS (M + H)+ Observ. | 528 |
| Retention Time | 2.388 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.73-7.46 (m, 4H), 7.10-6.94 (m, 1H), 6.89 (s, 1H), 6.85-6.77 (m, 1H), 5.34 (s, 1H), 4.49-4.03 (m, 4H), 2.94-2.84 (m, 4H), 2.68 (s, 1H), 2.22-1.89 (m, 4H), 1.04 (s, 9H).

Example 114

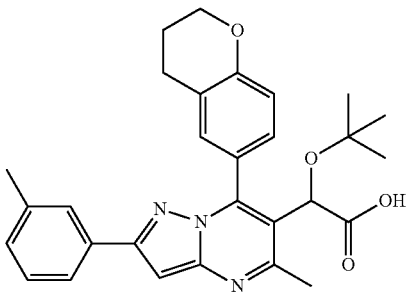 [SMILES: Cc1cccc(-c2cc3nc(C)c(C(OC(C)(C)C)C(=O)O)c(-c4ccc5c(c4)CCCO5)n3n2)c1]

2-tert-Butoxy-2-(7-(chroman-6-yl)-5-methyl-2-m-tolylpyrazolo[1,5-a]pyrimidin-6-yl)acetic acid, TFA salt

| | |
|---|---|
| MS (M + H)+ Calcd. | 486 |
| MS (M + H)+ Observ. | 486 |

173

-continued 2-tert-Butoxy-2-(7-(chroman-6-yl)-5-methyl-2-m-tolylpyrazolo[1,5-a]pyrimidin-6-yl)acetic acid, TFA salt

| Retention Time | 2.390 min |
|---|---|
| | LC Condition |

| Solvent A | 10% methanol:90% Water:0.1% TFA |
|---|---|
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |

174

-continued 2-tert-Butoxy-2-(7-(chroman-6-yl)-5-methyl-2-m-tolylpyrazolo[1,5-a]pyrimidin-6-yl)acetic acid, TFA salt

| Solvent Pair | methanol:Water:TFA |
|---|---|
| Column | Phenomenex Luna 2.0 × 30 mm 3 um |

$^1$H NMR (500 MHz, CHLOROFORM-d) δ 7.68-7.67 (m, 2H), 7.57-7.51 (m, 2H), 7.32-7.27 (m, 1H), 7.19 (t, J=7.0 Hz, 1H), 7.06-6.96 (m, 2H), 5.33 (s, 1H), 4.38-4.26 (m, 2H), 2.86-2.84 (m, 2H), 2.73 (s, 3H), 2.38 (s, 3H), 2.10-2.05 (m, 2H), 1.02 (s, 9H).

Scheme 10

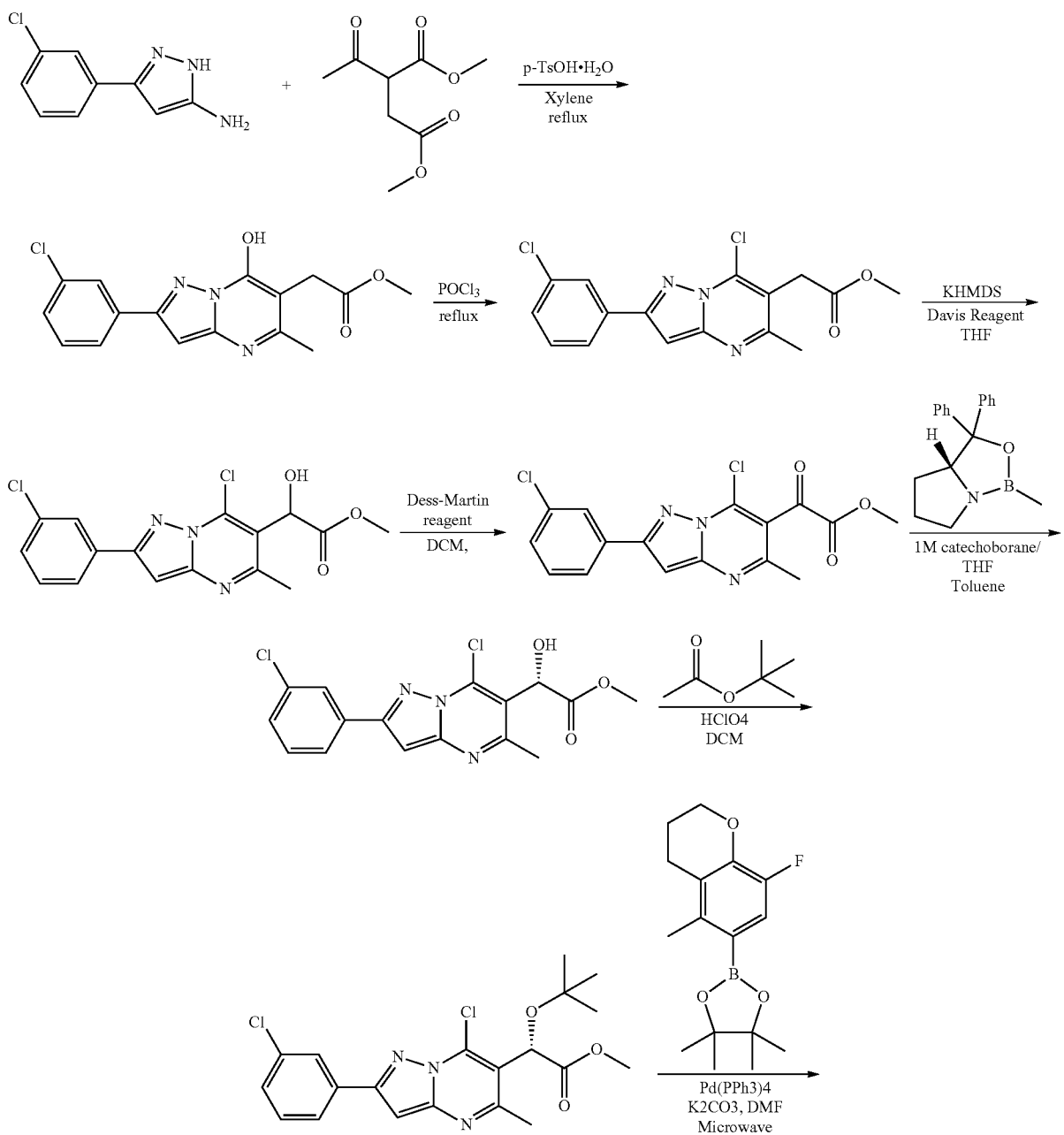

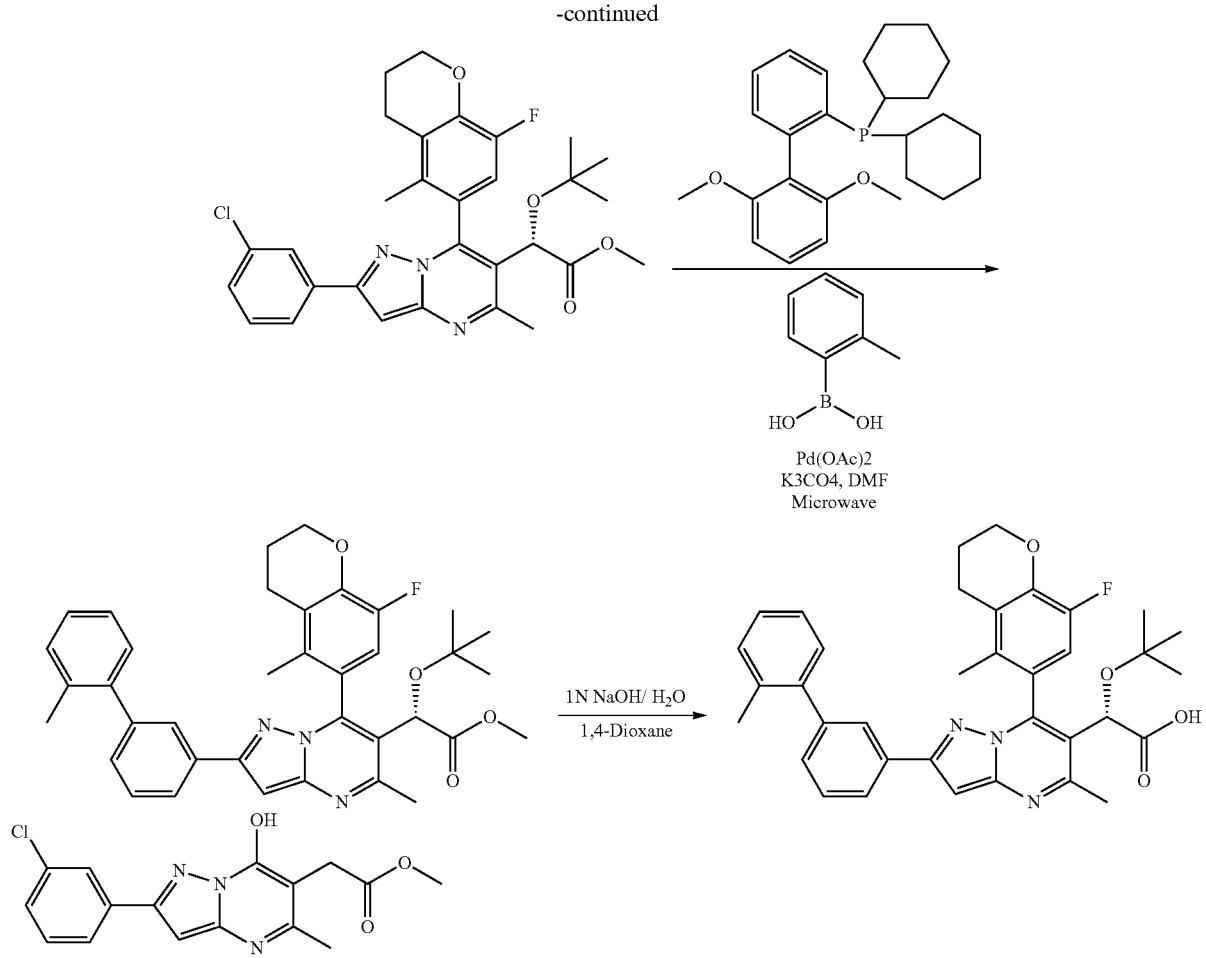

Methyl 2-(2-(3-chlorophenyl)-7-hydroxy-5-methylpyrazolo[1,5-a]pyrimidin-6-yl)acetate To a solution of 3-(3-chlorophenyl)-1H-pyrazol-5-amine (23 g, 119 mmol), dimethyl 2-acetylsuccinate (22.35 g, 119 mmol) in o-Xylene (200 mL) was added p-toluenesulfonic acid monohydrate (100 mg, 0.526 mmol). The reaction mixture was heated at reflux under a Dean-Stark trap for 2 h. The solid was filtered and washed with hexanes to afford (39 g, 99%) of the title compound. $^1$H NMR (500 MHz, METHANOL-$d_4$) δ 8.14-7.95 (m, 1H), 7.93-7.79 (m, 1H), 7.51-7.27 (m, 2H), 6.62-6.35 (m, 1H), 3.72 (s, 3H), 3.67 (s, 2H), 2.39 (s, 3H).

| Methyl 2-(2-(3-chlorophenyl)-7-hydroxy-5-methylpyrazolo[1,5-a]pyrimidin-6-yl)acetate. | |
|---|---|
| MS (M + H)$^+$ Calcd. | 332 |
| MS (M + H)$^+$ Observ. | 332 |
| Retention Time | 1.810 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

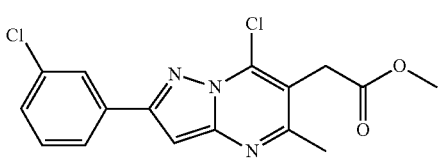 [SMILES: COC(=O)Cc1c(C)nc2cc(-c3cccc(Cl)c3)nn2c1Cl]

Methyl 2-(7-chloro-2-(3-chlorophenyl)-5-methylpyrazolo[1,5-a]pyrimidin-6-yl)acetate To 2-(2-(3-chlorophenyl)-5-methyl-7-oxo-4,7-dihydropyrazolo[1,5-a]pyrimidin-6-yl)acetate (12 g, 36.2 mmol) was added POCl$_3$ (50 mL). The reaction mixture was heated at reflux for 2.5 h. After cooling, the reaction mixture was added drop-wise to ice-water. A brown solid precipitated. The solid was filtered and washed with water, then dissolved in ethyl acetate. The organic solution was washed with saturated NaHCO$_3$ and dried over sodium sulfate. The solvent was evaporated to give the title compound (11.9 g, 94%). $^1$H NMR (400 MHz, CHLOROFORM-d) δ 8.03 (t, J=1.8 Hz, 1H), 7.94-7.82 (m, 1H), 7.48-7.34 (m, 2H), 6.94 (s, 1H), 3.93 (s, 2H), 3.78 (s, 3H), 2.63 (s, 3H).

| Methyl 2-(7-chloro-2-(3-chlorophenyl)-5-methylpyrazolo[1,5-a]pyrimidin-6-yl)acetate. | |
|---|---|
| MS (M + H)$^+$ Calcd. | 350 |
| MS (M + H)$^+$ Observ. | 350 |
| Retention Time | 2.185 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

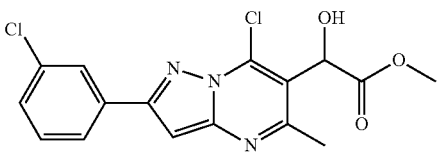 [SMILES: COC(=O)C(O)c1c(C)nc2cc(-c3cccc(Cl)c3)nn2c1Cl]

Methyl 2-(7-chloro-2-(3-chlorophenyl)-5-methylpyrazolo[1,5-a]pyrimidin-6-yl)-2-hydroxyacetate To a stirred solution of methyl 2-(7-chloro-2-(3-chlorophenyl)-5-methylpyrazolo[1,5-a]pyrimidin-6-yl)acetate (7.8 g, 22.27 mmol) in THF (40 mL) at −78° C. was added KHMDS (44.5 mL, 22.27 mmol) dropwise over 30 min. The mixture was stirred at −78° C. for 30 min. A solution of 3-phenyl-2-(phenylsulfonyl)-1,2-oxaziridine (8.73 g, 33.4 mmol) in THF (50 mL) was added over 30 min and the reaction mixture was stirred for additional 2 h at −78° C. The reaction mixture was quenched with saturated NH$_4$Cl aqueous solution (40 mL). The reaction mixture was allowed to warm to room temperature and then diluted with ethyl acetate (200 mL). The organic phase was washed with water and brine and dried with sodium sulfate. The solvent was evaporated. Purification by silica gel chromatography provided the title compound (4.2 g, 51.5%). $^1$H NMR (500 MHz, CHLOROFORM-d) δ 8.05-7.97 (m, 1H), 7.88 (dt, J=6.7, 1.8 Hz, 1H), 7.44-7.38 (m, 2H), 6.93 (s, 1H), 5.76 (s, 1H), 3.84 (s, 3H), 2.62 (s, 3H).

| Methyl 2-(7-chloro-2-(3-chlorophenyl)-5-methylpyrazolo[1,5-a]pyrimidin-6-yl)-2-hydroxyacetate | |
|---|---|
| MS (M + H)$^+$ Calcd. | 366 |
| MS (M + H)$^+$ Observ. | 366 |
| Retention Time | 2.078 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

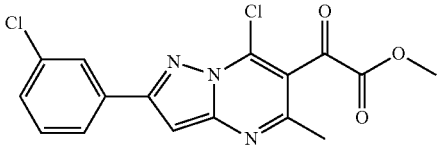 [SMILES: COC(=O)C(=O)c1c(C)nc2cc(-c3cccc(Cl)c3)nn2c1Cl]

Methyl 2-(7-chloro-2-(3-chlorophenyl)-5-methylpyrazolo[1,5-a]pyrimidin-6-yl)-2-oxoacetate To a mixture of methyl 2-(7-chloro-2-(3-chlorophenyl)-5-methylpyrazolo[1,5-a]pyrimidin-6-yl)-2-hydroxyacetate (5 g, 13.65 mmol) in CH$_2$Cl$_2$ (20 mL) was added Dess-Martin-Periodinane (6.37 g, 15.02 mmol) and the reaction mixture was stirred at room temp for 1 h. The reaction mixture was diluted with ethyl acetate (100 mL). The organic layer was washed with saturated NaHCO$_3$ solution (100 mL) and dried (Na$_2$SO$_4$). The solvent was evaporated and the residue was purified by a quick silica gel chromatography to afford (3.8 g, 76%) of the title compound. $^1$H NMR (500 MHz, CHLOROFORM-d) δ 8.10-7.98 (m, 1H), 7.89 (td, J=4.4, 1.5 Hz, 1H), 7.51-7.36 (m, 2H), 7.00 (s, 1H), 4.00 (s, 3H), 2.62 (s, 3H).

| Methyl 2-(7-chloro-2-(3-chlorophenyl)-5-methylpyrazolo[1,5-a]pyrimidin-6-yl)-2-oxoacetate | |
|---|---|
| MS (M + H)$^+$ Calcd. | 364 |
| MS (M + H)$^+$ Observ. | 364 |
| Retention Time | 2.270 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

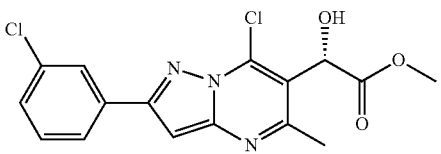 [SMILES: COC(=O)[C@@H](O)c1c(C)nc2cc(-c3cccc(Cl)c3)nn2c1Cl]

(S)-methyl 2-(7-chloro-2-(3-chlorophenyl)-5-methylpyrazolo[1,5-a]pyrimidin-6-yl)-2-hydroxyacetate To a stirred solution of methyl 2-(7-chloro-2-(3-chlorophenyl)-5-methylpyrazolo[1,5-a]pyrimidin-6-yl)-2-oxoacetate (1.8 g, 4.94 mmol) in anhydrous toluene (30 mL) was added 1.1M (R)-1-methyl-3,3-diphenylhexahydropyrrolo[1,2-c][1,3,2]oxazaborole/toluene (1.797 mL, 1.977 mmol). The mixture was cooled to −40° C. (acetonitrile/dry ice bath) and a solution of 50% (by weight) catechoborane in toluene (1.695 mL, 6.92 mmol) was added over 30 min. After stirred at −45−−35° C. for 2 hrs, the reaction mixture was stirred at −25° C.−−15° C. for additional 1 h. Saturated $Na_2CO_3$ solution (20 mL) was added to quench the reaction. The mixture was stirred vigorously for 30 min and extracted with EtOAc. The organic layer was washed with saturated $Na_2CO_3$ solution and dried ($Na_2SO_4$). The solvent was evaporated and the residue was purified by silica gel chromatography (15-50% EtOAc/hexane) to afford (1.5 g, 83%) of the title compound. $^1$H NMR (500 MHz, CHLOROFORM-d) δ 8.05-7.97 (m, 1H), 7.88 (dt, J=6.7, 1.8 Hz, 1H), 7.44-7.38 (m, 2H), 6.93 (s, 1H), 5.76 (s, 1H), 3.84 (s, 3H), 2.62 (s, 3H).

| (S)-Methyl 2-(7-chloro-2-(3-chlorophenyl)-5-methylpyrazolo[1,5-a]pyrimidin-6-yl)-2-hydroxyacetate | |
|---|---|
| MS (M + H)$^+$ Calcd. | 366 |
| MS (M + H)$^+$ Observ. | 366 |
| Retention Time | 2.075 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

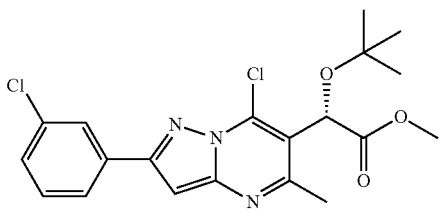 [SMILES: COC(=O)[C@@H](OC(C)(C)C)c1c(C)nc2cc(-c3cccc(Cl)c3)nn2c1Cl]

(S)-Methyl 2-(tert-butoxy)-2-(7-chloro-2-(3-chlorophenyl)-5-methylpyrazolo[1,5-a]pyrimidin-6-yl)acetate To a solution of (S)-methyl 2-(7-chloro-2-(3-chlorophenyl)-5-methylpyrazolo[1,5-a]pyrimidin-6-yl)-2-hydroxyacetate (1.0 g, 2.73 mmol) in $CH_2Cl_2$ (100 mL) at room temperature was added tert-butyl acetate (20 mL) followed by perchloric acid (0.282 mL, 3.28 mmol). The reaction mixture was stirred for 16 h at room temperature. The reaction mixture was quenched with water and diluted with ethyl acetate. The organic phase was washed with saturated $NaHCO_3$ and dried over sodium sulfate. The solvent was evaporated. Purification by silica gel chromatography provided the title compound (520 mg, 50%). $^1$H NMR (400 MHz, CHLOROFORM-d) δ 8.07-8.00 (m, 1H), 7.89 (dt, J=6.7, 1.9 Hz, 1H), 7.48-7.37 (m, 2H), 6.93 (s, 1H), 5.68 (s, 1H), 3.75 (s, 3H), 2.69 (s, 3H), 1.29 (s, 9H).

| (S)-Methyl 2-(tert-butoxy)-2-(7-chloro-2-(3-chlorophenyl)-5-methylpyrazolo[1,5-a]pyrimidin-6-yl)acetate | |
|---|---|
| MS (M + H)$^+$ Calcd. | 422 |
| MS (M + H)$^+$ Observ. | 422 |
| Retention Time | 2.425 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

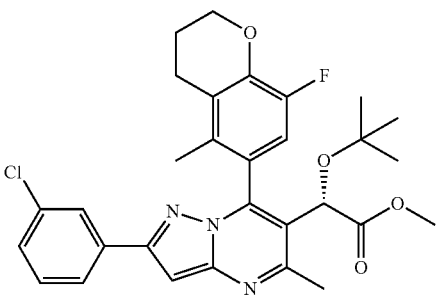 [SMILES: COC(=O)[C@@H](OC(C)(C)C)c1c(C)nc2cc(-c3cccc(Cl)c3)nn2c1-c1cc(F)c2c(c1C)CCCO2]

(2S)-Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate To a 2-5 ml microwave tube was added (S)-methyl 2-(tert-butoxy)-2-(7-chloro-2-(3-chlorophenyl)-5-methylpyrazolo[1,5-a]pyrimidin-6-yl)acetate (420 mg, 0.995 mmol), tetrakis(triphenylphosphine)palladium(0) (115 mg, 0.099 mmol), 2-(8-fluoro-5-methylchroman-6-yl)-4,4,5,5-tetramethyl-1,3,2-dioxaborolane (320 mg, 1.094 mmol), DMF (4 mL), followed by 2M $K_2CO_3$ solution (400 µl). The reaction mixture was heated in a microwave reactor at 125° C. for 45 min. The reaction mixture was filtered and the filtrate was purified by silica gel chromatography to afford (204 mg, 37.2%) of the title compound. Enantiomeric Excess was determined by Chiral SFC method: Chiralpak AD-H analytical column, 4.6× 250 mm, 5 µm. Mobile Phase: 15% MeOH in $CO_2$. Temp: 35° C. Flow rate: 2.0 mL/min. for 10 min. UV monitored @ 266 nm. Injection: 5 uL of ~2.0 mg/mL solution in 50:50 MeOH:$CHCl_3$. The enantiomeric Excess is 93.0%. $^1$H NMR (500 MHz, CHLOROFORM-d) δ 7.83-7.78 (m, 1H), 7.69 (dt, J=6.7, 1.8 Hz, 1H), 7.35-7.28 (m, 2H), 6.87 (d, J=10.7 Hz, 1H), 6.84 (s, 1H), 5.00 (s, 1H), 4.48-4.26 (m, 2H), 3.64 (s, 3H), 2.85-2.67 (m, 5H), 2.30-2.13 (m, 2H), 1.84 (s, 3H), 1.16 (s, 9H).

| (2S)-Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate | |
|---|---|
| MS (M + H)$^+$ Calcd. | 552 |
| MS (M + H)$^+$ Observ. | 552 |
| Retention Time | 2.400 min |

-continued (2S)-Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate

| | LC Condition |
|---|---|
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

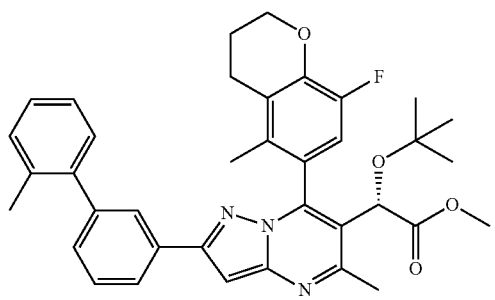 [SMILES: COC(=O)[C@@H](OC(C)(C)C)c1c(C)nc2cc(-c3cccc(-c4ccccc4C)c3)nn2c1-c1cc(F)c2c(c1C)CCCO2]

(2S)-Methyl 2-(tert-butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetate To a 2-5 ml microwave tube was added dicyclohexyl(2',6'-dimethoxy-[1,1'-biphenyl]-2-yl)phosphine (595 mg, 1.449 mmol), PALLADIUM(II) ACETATE (163 mg, 0.725 mmol), o-tolylboronic acid (296 mg, 2.174 mmol) and (2S)-methyl 2-(tert-butoxy)-2-(2-(3-chlorophenyl)-7-(8-fluoro-5-methylchroman-6-yl)-5-methylpyrazolo[1,5-a]pyrimidin-6-yl)acetate (400 mg, 0.725 mmol) in DMF (1.5 mL), followed by 2M K₃PO₄ solution (200 µl). The reaction mixture was heated in a microwave reactor at 130° C. for 30 min. The reaction mixture was filtered and the filtrate was purified by silica gel chromatography to afford (225.6 mg, 51.2%) of the title compound. ¹H NMR (500 MHz, CHLOROFORM-d) δ 7.86-7.76 (m, 2H), 7.42 (t, J=7.8 Hz, 1H), 7.29-7.26 (m, 5H), 6.88-6.86 (m, 2H), 4.99 (s, 1H), 4.39-4.27 (m, 2H), 3.64 (s, 3H), 2.83-2.70 (m, 5H), 2.26 (s, 3H), 2.22-2.13 (m, 2H), 1.84 (s, 3H), 1.16 (s, 9H).

| (2S)-Methyl 2-(tert-butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetate | |
|---|---|
| MS (M + H)⁺ Calcd. | 608 |
| MS (M + H)⁺ Observ. | 608 |
| Retention Time | 2.686 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |

-continued (2S)-Methyl 2-(tert-butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetate

| Solvent Pair | methanol:Water:TFA |
|---|---|
| Column | Phenomenex Luna 2.0 × 30 mm 3 um |

Example 115

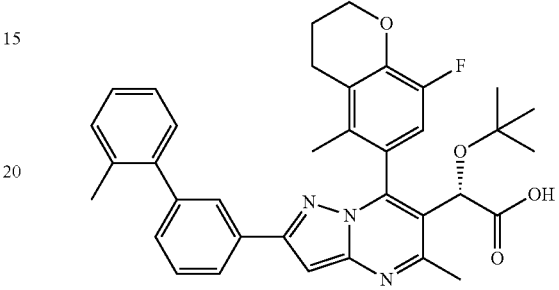

(2S)-2-(tert-Butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetic acid To a solution of (2S)-methyl 2-(tert-butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetate (1.28 g, 2.1 mmol) in dioxane (12 mL) was added 1 N NaOH aqueous solution (9 mL, 9 mmol). The reaction mixture was stirred at 50° C. for 2 h. The reaction mixture was diluted with water (50 ml) and neutralized with acetic acid. The resulted mixture was extracted with ethyl acetate (3×100 ml). The organic phase was combined and dried by sodium sulfate. The solvents were evaporated and the crude product was purified by preparative HPLC to afford (840 mg, 66%) of the title compound. Preparative HPLC condition: Waters Sunfire OBD C18 30×100 mm 5 u, 15 to 60% B over 18 minute gradient, 2 minute hold time, A=5% acetonitrile 95% water 10 mM Ammonium Acetate, B=95% acetonitrile 5% water 10 mM Ammonium Acetate. Flow rate: 40 ml/min. ¹H NMR (400 MHz, DMSO-d₆) δ 7.86-7.75 (m, 2H), 7.50 (t, J=7.7 Hz, 1H), 7.40-7.22 (m, 5H), 7.18 (s, 1H), 7.09 (d, J=11.0 Hz, 1H), 4.83 (s, 1H), 4.34-4.22 (m, 2H), 2.82-2.66 (m, 5H), 2.24 (s, 3H), 2.13-2.02 (m, 2H), 1.83 (s, 3H), 1.09 (s, 9H).

| (2S)-2-(tert-Butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetic acid | |
|---|---|
| MS (M + H)⁺ Calcd. | 594 |
| MS (M + H)⁺ Observ. | 594 |
| Retention Time | 2.322 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |

183
-continued (2S)-2-(tert-Butoxy)-2-(7-(8-fluoro-5-methylchroman-6-yl)-5-methyl-2-(2'-methyl-[1,1'-biphenyl]-3-yl)pyrazolo[1,5-a]pyrimidin-6-yl)acetic acid

| Solvent Pair | methanol:Water:TFA |
|---|---|
| Column | Phenomenex Luna 2.0 × 30 mm 3 um |

Example 116-120 were synthesized using the procedure described above for example 115.

Example 116

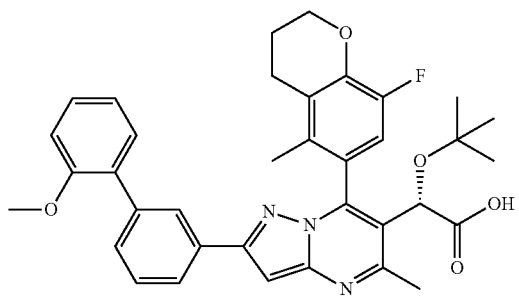 [SMILES: COc1ccccc1-c1cccc(-c2cc3nc(C)c([C@H](OC(C)(C)C)C(=O)O)c(-c4cc(F)c5c(c4C)CCCO5)n3n2)c1]

$^1$H NMR (500 MHz, CHLOROFORM-d) δ 8.00-7.95 (m, 1H), 7.79 (d, J=7.6 Hz, 1H), 7.51-7.47 (m, 1H), 7.45-7.39 (m, 1H), 7.37-7.31 (m, 2H), 7.08-6.97 (m, 2H), 6.93 (d, J=10.7 Hz, 1H), 6.90 (s, 1H), 5.08 (s, 1H), 4.39-4.24 (m, 2H), 3.79 (s, 3H), 2.82-2.64 (m, 5H), 2.15 (d, J=3.7 Hz, 2H), 1.92 (s, 3H), 1.21 (s, 9H).

(2S)-2-(tert-Butoxy)-2-(7-(8-fluoro-5-methylchroman-6-yl)-2-(2'-methoxy-[1,1'-biphenyl]-3-yl)-5-methylpyrazolo[1,5-a]pyrimidin-6-yl)acetic acid

| MS (M + H)$^+$ Calcd. | 610 |
|---|---|
| MS (M + H)$^+$ Observ. | 610 |
| Retention Time | 2.450 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

184

Example 117

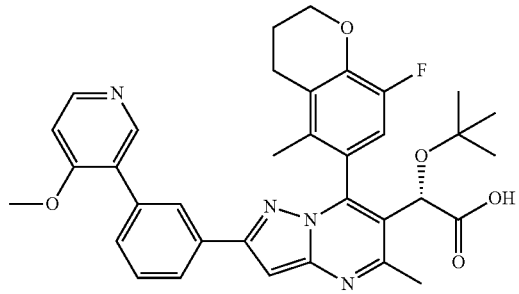

(2S)-2-(tert-Butoxy)-2-(7-(8-fluoro-5-methylchroman-6-yl)-2-(3-(4-methoxypyridin-3-yl)phenyl)-5-methylpyrazolo[1,5-a]pyrimidin-6-yl)acetic acid

| MS (M + H)$^+$ Calcd. | 611 |
|---|---|
| MS (M + H)$^+$ Observ. | 611 |
| Retention Time | 1.478 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex Luna 2.0 × 30 mm 3 um |

$^1$H NMR (500 MHz, CHLOROFORM-d) δ 8.52 (d, J=5.8 Hz, 1H), 8.35 (s, 1H), 7.94-7.74 (m, 2H), 7.55-7.38 (m, 2H), 7.01-6.77 (m, 3H), 5.01 (s, 1H), 4.38-4.20 (m, 2H), 3.87 (s, 3H), 2.84-2.63 (m, 5H), 2.20-2.02 (m, 2H), 1.89 (s, 3H), 1.17 (s, 9H).

Example 118

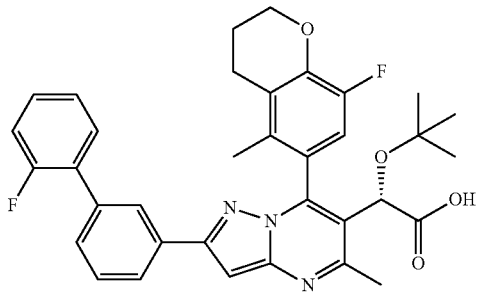 [SMILES: Cc1nc2cc(-c3cccc(-c4ccccc4F)c3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(2'-fluoro-[1,1'-biphenyl]-3-yl)-5-methylpyrazolo[1,5-a]pyrimidin-6-yl)acetic acid

| MS (M + H)$^+$ Calcd. | 598 |
|---|---|
| MS (M + H)$^+$ Observ. | 598 |
| Retention Time | 2.485 min |

-continued (2S)-2-(tert-Butoxy)-2-(7-(8-fluoro-5-methylchroman-6-yl)-2-(2'-fluoro-[1,1'-biphenyl]-3-yl)-5-methylpyrazolo[1,5-a]pyrimidin-6-yl)acetic acid

| LC Condition | |
|---|---|
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.95 (d, J=1.2 Hz, 1H), 7.88-7.75 (m, 1H), 7.57-7.40 (m, 3H), 7.37-7.29 (m, 1H), 7.24-7.12 (m, 2H), 7.01-6.82 (m, 2H), 5.06 (s, 1H), 4.36-4.24 (m, 2H), 2.80-2.63 (m, 5H), 2.13 (dd, J=6.1, 3.1 Hz, 2H), 1.89 (s, 3H), 1.17 (s, 9H).

Example 119

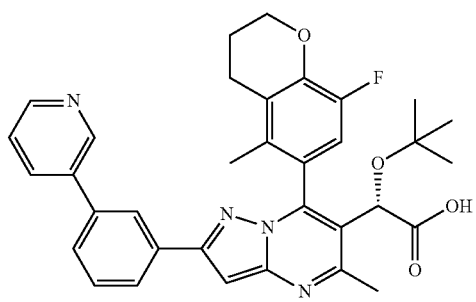

| (2S)-2-(tert-Butoxy)-2-(7-(8-fluoro-5-methylchroman-6-yl)-5-methyl-2-(3-(pyridin-3-yl)phenyl)pyrazolo[1,5-a]pyrimidin-6-yl)acetic acid | |
|---|---|
| MS (M + H)$^+$ Calcd. | 581 |
| MS (M + H)$^+$ Observ. | 581 |
| Retention Time | 1.997 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 8.87 (d, J=1.8 Hz, 1H), 8.63 (dd, J=4.8, 1.5 Hz, 1H), 8.07-7.83 (m, 3H), 7.61-7.37 (m, 3H), 7.03-6.81 (m, 2H), 5.10 (s, 1H), 4.43-4.25 (m, 2H), 2.86-2.69 (m, 5H), 2.18-2.16 (m, 2H), 1.96 (s, 3H), 1.23 (s, 9H).

Example 120

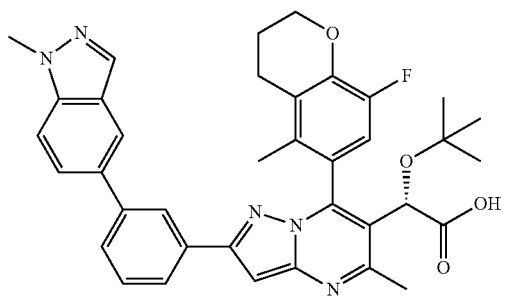 [SMILES: Cc1nc2cc(-c3cccc(-c4ccc5c(cnn5C)c4)c3)nn2c(-c2cc(F)c3c(c2C)CCCO3)c1[C@H](OC(C)(C)C)C(=O)O]

| (2S)-2-(tert-Butoxy)-2-(7-(8-fluoro-5-methylchroman-6-yl)-5-methyl-2-(3-(1-methyl-1H-indazol-5-yl)phenyl)pyrazolo[1,5-a]pyrimidin-6-yl)acetic acid | |
|---|---|
| MS (M + H)$^+$ Calcd. | 634 |
| MS (M + H)$^+$ Observ. | 634 |
| Retention Time | 2.49 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 8.09-8.00 (m, 2H), 7.93 (s, 1H), 7.81 (d, J=7.9 Hz, 1H), 7.67 (dd, J=8.5, 1.5 Hz, 1H), 7.59 (d, J=7.6 Hz, 1H), 7.52-7.42 (m, 2H), 7.00-6.90 (m, 2H), 5.09 (s, 1H), 4.37-4.27 (m, 2H), 4.11 (s, 3H), 2.80-2.67 (m, 5H), 2.21-2.11 (m, 2H), 1.94 (s, 1H), 1.21 (s, 9H).

Example 121-132

Scheme 11

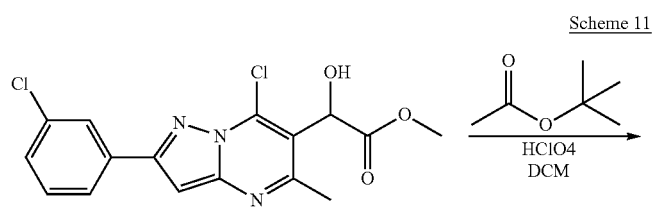

-continued
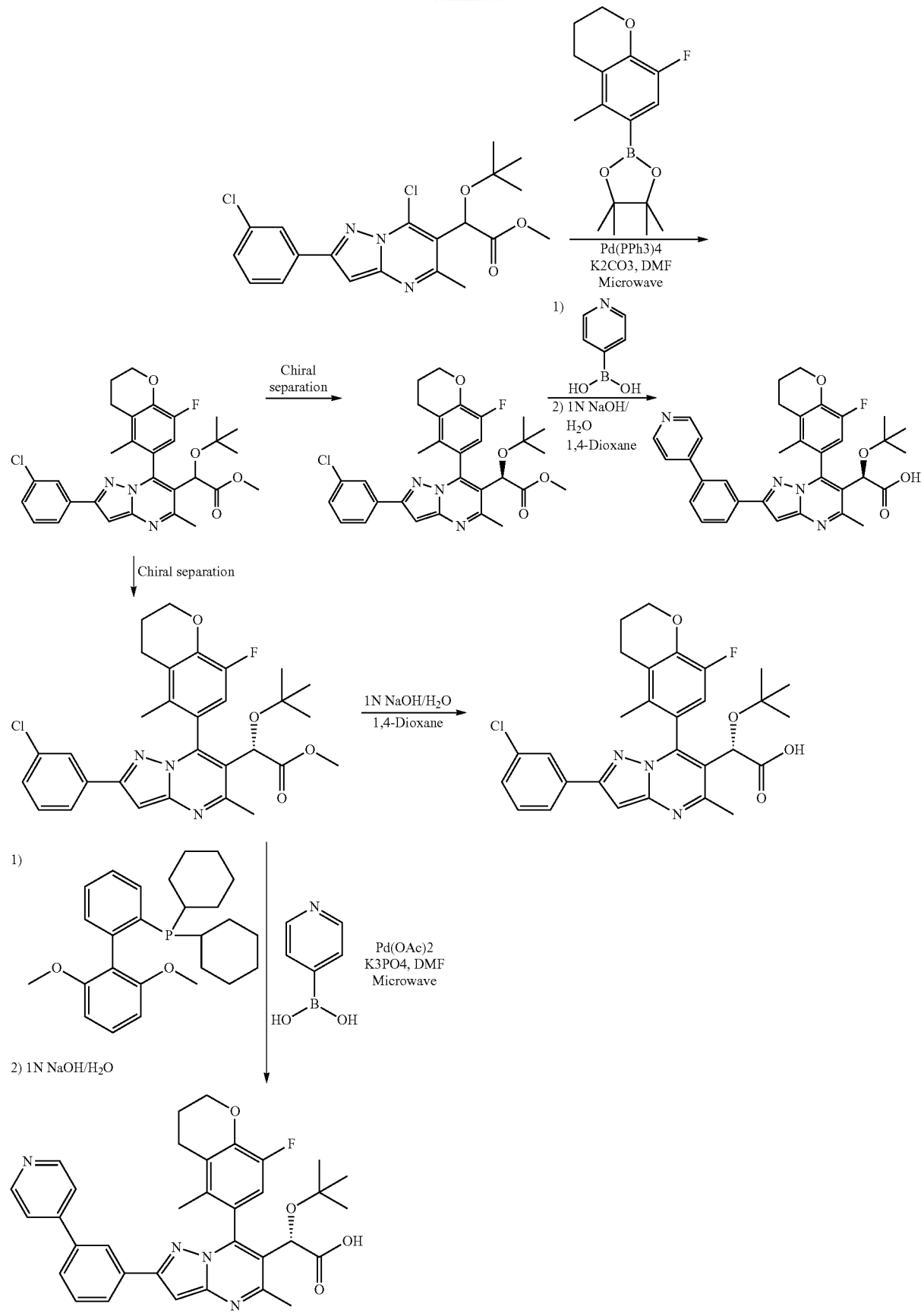

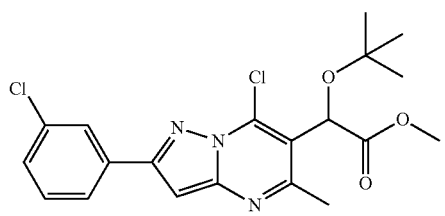

Methyl 2-(tert-butoxy)-2-(7-chloro-2-(3-chlorophenyl)-5-methylpyrazolo[1,5-a]pyrimidin-6-yl)acetate To a suspension of methyl 2-(7-chloro-2-(3-chlorophenyl)-5-methylpyrazolo[1,5-a]pyrimidin-6-yl)-2-hydroxyacetate (3550 mg, 9.69 mmol) in tert-butyl acetate (50 mL, 9.69 mmol) at room temperature was added $CH_2Cl_2$ (30 mL) followed by perchloric acid (1.250 mL, 14.54 mmol). The reaction mixture was stirred for 5 h at room temperature. The reaction mixture was quenched with water and diluted with ethyl acetate. The organic phase was washed with saturated $NaHCO_3$ and dried over sodium sulfate. The solvent was evaporated. Purification by silica gel chromatography provided the title compound (2.7 mg, 66%). $^1H$ NMR (400 MHz, CHLOROFORM-d) δ 8.07-8.00 (m, 1H), 7.89 (dt, J=6.7, 1.9 Hz, 1H), 7.48-7.37 (m, 2H), 6.93 (s, 1H), 5.68 (s, 1H), 3.75 (s, 3H), 2.69 (s, 3H), 1.29 (s, 9H).

| Methyl 2-(tert-butoxy)-2-(7-chloro-2-(3-chlorophenyl)-5-methylpyrazolo[1,5-a]pyrimidin-6-yl)acetate | |
|---|---|
| MS (M + H)⁺ Calcd. | 422 |
| MS (M + H)⁺ Observ. | 422 |
| Retention Time | 2.377 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

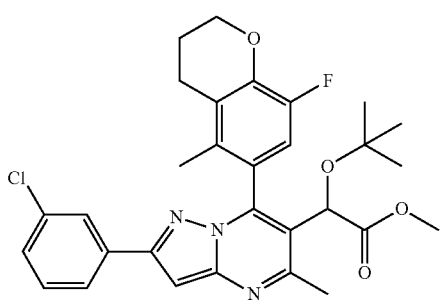 [SMILES: COC(=O)C(OC(C)(C)C)c1c(C)nc2cc(-c3cccc(Cl)c3)nn2c1-c1cc(F)c2c(c1C)CCCO2]

Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate To a 2-5 ml microwave tube was added methyl 2-(tert-butoxy)-2-(7-chloro-2-(3-chlorophenyl)-5-methylpyrazolo[1,5-a]pyrimidin-6-yl)acetate (200 mg, 0.474 mmol), tetrakis(triphenylphosphine)palladium(0) (55 mg, 0.047 mmol), 2-(8-fluoro-5-methylchroman-6-yl)-4,4,5,5-tetramethyl-1,3,2-dioxaborolane (180 mg, 0.616 mmol), DMF (3 mL), followed by 2M $K_2CO_3$ solution (300 µl). The reaction mixture was heated in a microwave reactor at 115° C. for 45 min. The reaction mixture was filtered and the filtrate was purified by silica gel chromatography to afford (128 mg, 48.9%) of the title compound. $^1H$ NMR (400 MHz, CHLOROFORM-d) δ 7.82 (s, 1H), 7.76-7.65 (m, 1H), 7.41-7.29 (m, 2H), 7.01-6.73 (m, 2H), 5.02 (s, 1H), 4.37 (dt, J=6.5, 3.5 Hz, 2H), 3.66 (s, 3H), 2.93-2.69 (m, 5H), 2.21 (dd, J=5.6, 2.4 Hz, 2H), 1.86 (s, 3H), 1.18 (s, 9H).

| Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate | |
|---|---|
| MS (M + H)⁺ Calcd. | 552 |
| MS (M + H)⁺ Observ. | 552 |
| Retention Time | 2.502 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

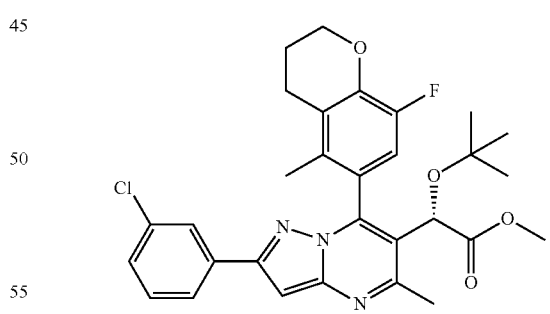

(2S)-Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate The title compound was separated from the racemic ester using a chiral column and (2S)-methyl 2-(tert-butoxy)-2-(2-(3-chlorophenyl)-7-(8-fluoro-5-methylchroman-6-yl)-5-methylpyrazolo[1,5-a]pyrimidin-6-yl)acetate was isolated with 100% enantiomeric excess. Chiral separation method:

Chiralpak AD-H preparative column, 30×250 mm, 5 µm. Mobile Phase: 15% MeOH in CO₂ @ 150 Bar. Temp: 35° C. Flow rate: 70.0 mL/min. for 13 min. UV was monitored @ 266 nm. provided the title compound with 100% enantiomeric excess. Retention time: 5.02 min. Enantiomeric Excess was determined by Chiral SFC method: Chiralpak AD-H analytical column, 4.6×250 mm, 5 µm. Mobile Phase: 15% MeOH in CO₂. Temp: 35° C. Flow rate: 2.0 mL/min. for 10 min. UV monitored @ 266 nm. Injection: 5 uL of ~2.0 mg/mL solution in 50:50 MeOH:CHCl₃.

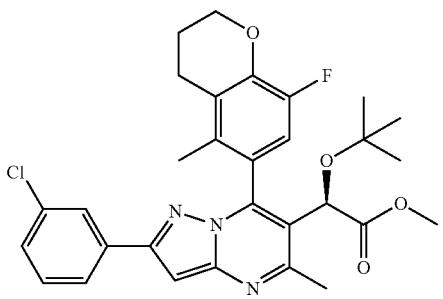 [SMILES: COC(=O)[C@H](OC(C)(C)C)c1c(C)nc2cc(-c3cccc(Cl)c3)nn2c1-c1cc(F)c2c(c1C)CCCO2]

(2R)-Methyl 2-(tert-butoxy)-2-(2-(3-chlorophenyl)-7-(8-fluoro-5-methylchroman-6-yl)-5-methylpyrazolo[1,5-a]pyrimidin-6-yl)acetate The title compound was separated from the racemic ester using a chiral column and (2R)-methyl 2-(tert-butoxy)-2-(2-(3-chlorophenyl)-7-(8-fluoro-5-methylchroman-6-yl)-5-methylpyrazolo[1,5-a]pyrimidin-6-yl)acetate was isolated with 100% enantiomeric excess. Chiral separation method: Chiralpak AD-H preparative column, 30×250 mm, 5 µm. Mobile Phase: 15% MeOH in CO₂ @ 150 Bar. Temp: 35° C. Flow rate: 70.0 mL/min. for 13 min. UV was monitored @ 266 nm. provided the title compound with 100% enantiomeric excess. Retention time: 8.41 min. Enantiomeric Excess was determined by Chiral SFC method: Chiralpak AD-H analytical column, 4.6×250 mm, 5 µm. Mobile Phase: 15% MeOH in CO₂. Temp: 35° C. Flow rate: 2.0 mL/min. for 10 min. UV monitored @ 266 nm. Injection: 5 uL of ~2.0 mg/mL solution in 50:50 MeOH:CHCl3.

Example 121

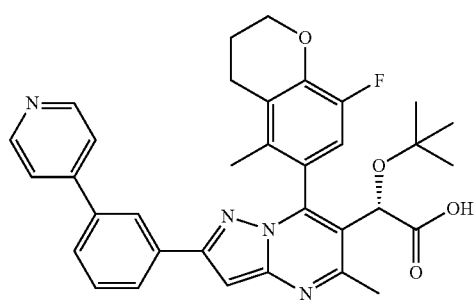 [SMILES: Cc1nc2cc(-c3cccc(-c4ccncc4)c3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-5-methyl-2-(3-(pyridin-4-yl)phenyl)pyrazolo[1,5-a]pyrimidin-6-yl)acetic acid, TFA salt The title compound was synthesized from (2S)-methyl 2-(tert-butoxy)-2-(2-(3-chlorophenyl)-7-(8-fluoro-5-meth-ylchroman-6-yl)-5-methylpyrazolo[1,5-a]pyrimidin-6-yl)acetate using the procedure described for example 115.

| (2S)-2-(tert-Butoxy)-2-(7-(8-fluoro-5-methylchroman-6-yl)-5-methyl-2-(3-(pyridin-4-yl)phenyl)pyrazolo[1,5-a]pyrimidin-6-yl)acetic acid, TFA salt | |
|---|---|
| MS (M + H)⁺ Calcd. | 581 |
| MS (M + H)⁺ Observ. | 581 |
| Retention Time | 2.000 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | methanol: Water: TFA |
| Column | Phenomenex Luna 2.0 × 30 mm 3 um |

¹H NMR (500 MHz, CHLOROFORM-d) δ 8.91 (d, J=6.41 Hz, 2H), 8.13-8.05 (m, 4H), 7.75-7.60 (m, 2H), 7.00 (s, 1H), 6.92 (d, J=10.38 Hz, 1H), 5.09 (s, 1H), 4.33 (t, J=5.04 Hz, 2H), 2.79-2.69 (m, 5H), 2.22-2.11 (m, 2H), 1.95 (s, 3H), 1.21 (s, 9H).

Example 122

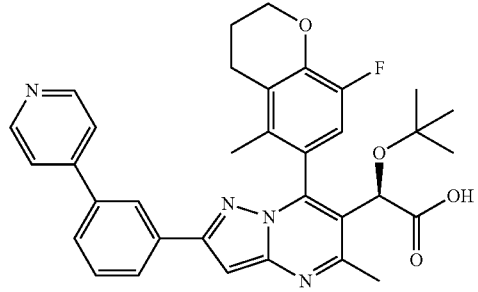

(2R)-2-(tert-Butoxy)-2-(7-(8-fluoro-5-methylchroman-6-yl)-5-methyl-2-(3-(pyridin-4-yl)phenyl)pyrazolo[1,5-a]pyrimidin-6-yl)acetic acid, TFA salt The title compound was synthesized from (2R)-methyl 2-(tert-butoxy)-2-(2-(3-chlorophenyl)-7-(8-fluoro-5-meth-ylchroman-6-yl)-5-methylpyrazolo[1,5-a]pyrimidin-6-yl)acetate using the procedure described for example 115.

| (2R)-2-(tert-Butoxy)-2-(7-(8-fluoro-5-methylchroman-6-yl)-5-methyl-2-(3-(pyridin-4-yl)phenyl)pyrazolo[1,5-a]pyrimidin-6-yl)acetic acid, TFA salt | |
|---|---|
| MS (M + H)⁺ Calcd. | 581 |
| MS (M + H)⁺ Observ. | 581 |
| Retention Time | 1.983 min |
| | LC Condition |
| Solvent A | 10% methanol: 90% Water: 0.1% TFA |
| Solvent B | 90% methanol: 10% Water: 0.1% TFA |
| Start % B | 0 |
| Final % B | 100 |
| Gradient Time | 2 min |
| Flow Rate | 1 mL/min |
| Wavelength | 220 |

-continued (2R)-2-(tert-Butoxy)-2-(7-(8-fluoro-5-methylchroman-6-yl)-5-methyl-2-(3-(pyridin-4-yl)phenyl)pyrazolo[1,5-a]pyrimidin-6-yl)acetic acid, TFA salt

| | |
|---|---|
| Solvent Pair | methanol: Water: TFA |
| Column | Phenomenex Luna 2.0 × 30 mm 3 um |

$^1$H NMR (500 MHz, CHLOROFORM-d) δ 8.95 (d, J=5.2 Hz, 2H), 8.33-7.94 (m, 4H), 7.83-7.53 (m, 2H), 7.05 (s, 1H), 6.92 (d, J=10.7 Hz, 1H), 5.10 (s, 1H), 4.33 (t, J=4.9 Hz, 2H), 2.93-2.58 (m, 5H), 2.31-2.05 (m, 2H), 1.94 (s, 3H), 1.21 (s, 9H).

Example 123

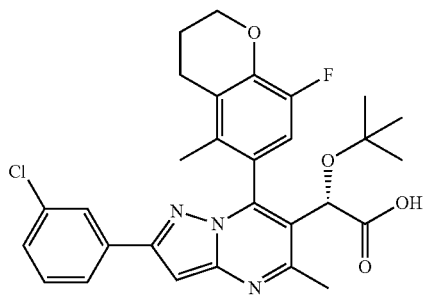 [SMILES: Cc1nc2cc(-c3cccc(Cl)c3)nn2c(-c2cc(F)c3c(c2C)CCCO3)c1[C@H](OC(C)(C)C)C(=O)O]

(2S)-2-(tert-Butoxy)-2-(2-(3-chlorophenyl)-7-(8-fluoro-5-methylchroman-6-yl)-5-methylpyrazolo[1,5-a]pyrimidin-6-yl)acetic acid, TFA salt The title compound was hydrolyzed from (2S)-methyl 2-(tert-butoxy)-2-(2-(3-chlorophenyl)-7-(8-fluoro-5-methylchroman-6-yl)-5-methylpyrazolo[1,5-a]pyrimidin-6-yl)acetate using the procedure described for example 115.

| (2S)-2-(tert-Butoxy)-2-(2-(3-chlorophenyl)-7-(8-fluoro-5-methylchroman-6-yl)-5-methylpyrazolo[1,5-a]pyrimidin-6-yl)acetic acid, TFA salt | |
|---|---|
| MS (M + H)$^+$ Calcd. | 538 |
| MS (M + H)$^+$ Observ. | 538 |
| Retention Time | 2.083 min |
| | LC Condition |
| Solvent A | 10% acetonitrile: 90% Water: 0.1% TFA |
| Solvent B | 90% acetonitrile: 10% Water: 0.1% TFA |
| Start % B | 0 |
| Final % B | 100 |
| Gradient Time | 2 min |
| Flow Rate | 1 mL/min |
| Wavelength | 220 |
| Solvent Pair | acetonitrile: Water: TFA |
| Column | Phenomenex Luna 2.0 × 30 mm 3 um |

$^1$H NMR (500 MHz, CHLOROFORM-d) δ 7.81 (s, 1H), 7.74-7.61 (m, 1H), 7.41-7.28 (m, 2H), 7.03-6.81 (m, 2H), 5.09 (s, 1H), 4.56-4.21 (m, 2H), 2.88-2.61 (m, 5H), 2.30-2.07 (m, 2H), 1.91 (s, 3H), 1.21 (s, 9H).

Example 124-131 were synthesized using the procedure described above for Example 121.

Example 124

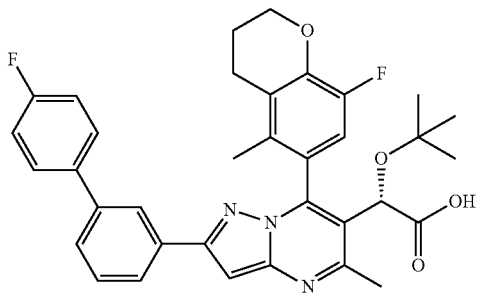 [SMILES: Cc1nc2cc(-c3cccc(-c4ccc(F)cc4)c3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(4'-fluoro-[1,1'-biphenyl]-3-yl)-5-methylpyrazolo[1,5-a]pyrimidin-6-yl)acetic acid, TFA salt

| | |
|---|---|
| MS (M + H)$^+$ Calcd. | 598 |
| MS (M + H)$^+$ Observ. | 598 |
| Retention Time | 2.492 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.99-7.88 (m, 1H), 7.80 (d, J=7.6 Hz, 1H), 7.64-7.39 (m, 4H), 7.19-7.08 (m, 2H), 7.00 (s, 1H), 6.93 (d, J=10.7 Hz, 1H), 5.10 (s, 1H), 4.32 (dt, J=6.8, 3.2 Hz, 2H), 2.79-2.66 (m, 5H), 2.15 (dd, J=6.3, 4.1 Hz, 2H), 1.92 (s, 3H), 1.21 (s, 9H).

Example 125

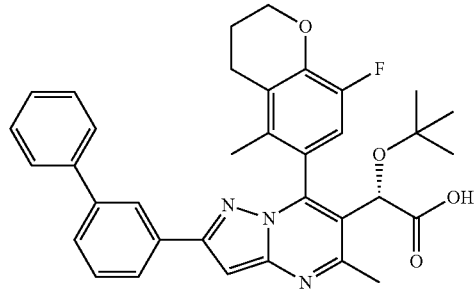

(2S)-2-(2-([1,1'-Biphenyl]-3-yl)-7-(8-fluoro-5-methylchroman-6-yl)-5-methylpyrazolo[1,5-a]pyrimidin-6-yl)-2-(tert-butoxy)acetic acid

| | |
|---|---|
| MS (M + H)+ Calcd. | 580 |
| MS (M + H)+ Observ. | 580 |
| Retention Time | 2.503 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 8.05-7.98 (m, 1H), 7.81 (d, J=7.6 Hz, 1H), 7.65-7.58 (m, 2H), 7.55 (d, J=7.6 Hz, 1H), 7.46 (t, J=7.5 Hz, 3H), 7.40-7.33 (m, 1H), 6.98-6.90 (m, 2H), 5.09 (s, 1H), 4.38-4.27 (m, 2H), 2.82-2.66 (m, 5H), 2.15 (d, J=6.1 Hz, 2H), 1.93 (s, 3H), 1.21 (s, 9H).

Example 126

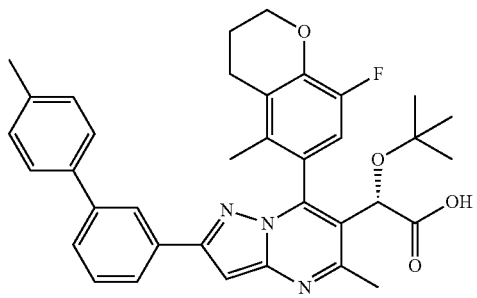 [SMILES: Cc1ccc(-c2cccc(-c3cc4nc(C)c([C@H](OC(C)(C)C)C(=O)O)c(-c5cc(F)c6c(c5C)CCCO6)n4n3)c2)cc1]

(2S)-2-(tert-Butoxy)-2-(7-(8-fluoro-5-methylchroman-6-yl)-2-(4'-methyl-[1,1'-biphenyl]-3-yl)-5-methylpyrazolo[1,5-a]pyrimidin-6-yl)acetic acid, TFA salt

| | |
|---|---|
| MS (M + H)+ Calcd. | 594 |
| MS (M + H)+ Observ. | 594 |
| Retention Time | 2.570 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (500 MHz, CHLOROFORM-d) δ 7.98 (t, J=1.5 Hz, 1H), 7.78 (d, J=7.9 Hz, 1H), 7.60-7.38 (m, 4H), 7.29-7.23 (m, 2H), 7.03-6.97 (m, 1H), 6.96-6.88 (m, 1H), 5.09 (s, 1H), 4.45-4.20 (m, 2H), 2.79-2.67 (m, 5H), 2.40 (s, 3H), 2.14 (d, J=5.8 Hz, 2H), 1.90 (s, 3H), 1.21 (s, 9H).

Example 127

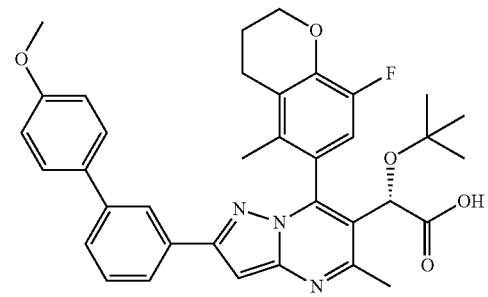 [SMILES: COc1ccc(-c2cccc(-c3cc4nc(C)c([C@H](OC(C)(C)C)C(=O)O)c(-c5cc(F)c6c(c5C)CCCO6)n4n3)c2)cc1]

(2S)-2-(tert-Butoxy)-2-(7-(8-fluoro-5-methylchroman-6-yl)-2-(4'-methoxy-[1,1'-biphenyl]-3-yl)-5-methylpyrazolo[1,5-a]pyrimidin-6-yl)acetic acid, TFA salt

| | |
|---|---|
| MS (M + H)+ Calcd. | 610 |
| MS (M + H)+ Observ. | 610 |
| Retention Time | 2.468 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

$^1$H NMR (400 MHz, CHLOROFORM-d) δ 7.97 (t, J=1.5 Hz, 1H), 7.77 (d, J=7.5 Hz, 1H), 7.63-7.39 (m, 4H), 7.11-6.81 (m, 4H), 5.11 (s, 1H), 4.43-4.30 (m, 2H), 3.88 (s, 3H), 2.80 (s, 3H), 2.72 (t, J=6.4 Hz, 2H), 2.15 (dd, J=6.3, 4.3 Hz, 2H), 1.89 (s, 3H), 1.23 (s, 9H).

Example 128

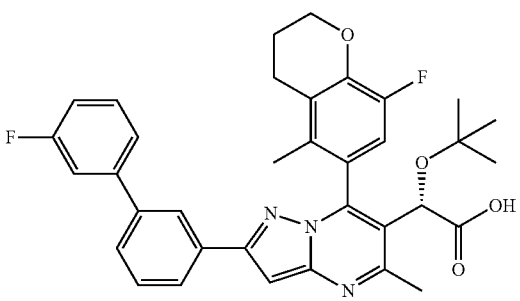

1H), 7.00 (s, 1H), 6.95-6.87 (m, 2H), 5.09 (s, 1H), 4.40-4.26 (m, 2H), 3.86 (s, 3H), 2.78-2.67 (m, 5H), 2.22-2.06 (m, 2H), 1.89 (s, 3H), 1.21 (s, 9H).

Example 130

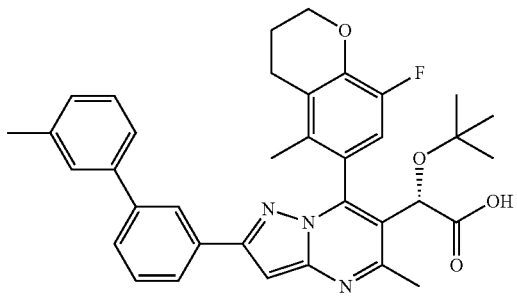

| (2S)-2-(tert-Butoxy)-2-(7-(8-fluoro-5-methylchroman-6-yl)-2-(3'-fluoro-[1,1'-biphenyl]-3-yl)-5-methylpyrazolo[1,5-a]pyrimidin-6-yl)acetic acid, TFA salt | |
|---|---|
| MS (M + H)+ Calcd. | 598 |
| MS (M + H)+ Observ. | 598 |
| Retention Time | 2.61 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

¹H NMR (500 MHz, CHLOROFORM-d) δ 7.97 (t, J=1.5 Hz, 1H), 7.86-7.79 (m, 1H), 7.55 (dt, J=7.9, 1.4 Hz, 1H), 7.51-7.35 (m, 3H), 7.32-7.27 (m, 1H), 7.10-7.03 (m, 1H), 7.01 (s, 1H), 6.93 (d, J=10.7 Hz, 1H), 5.10 (s, 1H), 4.32 (m, 2H), 2.82-2.66 (m, 5H), 2.14 (dd, J=6.4, 3.7 Hz, 2H), 1.90 (s, 3H), 1.21 (s, 9H).

Example 129

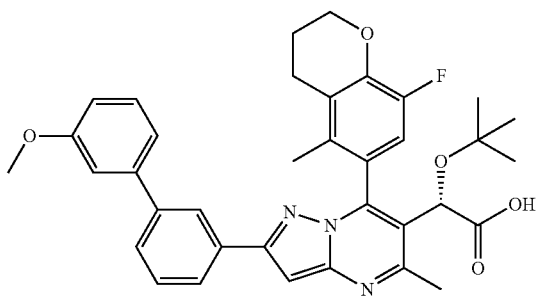 [SMILES: COc1cccc(-c2cccc(-c3cc4nc(C)c([C@H](OC(C)(C)C)C(=O)O)c(-c5cc(F)c6c(c5C)CCCO6)n4n3)c2)c1]

| (2S)-2-(tert-Butoxy)-2-(7-(8-fluoro-5-methylchroman-6-yl)-2-(3'-methoxy-[1,1'-biphenyl]-3-yl)-5-methylpyrazolo[1,5-a]pyrimidin-6-yl)acetic acid, TFA salt | |
|---|---|
| MS (M + H)+ Calcd. | 610 |
| MS (M + H)+ Observ. | 610 |
| Retention Time | 2.59 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

¹H NMR (500 MHz, CHLOROFORM-d) δ 7.99 (s, 1H), 7.80 (d, J=7.6 Hz, 1H), 7.60-7.52 (m, 1H), 7.49-7.41 (m, 1H), 7.37 (t, J=7.9 Hz, 1H), 7.19 (d, J=7.6 Hz, 1H), 7.14-7.09 (m,

| (2S)-2-(tert-Butoxy)-2-(7-(8-fluoro-5-methylchroman-6-yl)-2-(3'-methyl-[1,1'-biphenyl]-3-yl)-5-methylpyrazolo[1,5-a]pyrimidin-6-yl)acetic acid, TFA salt | |
|---|---|
| MS (M + H)+ Calcd. | 594 |
| MS (M + H)+ Observ. | 594 |
| Retention Time | 2.565 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

¹H NMR (500 MHz, CHLOROFORM-d) δ 7.98 (s, 1H), 7.79 (d, J=7.6 Hz, 1H), 7.55 (d, J=7.6 Hz, 1H), 7.48-7.31 (m, 4H), 7.19 (d, J=7.3 Hz, 1H), 7.00 (s, 1H), 6.93 (d, J=10.7 Hz, 1H), 5.10 (s, 1H), 4.37-4.27 (m, 2H), 2.78-2.68 (m, 5H), 2.43 (s, 3H), 2.14 (d, J=3.4 Hz, 2H), 1.90 (s, 3H), 1.22 (s, 9H).

Example 131

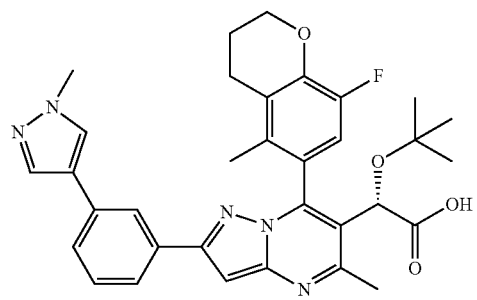 [SMILES: Cc1nc2cc(-c3cccc(-c4cnn(C)c4)c3)nn2c(-c2cc(F)c3c(c2C)CCCO3)c1[C@H](OC(C)(C)C)C(=O)O]

| (2S)-2-(tert-Butoxy)-2-(7-(8-fluoro-5-methylchroman-6-yl)-5-methyl-2-(3-(1-methyl-1H-pyrazol-4-yl)phenyl)pyrazolo[1,5-a]pyrimidin-6-yl)acetic acid, TFA salt | |
|---|---|
| MS (M + H)$^+$ Calcd. | 584 |
| MS (M + H)$^+$ Observ. | 584 |
| Retention Time | 1.752 min |
| | LC Condition |
| Solvent A | 10% acetonitrile:90% Water:0.1% TFA |
| Solvent B | 90% acetonitrile:10% Water:0.1% TFA |
| Start % B | 0 |
| Final % B | 100 |
| Gradient Time | 2 min |
| Flow Rate | 1 mL/min |
| Wavelength | 220 |
| Solvent Pair | acetonitrile:Water:TFA |
| Column | Phenomenex Luna 2.0 × 30 mm 3 um |

$^1$H NMR (500 MHz, CHLOROFORM-d) δ 7.96-7.80 (m, 2H), 7.75-7.61 (m, 2H), 7.53-7.33 (m, 2H), 7.03 (s, 1H), 6.92 (d, J=10.7 Hz, 1H), 5.09 (s, 1H), 4.32 (t, J=4.1 Hz, 2H), 4.02 (s, 3H), 2.86-2.64 (m, 5H), 2.24-2.06 (m, 2H), 1.89 (s, 3H), 1.21 (s, 9H).

Scheme 12

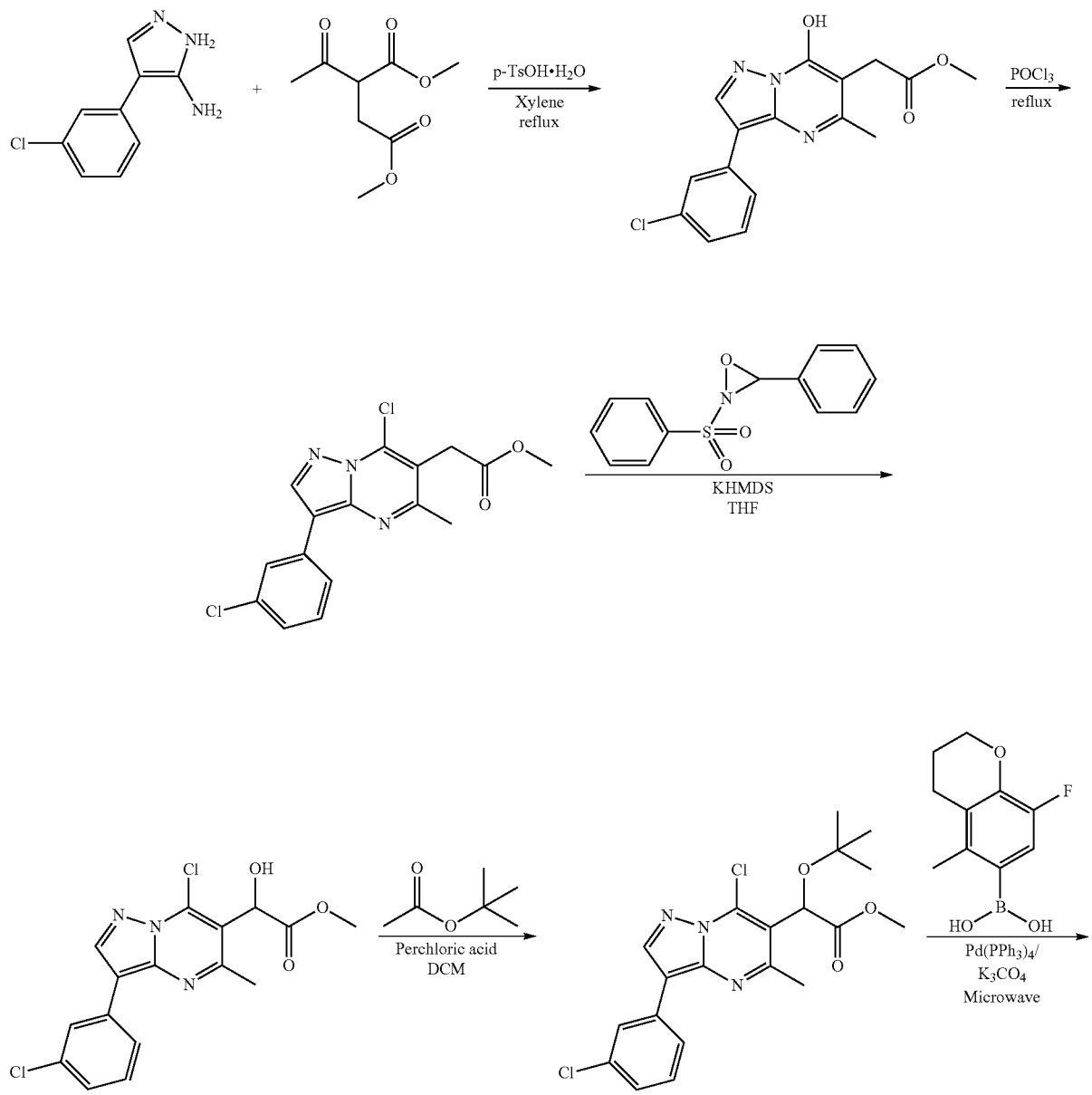

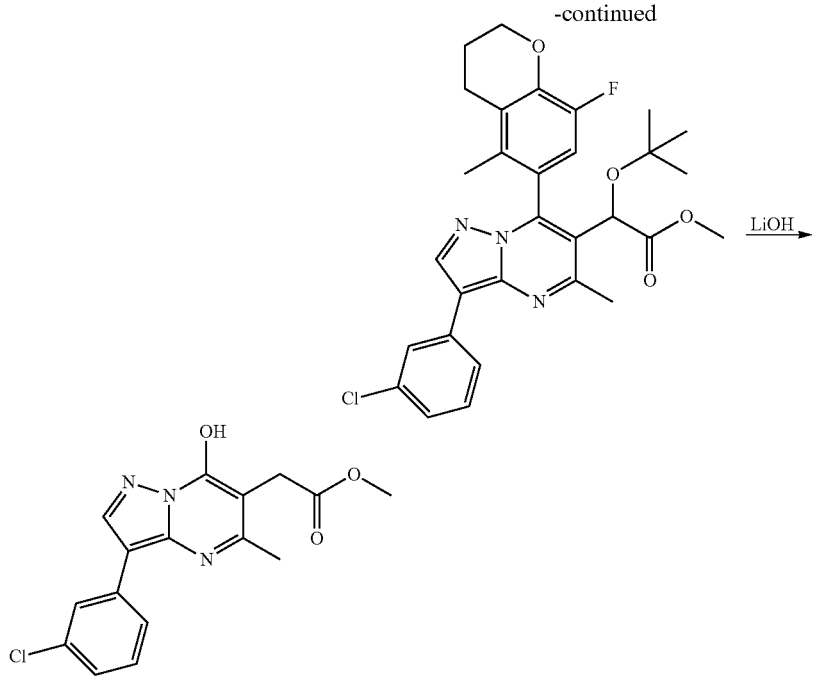

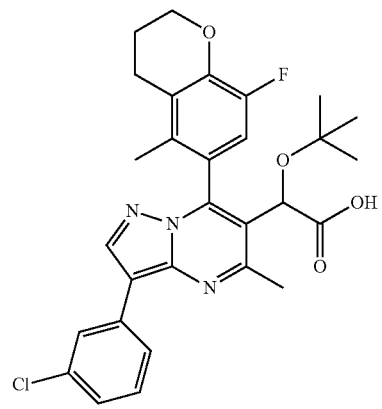

Methyl 2(3-(3-chlorophenyl)-(7-hydroxy-5-methylpyrazolo[1,5-a]pyrimidin-6-yl)acetate To a solution of 4-(3-chlorophenyl)-1H-pyrazol-5-amine (1 g, 5.2 mmol) and dimethyl 2-acetylsuccinate (2.92 g, 15.5 mmol) in xylene (100 mL) was added p-toluenesulfonic acid monohydrate (10 mg, 0.052 mmol). The reaction mixture was heated at reflux under a Dean-Stark trap for 2 hrs. The solid was filtered and washed by hexanes to afford (1.3 g, 76%) of the title compound. $^1$H-NMR (500 MHz, DMSO-d$_6$) δ ppm 2.39 (s, 3H), 3.59 (s, 2H), 3.63 (s, 3H), 7.37 (s, 1H), 7.48 (s, 1H), 7.54 (s, 1H), 7.56 (s, 1H), 7.64 (d, 1H), 8.19 (s, 1H), 11.94 (s, 1H).

| Methyl2(3-(3-chlorophenyl)-(7-hydroxy-5-methylpyrazolo[1,5-a]pyrimidin-6-yl)acetate | |
|---|---|
| MS (M + H)$^+$ Calcd. | 332 |
| MS (M + H)$^+$ Observ. | 332 |
| Retention Time | 1.81 min |
| | LC Condition |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

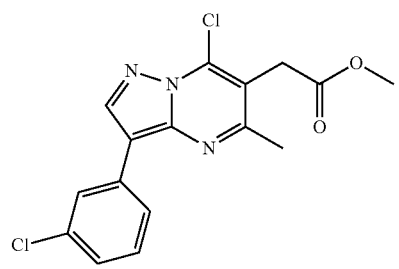 [SMILES: COC(=O)Cc1c(C)nc2c(-c3cccc(Cl)c3)cnn2c1Cl]

Methyl 2-(7-chloro-3-(3-chlorophenyl)-5-methylpyrazolo[1,5-a]pyrimidin-6-yl)acetate To methyl 2-(3-(3-chlorophenyl)-(7-hydroxy-5-methylpyrazolo[1,5-a]pyrimidin-6-yl)acetate (1.3 g, 3.92 mmol) was added POCl$_3$ (4 mL). The reaction mixture was heated at reflux for 1 h. After cooling, the reaction mixture was added drop-wise to ice-water. A brown solid precipitated. The solid were filtered and washed with water, then dissolved in ethyl acetate. The organic solution was washed with saturated NaHCO$_3$ and dried over sodium sulfate. The solvent was evaporated to give the title compound (1.3 g, 90%). Used as is in the next step.

| Methyl 2-(7-chloro-3-(3-chlorophenyl)-5-methylpyrazolo[1,5-a]pyrimidin-6-yl)acetate. | |
|---|---|
| MS (M + H)$^+$ Calcd. | 351 |
| MS (M + H)$^+$ Observ. | 351 |
| Retention Time | 2.1 min |
| | LC Condition |
| Solvent A | 10% Methanol:90% Water:0.1% TFA |
| Solvent B | 90% Methanol:10% Water:0.1% TFA |
| Start % B | 0 |

-continued

| Methyl 2-(7-chloro-3-(3-chlorophenyl)-5-methylpyrazolo[1,5-a]pyrimidin-6-yl)acetate. ||
|---|---|
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

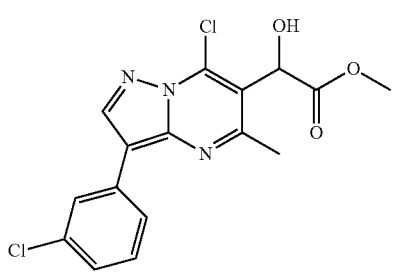 [SMILES: COC(=O)C(O)c1c(C)nc2c(-c3cccc(Cl)c3)cnn2c1Cl]

Methyl 2-(7-chloro-3-(3-chlorophenyl)-5-methyl-3-phenylpyrazolo[1,5-a]pyrimidin-6-yl)-2-hydroxyacetate To a stirred solution of KHMDS (0.5 M in toluene, 7.4 mL) in THF (20 mL) at −78° C. was added a solution of methyl 2-(7-chloro-3-(3-chlorophenyl)-5-methylpyrazolo[1,5-a]pyrimidin-6-yl)acetate (1.3 g, 3.7 mmol) in THF (20 mL) over 20 mins. The reaction mixture was stirred at −78° C. for 30 min. A solution of 3-phenyl-2-(phenylsulfonyl)-1,2-oxaziridine (1.16 g, 4.45 mmol) in THF (20 mL) was added over 10 min and the resulted reaction mixture was stirred for an additional 30 min at −78° C. The reaction mixture was quenched with saturated NH$_4$Cl aqueous solution (2 mL). The mixture was allowed to warm up to room temperature and diluted with EtOAc (100 mL). The organic phase was washed with water and brine and dried with sodium sulfate. The solvent was evaporated. Purification by silica gel chromatography provided the title compound (0.4 mg, 30%). Used as is in the next step.

| Methyl 2-(7-chloro-3-(3-chlorophenyl)-5-methyl-3-phenylpyrazolo[1,5-a]pyrimidin-6-yl)-2-hydroxyacetate. ||
|---|---|
| MS (M + H)$^+$ Calcd. | 366 |
| MS (M + H)$^+$ Observ. | 366 |
| Retention Time | 2.15 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

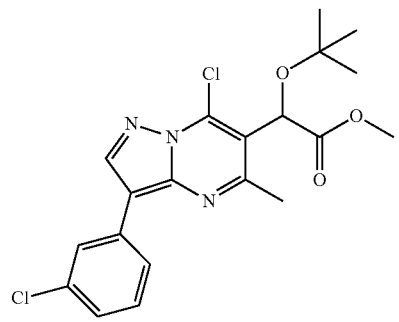 [SMILES: COC(=O)C(OC(C)(C)C)c1c(C)nc2c(-c3cccc(Cl)c3)cnn2c1Cl]

Methyl 2-tert-butoxy-2-(7-chloro-3-(3-chlorophenyl)-5-methylpyrazolo[1,5-a]pyrimidin-6-yl)acetate To a suspension of methyl 2-(7-chloro-3-(3-chlorophenyl)-5-methyl-3-phenylpyrazolo[1,5-a]pyrimidin-6-yl)-2-hydroxyacetate (400 mg, 1.09 mmol) in tert-butyl acetate (5 mL) at room temperature was added CH$_2$Cl$_2$ (15 mL) followed by perchloric acid (165 mg, 1.6 mmol). The reaction mixture was stirred for 2 h at room temperature. The reaction mixture was diluted with ethyl acetate (15 mL). The organic phase was washed with saturated NaHCO$_3$ (2×10 mL), followed by water (1×10 mL) and dried over sodium sulfate. The solvent was evaporated. Purification by silica gel chromatography provided the title compound (300 mg, 65%). Used as is in the next step.

| Methyl 2-tert-butoxy-2-(7-chloro-3-(3chlorophenyl)-5-methylpyrazolo[1,5-a]pyrimidin-6-yl)acetate ||
|---|---|
| MS (M + H)$^+$ Calcd. | 422 |
| MS (M + H)$^+$ Observ. | 422 |
| Retention Time | 2.45 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

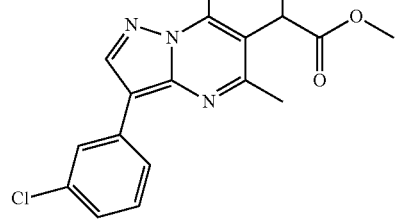

Methyl 2-tert-butoxy-2-(3-(3-chorophenyl)-7-(8-fluoro-5-methylchroman-6-yl)-5-methylpyrazolo[1,5-a]pyrimidin-6-yl)acetate, TFA salt To a 2-5 mL microwave tube was added methyl 2-tert-butoxy-2-(7-chloro-3-(3-chlorophenyl)-5-methylpyrazolo[1,5-a]pyrimidin-6-yl)acetate (25 mg, 0.059 mmol), tetrakis(triphenylphosphine)palladium(0) (10 mg, 8.88 µmol), 8-fluoro-5-methylchroman-6-ylboronic acid (17 mg, 0.059 mmol), dioxane (1.5 mL), followed by 2M K$_3$PO$_4$ solution (77 uL). The reaction mixture was heated in a microwave reactor at 130° C. for 30 min. The reaction mixture was filtered and the filtrate was purified by preparative HPLC to afford (13 mg, 38%) of the title compound as the TFA salt. Preparative HPLC condition: Phenomenex Luna C18 30×100 mm S10, 30 to 100% B over 17 min gradient, 5 min hold time, A=10% methanol 90% water 0.1% TFA, B=90% methanol 10% water 0.1% TFA. Flow rate: 40 mL/min. Used as is in the next step.

| Methyl 2-tert-butoxy-2-(3-(3-chorophenyl)-7-(8-fluoro-5-methylchroman-6-yl)-5-methylpyrazolo[1,5-a]pyrimidin-6-yl)acetate, TFA salt. | |
|---|---|
| MS (M + H)$^+$ Calcd. | 552 |
| MS (M + H)$^+$ Observ. | 552 |
| Retention Time | 2.55 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 132

Scheme 13

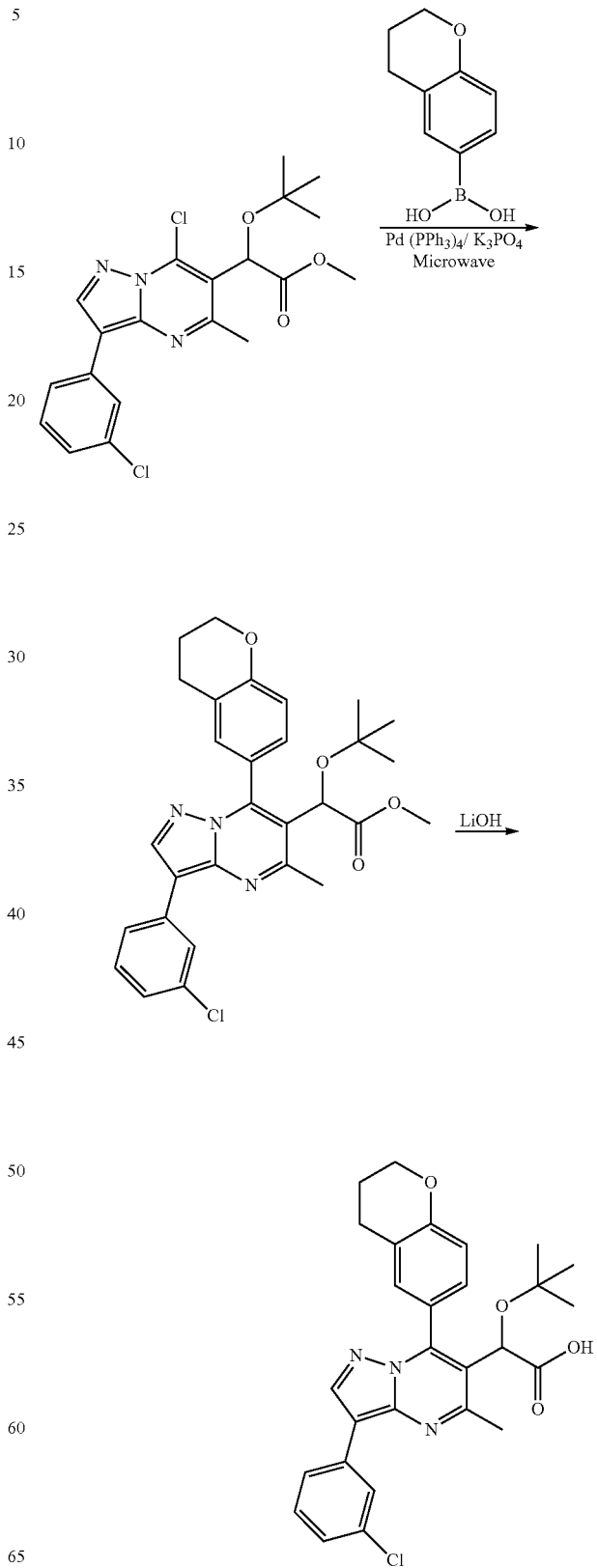

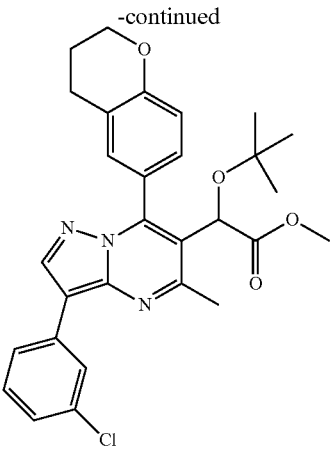

Methyl 2-tert-butoxy-2-(3-(3-chlorophenyl)-7-(chroman-6-yl)-5-methylpyrazolo[1,5-a]pyrimidin-6-yl)acetate, TFA salt To a 2-5 mL microwave tube was added methyl 2-tert-butoxy-2-(7-chloro-3-(3-chlorophenyl)-5-methylpyrazolo[1,5-a]pyrimidin-6-yl)acetate (25 mg, 0.059 mmol), tetrakis(triphenylphosphine)palladium(0) (6 mg, 0.005 μmol), 2-(chroman-6-yl)-4,4,5,5-tetramethyl-1,3,2-dioxaborolane (15 mg, 0.059 mmol), dioxane (1.5 mL), followed by 2M K$_3$PO$_4$ solution (77 uL). The reaction mixture was heated in a microwave reactor at 130° C. for 30 min. The reaction was filtered and the filtrate was purified by preparative HPLC to afford (12 mg, 39%) of the title compound as the TFA salt. Preparative HPLC condition: Phenomenex Luna C18 30×100 mm S10, 30 to 100% B over 17 min gradient, 5 min hold time, A=10% methanol 90% water 0.1% TFA, B=90% methanol 10% water 0.1% TFA. Flow rate: 40 mL/min. Compound used as is in the next step.

2-tert-Butoxy-2-(3-(3-chlorophenyl)-(7-(8-fluoro-5-methylchroman-6-yl)-5-methylpyrazolo[1,5-a]pyrimidin-6-yl)acetic acid To a solution of methyl 2-tert-butoxy-2-(3-(3-chorophenyl)-7-(8-fluoro-5-methylchroman-6-yl)-5-methylpyrazolo[1,5-a]pyrimidin-6-yl)acetate, TFA salt (13 mg, 0.027 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (3 mg, 30%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (500 MHz, DMSO-d$_6$) δ ppm 0.99 (9H, br. s.), 2.07 (2H, br. s.), 2.74 (3H, br. s.), 2.82-2.96 (2H, m), 4.29 (2H, br. s.), 5.21 (1H, s), 6.98 (1H, s), 7.24 (1H, s), 7.41 (4H, s), 8.11 (2H, s), 8.38 (1H, s).

2-tert-Butoxy-2-(3-(3-chorophenyl)-7-(8-fluoro-5-methylchroman-6-yl)-5-methylpyrazolo[1,5-a]pyrimidin-6-yl)acetic acid.

| | |
|---|---|
| MS (M + H)$^+$ Calcd. | 539 |
| MS (M + H)$^+$ Observ. | 539 |
| Retention Time | 2.55 min |

| LC Condition | |
|---|---|
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

Methyl 2-tert-butoxy-2-(3-(3-chlorophenyl)-7-(chroman-6-yl)-5-methylpyrazolo[1,5-a]pyrimidin-6-yl)acetate, TFA salt.

| | |
|---|---|
| MS (M + H)$^+$ Calcd. | 520 |
| MS (M + H)$^+$ Observ. | 520 |
| Retention Time | 2.56 min |

| LC Condition | |
|---|---|
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 133

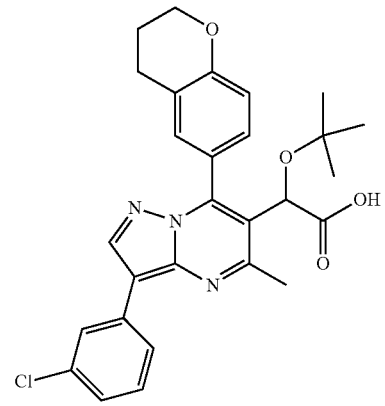 [SMILES: Cc1nc2c(-c3cccc(Cl)c3)cnn2c(-c2ccc3c(c2)CCCO3)c1C(OC(C)(C)C)C(=O)O]

2-tert-Butoxy-2-(3-(3-chlorophenyl)-(7-chroman-6-yl)-5-methylpyrazolo[1,5-a]pyrimidin-6-yl)acetic acid To a solution of methyl 2-tert-butoxy-2-(3-(3-chorophenyl)-7-chroman-6-yl)-5-methylpyrazolo[1,5-a]pyrimidin-6-yl)acetate, TFA salt (13 mg, 0.027 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (6.3 mg, 63%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (500 MHz, DMSO-d$_6$) δ ppm 0.91 (9H, br.

s.), 2.07 (2H, br. s.), 2.74 (3H, br. s.), 2.82-2.96 (2H, m), 4.27 (2H, br. s.), 5.03 (1H, s), 6.98 (1H, s), 7.28 (1H, s), 7.41 (3H, s), 8.11 (1H, s), 8.16 (1H, s), 8.17 (1H, s), 8.26 (1H, s).

| 2-tert-Butoxy-2-(3-(3-chorophenyl)-7-(8-fluoro-5-methylchroman-6-yl)-5-methylpyrazolo[1,5-a]pyrimidin-6-yl)acetic acid. | |
|---|---|
| MS (M + H)+ Calcd. | 505 |
| MS (M + H)+ Observ. | 505 |
| Retention Time | 2.86 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

Scheme 14

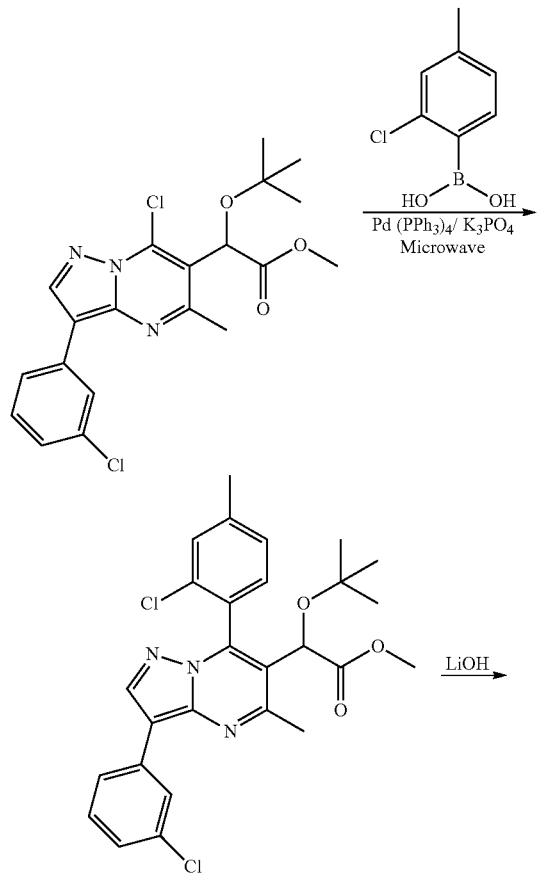

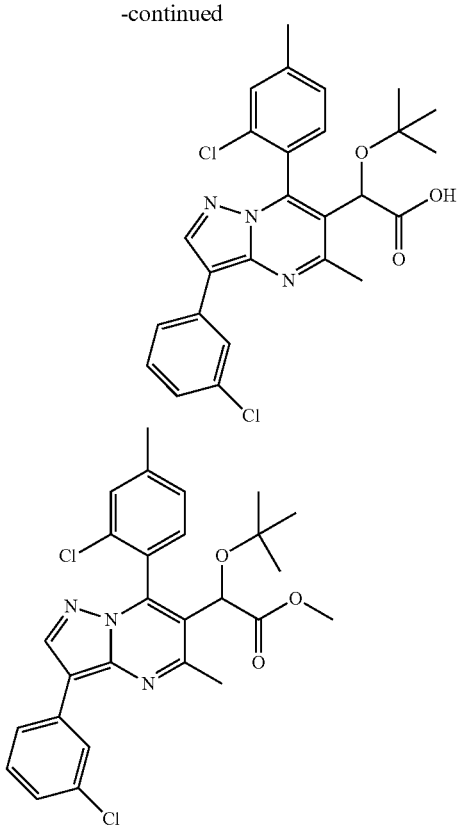

Methyl 2-tert-butoxy-2-(7-(2-chloro-4-methylphenyl)-3-(3-chlorophenyl)-5-methylpyrazolo[1,5-a]pyrimidin-6-yl)acetate, TFA salt To a 2-5 mL microwave tube was added methyl 2-tert-butoxy-2-(7-chloro-3-(3-chlorophenyl)-5-methylpyrazolo[1,5-a]pyrimidin-6-yl)acetate (25 mg, 0.059 mmol), tetrakis(triphenylphosphine)palladium(0) (10 mg, 0.008 µmol), 2-(2-chloro-4-methylphenyl)-4,4,5,5-tetramethyl-1,3,2-dioxaborolane (15 mg, 0.059 mmol), dioxane (1.5 mL), followed by 2M K₃PO₄ solution (77 uL). The reaction mixture was heated in a microwave reactor at 130° C. for 30 min. The reaction was filtered and the filtrate was purified by preparative HPLC to afford (12 mg, 39%) of the title compound as the TFA salt. Preparative HPLC condition: Phenomenex Luna C18 30×100 mm S10, 30 to 100% B over 17 mingradient, 5 min hold time, A=10% methanol 90% water 0.1% TFA, B=90% methanol 10% water 0.1% TFA. Flow rate: 40 mL/min. Compound used as is in the next step.

| Methyl 2-tert-butoxy-2-(7-(2-chloro-4-methylphenyl)-3-(3chlorophenyl)-5-methylpyrazolo[1,5-a]pyrimidin-6-yl)acetate, TFA salt. | |
|---|---|
| MS (M + H)+ Calcd. | 512 |
| MS (M + H)+ Observ. | 512 |
| Retention Time | 2.55 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |

| Methyl 2-tert-butoxy-2-(7-(2-chloro-4-methylphenyl)-3-(3chlorophenyl)-5-methylpyrazolo[1,5-a]pyrimidin-6-yl)acetate, TFA salt. | |
|---|---|
| Flow Rate | 1 mL/min |
| Wavelength | 220 |
| Solvent Pair | methanol:Water:TFA |
| Column | Phenomenex Luna 2.0 × 30 mm 3 um |

Example 134

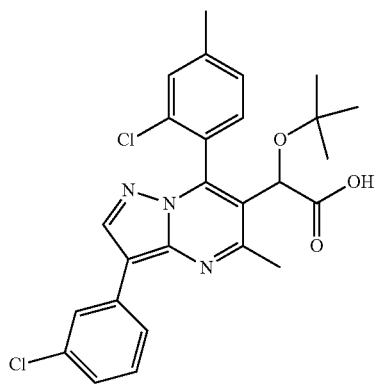 [SMILES: Cc1ccc(-c2c(C(OC(C)(C)C)C(=O)O)c(C)nc3c(-c4cccc(Cl)c4)cnn23)c(Cl)c1]

2-tert-Butoxy-2-(7-(2-chloro-4-methylphenyl)-3-(3-chlorophenyl)-5-methylpyrazolo[1,5-a]pyrimidin-6-yl)acetic acid To a solution of methyl 2-tert-butoxy-2-(7-(2-chloro-4-methylphenyl)-3-(3-chlorophenyl)-5-methylpyrazolo[1,5-a]pyrimidin-6-yl)acetate, TFA salt (10 mg, 0.027 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (3 mg, 30%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-$d_6$) δ ppm 1.02 (9H, br. s.), 2.54 (3H, br. s.), 2.82-2.96 (3H, m), 4.77 (1H, br. s.), 7.28 (1H, s), 7.41 (3H, s), 8.11 (1H, s), 8.16 (1H, s), 8.17 (1H, s), 8.26 (1H, s).

| 2-tert-Butoxy-2-(7-(2-chloro-4-methylphenyl)-3-(3chlorophenyl)-5-methylpyrazolo[1,5-a]pyrimidin-6-yl)acetic acid. | |
|---|---|
| MS (M + H)$^+$ Calcd. | 498 |
| MS (M + H)$^+$ Observ. | 498 |
| Retention Time | 3.07 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |

| 2-tert-Butoxy-2-(7-(2-chloro-4-methylphenyl)-3-(3chlorophenyl)-5-methylpyrazolo[1,5-a]pyrimidin-6-yl)acetic acid. | |
|---|---|
| Solvent Pair | Acetonitrile:Water:ammonium acetate |
| Column | Waters BEH C18, 2.0 × 50 mm |

Scheme 15

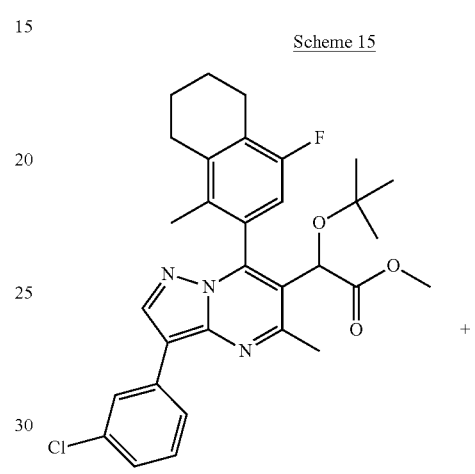

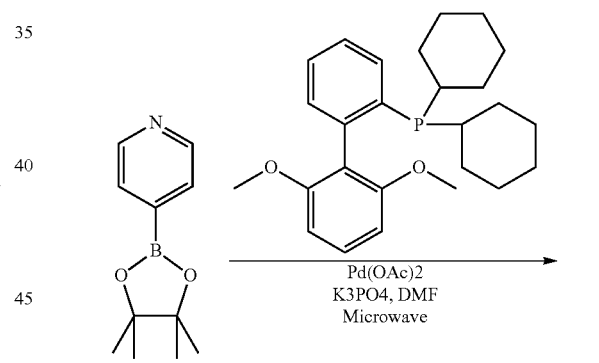

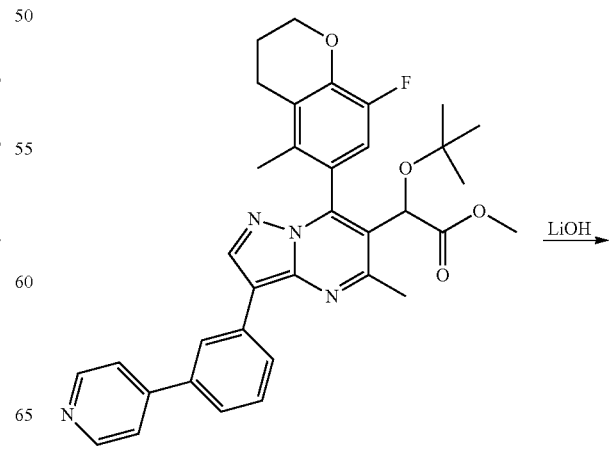

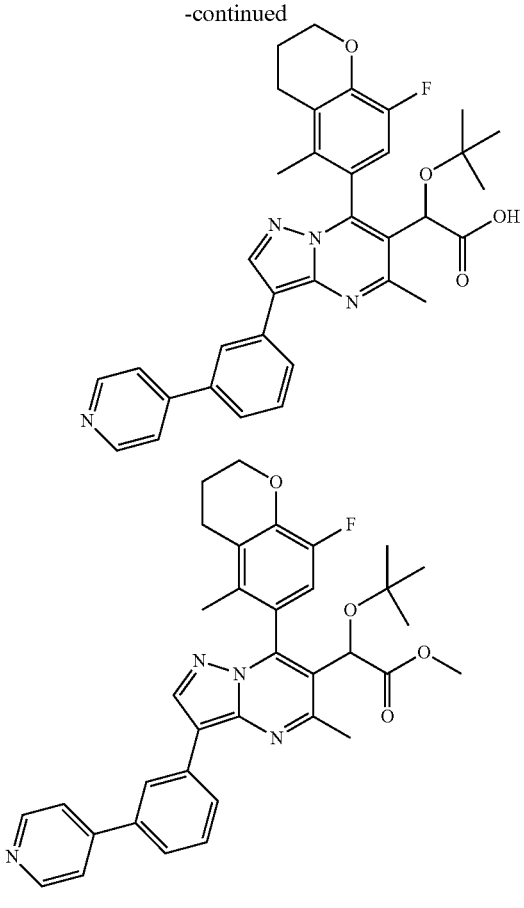

Methyl 2-(tert-butoxy)-2-(7-(8-fluoro-5-methylchroman-6-yl)-5-methyl-3-(3-(pyridin-4-yl)phenyl)pyrazolo[1,5-a]pyrimidin-6-yl)acetate To a 2-5 ml microwave tube was added methyl 2-tert-butoxy-2-(3-(3-chorophenyl)-7-(8-fluoro-5-methylchroman-6-yl)-5-methylpyrazolo[1,5-a]pyrimidin-6-yl)acetate, TFA salt. (45 mg, 0.082 mmol), dicyclohexyl(2',6'-dimethoxy-[1,1'-biphenyl]-2-yl)phosphine (16.73 mg, 0.045 mmol), palladium (II) acetate (9.15 mg, 0.045 mmol), and 4-(4,4,5,5-tetramethyl-1,3,2-dioxaborolan-2-yl)pyridine (37.1 mg, 0.181 mmol) in DMF (2 mL), followed by 2M $K_3PO_4$ (50 uL). The reaction mixture was heated by microwave at 130° C. for 30 mins. The reaction mixture was filtered and the filtrate was purified by preparative HPLC to afford (10 mg, 20%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. Compound is used as is in the next step.

| Methyl 2-(tert-butoxy)-2-(7-(8-fluoro-5-methylchroman-6-yl)-5-methyl-3-(3-(pyridin-4-yl)phenyl)pyrazolo[1,5-a]pyrimidin-6-yl)acetate. | |
|---|---|
| MS (M + H)+ Calcd. | 595 |
| MS (M + H)+ Observ. | 595 |
| Retention Time | 2.07 min |

| Methyl 2-(tert-butoxy)-2-(7-(8-fluoro-5-methylchroman-6-yl)-5-methyl-3-(3-(pyridin-4-yl)phenyl)pyrazolo[1,5-a]pyrimidin-6-yl)acetate. | |
|---|---|
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

Example 135

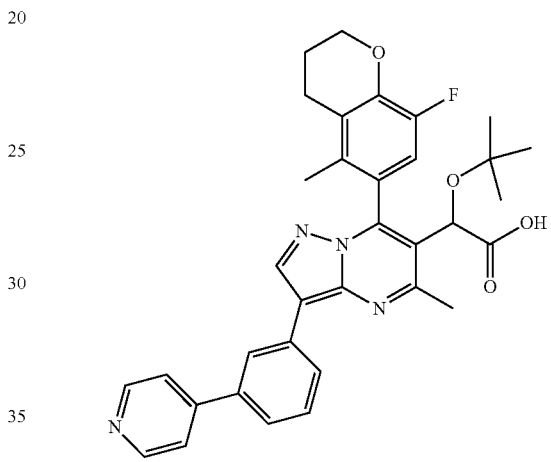

2-(tert-Butoxy)-2-(7-(8-fluoro-5-methylchroman-6-yl)-5-methyl-3-(3-(pyridin-4-yl)phenyl)pyrazolo[1,5-a]pyrimidin-6-yl)acetic acid To a solution of methyl 2-(tert-butoxy)-2-(7-(8-fluoro-5-methylchroman-6-yl)-5-methyl-3-(3-(pyridin-4-yl)phenyl)pyrazolo[1,5-a]pyrimidin-6-yl)acetate. TFA salt (8 mg, 0.013 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (4 mg, 50%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-$d_6$) δ ppm 1.1 (9H, br. s.), 2.51 (4H, br. s.), 2.74 (3H, br. s.), 2.82-3.1 (5H, m), 4.29 (1H, br. s.), 6.98 (1H, s), 7.61 (2H, m), 7.81 (2H, m), 8.31 (1H, m), 8.5 (1H, s), 8.7 (3H, m).

| 2-(tert-Butoxy)-2-(7-(8-fluoro-5-methylchroman-6-yl)-5-methyl-3-(3-(pyridin-4-yl)phenyl)pyrazolo[1,5-a]pyrimidin-6-yl)acetic acid | |
|---|---|
| MS (M + H)+ Calcd. | 581 |
| MS (M + H)+ Observ. | 581 |
| Retention Time | 2.03 min |

2-(tert-Butoxy)-2-(7-(8-fluoro-5-methylchroman-6-yl)-5-methyl-3-(3-(pyridin-4-yl)phenyl)pyrazolo[1,5-a]pyrimidin-6-yl)acetic acid LC Condition

| | |
|---|---|
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

Scheme 16

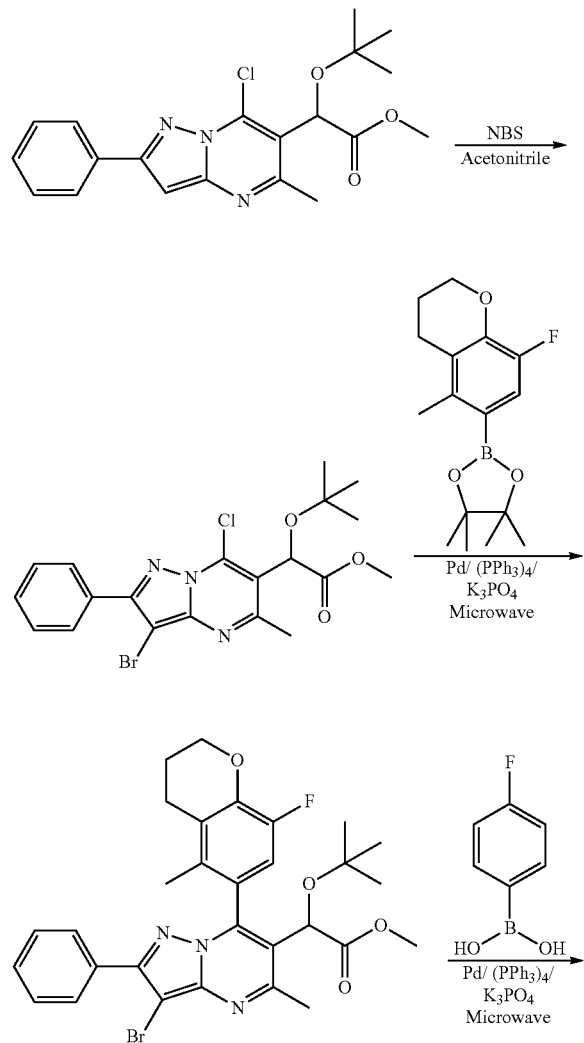

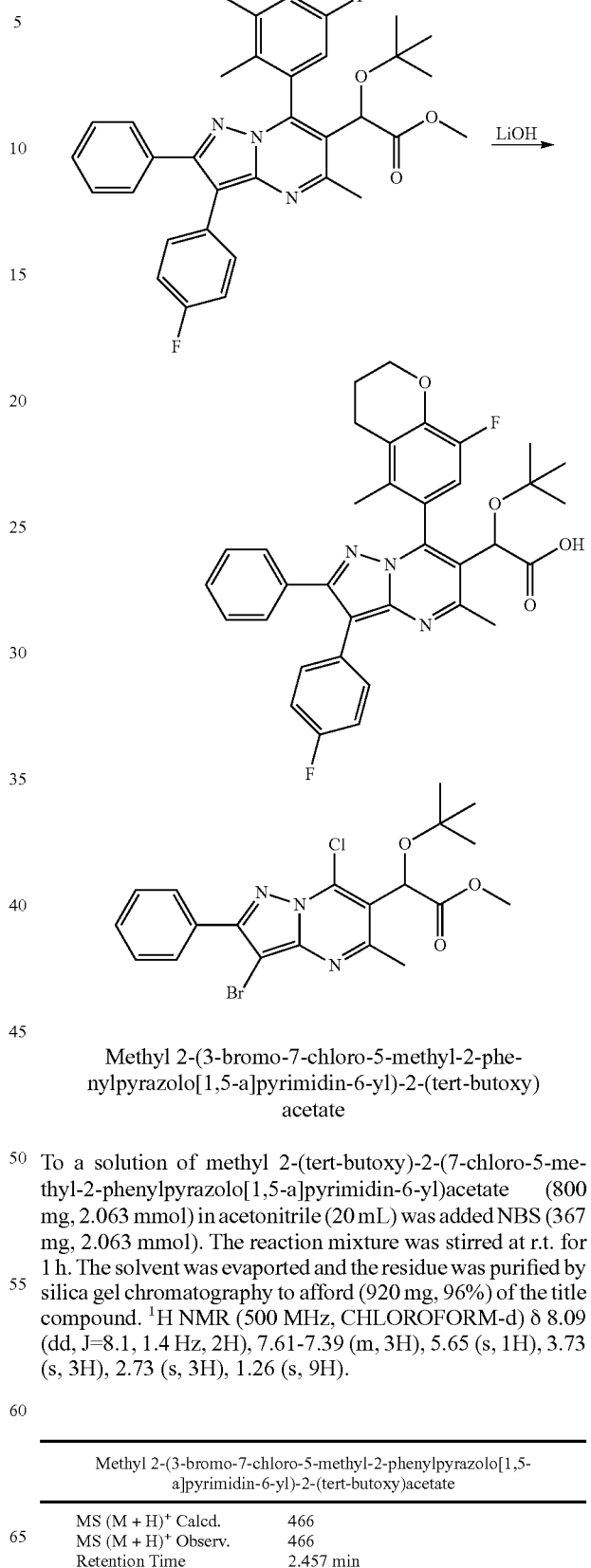

Methyl 2-(3-bromo-7-chloro-5-methyl-2-phenylpyrazolo[1,5-a]pyrimidin-6-yl)-2-(tert-butoxy)acetate To a solution of methyl 2-(tert-butoxy)-2-(7-chloro-5-methyl-2-phenylpyrazolo[1,5-a]pyrimidin-6-yl)acetate (800 mg, 2.063 mmol) in acetonitrile (20 mL) was added NBS (367 mg, 2.063 mmol). The reaction mixture was stirred at r.t. for 1 h. The solvent was evaported and the residue was purified by silica gel chromatography to afford (920 mg, 96%) of the title compound. $^1$H NMR (500 MHz, CHLOROFORM-d) δ 8.09 (dd, J=8.1, 1.4 Hz, 2H), 7.61-7.39 (m, 3H), 5.65 (s, 1H), 3.73 (s, 3H), 2.73 (s, 3H), 1.26 (s, 9H).

| Methyl 2-(3-bromo-7-chloro-5-methyl-2-phenylpyrazolo[1,5-a]pyrimidin-6-yl)-2-(tert-butoxy)acetate | |
|---|---|
| MS (M + H)$^+$ Calcd. | 466 |
| MS (M + H)$^+$ Observ. | 466 |
| Retention Time | 2.457 min |

Methyl 2-(3-bromo-7-chloro-5-methyl-2-phenylpyrazolo[1,5-a]pyrimidin-6-yl)-2-(tert-butoxy)acetate

| LC Condition | |
|---|---|
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

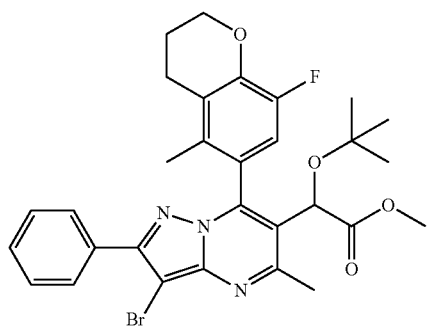 [SMILES: COC(=O)C(OC(C)(C)C)c1c(C)nc2c(Br)c(-c3ccccc3)nn2c1-c1cc(F)c2c(c1C)CCCO2]

Methyl 2-(3-bromo-7-(8-fluoro-5-methylchroman-6-yl)-5-methyl-2-phenylpyrazolo[1,5-a]pyrimidin-6-yl)-2-(tert-butoxy)acetate To a 2-5 ml microwave tube was added methyl 2-(3-bromo-7-chloro-5-methyl-2-phenylpyrazolo[1,5-a]pyrimidin-6-yl)-2-(tert-butoxy)acetate (290 mg, 0.621 mmol), tetrakis(triphenylphosphine)palladium(0) (71.8 mg, 0.062 mmol), 2-(8-fluoro-5-methylchroman-6-yl)-4,4,5,5-tetramethyl-1,3,2-dioxaborolane (200 mg, 0.683 mmol), DMF (2 mL) followed by 2M $K_2CO_3$ solution (200 µl). The reaction mixture was heated in a microwave reactor at 110° C. for 40 min. The reaction mixture was filtered and the filtrate was purified by silica gel chromatography to afford (35 mg, 9.4%) of the title compound. $^1$H NMR (500 MHz, CHLOROFORM-d) δ 7.90 (dd, J=8.1, 1.4 Hz, 2H), 7.53-7.32 (m, 3H), 6.86 (d, J=10.7 Hz, 1H), 5.02 (s, 1H), 4.48-4.18 (m, 2H), 3.64 (s, 3H), 2.82 (s, 3H), 2.75 (t, J=6.4 Hz, 2H), 2.20-2.12 (m, 2H), 1.84 (s, 3H), 1.16 (s, 9H).

| Methyl 2-(3-bromo-7-(8-fluoro-5-methylchroman-6-yl)-5-methyl-2-phenylpyrazolo[1,5-a]pyrimidin-6-yl)-2-(tert-butoxy)acetate | |
|---|---|
| MS (M + H)$^+$ Calcd. | 596 |
| MS (M + H)$^+$ Observ. | 596 |
| Retention Time | 2.515 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |

Methyl 2-(3-bromo-7-(8-fluoro-5-methylchroman-6-yl)-5-methyl-2-phenylpyrazolo[1,5-a]pyrimidin-6-yl)-2-(tert-butoxy)acetate

| Solvent Pair | Methanol:Water:TFA |
|---|---|
| Column | Phenomenex Luna 2.0 × 30 mm 3 um |

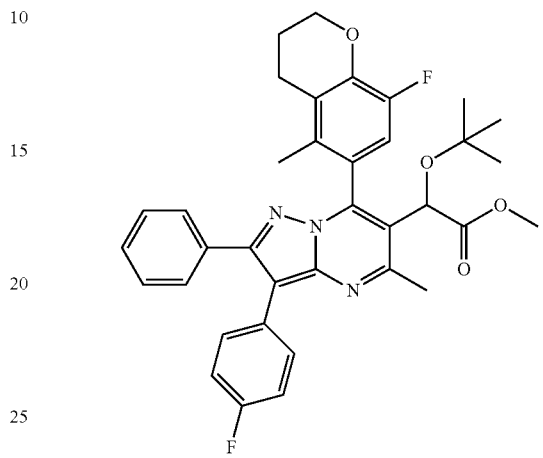

Methyl 2-(tert-butoxy)-2-(7-(8-fluoro-5-methylchroman-6-yl)-3-(4-fluorophenyl)-5-methyl-2-phenylpyrazolo[1,5-a]pyrimidin-6-yl)acetate, TFA salt To a 2-5 ml microwave tube was added dicyclohexyl(2',6'-dimethoxy-[1,1'-biphenyl]-2-yl)phosphine (12 mg, 0.029 mmol), palladium acetate (6.59 mg, 0.029 mmol), (4-fluorophenyl)boronic acid (16.42 mg, 0.117 mmol) and methyl 2-(3-bromo-7-(8-fluoro-5-methylchroman-6-yl)-5-methyl-2-phenylpyrazolo[1,5-a]pyrimidin-6-yl)-2-(tert-butoxy)acetate (35 mg, 0.059 mmol), DMF (1 mL), followed by 2M $K_3PO_4$ (50 µl). The reaction mixture was heated in a microwave reactor at 120° C. for 20 min. The reaction mixture was filtered and the filtrate was purified by PrepHPLC to afford (24 mg, 56.4%) of the title compound as TFA salt. $^1$H NMR (400 MHz, CHLOROFORM-d) δ 7.58-7.44 (m, 4H), 7.35-7.29 (m, 3H), 7.12-7.02 (m, 2H), 6.93 (d, J=10.8 Hz, 1H), 5.04 (s, 1H), 4.38-4.30 (m, 2H), 3.66 (s, 3H), 2.83-2.72 (m, 5H), 2.25-2.12 (m, 2H), 1.92 (s, 3H), 1.19 (s, 9H).

| Methyl 2-(tert-butoxy)-2-(7-(8-fluoro-5-methylchroman-6-yl)-3-(4-fluorophenyl)-5-methyl-2-phenylpyrazolo[1,5-a]pyrimidin-6-yl)acetate, TFA salt. | |
|---|---|
| MS (M + H)$^+$ Calcd. | 612 |
| MS (M + H)$^+$ Observ. | 612 |
| Retention Time | 2.621 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 136

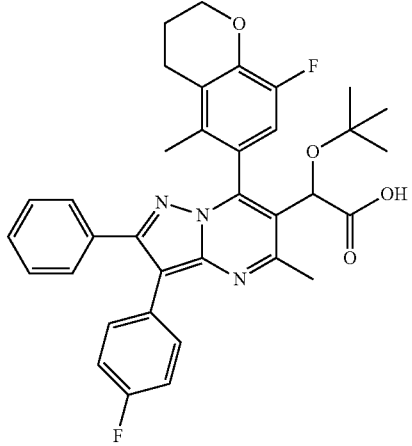 [SMILES: Cc1nc2c(-c3ccc(F)cc3)c(-c3ccccc3)nn2c(-c2cc(F)c3c(c2C)CCCO3)c1C(OC(C)(C)C)C(=O)O]

2-(tert-Butoxy)-2-(7-(8-fluoro-5-methylchroman-6-yl)-3-(4-fluorophenyl)-5-methyl-2-phenylpyrazolo[1,5-a]pyrimidin-6-yl)acetic acid To a solution of methyl 2-(tert-butoxy)-2-(7-(8-fluoro-5-methylchroman-6-yl)-3-(4-fluorophenyl)-5-methyl-2-phenylpyrazolo[1,5-a]pyrimidin-6-yl)acetate, TFA salt (22 mg, 0.030 mmol) in Dioxane (0.8 mL) was added 1N NaOH aqueous solution (0.8 mL, 0.8 mmol). The reaction mixture was stirred at 50° C. for 4 h. The reaction mixture was filtered and purified by preparative HPLC to afford (17 mg, 94%) of the title compound. Preparative HPLC condition: Waters Sunfire OBD C18 30×100 mm 5 u, 15 to 60% B over 18 minute gradient, 2 minute hold time, A=5% acetonitrile 95% water 10 mM Ammonium Acetate, B=95% acetonitrile 5% water 10 mM Ammonium Acetate. Flow rate: 40 ml/min. $^1$H NMR (400 MHz, DMSO-$d_6$) δ 7.97 (s, 1H), 7.48 (dd, J=8.5, 5.5 Hz, 2H), 7.37 (s, 5H), 7.24 (t, J=8.8 Hz, 2H), 7.13 (d, J=11.3 Hz, 1H), 4.83 (s, 1H), 4.27 (t, J=4.9 Hz, 2H), 2.70 (s, 3H), 2.16-1.96 (m, J=4.5 Hz, 2H), 1.86 (s, 3H), 1.09 (s, 9H).

| 2-(tert-Butoxy)-2-(7-(8-fluoro-5-methylchroman-6-yl)-3-(4-fluorophenyl)-5-methyl-2-phenylpyrazolo[1,5-a]pyrimidin-6-yl)acetic acid | |
|---|---|
| MS (M + H)$^+$ Calcd. | 598 |
| MS (M + H)$^+$ Observ. | 598 |
| Retention Time | 3.29 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

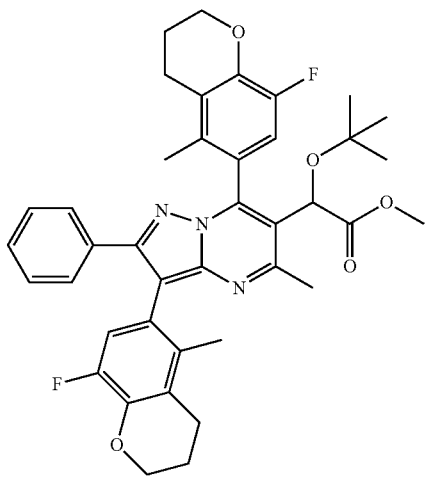 [SMILES: COC(=O)C(OC(C)(C)C)c1c(C)nc2c(-c3cc(F)c4c(c3C)CCCO4)c(-c3ccccc3)nn2c1-c1cc(F)c2c(c1C)CCCO2]

Methyl 2-(3,7-bis(8-fluoro-5-methylchroman-6-yl)-5-methyl-2-phenylpyrazolo[1,5-a]pyrimidin-6-yl)-2-(tert-butoxy)acetate, TFA salt To a 2-5 ml microwave tube was added dicyclohexyl(2',6'-dimethoxy-[1,1'-biphenyl]-2-yl)phosphine (12 mg, 0.029 mmol), palladium acetate (6.59 mg, 0.029 mmol), 8-fluoro-5-methylchroman-6-yl boronic acid (17 mg, 0.059 mmol), and methyl 2-(3-bromo-7-(8-fluoro-5-methylchroman-6-yl)-5-methyl-2-phenylpyrazolo[1,5-a]pyrimidin-6-yl)-2-(tert-butoxy)acetate (35 mg, 0.059 mmol), DMF (1 mL), followed by 2M $K_3PO_4$ (50 μl). The reaction mixture was heated in a microwave reactor at 120° C. for 20 min. The reaction mixture was filtered and the filtrate was purified by PrepHPLC to afford (24 mg, 56.4%) of the title compound as TFA salt. Used as is in the next step.

| Methyl 2-(3,7-bis(8-fluoro-5-methylchroman-6-yl)-5-methyl-2-phenylpyrazolo[1,5-a]pyrimidin-6-yl)-2-(tert-butoxy)acetate, TFA salt. | |
|---|---|
| MS (M + H)$^+$ Calcd. | 682 |
| MS (M + H)$^+$ Observ. | 682 |
| Retention Time | 2.4 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 137

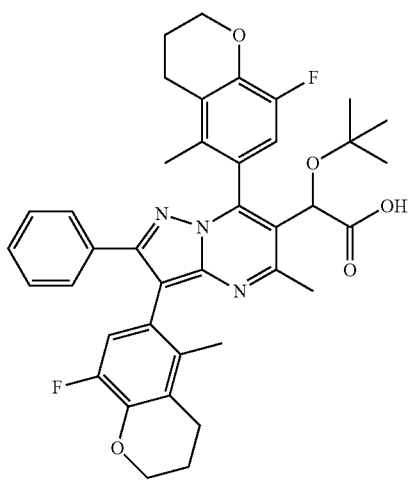 [SMILES: Cc1nc2c(-c3cc(F)c4c(c3C)CCCO4)c(-c3ccccc3)nn2c(-c2cc(F)c3c(c2C)CCCO3)c1C(OC(C)(C)C)C(=O)O]

2-(3,7-Bis(8-fluoro-5-methylchroman-6-yl)-5-methyl-2-phenylpyrazolo[1,5-a]pyrimidin-6-yl)-2-(tert-butoxy)acetic acid To a solution of methyl 2-(3,7-bis(8-fluoro-5-methylchroman-6-yl)-5-methyl-2-phenylpyrazolo[1,5-a]pyrimidin-6-yl)-2-(tert-butoxy)acetate, TFA salt, (10 mg, 0.030 mmol) in Dioxane (0.8 mL) was added 1 N LiOH aqueous solution (0.8 mL, 0.8 mmol). The reaction mixture was stirred at 50° C. for 4 h. The reaction mixture was filtered and purified by preparative HPLC to afford (5 mg, 94%) of the title compound. Preparative HPLC condition: Waters Sunfire OBD C18 30×100 mm 5 u, 15 to 60% B over 18 minute gradient, 2 minute hold time, A=5% acetonitrile 95% water 10 mM Ammonium Acetate, B=95% acetonitrile 5% water 10 mM Ammonium Acetate. Flow rate: 40 ml/min. $^1$H NMR (400 MHz, DMSO-$d_6$) δ 7.97 (s, 1H), 7.34 (dd, J=8.5, 5.5 Hz, 1H), 7.30 (s, 3H), 7.29 (t, J=8.8 Hz, 1H), 6.95 (d, J=11.3 Hz, 1H), 4.83 (s, 1H), 4.27 (t, J=4.9 Hz, 4H), 2.70 (s, 6H), 2.5-1.96 (m, J=4.5 Hz, 8H), 1.86 (s, 3H), 1.09 (s, 9H).

| 2-(3,7-Bis(8-fluoro-5-methylchroman-6-yl)-5-methyl-2-phenylpyrazolo[1,5-a]pyrimidin-6-yl)-2-(tert-butoxy)acetic acid. | |
|---|---|
| MS (M + H)$^+$ Calcd. | 668 |
| MS (M + H)$^+$ Observ. | 668 |
| Retention Time | 2.44 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-µm particles |

Scheme 17

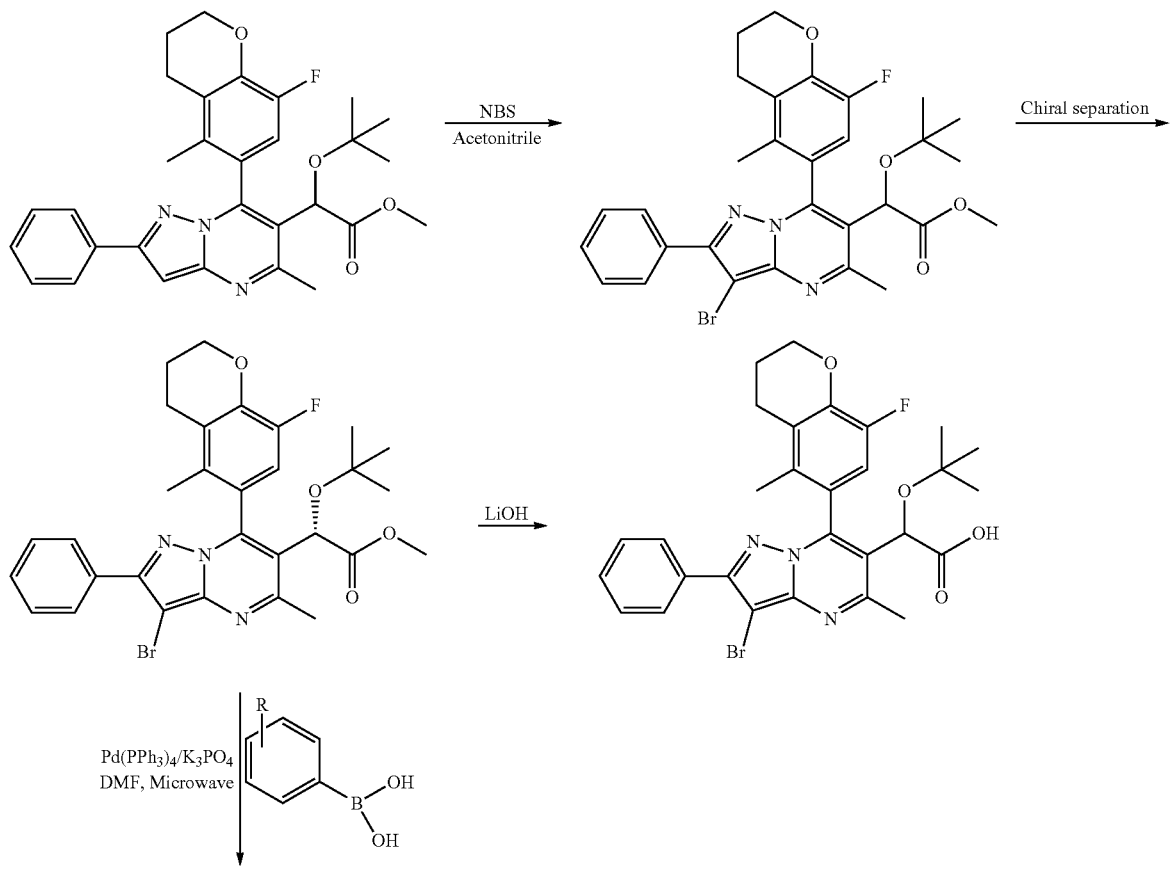

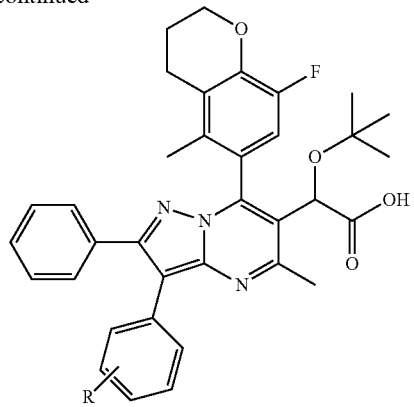

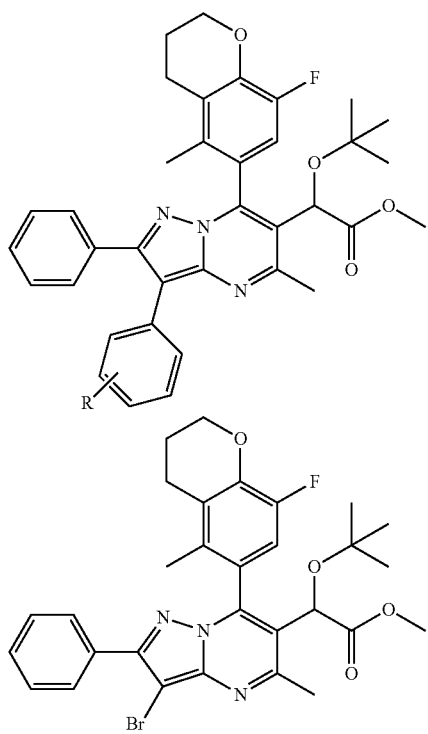

Methyl 2-(3-bromo-7-(8-fluoro-5-methylchroman-6-yl)-5-methyl-2-phenylpyrazolo[1,5-a]pyrimidin-6-yl)-2-(tert-butoxy)acetate To a solution of methyl 2-(tert-butoxy)-2-(7-(8-fluoro-5-methylchroman-6-yl)-3,5-dimethyl-2-phenylpyrazolo[1,5-a]pyrimidin-6-yl)acetate (350 mg, 0.676 mmol) in acetonitrile (20 mL) was added N-bromosuccinimide (119 mg, 0.676 mmol). The reaction mixture was stirred at r.t. for 1 h. The solvent was evaported and the residue was purified by silica gel chromatography to afford (210 mg, 52%) of the title compound.

$^1$H NMR (500 MHz, CHLOROFORM-d) δ 1.16 (s, 9H), 1.56 (s, 2H), 1.84 (s, 3H), 2.15 (br. s., 2H), 2.77 (d, 5H), 3.64 (s, 3H), 4.32 (s, 2H), 5.02 (s, 1H), 6.85 (s, 1H), 7.90 (s, 2H).

| Methyl 2-(3-bromo-7-chloro-5-methyl-2-phenylpyrazolo[1,5-a]pyrimidin-6-yl)-2-(tert-butoxy)acetate | |
|---|---|
| MS (M + H)$^+$ Calcd. | 596 |
| MS (M + H)$^+$ Observ. | 596 |
| Retention Time | 2.93 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

(2S)-Methyl 2-(3-bromo-7-(8-fluoro-5-methylchroman-6-yl)-5-methyl-2-phenylpyrazolo[1,5-a]pyrimidin-6-yl)-2-(tert-butoxy)acetate Chiral separation of methyl 2-(3-bromo-7-(8-fluoro-5-methylchroman-6-yl)-5-methyl-2-phenylpyrazolo[1,5-a]pyrimidin-6-yl)-2-(tert-butoxy)acetate using preparative chiral SFC resulted in the title compound 100 mg, RT 5.43 min (50% yield). Preparative chiral SFC condition: Chiralpak AD-H preparative column, 30×250 mm, 5 μm, Mobile Phase: 15% MeOH in CO$_2$ @ 150 Bar, Temp: 35° C., Flow rate: 70 mL/min for 10 min. UV monitored at 264 nm. Injection 0.35 mL of 35 mg/mL solution in 2:1 chloroform:methanol using stacked injections.

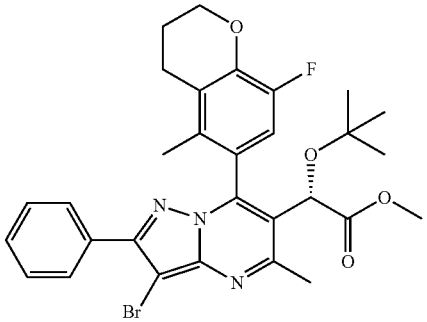 [SMILES: COC(=O)[C@@H](OC(C)(C)C)c1c(C)nc2c(Br)c(-c3ccccc3)nn2c1-c1cc(F)c2c(c1C)CCCO2]

$^1$H NMR (500 MHz, CHLOROFORM-d) δ 1.16 (s, 9H), 1.56 (s, 2H), 1.84 (s, 3H), 2.15 (br. s., 2H), 2.77 (d, 5H), 3.64 (s, 3H), 4.32 (s, 2H), 5.02 (s, 1H), 6.85 (s, 1H), 7.90 (s, 2H).

Example 138

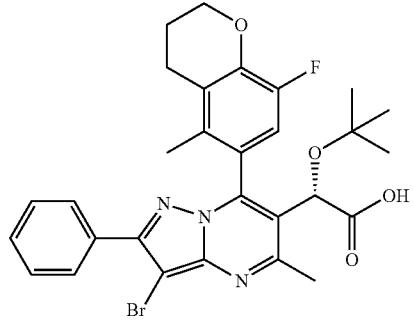 [SMILES: Cc1nc2c(Br)c(-c3ccccc3)nn2c(-c2cc(F)c3c(c2C)CCCO3)c1[C@H](OC(C)(C)C)C(=O)O]

(2S)-2-(3-Bromo-7-(8-fluoro-5-methylchroman-6-yl)-5-methyl-2-phenylpyrazolo[1,5-a]pyrimidin-6-yl)-2-(tert-butoxy)acetic acid To a solution of (2S)-methyl 2-(3-bromo-7-(8-fluoro-5-methylchroman-6-yl)-5-methyl-2-phenylpyrazolo[1,5-a]pyrimidin-6-yl)-2-(tert-butoxy)acetate. TFA salt, (10 mg, 0.017 mmol) in dioxane (0.5 mL) was added 1.0 N LiOH aqueous solution (0.5 mL, 0.5 mmol). The reaction mixture was stirred at 60° C. for 48 h. The reaction mixture was filtered and the filtrate was purified by preparative HPLC to afford (5 mg, 50%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H NMR (400 MHz, DMSO-$d_6$) δ 1.16 (s, 9H), 1.56 (s, 2H), 1.84 (s, 3H), 2.15 (br. s., 2H), 2.77 (d, 5H), 4.32 (s, 2H), 5.02 (s, 1H), 6.85 (s, 1H), 7.90 (s, 2H).

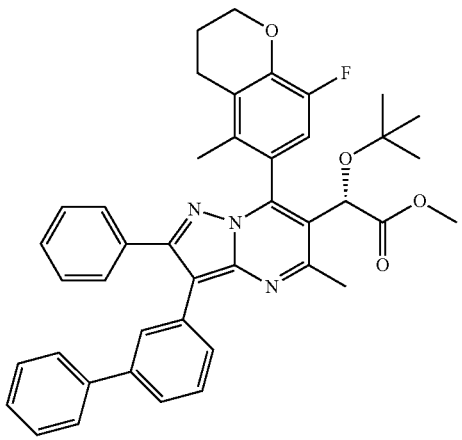 [SMILES: COC(=O)[C@@H](OC(C)(C)C)c1c(C)nc2c(-c3cccc(-c4ccccc4)c3)c(-c3ccccc3)nn2c1-c1cc(F)c2c(c1C)CCCO2]

(2S)-Methyl 2-(3-([1,1'-biphenyl]-3-yl)-7-(8-fluoro-5-methylchroman-6-yl)-5-methyl-2-phenylpyrazolo[1,5-a]pyrimidin-6-yl)-2-(tert-butoxy)acetate, TFA salt To a 2-5 ml microwave tube was added tetrakis(triphenylphosphine)palladium(0) (5.8 mg, 0.029 mmol), (1,1'-biphenyl)-3-ylboronic acid (7 mg, 0.117 mmol) and (2S)-methyl 2-(3-bromo-7-(8-fluoro-5-methylchroman-6-yl)-5-methyl-2-phenylpyrazolo[1,5-a]pyrimidin-6-yl)-2-(tert-butoxy)acetate (20 mg, 0.034 mmol), DMF (1 mL), followed by 2M $K_3PO_4$ (50 µl). The reaction mixture was heated in a microwave reactor at 130° C. for 20 min. The reaction mixture was filtered and the filtrate was purified by PrepHPLC to afford (20 mg, 77%) of the title compound as TFA salt. $^1$H NMR (400 MHz, CHLOROFORM-d) δ 7.7 (s, 1H), 7.5-7.25 (m, 13H), 6.93 (s, 1H), 5.04 (s, 1H), 4.31-4.30 (m, 2H), 3.66 (s, 3H), 2.74-2.79 (m, 5H), 2.25-2.12 (m, 2H), 1.92 (s, 3H), 1.17 (s, 9H).

| (2S)-2-(3-Bromo-7-(8-fluoro-5-methylchroman-6-yl)-5-methyl-2-phenylpyrazolo[1,5-a]pyrimidin-6-yl)-2-(tert-butoxy)acetic acid. | |
|---|---|
| MS (M + H)$^+$ Calcd. | 584 |
| MS (M + H)$^+$ Observ. | 584 |
| Retention Time | 2.81 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

| (2S)-Methyl 2-(3-([1,1'-biphenyl]-3-yl)-7-(8-fluoro-5-methylchroman-6-yl)-5-methyl-2-phenylpyrazolo[1,5-a]pyrimidin-6-yl)-2-(tert-butoxy)acetate, TFA salt. | |
|---|---|
| MS (M + H)$^+$ Calcd. | 670 |
| MS (M + H)$^+$ Observ. | 670 |
| Retention Time | 2.641 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 139

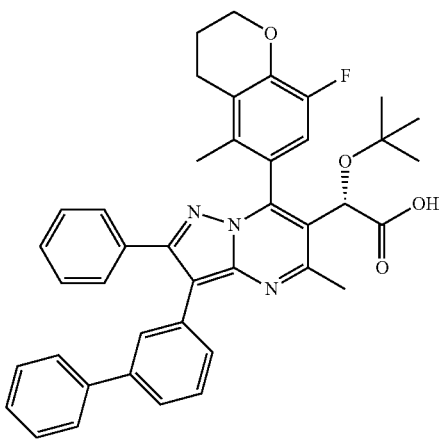 [SMILES: Cc1nc2c(-c3cccc(-c4ccccc4)c3)c(-c3ccccc3)nn2c(-c2cc(F)c3c(c2C)CCCO3)c1[C@H](OC(C)(C)C)C(=O)O]

(2S)-2-(3-([1,1'-Biphenyl]-3-yl)-7-(8-fluoro-5-methylchroman-6-yl)-5-methyl-2-phenylpyrazolo[1,5-a]pyrimidin-6-yl)-2-(tert-butoxy)acetic acid To a solution of (2S)-methyl 2-(3-([1,1'-biphenyl]-3-yl)-7-(8-fluoro-5-methylchroman-6-yl)-5-methyl-2-phenylpyrazolo[1,5-a]pyrimidin-6-yl)-2-(tert-butoxy)acetate, TFA salt. (20 mg, 0.030 mmol) in dioxane (0.5 mL) was added 1.0 N LiOH aqueous solution (0.5 mL, 0.5 mmol). The reaction mixture was stirred at 60° C. for 48 h. The reaction mixture was filtered and the filtrate was purified by preparative HPLC to afford (5 mg, 25%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min.

$^1$H NMR (400 MHz, DMSO-$d_6$) δ 7.7 (s, 1H), 7.5-7.25 (m, 13H), 6.93 (s, 1H), 5.04 (s, 1H), 4.31-4.30 (m, 2H), 2.74-2.79 (m, 5H), 2.25-2.12 (m, 2H), 1.92 (s, 3H), 1.17 (s, 9H).

| (2S)-2-(3-([1,1'-Biphenyl]-3-yl)-7-(8-fluoro-5-methylchroman-6-yl)-5-methyl-2-phenylpyrazolo[1,5-a]pyrimidin-6-yl)-2-(tert-butoxy)acetic acid. | |
|---|---|
| MS (M + H)$^+$ Calcd. | 655 |
| MS (M + H)$^+$ Observ. | 655 |
| Retention Time | 3.5 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

Examples 140-142 were prepared using the procedure similar to example 139

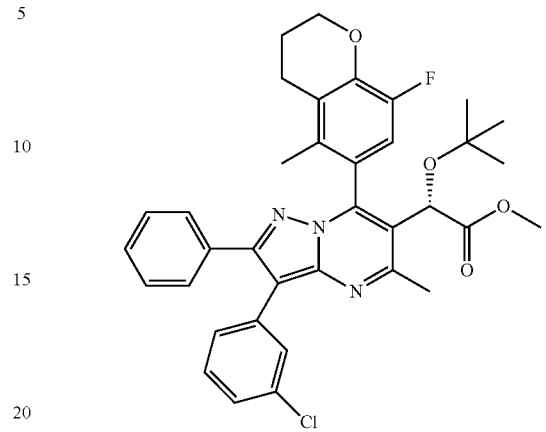

(2S)-Methyl 2-(tert-butoxy)-2-(3-(3-chlorophenyl)-7-(8-fluoro-5-methylchroman-6-yl)-5-methyl-2-phenylpyrazolo[1,5-a]pyrimidin-6-yl)acetate, TFA salt To a 2-5 ml microwave tube was added tetrakis(triphenylphosphine)palladium(0) (5.8 mg, 0.005 mmol), (3-chlorphenyl)-boronic acid (5.2 mg, 0.034 mmol) and (2S)-methyl 2-(3-bromo-7-(8-fluoro-5-methylchroman-6-yl)-5-methyl-2-phenylpyrazolo[1,5-a]pyrimidin-6-yl)-2-(tert-butoxy)acetate (20 mg, 0.034 mmol), DMF (1 mL), followed by 2M $K_3PO_4$ (50 µl). The reaction mixture was heated in a microwave reactor at 130° C. for 30 min. The reaction mixture was filtered and the filtrate was purified by PrepHPLC to afford (10 mg, 48%) of the title compound as TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. Product used as is in the next reaction.

| (2S)-Methyl 2-(tert-butoxy)-2-(3-(3-chlorophenyl)-7-(8-fluoro-5-methylchroman-6-yl)-5-methyl-2-phenylpyrazolo[1,5-a]pyrimidin-6-yl)acetate, TFA salt. | |
|---|---|
| MS (M + H)$^+$ Calcd. | 628 |
| MS (M + H)$^+$ Observ. | 628 |
| Retention Time | 2.59 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 140

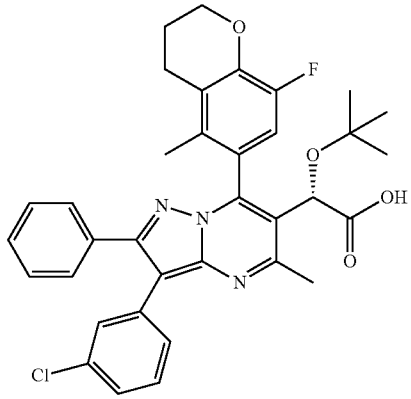 [SMILES: Cc1nc2c(-c3cccc(Cl)c3)c(-c3ccccc3)nn2c(-c2cc(F)c3c(c2C)CCCO3)c1[C@H](OC(C)(C)C)C(=O)O]

(2S)-2-(tert-Butoxy)-2-(3-(3-chlorophenyl)-7-(8-fluoro-5-methylchroman-6-yl)-5-methyl-2-phenylpyrazolo[1,5-a]pyrimidin-6-yl)acetic acid To a solution of (2S)-methyl 2-(3-([1,1'-biphenyl]-3-yl)-7-(8-fluoro-5-methylchroman-6-yl)-5-methyl-2-phenylpyrazolo[1,5-a]pyrimidin-6-yl)-2-(tert-butoxy)acetate, TFA salt (10 mg, 0.016 mmol) in dioxane (0.5 mL) was added 1.0 N LiOH aqueous solution (0.5 mL, 0.5 mmol). The reaction mixture was stirred at 60° C. for 48 h. The reaction mixture was filtered and the filtrate was purified by preparative HPLC to afford (3 mg, 30%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-$d_6$) δ ppm 1.084 (9H, br. s.), 1.866 (2H, br. s.), 2.51 (2H, br. s.), 2.71 (3H, br. s.) 2.82-2.96 (2H, m), 4.29 (2H, br. s.), 4.6 (1H, s), 7.06 (1H, s), 7.33-7.39 (8H, m), 7.54 (1H, s).

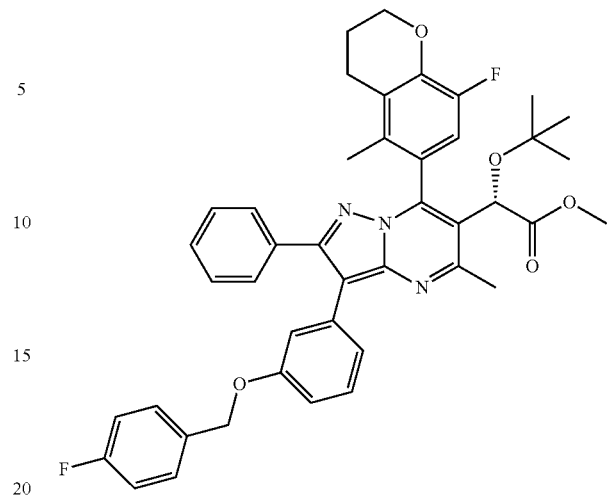

(2S)-Methyl 2-(tert-butoxy)-2-(7-(8-fluoro-5-methylchroman-6-yl)-3-(3-((4-fluorobenzyl)oxy)phenyl)-5-methyl-2-phenylpyrazolo[1,5-a]pyrimidin-6-yl)acetate, TFA salt To a 2-5 ml microwave tube was added tetrakis(triphenylphosphine)palladium(0) (5.8 mg, 0.005 mmol), (3-((4-fluorobenzyl)oxy)phenyl)boronic acid (8.3 mg, 0.034 mmol) and (2S)-methyl 2-(3-bromo-7-(8-fluoro-5-methylchroman-6-yl)-5-methyl-2-phenylpyrazolo[1,5-a]pyrimidin-6-yl)-2-(tert-butoxy)acetate (20 mg, 0.034 mmol), DMF (1 mL), followed by 2M $K_3PO_4$ (50 μl). The reaction mixture was heated in a microwave reactor at 130° C. for 30 min. The reaction mixture was filtered and the filtrate was purified by PrepHPLC to afford (10 mg, 48%) of the title compound as TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. Product used as is in the next reaction.

| (2S)-2-(tert-Butoxy)-2-(3-(3-chlorophenyl)-7-(8-fluoro-5-methylchroman-6-yl)-5-methyl-2-phenylpyrazolo[1,5-a]pyrimidin-6-yl)acetic acid | |
|---|---|
| MS (M + H)$^+$ Calcd. | 614 |
| MS (M + H)$^+$ Observ. | 614 |
| Retention Time | 2.59 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

| (2S)-Methyl 2-(tert-butoxy)-2-(7-(8-fluoro-5-methylchroman-6-yl)-3-(3-((4-fluorobenzyl)oxy)phenyl)-5-methyl-2-phenylpyrazolo[1,5-a]pyrimidin-6-yl)acetate, TFA salt | |
|---|---|
| MS (M + H)$^+$ Calcd. | 718 |
| MS (M + H)$^+$ Observ. | 718 |
| Retention Time | 2.91 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 141

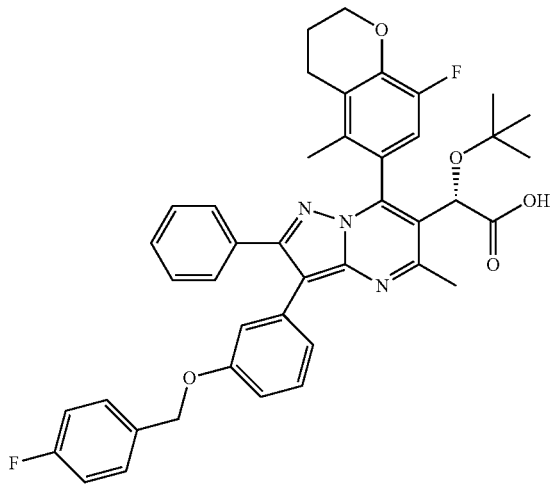 [SMILES: Cc1nc2c(-c3cccc(OCc4ccc(F)cc4)c3)c(-c3ccccc3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-3-(3-((4-fluorobenzyl)oxy)phenyl)-5-methyl-2-phenylpyrazolo[1,5-a]pyrimidin-6-yl)acetic acid To a solution of (2S)-methyl 2-(tert-butoxy)-2-(7-(8-fluoro-5-methylchroman-6-yl)-3-(3-((4-fluorobenzyl)oxy)phenyl)-5-methyl-2-phenylpyrazolo[1,5-a]pyrimidin-6-yl)acetate TFA salt (10 mg, 0.014 mmol) in dioxane (0.5 mL) was added 1.0 N LiOH aqueous solution (0.5 mL, 0.5 mmol). The reaction mixture was stirred at 60° C. for 48 h. The reaction mixture was filtered and the filtrate was purified by preparative HPLC to afford (5 mg, 50%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-$d_6$) δ ppm 1.087 (9H, br. s.), 1.88 (2H, br. s.), 2.51 (2H, br. s.), 2.71 (3H, br. s.) 2.82-2.96 (2H, m), 4.29 (2H, br. s.), 4.6 (1H, s), 5.02 (2H, s), 6.9 (1H, s), 7.14-7.47 (12H, m), 7.97 (1H, s).

| (2S)-2-(tert-Butoxy)-2-(7-(8-fluoro-5-methylchroman-6-yl)-3-(3-((4-fluorobenzyl)oxy)phenyl)-5-methyl-2-phenylpyrazolo[1,5-a]pyrimidin-6-yl)acetic acid | |
|---|---|
| MS (M + H)$^+$ Calcd. | 704 |
| MS (M + H)$^+$ Observ. | 704 |
| Retention Time | 3.56 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

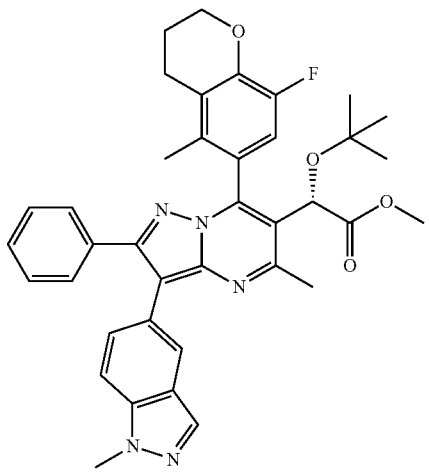 [SMILES: COC(=O)[C@@H](OC(C)(C)C)c1c(C)nc2c(-c3ccc4c(cnn4C)c3)c(-c3ccccc3)nn2c1-c1cc(F)c2c(c1C)CCCO2]

(2S)-Methyl 2-(tert-butoxy)-2-(7-(8-fluoro-5-methylchroman-6-yl)-5-methyl-3-(1-methyl-1H-indazol-5-yl)-2-phenylpyrazolo[1,5-a]pyrimidin-6-yl)acetate, TFA salt To a 2-5 ml microwave tube was added tetrakis(triphenylphosphine)palladium(0) (5.8 mg, 0.005 mmol), (1-methyl-1H-indazol-5-yl)boronic acid (5.2 mg, 0.034 mmol) and (2S)-methyl 2-(3-bromo-7-(8-fluoro-5-methylchroman-6-yl)-5-methyl-2-phenylpyrazolo[1,5-a]pyrimidin-6-yl)-2-(tert-butoxy)acetate (20 mg, 0.034 mmol), DMF (1 mL), followed by 2M K$_3$PO$_4$ (50 µl). The reaction mixture was heated in a microwave reactor at 130° C. for 30 min. The reaction mixture was filtered and the filtrate was purified by PrepHPLC to afford (10 mg, 48%) of the title compound as TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min.

| (2S)-methyl 2-(tert-butoxy)-2-(7-(8-fluoro-5-methylchroman-6-yl)-5-methyl-3-(1-methyl-1H-indazol-5-yl)-2-phenylpyrazolo[1,5-a]pyrimidin-6-yl)acetate, TFA salt. | |
|---|---|
| MS (M + H)$^+$ Calcd. | 648 |
| MS (M + H)$^+$ Observ. | 648 |
| Retention Time | 2.3 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 142

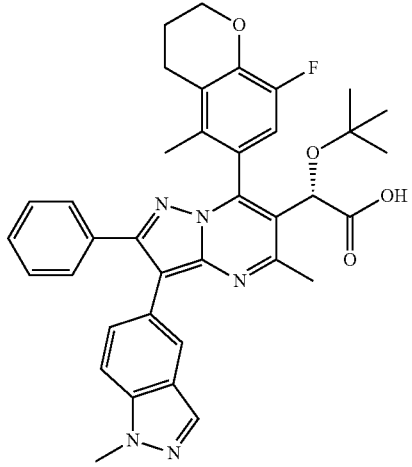 [SMILES: Cc1nc2c(-c3ccc4c(cnn4C)c3)c(-c3ccccc3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-5-methyl-3-(1-methyl-1H-indazol-5-yl)-2-phenylpyrazolo[1,5-a]pyrimidin-6-yl)acetic acid To a solution of (2S)-methyl 2-(tert-butoxy)-2-(7-(8-fluoro-5-methylchroman-6-yl)-5-methyl-3-(1-methyl-1H-indazol-5-yl)-2-phenylpyrazolo[1,5-a]pyrimidin-6-yl)acetate, TFA salt (10 mg, 0.014 mmol) in dioxane (0.5 mL) was added 1.0 N LiOH aqueous solution (0.5 mL, 0.5 mmol). The reaction mixture was stirred at 80° C. for 3 h. The reaction mixture was filtered and the filtrate was purified by preparative HPLC to afford (3 mg, 30%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-d$_6$) δ ppm 1.09 (9H, br. s.), 1.88 (2H, br. s.), 2.51 (2H, br. s.), 2.71 (3H, br. s.) 2.82-2.96 (2H, m), 4.29 (2H, br. s.), 4.6 (1H, s), 5.02 (2H, s), 6.9 (1H, s), 7.14-7.47 (8H, m), 7.97 (1H, s).

| (2S)-2-(tert-Butoxy)-2-(7-(8-fluoro-5-methylchroman-6-yl)-3-(3-((4-fluorobenzyl)oxy)phenyl)-5-methyl-2-phenylpyrazolo[1,5-a]pyrimidin-6-yl)acetic acid | |
|---|---|
| MS (M + H)$^+$ Calcd. | 704 |
| MS (M + H)$^+$ Observ. | 704 |
| Retention Time | 3.56 min |
| | LC Condition |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

Scheme 18

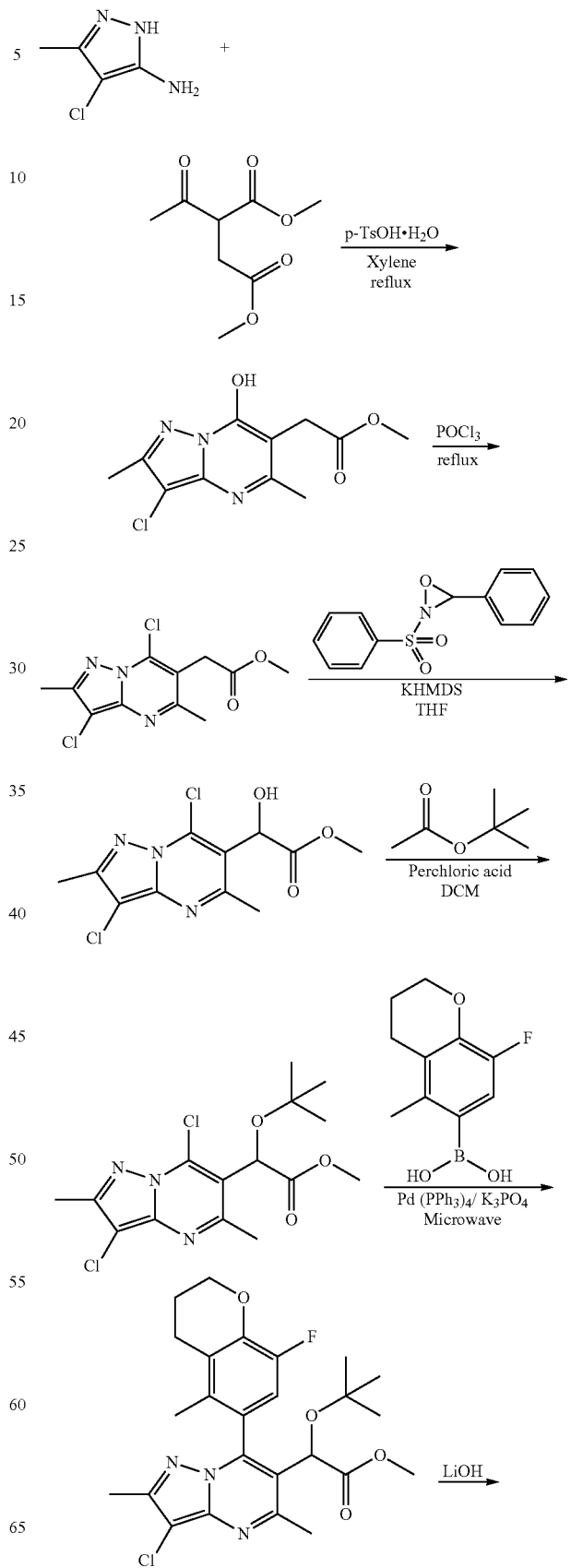

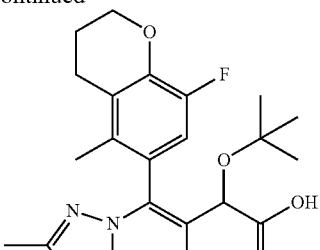

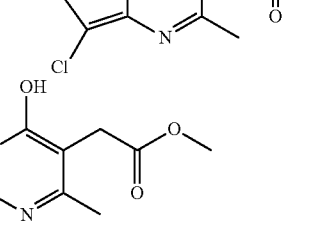

Methyl 2-(3-chloro-7-hydroxy-2,5-di-methylpyrazolo[1,5-a]pyrimidin-6-yl)acetate

To a solution of 4-chloro-3-methyl-1H-pyrazol-5-amine (0.263 g, 2 mmol) and dimethyl 2-acetylsuccinate (1.3 g, 6 mmol) in xylene (50 mL) was added p-toluenesulfonic acid monohydrate (4 mg, 0.02 mmol). The reaction mixture was heated at reflux under a Dean-Stark trap for 2 hrs. The solid was filtered and washed by hexanes to afford (0.31 g, 58%) of the title compound. $^1$H-NMR (500 MHz, DMSO-$d_6$) δ ppm 2.28 (s, 3H), 2.33 (s, 3H), 3.54 (s, 2H), 3.61 (s, 3H).

| Methyl 2-(3chloro-7-hydroxy-2,5-di-methylpyrazolo[1,5-a]pyrimidin-6-yl)acetate. | |
|---|---|
| MS (M + H)$^+$ Calcd. | 270 |
| MS (M + H)$^+$ Observ. | 270 |
| Retention Time | 1.4 min |
| | LC Condition |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

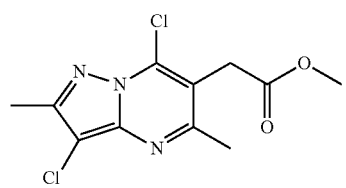

Methyl 2-(3,7-dichloro-2,5-dimethylpyrazolo[1,5-a]pyrimidin-6-yl)acetate

To a solution of methyl 2-(3-chloro-7-hydroxy-2,5-di-methylpyrazolo[1,5-a]pyrimidin-6-yl)acetate (0.160 g, 0.6 mmol) was added POCl$_3$ (1 mL). The reaction mixture was heated at reflux for 1 h. After cooling, the reaction mixture was added drop-wise to ice-water. A brown solid precipitated. The solid were filtered and washed with water, then dissolved in ethyl acetate. The organic solution was washed with saturated NaHCO$_3$ and dried over sodium sulfate. The solvent was evaporated to give the title compound (0.1 g, 59%). NMR (500 MHz, DMSO-$d_6$) δ ppm 2.44 (s, 3H), 2.57 (s, 3H), 3.68 (s, 3H), 4.00 (s, 2H). Used as is in the next step.

| Methyl 2-(3,7-dichloro-2,5-dimethylpyrazolo[1,5-a]pyrimidin-6-yl)acetate. | |
|---|---|
| MS (M + H)$^+$ Calcd. | 287 |
| MS (M + H)$^+$ Observ. | 287 |
| Retention Time | 1.82 min |
| | LC Condition |
| Solvent A | 10% Methanol:90% Water:0.1% TFA |
| Solvent B | 90% Methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | Methanol:Water:TFA |
| Column | Phenomenex Luna 2.0 × 30 mm 3 um |

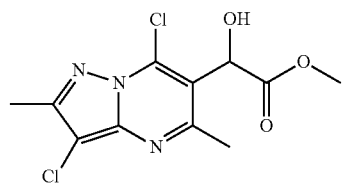

Methyl 2-(3,7-dichloro-2,5-dimethylpyrazolo[1,5-a]pyrimidin-6-yl)-2-hydroxyacetate To a stirred solution of KHMDS (0.5 M in toluene, 1.04 mL) in THF (5 mL) at −78° C. was added a solution of methyl 2-(3,7-dichloro-2,5-dimethylpyrazolo[1,5-a]pyrimidin-6-yl)acetate (0.15 g, 0.5 mmol) in THF (5 mL) over 20 mins. The reaction mixture was stirred at −78° C. for 30 min. A solution of 3-phenyl-2-(phenylsulfonyl)-1,2-oxaziridine (0.16 g, 0.63 mmol) in THF (5 mL) was added over 10 min and the resulted reaction mixture was stirred for an additional 30 min at −78° C. The reaction mixture was quenched with saturated NH$_4$Cl aqueous solution (2 mL). The mixture was allowed to warm up to room temperature and diluted with EtOAc (100 mL). The organic phase was washed with water and brine and dried with sodium sulfate. The solvent was evaporated. Purification by silica gel chromatography provided the title compound (80 mg, 30%). Used as is in the next step.

| Methyl 2-(3,7-dichloro-2,5-dimethylpyrazolo[1,5-a]pyrimidin-6-yl)-2-hydroxyacetate | |
|---|---|
| MS (M + H)$^+$ Calcd. | 304 |
| MS (M + H)$^+$ Observ. | 304 |
| Retention Time | 1.73 min |
| | LC Condition |
| Solvent A | 10% methanol:90% Water:0.1% TFA |
| Solvent B | 90% methanol:10% Water:0.1% TFA |

| Methyl 2-(3,7-dichloro-2,5-dimethylpyrazolo[1,5-a]pyrimidin-6-yl)-2-hydroxyacetate | |
|---|---|
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

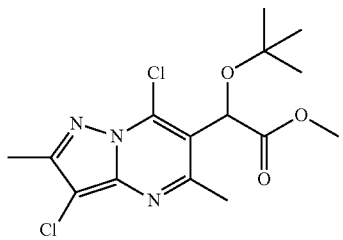

Methyl 2-tert-butoxy-2-(3,7-dichloro-2,5-dimethylpyrazolo[1,5-a]pyrimidin-6-yl)acetate To a suspension of methyl 2-(3,7-dichloro-2,5-dimethylpyrazolo[1,5-a]pyrimidin-6-yl)-2-hydroxyacetate (80 mg, 0.26 mmol) in tert-butyl acetate (1.5 mL) at room temperature was added CH$_2$Cl$_2$ (1.5 mL) followed by perchloric acid (40 mg, 2.1 mmol). The reaction mixture was stirred for 2 h at room temperature. The reaction mixture was diluted with ethyl acetate (15 mL). The organic phase was washed with saturated NaHCO$_3$ (2×10 mL), followed by water (1×10 mL) and dried over sodium sulfate. The solvent was evaporated. Purification by silica gel chromatography provided the title compound (85 mg, 90%). Used as is in the next step.

| Methyl 2-tert-butoxy-2-(3,7-dichloro-2,5-dimethylpyrazolo[1,5-a]pyrimidin-6-yl)acetate | |
|---|---|
| MS (M + H)$^+$ Calcd. | 360 |
| MS (M + H)$^+$ Observ. | 360 |
| Retention Time | 2.2 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

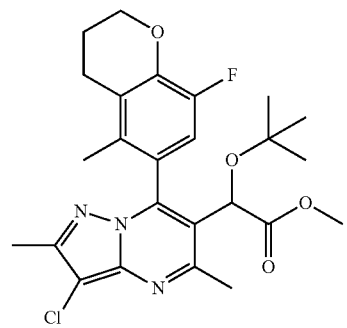

Methyl 2-tert-butoxy-2-(3-chloro-7-(8-fluoro-5-methylchroman-6-yl)-2,5-dimethylpyrazolo[1,5-a]pyrimidin-6-yl)acetate, TFA salt To a 2-5 mL microwave tube was added methyl 2-tert-butoxy-2-(3,7-dichloro-2,5-dimethylpyrazolo[1,5-a]pyrimidin-6-yl)acetate. (25 mg, 0.069 mmol), tetrakis(triphenylphosphine) palladium(0) (10 mg, 8.88 mmol), 8-fluoro-5-methylchroman-6-ylboronic acid (20 mg, 0.069 mmol), dioxane (1.5 mL), followed by 2M K$_3$PO$_4$ solution (77 uL). The reaction mixture was heated in a microwave reactor at 130° C. for 30 min. The reaction mixture was filtered and the filtrate was purified by preparative HPLC to afford (7 mg, 21%) of the title compound as the TFA salt. Preparative HPLC condition: Phenomenex Luna C18 30×100 mm S10, 30 to 100% B over 17 min gradient, 5 min hold time, A=10% methanol 90% water 0.1% TFA, B=90% methanol 10% water 0.1% TFA. Flow rate: 40 mL/min.

| Methyl 2-tert-butoxy-2-(3-chloro-7-(8-fluoro-5-methylchroman-6-yl)-2,5-dimethylpyrazolo[1,5-a]pyrimidin-6-yl)acetate, TFA salt | |
|---|---|
| MS (M + H)$^+$ Calcd. | 490 |
| MS (M + H)$^+$ Observ. | 490 |
| Retention Time | 2.36 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 143

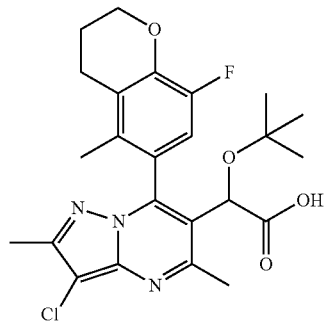 [SMILES: Cc1nc2c(Cl)c(C)nn2c(-c2cc(F)c3c(c2C)CCCO3)c1C(OC(C)(C)C)C(=O)O]

2-(tert-Butoxy)-2-(3-chloro-7-(8-fluoro-5-methyl-chroman-6-yl)-2,5-dimethylpyrazolo[1,5-a]pyrimidin-6-yl)acetic acid To a solution of methyl 2-tert-butoxy-2-(3-chloro-7-(8-fluoro-5-methylchroman-6-yl)-2,5-dimethylpyrazolo[1,5-a]pyrimidin-6-yl)acetate, (5 mg, 10 umol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (3 mg, 60%) of the title compound. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-$d_6$) δ ppm 1.03 (9H, br. s.), 1.8 (2H, s), 2.28 (2H, br. s.), 2.52 (3H, s), 2.74 (3H, br. s.), 2.96 (3H, s), 4.29 (2H, br. s.), 4.7 (1H, s), 6.98 (1H, s), 7.96 (1H, s).

| 2-(tert-Butoxy)-2-(3-chloro-7-(8-fluoro-5-methylchroman-6-yl)-2,5-dimethylpyrazolo[1,5-a]pyrimidin-6-yl)acetic acid | |
|---|---|
| MS (M + H)$^+$ Calcd. | 476 |
| MS (M + H)$^+$ Observ. | 476 |
| Retention Time | 2.3 min |
| LC Condition | |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water:ammonium acetate |
| Column | Waters BEH C18, 2.0 × 50 mm |

Scheme 19

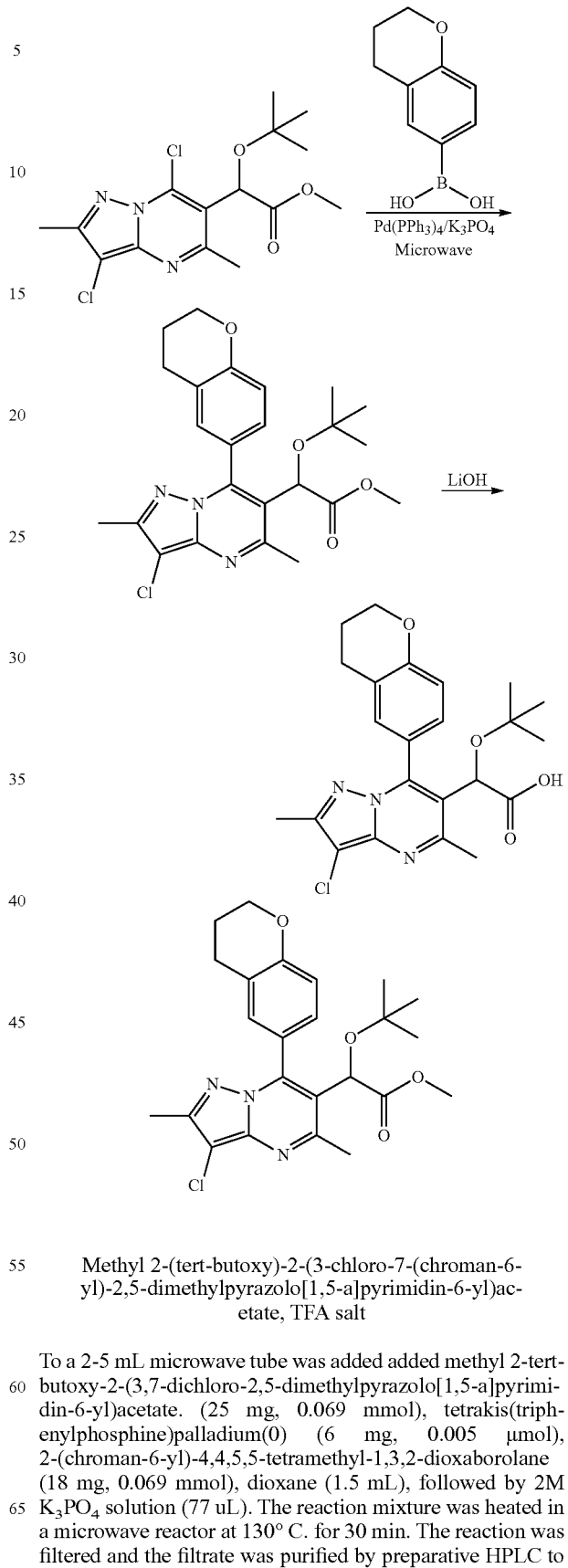

Methyl 2-(tert-butoxy)-2-(3-chloro-7-(chroman-6-yl)-2,5-dimethylpyrazolo[1,5-a]pyrimidin-6-yl)acetate, TFA salt To a 2-5 mL microwave tube was added added methyl 2-tert-butoxy-2-(3,7-dichloro-2,5-dimethylpyrazolo[1,5-a]pyrimidin-6-yl)acetate. (25 mg, 0.069 mmol), tetrakis(triphenylphosphine)palladium(0) (6 mg, 0.005 μmol), 2-(chroman-6-yl)-4,4,5,5-tetramethyl-1,3,2-dioxaborolane (18 mg, 0.069 mmol), dioxane (1.5 mL), followed by 2M K$_3$PO$_4$ solution (77 uL). The reaction mixture was heated in a microwave reactor at 130° C. for 30 min. The reaction was filtered and the filtrate was purified by preparative HPLC to afford (7 mg, 22%) of the title compound as the TFA salt. Preparative HPLC condition: Phenomenex Luna C18 30×100 mm S10, 30 to 100% B over 17 min gradient, 5 min hold time, A=10% methanol 90% water 0.1% TFA, B=90% methanol 10% water 0.1% TFA. Flow rate: 40 mL/min. Compound used as is in the next step.

| Methyl 2-(tert-butoxy)2-(3-chloro-7-(chroman-6-yl)-2,5-dimethylpyrazolo[1,5-a]pyrimidin-6-yl)acetate, TFA salt | |
|---|---|
| MS (M + H)+ Calcd. | 458 |
| MS (M + H)+ Observ. | 458 |
| Retention Time | 2.27 min |
| | LC Condition |
| Solvent A | 10% methanol:90% Water:0.1% TFA |
| Solvent B | 90% methanol:10% Water:0.1% TFA |
| Start % B | 0 |
| Final % B | 100 |
| Gradient Time | 2 min |
| Flow Rate | 1 mL/min |
| Wavelength | 220 |
| Solvent Pair | methanol:Water:TFA |
| Column | Phenomenex Luna 2.0 × 30 mm 3 um |

Example 144

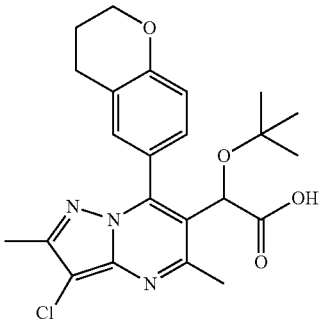 [SMILES: Cc1nc2c(Cl)c(C)nn2c(-c2ccc3c(c2)CCCO3)c1C(OC(C)(C)C)C(=O)O]

2-(tert-Butoxy)2-(3-chloro-7-(chroman-6-yl)-2,5-dimethylpyrazolo[1,5-a]pyrimidin-6-yl)acetic acid To a solution of methyl 2-(tert-butoxy)-2-(3-chloro-7-(chroman-6-yl)-2,5-dimethylpyrazolo[1,5-a]pyrimidin-6-yl)acetate, TFA salt. (5 mg, 0.011 mmol) in dioxane (0.5 mL) was added 1.0 N LiOH aqueous solution (0.5 mL, 0.5 mmol). The reaction mixture was stirred at 50° C. for 2 h. The reaction mixture was filtered and the filtrate was purified by preparative HPLC to afford (1.5 mg, 30%) of the title compound as the TFA salt. Preparative HPLC condition: Phenomenex Luna C18 30×100 mm S10, 50 to 100% B over 22 min gradient, 6 min hold time, A=10% methanol 90% water 0.1% TFA, B=90% methanol 10% water 0.1% TFA. Flow rate: 40 mL/min. $^1$H-NMR (400 MHz, DMSO-d$_6$) δ ppm 0.846 (9H, br. s.), 1.8 (2H, s), 2.6 (2H, s), 2.74 (3H, br. s.), 2.96 (3H, s), 4.29 (2H, br. s.), 4.7 (1H, s), 6.98 (1H, s), 7.4 (1H, br. s.), 7.8 (1H, brs), 7.96 (1H, s).

| 2-(tert-Butoxy)2-(3-chloro-7-(chroman-6-yl)-2,5-dimethylpyrazolo[1,5-a]pyrimidin-6-yl)acetic acid | |
|---|---|
| MS (M + H)+ Calcd. | 443 |
| MS (M + H)+ Observ. | 443 |
| Retention Time | 2.26 min |
| | LC Condition |
| Solvent A | 5% Acetonitrile:95% Water:10 mM ammonium acetate |
| Solvent B | 95% Acetonitrile:5% Water:10 mM ammonium acetate |
| Start % B | 0 |
| Final % B | 100 |
| Gradient Time | 2 min |
| Flow Rate | 1 mL/min |
| Wavelength | 220 |
| Solvent Pair | Acetonitrile:Water ammonium acetate |
| Column | Waters BEH C18, 2.0 × 50 mm |

Examples 145-149 were prepared using the following intermediates

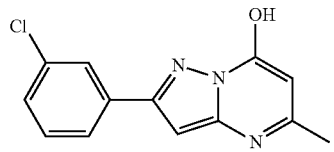 [SMILES: Cc1cc(O)n2nc(-c3cccc(Cl)c3)cc2n1]

2-(3-Chlorophenyl)-5-methylpyrazolo[1,5-a]pyrimidin-7-ol

A suspension of 3-(3-chlorophenyl)-1H-pyrazol-5-amine (10 g, 51.6 mmol) and ethyl 3-oxobutanoate (26.3 ml, 207 mmol) in o-xylene (200 mL) was heated at reflux (oil bath temp: 155-160° C.) for 20 h. Note: The reaction turned clear solution between 60-70° C. and solids started crashing out at 130° C. Then, cooled, diluted with hexanes (100 mL), filtered, washed with hexanes (100 mL) and dried to afford 2-(3-chlorophenyl)-5-methylpyrazolo[1,5-a]pyrimidin-7-ol (11.8 g, 45.4 mmol, 88% yield) as off-white solid. $^1$H NMR (400 MHz, DMSO-d$_6$) δ: 12.46 (s, 1H), 8.05 (s, 1H), 8.00-7.95 (m, 1H), 7.56-7.45 (m, 2H), 6.70 (s, 1H), 5.64 (s, 1H), 2.33 (s, 3H). LCMS (M+H) calcd for $C_{13}H_{11}ClN_6O$: 260.06. found: 260.1.

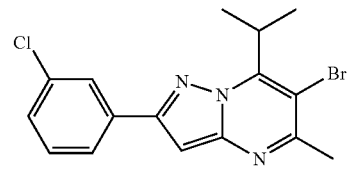 [SMILES: Cc1nc2cc(-c3cccc(Cl)c3)nn2c(C(C)C)c1Br]

6-Bromo-7-chloro-2-(3-chlorophenyl)-5-methylpyrazolo[1,5-a]pyrimidine

To a stirred slurry of 2-(3-chlorophenyl)-5-methylpyrazolo [1,5-a]pyrimidin-7-ol (8.83 g, 34 mmol) in CH$_2$Cl$_2$ (150 mL) was added added dropwise a solution of bromine (1.804 ml, 35.0 mmol) in CH$_2$Cl$_2$ (50 mL) over 15 min. After 1 h, the reaction mixture was concentrated to give 6-bromo-2-(3-chlorophenyl)-5-methylpyrazolo[1,5-a]pyrimidin-7-ol, hydrobromide (14.2 g) as brown solid. LCMS of this solid showed presence of unreacted material and two new products, the expecteded monobrominated and dibrominated products. So, this solid resuspended in MeOH/CH$_2$Cl$_2$ (1:1, 100 mL) and a solution of briomine in CH$_2$Cl$_2$ (1.4 mL) was added over 5 min. After 1 h, the reaction mixture was concentrated and the resulting tan solid was used in the next step without purification.

To the above crude product was added N,N-diethylaniline (16.23 ml, 102 mmol) and POCl$_3$ (47.5 ml, 510 mmol) and the mixture was stirred at 120° C. for 16 h. Then, cooled, concentrated and the dark residue taken up in EtOAc (250 mL) and stirred with ice-water for 30 min. Aqueous layer separated and organic layer washed with water (2×50 mL). The combine aqueous layers extracted with EtOAc (100 mL) and the combine organic layers washed with brine (50 mL), dried (Na$_2$SO$_4$/C), filtered and concentrated to give dark paste. Purification by flash column chromatography on silica gel column using 5-10% EtOAc/Hex/5% CH$_2$Cl$_2$ (2.5% increment/lit) provided 6-bromo-7-chloro-2-(3-chlorophenyl)-5-methylpyrazolo[1,5-a]pyrimidine (2.003 g, 5.61 mmol, 16.50% yield) as pale yellow solid. $^1$H NMR (500 MHz, CDCl$_3$) δ: 8.00 (s, 1H), 7.89-7.83 (m, 1H), 7.43-7.36 (m, 2H), 6.94 (s, 1H), 2.78 (s, 3H). LCMS (M+H) calcd for C$_{13}$H$_9$BrCl$_2$N$_3$: 355.94. found: 358.0.

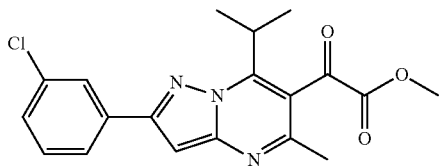 [SMILES: COC(=O)C(=O)c1c(C)nc2cc(-c3cccc(Cl)c3)nn2c1C(C)C]

Methyl 2-(2-(3-chlorophenyl)-7-isopropyl-5-methylpyrazolo[1,5-a]pyrimidin-6-yl)-2-oxoacetate A 100 mL RB-flask was charged with 6-bromo-7-chloro-2-(3-chlorophenyl)-5-methylpyrazolo[1,5-a]pyrimidine (0.918 g, 2.57 mmol) and copper(I) bromide (0.092 g, 0.643 mmol) was added anhydrous THF (30 mL). To the resulting mixture was added 1M iPrMgCl—LiCl/THF (3.34 ml, 3.34 mmol) over 5 min. After 1 h, methyl 2-chloro-2-oxoacetate (0.501 ml, 5.45 mmol) was added at once to the dark reaction mixture and stirred for additional 1 h. Then, the resulting homogeneous orange brown reaction mixture was quenched with sat NaHCO$_3$ (1 mL), diluted with Et$_2$O (75 mL), washed with water (2×25 mL), brine (25 mL), dried (Na$_2$SO$_4$/C), filtered and concentrated to give yellow residue. This residue was purified on silica gel column using 5-30% EtOAc/Hex (5% increment per 500 mL) to give methyl 2-(2-(3-chlorophenyl)-7-isopropyl-5-methylpyrazolo[1,5-a]pyrimidin-6-yl)-2-oxoacetate (0.1402 g, 0.377 mmol, 14.67% yield) as yellow solid; $^1$H NMR (500 MHz, CDCl$_3$) δ: 8.01-7.98 (m, 1H), 7.87 (dt, J=7.0, 1.7 Hz, 1H), 7.43-7.38 (m, 2H), 6.87 (s, 1H), 3.98 (s, 3H), 3.43-3.34 (m, 1H), 2.47 (s, 3H), 1.62 (d, J=7.0 Hz, 6H). LCMS (M+H) calcd for C$_{17}$H$_{16}$N$_3$O$_2$: 372.11. found: 372.2.

(S)-Methyl 2-(2-(3-chlorophenyl)-7-isopropyl-5-methylpyrazolo[1,5-a]pyrimidin-6-yl)-2-hydroxyacetate To a stirred yellow solution of methyl 2-(2-(3-chlorophenyl)-7-isopropyl-5-methylpyrazolo[1,5-a]pyrimidin-6-yl)-2-oxoacetate (0.103 g, 0.277 mmol) in anhydrous toluene (5 mL) was added 1.1M (R)-1-methyl-3,3-diphenylhexahydropyrrolo[1,2-c][1,3,2]oxazaborole/toluene (0.101 ml, 0.111 mmol). The mixture was cooled to −35° C. and a solution of 1M catechoborane/THF (0.388 ml, 0.388 mmol) was added over 10 min. After 30 min, the reaction mixture was slowly warmed to −15 C and diluted with EtOAc (5 mL) and sat. Na$_2$CO$_3$ (2 mL). The mixture was stirred vigorously for 30 min, and the organic phase washed with sat Na$_2$CO$_3$ (2×5 mL), dried (Na2SO4), filtered, concentrated and the residue was purified by prep-HPLC to give (S)-methyl 2-(2-(3-chlorophenyl)-7-isopropyl-5-methylpyrazolo[1,5-a]pyrimidin-6-yl)-2-hydroxyacetate (0.0693 g, 0.185 mmol, 66.9% yield) as white solid. $^1$H NMR (500 MHz, CDCl$_3$) δ: 7.99 (t, J=1.5 Hz, 1H), 7.86 (dt, J=7.4, 1.5 Hz, 1H), 7.41-7.33 (m, 2H), 6.80 (s, 1H), 5.63 (s, 1H), 3.81 (s, 3H), 3.40 (br. s., 1H), 2.62 (s, 3H), 1.68 (d, J=7.0 Hz, 3H), 1.59 (d, J=7.0 Hz, 3H). LCMS (M+H) calcd for C$_{19}$H$_{21}$ClN$_3$O$_3$: 374.13. found: 374.2.

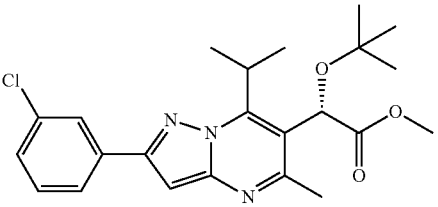

(S)-Methyl 2-(tert-butoxy)-2-(2-(3-chlorophenyl)-7-isopropyl-5-methylpyrazolo[1,5-a]pyrimidin-6-yl) acetate To a stirred solution of (S)-methyl 2-(2-(3-chlorophenyl)-7-isopropyl-5-methylpyrazolo[1,5-a]pyrimidin-6-yl)-2-hydroxyacetate (0.069 g, 0.185 mmol) and tert-butyl acetate (1.247 ml, 9.23 mmol) in CH$_2$Cl$_2$ (5 mL) was added 70% perchloric acid (0.048 ml, 0.554 mmol) at rt. After 3 h, the reaction mixture was diluted with Et$_2$O (35 mL), washed with sat Na$_2$CO$_3$ (2×5 mL), brine (5 mL), dried (Na$_2$SO$_4$), filtered and concentrated to give colorless paste which was purified by prep-HPLC to afford (S)-methyl 2-(tert-butoxy)-2-(2-(3-chlorophenyl)-7-isopropyl-5-methylpyrazolo[1,5-a]pyrimidin-6-yl)acetate (0.0496 g, 0.244 mmol, 62.5% yield) as white solid. $^1$H NMR (500 MHz, CDCl$_3$) δ: 7.98 (t, J=1.7 Hz, 1H), 7.87 (dt, J=7.6, 1.4 Hz, 1H), 7.41-7.32 (m, 2H), 6.77 (s, 1H), 5.42 (s, 1H), 4.07 (dt, J=13.6, 6.9 Hz, 1H), 3.71 (s, 3H), 2.73 (s, 3H), 1.68 (d, J=7.0 Hz, 3H), 1.56 (d, J=7.0 Hz, 3H), 1.26 (s, 9H). LCMS (M+H) calcd for C$_{23}$H$_{29}$ClN$_3$O$_3$: 430.19. found: 430.3.

Example 145

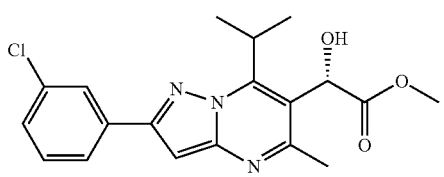 [SMILES: COC(=O)[C@@H](O)c1c(C)nc2cc(-c3cccc(Cl)c3)nn2c1C(C)C]

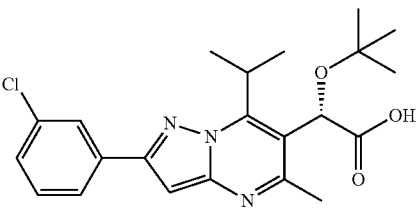 [SMILES: Cc1nc2cc(-c3cccc(Cl)c3)nn2c(C(C)C)c1[C@H](OC(C)(C)C)C(=O)O]

(S)-2-(tert-Butoxy)-2-(2-(3-chlorophenyl)-7-isopropyl-5-methylpyrazolo[1,5-a]pyrimidin-6-yl)acetic acid A solution of (S)-methyl 2-(tert-butoxy)-2-(2-(3-chlorophenyl)-7-isopropyl-5-methylpyrazolo[1,5-a]pyrimidin-6-yl)acetate (0.060 g, 0.140 mmol) and 1M NaOH (1 ml, 1.000 mmol) in MeOH (5 mL) was heated at 60° C. for 16 h. Then, the reaction mixture was cooled, neutralized with 1M HCl (1 mL), concentrated and the residue was diluted with Et$_2$O (25 mL), washed with 0.1M NH4OAc (5 mL), brine (5 mL), dried (Na$_2$SO$_4$), filtered and concentrated to give (S)-2-(tert-butoxy)-2-(2-(3-chlorophenyl)-7-isopropyl-5-methylpyrazolo[1,5-a]pyrimidin-6-yl)acetic acid (0.055 g, 0.131 mmol, 94% yield) as white solid and 98% ee. $^1$H NMR (500 MHz, CDCl$_3$) δ: 7.96 (s, 1H), 7.83 (d, J=7.0 Hz, 1H), 7.39-7.30 (m, 2H), 6.81 (s, 1H), 5.46 (br. s., 1H), 3.99 (br. s., 1H), 2.74 (br. s., 3H), 1.69 (d, J=6.4 Hz, 3H), 1.57 (br. s., 3H), 1.27 (s, 9H). LCMS (M+H) calcd for C$_{22}$H$_{27}$ClN$_3$O$_3$: 416.17. found: 416.3.

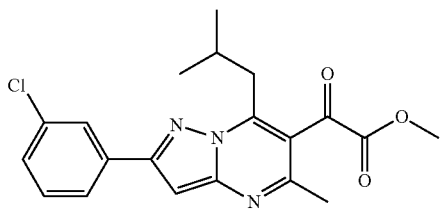 [SMILES: COC(=O)C(=O)c1c(C)nc2cc(-c3cccc(Cl)c3)nn2c1CC(C)C]

Methyl 2-(2-(3-chlorophenyl)-7-isobutyl-5-methylpyrazolo[1,5-a]pyrimidin-6-yl)-2-oxoacetate To a stirred solution of 6-bromo-7-chloro-2-(3-chlorophenyl)-5-methylpyrazolo[1,5-a]pyrimidine (0.179 g, 0.5 mmol), copper(I) bromide (0.036 g, 0.250 mmol) and 0.5M LiCl/THF (8 ml, 4.00 mmol) was added 2M i-BuMgCl/THF (2.000 ml, 4.00 mmol) over 5 min at rt. After 2 h, LCMS indicated presence of mostly the unreacted starting material. More iBuMgCl (1 ml) was added and continued stirring at rt for additional 4 h and methyl 2-chloro-2-oxoacetate (0.736 ml, 8.00 mmol) added at once to the reaction mixture, and stirred for additional 1 h. Then, the reaction was diluted with Et$_2$O (50 mL), quenched with Na$_2$CO$_3$ (1 mL), washed with 10 mL each water and brine, dried (Na$_2$SO$_4$), filtered and concentrated to give orange paste which was purified by prep-HPLC to afford methyl 2-(2-(3-chlorophenyl)-7-isobutyl-5-methylpyrazolo[1,5-a]pyrimidin-6-yl)-2-oxoacetate (0.0772 g, 0.170 mmol, 34.0% yield) as yellow oil which turned to yellow solid overtime and contaminated with about 15% of 2-(3-chlorophenyl)-7-isobutyl-5-methylpyrazolo[1,5-a]pyrimidine. $^1$H NMR (500 MHz, CDCl$_3$) δ: 7.98 (d, J=1.8 Hz, 1H), 7.87-7.83 (m, 1H), 7.41-7.31 (m, 2H), 6.87 (s, 1H), 3.97 (s, 3H), 3.13 (d, J=7.3 Hz, 2H), 2.51 (s, 3H), 2.44 (dt, J=13.7, 6.8 Hz, 1H), 0.97 (d, J=6.7 Hz, 6H). LCMS (M+H) calcd for C$_{20}$H$_{21}$ClN$_3$O$_3$: 386.13. found: 386.3.

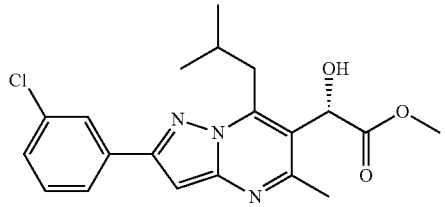 [SMILES: COC(=O)[C@@H](O)c1c(C)nc2cc(-c3cccc(Cl)c3)nn2c1CC(C)C]

(S)-Methyl 2-(2-(3-chlorophenyl)-7-isobutyl-5-methylpyrazolo[1,5-a]pyrimidin-6-yl)-2-hydroxyacetate To a stirred solution of methyl 2-(2-(3-chlorophenyl)-7-isobutyl-5-methylpyrazolo[1,5-a]pyrimidin-6-yl)-2-oxoacetate (0.077 g, 0.170 mmol) in toluene (3 mL) was added 1M (R)-1-methyl-3,3-diphenylhexahydropyrrolo[1,2-c][1,3,2]oxazaborole/toluene (0.034 ml, 0.034 mmol) at rt and cooled to −35° C. To this was added dropwise 1M catecholborane/THF (0.237 ml, 0.237 mmol) over 10 min. After stirring 30 min, the reaction mixture was slowly warm to −15° C. over 30 min and diluted with EtOAc (15 mL). Then, the mixture was vigorously stirred with sat Na$_2$CO$_3$ (2 mL) for 45 min. The aqueous layer separated and organic layer washed with sat sat Na$_2$CO$_3$ (2×5 mL), dried (Na$_2$SO$_4$), filtered, concentrated and the resulting yellow residue purified by prep-HPLC to afford (S)-methyl 2-(2-(3-chlorophenyl)-7-isobutyl-5-methylpyrazolo[1,5-a]pyrimidin-6-yl)-2-hydroxyacetate (0.0592 g, 0.153 mmol, 90% yield) as white solid. $^1$H NMR (500 MHz, CDCl$_3$) δ: 7.98 (t, J=1.7 Hz, 1H), 7.85 (dt, J=7.3, 1.5 Hz, 1H), 7.40-7.32 (m, 2H), 6.80 (s, 1H), 5.52 (s, 1H), 3.81 (s, 3H), 3.66 (br. s., 1H), 3.34-3.23 (m, 2H), 2.51 (s, 3H), 2.43 (dt, J=13.6, 6.9 Hz, 1H), 1.05 (d, J=6.7 Hz, 6H). LCMS (M+H) calcd for C$_{20}$H$_{23}$ClN$_3$O$_3$: 388.14. found: 388.3.

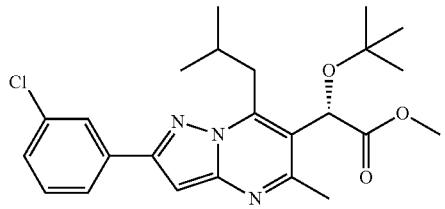 [SMILES: COC(=O)[C@@H](OC(C)(C)C)c1c(C)nc2cc(-c3cccc(Cl)c3)nn2c1CC(C)C]

(S)-Methyl 2-(tert-butoxy)-2-(2-(3-chlorophenyl)-7-isobutyl-5-methylpyrazolo[1,5-a]pyrimidin-6-yl)acetate To a stirred solution of (S)-methyl 2-(2-(3-chlorophenyl)-7-isobutyl-5-methylpyrazolo[1,5-a]pyrimidin-6-yl)-2-hydroxyacetate (0.059 g, 0.152 mmol) and tert-butyl acetate (1 ml, 7.40 mmol) in CH$_2$Cl$_2$ (3 mL) was added 70% perchloric aci (0.039 ml, 0.456 mmol) at rt. After 2 h, the reaction was diluted with Et$_2$O (50 mL), washed with sat. Na$_2$CO$_3$ (2×5 mL), dried (Na$_2$SO$_4$), filtered and concentrated to give yellow solid which was purified by prep-HPLC to afford (S)-methyl 2-(tert-butoxy)-2-(2-(3-chlorophenyl)-7-isobutyl-5-methylpyrazolo[1,5-a]pyrimidin-6-yl)acetate (0.0357 g, 0.080 mmol, 52.9% yield) as brown paste. $^1$H NMR (500 MHz, CDCl$_3$) δ: 7.97 (t, J=1.7 Hz, 1H), 7.86 (dt, J=7.6, 1.3 Hz, 1H), 7.40-7.31 (m, 2H), 6.79 (s, 1H), 5.36 (s, 1H), 3.70 (s, 3H), 3.53 (dd, J=13.4, 7.6 Hz, 1H), 3.14 (dd, J=13.4, 7.0 Hz, 1H), 2.69 (s, 3H), 2.65-2.54 (m, 1H), 1.25 (s, 9H), 1.03 (d, J=6.7

Hz, 3H), 0.98 (d, J=6.7 Hz, 3H). LCMS (M+H) calcd for C$_{24}$H$_{31}$ClN$_3$O$_3$: 444.21. found: 444.3.

Example 146

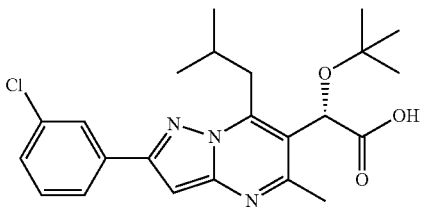 [SMILES: Cc1nc2cc(-c3cccc(Cl)c3)nn2c(CC(C)C)c1[C@H](OC(C)(C)C)C(=O)O]

(S)-2-(tert-Butoxy)-2-(2-(3-chlorophenyl)-7-isobutyl-5-methylpyrazolo[1,5-a]pyrimidin-6-yl)acetic acid A solution of (S)-methyl 2-(tert-butoxy)-2-(2-(3-chlorophenyl)-7-isobutyl-5-methylpyrazolo[1,5-a]pyrimidin-6-yl)acetate (0.035 g, 0.079 mmol) and 1M NaOH (0.788 ml, 0.788 mmol) in MeOH (5 mL) was heated at reflux for 4 h. Then, cooled, neutralized with 1M HCl (0.8 mL), concentrated and the residue was taken up in Et$_2$O (25 mL), washed with water (5 mL), brine (5 mL), dried (MgSO$_4$), filtered and concentrated to give (S)-2-(tert-butoxy)-2-(2-(3-chlorophenyl)-7-isobutyl-5-methylpyrazolo[1,5-a]pyrimidin-6-yl)acetic acid (0.0303 g, 0.069 mmol, 88% yield) as white solid. $^1$H NMR (500 MHz, CDCl$_3$) δ: 7.99-7.96 (m, 1H), 7.85 (dt, J=7.3, 1.4 Hz, 1H), 7.41-7.33 (m, 2H), 6.82 (s, 1H), 5.41 (s, 1H), 3.75-3.56 (m, 1H), 3.05-2.92 (m, 1H), 2.65 (s, 3H), 2.55 (br. s., 1H), 1.29 (s, 9H), 1.09 (d, J=6.7 Hz, 3H), 1.02 (d, J=6.4 Hz, 3H). LCMS (M+H) calcd for C$_{23}$H$_{29}$ClN$_3$O$_3$: 430.19. found: 430.3.

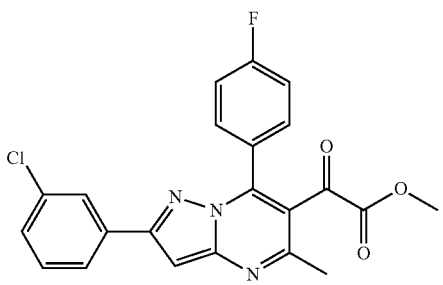 [SMILES: COC(=O)C(=O)c1c(C)nc2cc(-c3cccc(Cl)c3)nn2c1-c1ccc(F)cc1]

Methyl 2-(2-(3-chlorophenyl)-7-(4-fluorophenyl)-5-methylpyrazolo[1,5-a]pyrimidin-6-yl)-2-oxoacetate To a stirred mixture of 6-bromo-7-chloro-2-(3-chlorophenyl)-5-methylpyrazolo[1,5-a]pyrimidine (0.179 g, 0.5 mmol) and copper(I) bromide (0.072 g, 0.500 mmol) in THF (3 mL) was added dropwise a pre-mixed solution of 2M 4-fluorophenylmagnesium bromide/ether (3.00 ml, 6.00 mmol) and 0.5M LiCl/THF (6.00 ml, 3.00 mmol) over 15 min. After 2 h, added at once methyl 2-chloro-2-oxoacetate (0.368 ml, 4.00 mmol) to the dark solution. After 1 h, the reaction was diluted with Et$_2$O (50 mL), quenched with Na$_2$CO$_3$ (1 mL), washed with 10 mL each water and brine, dried (Na$_2$SO$_4$), filtered and concentrated to give orange paste which was purified by prep-HPLC to afford methyl 2-(2-(3-chlorophenyl)-7-(4-fluorophenyl)-5-methylpyrazolo[1,5-a]pyrimidin-6-yl)-2-oxoacetate (0.0644 g, 0.152 mmol, 30.4% yield) as yellow solid contaminated with some impurity. $^1$H NMR (500 MHz, CDCl$_3$) δ: 7.88 (s, 1H), 7.81-7.74 (m, 1H), 7.73-7.67 (m, 2H), 7.35 (d, J=5.2 Hz, 2H), 7.31-7.24 (m, 2H), 6.97 (s, 1H), 3.44 (s, 3H), 2.67 (s, 3H). LCMS (M+H) calcd for C$_{22}$H$_{16}$ClFN$_3$O$_3$: 424.09. found: 424.3. LCMS (M+H) calcd for C$_{22}$H$_{16}$ClFN$_3$O$_3$: 424.09. found: 424.3.

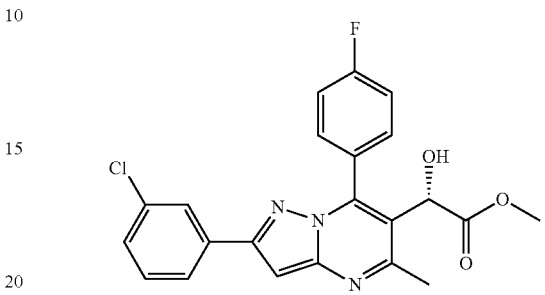

(S)-Methyl 2-(2-(3-chlorophenyl)-7-(4-fluorophenyl)-5-methylpyrazolo[1,5-a]pyrimidin-6-yl)-2-hydroxyacetate To a stirred solution of methyl 2-(2-(3-chlorophenyl)-7-(4-fluorophenyl)-5-methylpyrazolo[1,5-a]pyrimidin-6-yl)-2-oxoacetate (0.083 g, 0.196 mmol) in toluene (5 mL) was added 1M (R)-1-methyl-3,3-diphenylhexahydropyrrolo[1,2-c][1,3,2]oxazaborole/toluene (0.039 ml, 0.039 mmol) and cooled to −35° C. To this was added dropwise 1M catecholborane/THF (0.294 ml, 0.294 mmol) over 10 min and stirred for additional 20 min. Then, the reaction was slowly warmed to −15 C over 30 min, diluted with EtOAc (10 ml) and quenched with sat. Na$_2$CO$_3$ (5 mL). The resulting mixture was vigorously stirred for 30 min, aq. larer removed and organic layer washed with sat. Na$_2$CO$_3$ (2×5 mL), dried (Na$_2$SO$_4$), filtered, concentrated to yellow residue which was purified by prep-HPLC to afford (S)-methyl 2-(2-(3-chlorophenyl)-7-(4-fluorophenyl)-5-methylpyrazolo[1,5-a]pyrimidin-6-yl)-2-hydroxyacetate (0.08 g, 0.184 mmol, 94% yield) as solid. $^1$H NMR (500 MHz, CDCl$_3$) δ: 7.82 (s, 1H), 7.75-7.68 (m, 1H), 7.68-7.58 (m, 2H), 7.34-7.24 (m, 4H), 6.88 (s, 1H), 5.16 (s, 1H), 3.78 (s, 3H), 3.69-3.34 (br.s., 1H), 2.58 (s, 3H). LCMS (M+H) calcd for C$_{22}$H$_{18}$ClFN$_3$O$_3$: 426.1. found: 426.2.

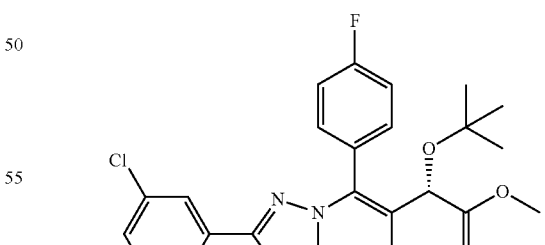

(S)-Methyl 2-(tert-butoxy)-2-(2-(3-chlorophenyl)-7-(4-fluorophenyl)-5-methylpyrazolo[1,5-a]pyrimidin-6-yl)acetate To a stirred solution of (S)-methyl 2-(2-(3-chlorophenyl)-7-(4-fluorophenyl)-5-methylpyrazolo[1,5-a]pyrimidin-6-yl)-

2-hydroxyacetate (0.06 g, 0.141 mmol) and tert-butyl acetate (0.952 ml, 7.04 mmol) in CH₂Cl₂ (3 mL) was added 70% perchloric acid (0.036 ml, 0.423 mmol) at rt. After 2 h, the reaction was diluted with Et₂O (50 mL), washed with sat. Na₂CO₃ (2×5 mL), dried (Na₂SO₄), filtered and concentrated to give yellow solid which was purified by prep-HPLC to afford (S)-methyl 2-(tert-butoxy)-2-(2-(3-chlorophenyl)-7-(4-fluorophenyl)-5-methylpyrazolo[1,5-a]pyrimidin-6-yl) acetate (0.0478 g, 0.099 mmol, 70.4% yield) as while solid. ¹H NMR (500 MHz, CDCl₃) δ: 7.83 (s, 1H), 7.77-7.69 (m, 2H), 7.67-7.62 (m, 1H), 7.35-7.26 (m, 4H), 6.87 (s, 1H), 5.07 (s, 1H), 3.81 (s, 3H), 2.66 (s, 3H), 0.96 (s, 9H). LCMS (M+H) calcd for C₂₆H₂₆ClFN₃O₃: 482.16. found: 482.3.

Example 147

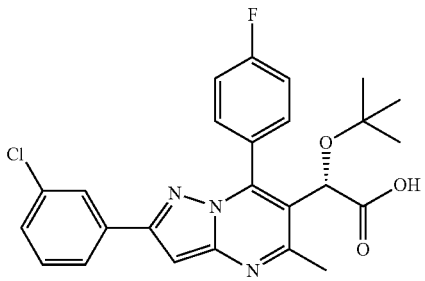 [SMILES: Cc1nc2cc(-c3cccc(Cl)c3)nn2c(-c2ccc(F)cc2)c1[C@H](OC(C)(C)C)C(=O)O]

(S)-2-(tert-Butoxy)-2-(2-(3-chlorophenyl)-7-(4-fluorophenyl)-5-methylpyrazolo[1,5-a]pyrimidin-6-yl) acetic acid A solution of (S)-methyl 2-(tert-butoxy)-2-(2-(3-chlorophenyl)-7-(4-fluorophenyl)-5-methylpyrazolo[1,5-a]pyrimidin-6-yl)acetate (0.0475 g, 0.099 mmol) and 1M NaOH (0.986 ml, 0.986 mmol) in MeOH was heated at reflux for 3 h. Then, cooled, neutralized with 1M HCl (1 mL), concentrated and the residue was taken up in Et₂O (25 mL), washed with water (5 mL), brine (5 mL), dried (MgSO₄), filtered and concentrated to give (S)-2-(tert-butoxy)-2-(2-(3-chlorophenyl)-7-(4-fluorophenyl)-5-methylpyrazolo[1,5-a]pyrimidin-6-yl) acetic acid (0.0407 g, 0.086 mmol, 87% yield) as while solid. ¹H NMR (500 MHz, 1₃) δ: 7.87-7.83 (m, 2H), 7.82-7.78 (m, 1H), 7.75-7.71 (m, 1H), 7.36-7.28 (m, 4H), 6.90 (s, 1H), 5.19 (s, 1H), 2.67 (s, 3H), 1.02 (s, 9H). LCMS (M+H) calcd for C₂₅H₂₄ClFN₃O₃: 468.15. found: 468.2.

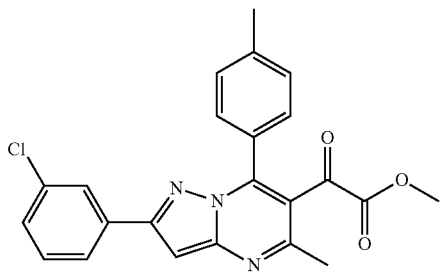 [SMILES: COC(=O)C(=O)c1c(C)nc2cc(-c3cccc(Cl)c3)nn2c1-c1ccc(C)cc1]

Methyl 2-(2-(3-chlorophenyl)-5-methyl-7-(p-tolyl) pyrazolo[1,5-a]pyrimidin-6-yl)-2-oxoacetate To a stirred mixture of 6-bromo-7-chloro-2-(3-chlorophenyl)-5-methylpyrazolo[1,5-a]pyrimidine (0.179 g, 0.5 mmol) and copper(I) bromide (0.036 g, 0.250 mmol) in THF (3 mL) was added dropwise over 10 min a pre-mixed solution of 1M p-tolylmagnesiumbromide/THF (3.00 ml, 3.00 mmol) and 0.5M LiCl/THF (6.00 ml, 3.00 mmol) at rt. After 2.5 h, methyl 2-chloro-2-oxoacetate (0.552 ml, 6 mmol) was added at once and stirred overnight at rt. Then, the reaction was diluted with Et₂O (50 mL), quenched with Na₂CO₃ (1 mL), washed with 10 mL each water and brine, dried (Na₂SO₄), filtered and concentrated to give orange paste which was purified by prep-HPLC to afford methyl 2-(2-(3-chlorophenyl)-5-methyl-7-(p-tolyl)pyrazolo[1,5-a]pyrimidin-6-yl)-2-oxoacetate (0.103 g, 0.123 mmol, 24.53% yield) as yellow solid which is contaminated with impurity. ¹H NMR (500 MHz, CDCl₃) δ: 7.95 (d, J=0.9 Hz, 1H), 7.81 (td, J=4.4, 1.5 Hz, 1H), 7.62 (d, J=8.2 Hz, 2H), 7.40 (d, J=7.6 Hz, 2H), 7.38-7.36 (m, 2H), 6.99 (s, 1H), 3.39 (s, 3H), 2.71 (s, 3H), 2.71 (s, 3H). LCMS (M+H) calcd for C₂₃H₁₉ClFN₃O₃: 420.11. found: 420.2.

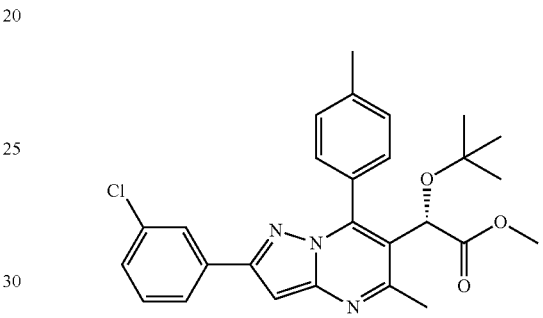

(S)-Methyl 2-(tert-butoxy)-2-(2-(3-chlorophenyl)-5-methyl-7-(p-tolyl)pyrazolo[1,5-a]pyrimidin-6-yl) acetate To a stirred solution of methyl 2-(2-(3-chlorophenyl)-5-methyl-7-(p-tolyl)pyrazolo[1,5-a]pyrimidin-6-yl)-2-oxoacetate (0.103 g, 0.123 mmol) and 1M (R)-1-methyl-3,3-diphenylhexahydropyrrolo[1,2-c][1,3,2]oxazaborole/toluene (0.025 ml, 0.025 mmol) in toluene (5 mL) at −35 C was added dropwise 1M catecholoborane/THF (0.245 ml, 0.245 mmol) over 5 min. After 30 min, the reaction mixture was warmed to −15° C., diluted with EtOAc (10 ml) and quenched with sat. Na₂CO₃ (5 mL). The resulting mixture was vigorously stirred for 30 min, aqueous layer removed and organic layer washed with sat. Na₂CO₃ (2×5 mL), dried (Na₂SO₄), filtered, concentrated to yellow residue which was purified by prep-HPLC to afford (S)-methyl 2-(2-(3-chlorophenyl)-5-methyl-7-(p-tolyl)pyrazolo[1,5-a]pyrimidin-6-yl)-2-hydroxyacetate as white solid.

To a stirred solution above solid (18 mg) in CH₂Cl₂ (3 mL) and tert-BuOAc (1 mL) was added 70% perchloric acid (0.025 mL) at rt and sealed for 1.5 h. Then, the reaction was diluted with Et₂O (25 mL), washed with sat. Na₂CO₃ (2×5 mL), dried (Na₂SO₄), filtered and concentrated to give yellow solid which was purified by prep-HPLC to afford (S)-methyl 2-(tert-butoxy)-2-(2-(3-chlorophenyl)-5-methyl-7-(p-tolyl) pyrazolo[1,5-a]pyrimidin-6-yl)acetate (0.01 g, 0.021 mmol, 17.06% yield) as pale yellow solid. ¹H NMR (500 MHz, CDCl₃) δ 7.86-7.83 (m, 1H), 7.73 (dt, J=6.6, 1.7 Hz, 1H), 7.62 (d, J=7.9 Hz, 1H), 7.50 (d, J=7.6 Hz, 1H), 7.40 (dd, J=12.5, 7.9 Hz, 2H), 7.32-7.27 (m, 2H), 6.86 (s, 1H), 5.14 (s, 1H), 3.80 (s, 3H), 2.65 (s, 3H), 2.51 (s, 3H), 0.95 (s, 9H). LCMS (M+H) calcd for $C_{27}H_{29}ClN_3O_3$: 478.19. found: 480.3.

Example 148

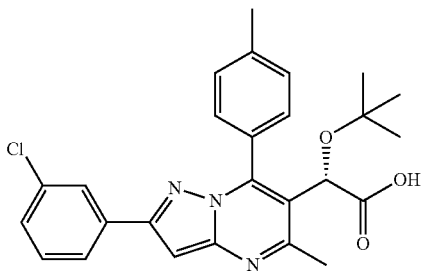 [SMILES: Cc1ccc(-c2c([C@H](OC(C)(C)C)C(=O)O)c(C)nc3cc(-c4cccc(Cl)c4)nn23)cc1]

(S)-2-(tert-Butoxy)-2-(2-(3-chlorophenyl)-5-methyl-7-(p-tolyl)pyrazolo[1,5-a]pyrimidin-6-yl)acetic acid A solution of (S)-methyl 2-(tert-butoxy)-2-(2-(3-chlorophenyl)-5-methyl-7-(p-tolyl)pyrazolo[1,5-a]pyrimidin-6-yl)acetate (0.01 g, 0.021 mmol) and 1M NaOH (0.209 ml, 0.209 mmol) in MeOH (3 mL) was heated at reflux for h. Then, cooled, neutralized with 1M HCl (1 mL), concentrated and the residue was taken up in Et₂O (25 mL), washed with water (5 mL), brine (5 mL), dried (MgSO₄), filtered and concentrated to give (S)-2-(tert-butoxy)-2-(2-(3-chlorophenyl)-5-methyl-7-(p-tolyl)pyrazolo[1,5-a]pyrimidin-6-yl)acetic acid (0.0082 g, 0.017 mmol, 80% yield) as pale yellow solid. ¹H NMR (500 MHz, CDCl₃) δ: 7.85 (s, 1H), 7.76-7.72 (m, 1H), 7.69 (t, J=6.1 Hz, 2H), 7.42 (dd, J=14.3, 8.2 Hz, 2H), 7.32-7.28 (m, 2H), 6.91 (s, 1H), 5.28 (s, 1H), 2.68 (s, 3H), 2.51 (s, 3H), 1.01 (s, 9H). LCMS (M+H) calcd for $C_{26}H_{22}ClN_3O_3$: 464.17. found: 464.3.

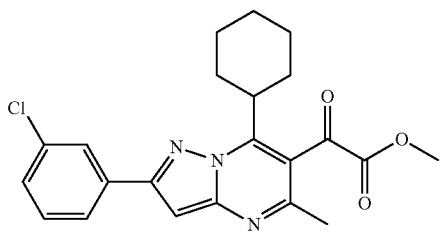 [SMILES: COC(=O)C(=O)c1c(C)nc2cc(-c3cccc(Cl)c3)nn2c1C1CCCCC1]

Methyl 2-(2-(3-chlorophenyl)-7-cyclohexyl-5-methylpyrazolo[1,5-a]pyrimidin-6-yl)-2-oxoacetate To a stirred mixture of 6-bromo-7-chloro-2-(3-chlorophenyl)-5-methylpyrazolo[1,5-a]pyrimidine (0.179 g, 0.5 mmol) and copper(I) bromide (0.036 g, 0.250 mmol) in THF (5 mL) was added dropwise a pre-mixed solution of 0.5M LiCl/THF (6.00 ml, 3.00 mmol) and 2M cyclohexylmagnesium chloride/ether (1.500 ml, 3.00 mmol) over 10 min at rt. After 1.5 h, methyl 2-chloro-2-oxoacetate (0.368 ml, 4.00 mmol) was added at once to the dark reaction mixture and stirred for 1 h. Then, the reaction was diluted with Et₂O (50 mL), quenched with Na₂CO₃ (1 mL), washed with 10 mL each water and brine, dried (Na₂SO₄), filtered and concentrated to give orange paste which was purified by prep-HPLC to afford methyl 24243-chlorophenyl)-7-cyclohexyl-5-methylpyrazolo[1,5-a]pyrimidin-6-yl)-2-oxoacetate (0.0943 g, 0.206 mmol, 41.2% yield) as yellow solid and contaminated with ~10% of 2-(3-chlorophenyl)-7-cyclohexyl-5-methylpyrazolo[1,5-a]pyrimidine. ¹H NMR (500 MHz, CDCl₃) δ: 7.98 (s, 1H), 7.89-7.85 (m, 1H), 7.43-7.38 (m, 2H), 6.86 (s, 1H), 3.98 (s, 3H), 3.11-2.95 (m, 1H), 2.46 (s, 3H), 1.95-1.88 (m, 2H), 1.82-1.7 (m, 2H), 1.46-1.23 (m, 6H). LCMS (M+H) calcd for $C_{22}H_{23}ClN_3O_3$: 412.14. found: 412.3.

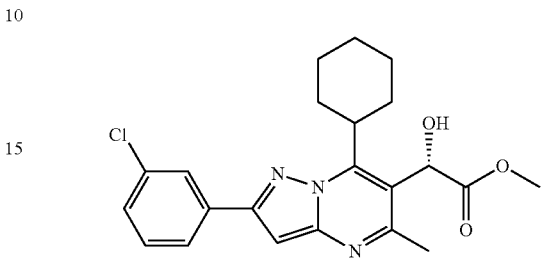

(S)-Methyl 2-(2-(3-chlorophenyl)-7-cyclohexyl-5-methylpyrazolo[1,5-a]pyrimidin-6-yl)-2-hydroxyacetate To a stirred solution of methyl 2-(2-(3-chlorophenyl)-7-cyclohexyl-5-methylpyrazolo[1,5-a]pyrimidin-6-yl)-2-oxoacetate (0.094 g, 0.205 mmol) in toluene (3 mL) was added 1M (R)-1-methyl-3,3-diphenylhexahydropyrrolo[1,2-c][1,3,2]oxazaborole/toluene (0.041 ml, 0.041 mmol) at rt and cooled to −35° C. To this was added dropwise 1M catecholborane/THF (0.288 ml, 0.288 mmol) over 10 min. After stirring 30 min, the reaction mixture was slowly warm to −15° C. over 30 min and diluted with EtOAc (15 mL). Then, the mixture was vigorously stirred with sat Na₂CO₃ (2 mL) for 45 min. The aq layer separated and org layer washed with sat sat Na₂CO₃ (2×5 mL), dried (Na2SO4), filtered, concentrated and the resulting yellow residue purified by prep-HPLC to afford (S)-methyl 2-(2-(3-chlorophenyl)-7-cyclohexyl-5-methylpyrazolo[1,5-a]pyrimidin-6-yl)-2-hydroxyacetate (0.0705 g, 0.170 mmol, 83% yield) as yellow solid. LCMS (M+H) calcd for $C_{22}H_{25}ClN_3O_3$: 414.16. found: 414.3.

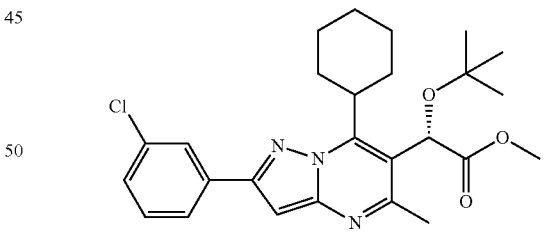

(S)-Methyl 2-(tert-butoxy)-2-(2-(3-chlorophenyl)-7-cyclohexyl-5-methylpyrazolo[1,5-a]pyrimidin-6-yl)acetate To a stirred solution of (S)-methyl 2-(2-(3-chlorophenyl)-7-cyclohexyl-5-methylpyrazolo[1,5-a]pyrimidin-6-yl)-2-hydroxyacetate (0.067 g, 0.162 mmol) and tert-butyl acetate (1 ml, 7.40 mmol) in CH₂Cl₂ (3 mL) was added 70% perchloric acid (0.042 ml, 0.486 mmol) at rt. After 2 h, the reaction was diluted with Et₂O (50 mL), washed with sat. Na₂CO₃ (2×5 mL), dried (Na₂SO₄), filtered and concentrated to give yellow solid which was purified by prep-HPLC to afford (S)-methyl 2-(tert-butoxy)-2-(2-(3-chlorophenyl)-7-cyclohexyl-5-methylpyrazolo[1,5-a]pyrimidin-6-yl)acetate (0.0481 g, 0.102 mmol, 63.2% yield) as white solid. ¹H NMR (500 MHz, CDCl₃) δ: 7.96 (t, J=1.5 Hz, 1H), 7.87 (dt, J=7.6, 1.3 Hz, 1H), 7.41-7.31 (m, 2H), 6.75 (s, 1H), 5.40 (s, 1H), 3.87-3.77 (m, 1H), 3.70 (s, 3H), 2.93-2.79 (m, 2H), 2.73 (s, 3H), 1.96-1.85 (m, 2H), 1.77-1.68 (m, 2H), 1.54-1.38 (m, 4H), 1.25 (s, 9H). LCMS (M+H) calcd for C₂₆H₃₃ClN₃O₃: 470.22. found: 472.4.

Example 149

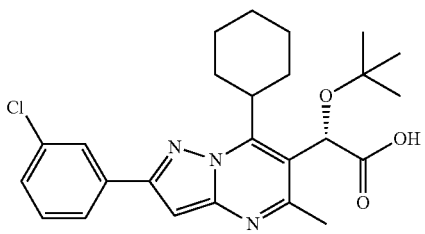 [SMILES: Cc1nc2cc(-c3cccc(Cl)c3)nn2c(C2CCCCC2)c1[C@H](OC(C)(C)C)C(=O)O]

(S)-2-(tert-Butoxy)-2-(2-(3-chlorophenyl)-7-cyclohexyl-5-methylpyrazolo[1,5-a]pyrimidin-6-yl)acetic acid A solution of (S)-methyl 2-(tert-butoxy)-2-(2-(3-chlorophenyl)-7-cyclohexyl-5-methylpyrazolo[1,5-a]pyrimidin-6-yl)acetate (0.048 g, 0.102 mmol) and 1M NaOH (1.021 ml, 1.021 mmol) in MeOH (5 mL) was heated at reflux for h. Then, cooled, neutralized with 1M HCl (0.8 mL), concentrated and the residue was taken up in Et₂O (25 mL), washed with water (5 mL), brine (5 mL), dried (MgSO₄), filtered and concentrated to give (S)-2-(tert-butoxy)-2-(2-(3-chlorophenyl)-7-cyclohexyl-5-methylpyrazolo[1,5-a]pyrimidin-6-yl)acetic acid (0.0426 g, 0.092 mmol, 90% yield) as light yellow solid. ¹H NMR (500 MHz, CDCl₃) δ: 7.95 (s, 1H), 7.86 (d, J=7.3 Hz, 1H), 7.42-7.32 (m, 2H), 6.77 (s, 1H), 5.46 (br. s., 1H), 3.43 (br. s., 1H), 2.97-2.84 (m, 2H), 2.72 (br. s., 3H), 1.98-1.70 (m, 4H), 1.58-1.32 (m, 4H), 1.28 (br. s., 9H). LCMS (M+H) calcd for C₂₅H₃₁ClN₃O₃: 456.21. found: 456.3.

Examples 150-157 were prepared using the synthetic route similar to Scheme 10.

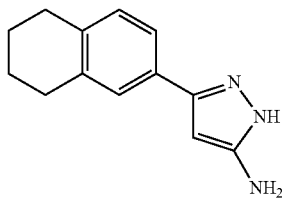 [SMILES: Nc1cc(-c2ccc3c(c2)CCCC3)n[nH]1]

3-(5,6,7,8-Tetrahydronaphthalen-2-yl)-1H-pyrazol-5-amine

Acetonitrile (21.48 mL, 411 mmol) was added to a stirred suspension of 60% NaH (7.05 g, 176 mmol) in dioxane (200 mL) and the resulting mixture was stirred at rt for 20 min. Solution of ethyl 5,6,7,8-tetrahydronaphthalene-2-carboxylate (12 g, 58.7 mmol) in dioxane (50 mL) was then added and the mixture was heated at reflux for 4 h. After cooling to rt, water followed by 1N HCl (100 mL) was added and the mixture was extracted twice with dichloromethane, dried (Na₂SO₄), filtered and concentrated to afford 3-oxo-3-(5,6,7,8-tetrahydronaphthalen-2-yl)propanenitrile as dark solid. A mixture of this syrup and hydrazine hydrate (2.77 mL, 88 mmol) in ethanol (200 mL) was refluxed for 16 h. The reaction mixture was then cooled to rt and concentrated in vacuo. The resulting crude was diluted with dichloromethane and washed with water, dried (Na₂SO₄), filtered, concentrated and purified by silica gel chromatography (5-10% CH₂Cl₂/MeOH) to afford desired 3-(5,6,7,8-tetrahydronaphthalen-2-yl)-1H-pyrazol-5-amine (6.1 g, 28.6 mmol, 48.7% yield) as yellow solid. ¹H NMR (400 MHz, CDCl₃) δ: 7.26 (d, J=3.5 Hz, 2H), 7.12 (d, J=7.8 Hz, 1H), 5.89 (s, 1H), 4.14 (br. s., 3H), 2.88-2.75 (m, 4H), 1.83 (dt, J=6.1, 3.4 Hz, 4H). LCMS (M+H)=214.2.

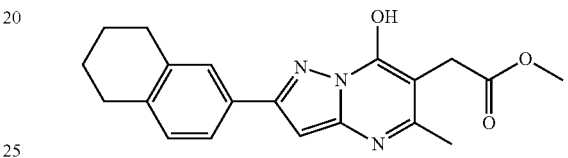

Methyl 2-(7-hydroxy-5-methyl-2-(5,6,7,8-tetrahydronaphthalen-2-yl)pyrazolo[1,5-a]pyrimidin-6-yl)acetate A suspension of 3-(5,6,7,8-tetrahydronaphthalen-2-yl)-1H-pyrazol-5-amine (6 g, 28.1 mmol), 1-ethyl 4-methyl 2-acetylsuccinate (24.52 mL, 141 mmol) and Ts-OH.H₂O (0.096 g, 0.506 mmol) in o-xylene (200 mL) was heated at 150° C. (oil bath temp) for 16 h. (Note: Mixture became homogeneous and in about 15 min slowly yellow solid started crashing out of the reaction.). Then, the reaction mixture was cooled, diluted with hexanes (300 mL), filtered, washed with hexanes and dried to afford methyl 2-(7-hydroxy-5-methyl-2-(5,6,7,8-tetrahydronaphthalen-2-yl)pyrazolo[1,5-a]pyrimidin-6-yl)acetate (8.4 g, 23.90 mmol, 85% yield) as light yellow solid. ¹H NMR (400 MHz, DMSO-d₆) δ: 12.35 (s, 1H), 7.78-7.62 (m, 2H), 7.15 (d, J=8.5 Hz, 1H), 6.52 (s, 1H), 3.64 (s, 3H), 3.58 (s, 2H), 2.82-2.77 (m, 4H), 2.33 (s, 3H), 1.78 (t, J=3.0 Hz, 4H). LCMS (M+H)=352.3.

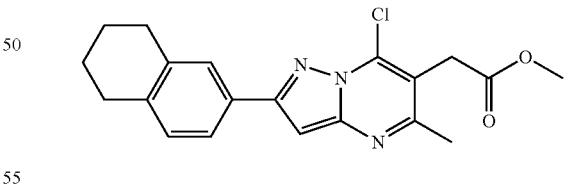

Methyl 2-(7-chloro-5-methyl-2-(5,6,7,8-tetrahydronaphthalen-2-yl)pyrazolo[1,5-a]pyrimidin-6-yl)acetate A mixture of methyl 2-(7-hydroxy-5-methyl-2-(5,6,7,8-tetrahydronaphthalen-2-yl)pyrazolo[1,5-a]pyrimidin-6-yl)acetate (8.4 g, 23.90 mmol) and phosphoryl trichloride (10.94 ml, 120 mmol) was refluxed for 4 h. Then, cooled, concentrated and the dark residue was taken up in EtOAc (500 mL) and stirred with ice-water for 30 min. Aqueous layer separated and organic layer washed with water (2×50 mL). The combine aqueous layers extracted with EtOAc (100 mL) and the combined organic layers washed with brine (100 mL), dried (Na₂SO₄/C), filtered and concentrated to give dark paste. Purification by flash column chromatography on silica gel using 5-20% EtOAc/Hex afforded methyl 2-(7-chloro-5-methyl-2-(5,6,7,8-tetrahydronaphthalen-2-yl)pyrazolo[1,5-a]pyrimidin-6-yl)acetate (5.6 g, 15.14 mmol, 63.3% yield) as off-white solid. ¹H NMR (500 MHz, CDCl₃) δ: 7.76-7.71 (m, 2H), 7.18 (d, J=7.6 Hz, 1H), 6.92 (s, 1H), 3.93 (s, 2H), 3.78 (s, 3H), 2.89-2.84 (m, 4H), 2.63 (s, 3H), 1.86 (dt, J=6.5, 3.3 Hz, 4H). LCMS (M+H)=370.11.

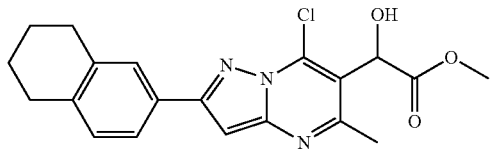 [SMILES: COC(=O)C(O)c1c(C)nc2cc(-c3ccc4c(c3)CCCC4)nn2c1Cl]

Methyl 2-(7-chloro-5-methyl-2-(5,6,7,8-tetrahydronaphthalen-2-yl)pyrazolo[1,5-a]pyrimidin-6-yl)-2-hydroxyacetate To a stirred solution of 0.9M KHMDS/THF (9.76 mL, 8.79 mmol) in THF (25 mL) at −78° C. was added dropwise a THF (25 mL) solution of methyl 2-(7-chloro-5-methyl-2-(5,6,7,8-tetrahydronaphthalen-2-yl)pyrazolo[1,5-a]pyrimidin-6-yl)acetate (2.5 g, 6.76 mmol) over 5 min. After 30 min, a THF (20 mL) solution of 3-phenyl-2-(phenylsulfonyl)-1,2-oxaziridine (2.296 g, 8.79 mmol) was added to the resulting red reaction mixture and stirred for additional 30 min at −78° C. Then, the resulting orange reaction mixture was quenched with sat. NH₄Cl (50 mL), diluted with EtOAc (200 mL), washed with water (100 mL), brine (100 mL), dried (Na₂SO₄), filtered and concentrated to give yellow solid. This was purified by flash column chromatography on silica gel column (5-40% EtOAc/hexane) to afford the 2.2 g desired methyl 2-(7-chloro-5-methyl-2-(5,6,7,8-tetrahydronaphthalen-2-yl)pyrazolo[1,5-a]pyrimidin-6-yl)-2-hydroxyacetate as off-white solid. Impurities were present by NMR and LCMS. Used in the next step without further purification. ¹H NMR (500 MHz, CDCl₃) δ: 7.77-7.71 (m, 2H), 7.19 (d, J=7.6 Hz, 1H), 6.93 (s, 1H), 5.78 (d, J=2.7 Hz, 1H), 3.86 (s, 3H), 3.56 (d, J=2.7 Hz, 1H), 2.89-1.81 (m, 4H), 2.64 (s, 3H), 1.86 (dt, J=6.5, 3.3 Hz, 4H). LCMS (M+H)=386.3.

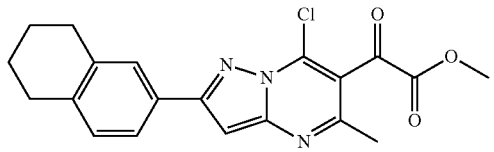 [SMILES: COC(=O)C(=O)c1c(C)nc2cc(-c3ccc4c(c3)CCCC4)nn2c1Cl]

Methyl 2-(7-chloro-5-methyl-2-(5,6,7,8-tetrahydronaphthalen-2-yl)pyrazolo[1,5-a]pyrimidin-6-yl)-2-oxoacetate To a mixture of methyl 2-(7-chloro-5-methyl-2-(5,6,7,8-tetrahydronaphthalen-2-yl)pyrazolo[1,5-a]pyrimidin-6-yl)-2-hydroxyacetate (2.5 g, 6.48 mmol) in CH₂Cl₂ (70 mL) was added Dess-Martin periodinane (3.02 g, 7.13 mmol) and the resulting mixture was stirred at rt for 1 hr. Then diluted with ethyl acetate (500 mL), washed with sat. NaHCO₃ (100 mL), dried (Na₂SO₄), filtered and concentrated. The residue was purified by silica gel chromatography (5-30% EtOAc/hexane) to afford desired methyl 2-(7-chloro-5-methyl-2-(5,6,7,8-tetrahydronaphthalen-2-yl)pyrazolo[1,5-a]pyrimidin-6-yl)-2-oxoacetate (1.1 g, 2.87 mmol, 44.2% yield) as off-white solid. 44% yield based on 2 steps. ¹H NMR (500 MHz, CDCl₃) δ: 7.77-7.71 (m, 2H), 7.20 (d, J=7.6 Hz, 1H), 7.00 (s, 1H), 4.02 (s, 3H), 2.89-2.83 (m, 4H), 2.64 (s, 3H), 1.86 (dt, J=6.5, 3.3 Hz, 4H). LCMS (M+H)=384.3.

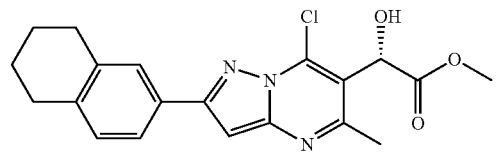

(S)-Methyl 2-(7-chloro-5-methyl-2-(5,6,7,8-tetrahydronaphthalen-2-yl)pyrazolo[1,5-a]pyrimidin-6-yl)-2-hydroxyacetate To a stirred yellow solution of methyl 2-(7-chloro-5-methyl-2-(5,6,7,8-tetrahydronaphthalen-2-yl)pyrazolo[1,5-a]pyrimidin-6-yl)-2-oxoacetate (1 g, 2.61 mmol) in anhydrous toluene (25 mL) was added 1.1M (R)-1-methyl-3,3-diphenylhexahydropyrrolo[1,2-c][1,3,2]oxazaborole/toluene (0.947 mL, 1.042 mmol). The mixture was cooled to −35° C. and a solution of 1M catechoborane/THF (3.65 mL, 3.65 mmol) was added over 10 min. After 30 min, the reaction mixture was slowly warmed to −15° C. and stirred for additional 30 min. Then, diluted with EtOAc (30 mL) and sat. Na₂CO₃ (10 mL), and the mixture was stirred vigorously for 30 min. The organic phase washed with sat Na₂CO₃ (2×5 mL), dried (Na₂SO₄), filtered, concentrated and the residue was purified by silica gel chromatography (5-70% EtOAc/hexane) to afford desired (S)-methyl 2-(7-chloro-5-methyl-2-(5,6,7,8-tetrahydronaphthalen-2-yl)pyrazolo[1,5-a]pyrimidin-6-yl)-2-hydroxyacetate (888 mg, 2.301 mmol, 88% yield) as off-white solid. EE=95.4%.

¹H NMR (500 MHz, CDCl₃) δ: 7.77-7.71 (m, 2H), 7.19 (d, J=7.6 Hz, 1H), 6.93 (s, 1H), 5.78 (d, J=2.7 Hz, 1H), 3.86 (s, 3H), 3.56 (d, J=2.7 Hz, 1H), 2.89-1.81 (m, 4H), 2.64 (s, 3H), 1.86 (dt, J=6.5, 3.3 Hz, 4H). LCMS (M+H)=386.3.

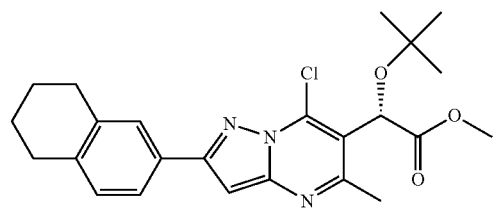 [SMILES: COC(=O)[C@@H](OC(C)(C)C)c1c(C)nc2cc(-c3ccc4c(c3)CCCC4)nn2c1Cl]

(S)-Methyl 2-(tert-butoxy)-2-(7-chloro-5-methyl-2-(5,6,7,8-tetrahydronaphthalen-2-yl)pyrazolo[1,5-a]pyrimidin-6-yl)acetate To a stirred solution of (S)-methyl 2-(7-chloro-5-methyl-2-(5,6,7,8-tetrahydronaphthalen-2-yl)pyrazolo[1,5-a]pyrimidin-6-yl)-2-hydroxyacetate (888 mg, 2.301 mmol) in CH₂Cl₂ (45 mL) and t-butyl acetate (21.76 mL, 161 mmol) at rt was added perchloric acid (0.593 mL, 6.90 mmol). After 2.5 h, the reaction mixture was diluted with CH₂Cl₂ (50 mL), carefully quenched with sat. NaHCO₃ (50 mL), organic layer separated and washed with brine (100 mL), dried (Na₂SO₄), filtered and concentrated to give yellow liquid. This was purified by flash column chromatography on silica gel column using (10-40% EtOAc/Hex as eluant) to afford the desired (S)-methyl 2-(tert-butoxy)-2-(7-chloro-5-methyl-2-(5,6,7,8-tetrahydronaphthalen-2-yl)pyrazolo[1,5-a]pyrimidin-6-yl)acetate (735 mg, 1.663 mmol, 72.3% yield) as white solid. 150 mg of starting material was also recovered. ¹H NMR (500 MHz, CDCl₃) δ: 7.76-7.70 (m, 2H), 7.18 (d, J=7.9 Hz, 1H), 6.91 (s, 1H), 5.68 (s, 1H), 3.76 (s, 3H), 2.89-2.84 (m, 4H), 2.68 (s, 3H), 1.89-1.83 (m, 4H), 1.30 (s, 9H). LCMS (M+H)=444.3.

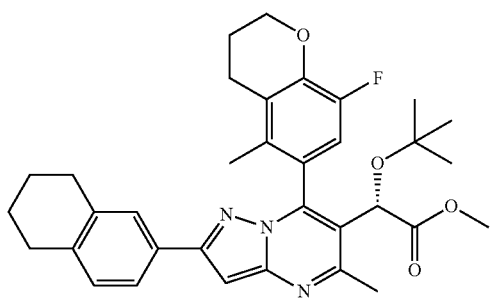 [SMILES: COC(=O)[C@@H](OC(C)(C)C)c1c(C)nc2cc(-c3ccc4c(c3)CCCC4)nn2c1-c1cc(F)c2c(c1C)CCCO2]

(2S)-Methyl 2-(tert-butoxy)-2-(7-(8-fluoro-5-methyl-chroman-6-yl)-5-methyl-2-(5,6,7,8-tetrahydronaphthalen-2-yl)pyrazolo[1,5-a]pyrimidin-6-yl)acetate A mixture of (S)-methyl 2-(tert-butoxy)-2-(7-chloro-5-methyl-2-(5,6,7,8-tetrahydronaphthalen-2-yl)pyrazolo[1,5-a]pyrimidin-6-yl)acetate (50 mg, 0.113 mmol), 2-(8-fluoro-5-methylchroman-6-yl)-4,4,5,5-tetramethyl-1,3,2-dioxaborolane (36.4 mg, 0.124 mmol) and 2M Na₂CO₃ (0.113 mL, 0.226 mmol) in DMF (1.5 mL) was added tetrakis(triphenylphosphine)pallafium(0) (13.07 mg, 0.011 mmol) and the mixture was subjected to microwave heating at 120° C. for 1 h. The mixture was then filtered and purified by prep HPLC to afford atrope isomer 1 (major, first eluting): (2S)-methyl 2-(tert-butoxy)-2-(7-(8-fluoro-5-methylchroman-6-yl)-5-methyl-2-(5,6,7,8-tetrahydronaphthalen-2-yl)pyrazolo[1,5-a]pyrimidin-6-yl)acetate (27 mg, 0.047 mmol, 41.7% yield) as white solid. ¹H NMR (500 MHz, CDCl₃) δ: 7.56 (d, J=7.9 Hz, 1H), 7.52 (s, 1H), 7.09 (d, J=7.9 Hz, 1H), 6.92 (d, J=10.7 Hz, 1H), 6.84 (s, 1H), 5.03 (s, 1H), 4.41-4.32 (m, 2H), 3.66 (s, 3H), 2.88-2.78 (m, 6H), 2.77 (s, 3H), 2.26-2.17 (m, 2H), 1.86 (s, 3H), 1.85-1.79 (m, 4H), 1.19 (s, 9H).

LCMS (M+H)=572.4. 5 mg of atrope isomer-2 (minor, second eluting) was also isolated. ¹H NMR (500 MHz, CDCl₃) δ: 7.59 (s, 1H), 7.54 (s, 1H), 7.20 (d, J=11.0 Hz, 1H), 7.11 (s, 1H), 6.85 (s, 1H), 5.08 (s, 1H), 4.42-4.32 (m, 2H), 3.81 (s, 3H), 2.86-2.78 (m, 6H), 2.68 (s, 3H), 2.23-2.16 (m, 2H), 1.84 (s, 3H), 1.83-1.78 (m, 4H), 1.01 (s, 9H). LCMS (M+H)=572.4.

The following intermediates were prepared according to the above procedure using appropriate boronate reagents.

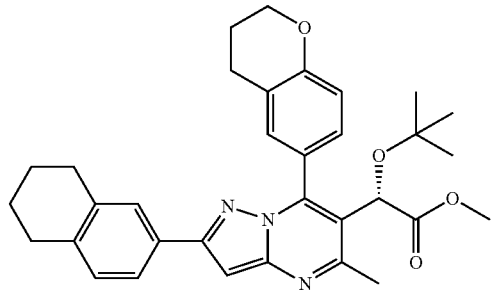 [SMILES: COC(=O)[C@@H](OC(C)(C)C)c1c(C)nc2cc(-c3ccc4c(c3)CCCC4)nn2c1-c1ccc2c(c1)CCCO2]

(S)-Methyl 2-(tert-butoxy)-2-(7-(chroman-6-yl)-5-methyl-2-(5,6,7,8-tetrahydronaphthalen-2-yl)pyrazolo[1,5-a]pyrimidin-6-yl)acetate ¹H NMR (500 MHz, CDCl₃) δ: 7.65-7.57 (m, 2H), 7.54-7.46 (m, 1H), 7.41-7.31 (m, 1H), 7.10 (t, J=7.0 Hz, 1H), 7.00 (dd, J=13.1, 8.2 Hz, 1H), 6.85 (s, 1H), 5.22 (d, J=5.2 Hz, 1H), 4.33 (t, J=5.0 Hz, 2H), 3.83 (d, J=5.8 Hz, 3H), 2.90-2.74 (m, 6H), 2.66 (d, J=4.6 Hz, 3H), 2.15-2.06 (m, 2H), 1.88-1.75 (m, 4H), 1.02-0.94 (m, 9H).

LCMS (M+H)=540.30.

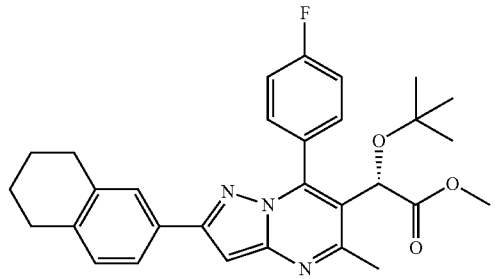 [SMILES: COC(=O)[C@@H](OC(C)(C)C)c1c(C)nc2cc(-c3ccc4c(c3)CCCC4)nn2c1-c1ccc(F)cc1]

(S)-Methyl 2-(tert-butoxy)-2-(7-(4-fluorophenyl)-5-methyl-2-(5,6,7,8-tetrahydronaphthalen-2-yl)pyrazolo[1,5-a]pyrimidin-6-yl)acetate ¹H NMR (500 MHz, CDCl₃) δ: 7.82-7.75 (m, 1H), 7.71-7.67 (m, 1H), 7.58 (d, J=7.6 Hz, 1H), 7.56 (s, 1H), 7.36-7.30 (m, 2H), 7.10 (d, J=7.9 Hz, 1H), 6.87 (s, 1H), 5.09 (s, 1H), 3.83 (s, 3H), 2.81 (d, J=14.0 Hz, 4H), 2.68 (s, 3H), 1.86-1.78 (m, 4H), 1.01-0.96 (m, 9H). LCMS (M+H)=502.25.

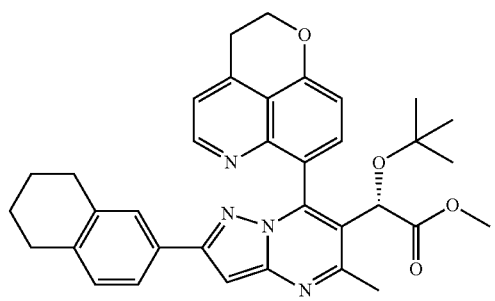 [SMILES: COC(=O)[C@@H](OC(C)(C)C)c1c(C)nc2cc(-c3ccc4c(c3)CCCC4)nn2c1-c1ccc2c3c(ccnc13)CCO2]

(2S)-Methyl 2-(tert-butoxy)-2-(7-(2,3-dihydropyrano[4,3,2-de]quinolin-7-yl)-5-methyl-2-(5,6,7,8-tetrahydronaphthalen-2-yl)pyrazolo[1,5-a]pyrimidin-6-yl)acetate ¹H NMR (500 MHz, CDCl₃) δ: 8.63 (br. s., 1H), 7.92-7.85 (m, 1H), 7.34 (d, J=8.5 Hz, 2H), 7.21-7.10 (m, 2H), 6.97 (br. s., 1H), 6.87 (br. s., 1H), 5.18 (s, 1H), 4.64-4.60 (m, 2H), 3.75 (s, 3H), 3.38-3.32 (m, 2H), 2.77 (s., 3H), 2.74-2.68 (m, 4H), 1.78-1.72 (m, 4H), 0.90 (s, 9H). LCMS (M+H)=577.4.

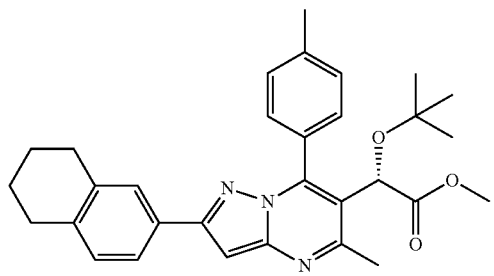 [SMILES: COC(=O)[C@@H](OC(C)(C)C)c1c(C)nc2cc(-c3ccc4c(c3)CCCC4)nn2c1-c1ccc(C)cc1]

(S)-Methyl 2-(tert-butoxy)-2-(5-methyl-2-(5,6,7,8-tetrahydronaphthalen-2-yl)-7-(p-tolyl)pyrazolo[1,5-a]pyrimidin-6-yl)acetate ¹H NMR (500 MHz, CDCl₃) δ: 7.67 (d, J=7.9 Hz, 1H), 7.59 (d, J=7.9 Hz, 1H), 7.57 (s, 1H), 7.54 (d, J=7.6 Hz, 1H), 7.41 (t, J=8.2 Hz, 2H), 7.08 (d, J=7.9 Hz, 1H), 6.86 (s, 1H), 5.17 (s, 1H), 3.83 (s, 3H), 2.80 (d, J=15.0 Hz, 4H), 2.67 (s, 3H), 2.53 (s, 3H), 1.82 (t, J=3.1 Hz, 4H), 0.97 (s, 9H).

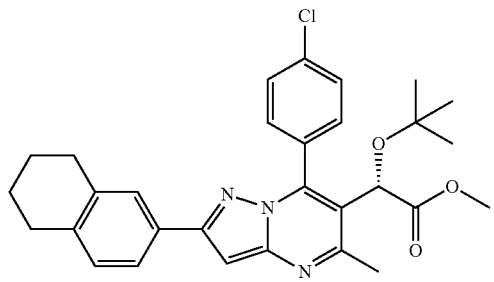 [SMILES: COC(=O)[C@@H](OC(C)(C)C)c1c(C)nc2cc(-c3ccc4c(c3)CCCC4)nn2c1-c1ccc(Cl)cc1]

(S)-Methyl 2-(tert-butoxy)-2-(7-(4-chlorophenyl)-5-methyl-2-(5,6,7,8-tetrahydronaphthalen-2-yl)pyrazolo[1,5-a]pyrimidin-6-yl)acetate ¹H NMR (500 MHz, CDCl₃) δ: 7.72 (d, J=7.6 Hz, 1H), 7.64-7.54 (m, 5H), 7.10 (d, J=7.9 Hz, 1H), 6.87 (s, 1H), 5.07 (s, 1H), 3.83 (s, 3H), 2.86-2.77 (m, 4H), 2.68 (s, 3H), 1.86-1.78 (m, 4H), 0.99 (s, 9H). LCMS (M+H)=518.4.

Example 150

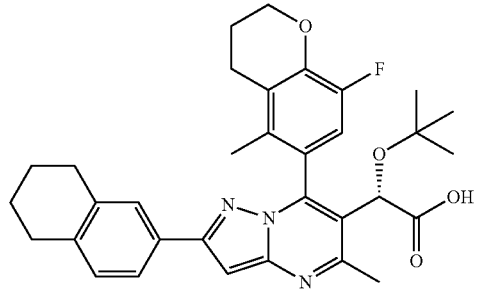 [SMILES: Cc1nc2cc(-c3ccc4c(c3)CCCC4)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-5-methyl-2-(5,6,7,8-tetrahydronaphthalen-2-yl)pyrazolo[1,5-a]pyrimidin-6-yl)acetic acid A solution of (2S)-methyl 2-(tert-butoxy)-2-(7-(8-fluoro-5-methylchroman-6-yl)-5-methyl-2-(5,6,7,8-tetrahydronaphthalen-2-yl)pyrazolo[1,5-a]pyrimidin-6-yl)acetate (22 mg, 0.038 mmol) and 1M NaOH (0.154 mL, 0.154 mmol) in MeOH (2 mL) was heated at 60° C. for 16 h. Then, the reaction mixture was cooled and purified by prep HPLC to afford (2S)-2-(tert-butoxy)-2-(7-(8-fluoro-5-methylchroman-6-yl)-5-methyl-2-(5,6,7,8-tetrahydronaphthalen-2-yl)pyrazolo[1,5-a]pyrimidin-6-yl)acetic acid (12 mg, 0.020 mmol, 53.1% yield) as white solid. ¹H NMR (500 MHz, CDCl₃) δ: 7.56 (d, J=7.9 Hz, 1H), 7.52 (s, 1H), 7.09 (d, J=7.9 Hz, 1H), 6.96 (d, J=10.7 Hz, 1H), 6.86 (s, 1H), 5.11 (s, 1H), 4.39-4.31 (m, 2H), 2.86-2.75 (m, 6H), 2.73 (s, 3H), 2.20-2.18 (m, 2H), 1.95 (s, 3H), 1.84-1.80 (m, 4H), 1.24 (s, 9H). LCMS (M+H)=558.4.

The following examples were prepared according to the procedure for Example 150 using appropriate esters.

Example 151

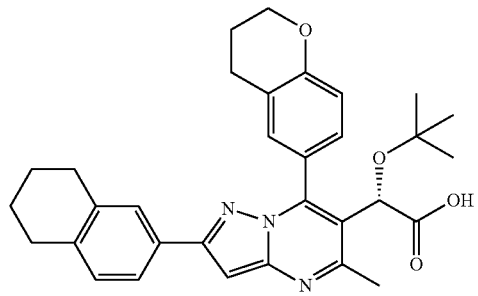 [SMILES: Cc1nc2cc(-c3ccc4c(c3)CCCC4)nn2c(-c2ccc3c(c2)CCCO3)c1[C@H](OC(C)(C)C)C(=O)O]

(S)-2-(tert-Butoxy)-2-(7-(chroman-6-yl)-5-methyl-2-(5,6,7,8-tetrahydronaphthalen-2-yl)pyrazolo[1,5-a]pyrimidin-6-yl)acetic acid ¹H NMR (400 MHz, DMSO-d₆) δ: 7.59-7.41 (m, 4H), 7.11 (d, J=8.0 Hz, 1H), 7.07-6.99 (m, 2H), 5.02 (s, 1H), 4.28 (br. s., 2H), 2.91 (s, 3H), 2.82-2.75 (m, 6H), 2.12-1.98 (m, 2H), 1.93 (s, 1H), 1.82-1.72 (m, 4H), 0.90 (s, 9H). LCMS (M+H)= 526.19.

Example 152

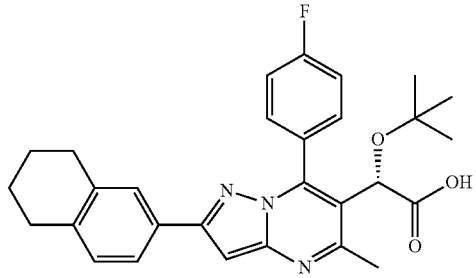

(S)-2-(tert-Butoxy)-2-(7-(4-fluorophenyl)-5-methyl-2-(5,6,7,8-tetrahydronaphthalen-2-yl)pyrazolo[1,5-a]pyrimidin-6-yl)acetic acid: ¹H NMR (400 MHz, DMSO-d₆) δ: 7.91-7.83 (m, 1H), 7.78-7.69 (m, 1H), 7.60-7.50 (m, 4H), 7.12 (s, 1H), 7.09 (s, 1H), 4.91 (s, 1H), 2.91 (s, 3H), 2.78-2.71 (m, 4H), 1.81-1.68 (m, 4H), 0.91 (s, 9H).

LCMS (M+H)=488.16.

Example 153

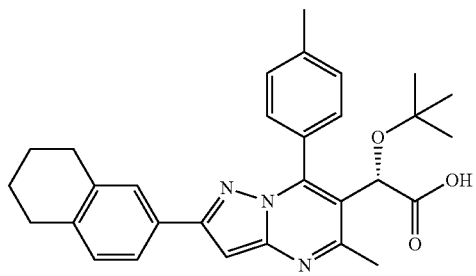 [SMILES: Cc1ccc(-c2c([C@H](OC(C)(C)C)C(=O)O)c(C)nc3cc(-c4ccc5c(c4)CCCC5)nn23)cc1]

(S)-2-(tert-Butoxy)-2-(5-methyl-2-(5,6,7,8-tetrahydronaphthalen-2-yl)-7-(p-tolyl)pyrazolo[1,5-a]pyrimidin-6-yl)acetic acid ¹H NMR (400 MHz, DMSO-d₆) δ: 7.67 (d, J=7.8 Hz, 1H), 7.63-7.54 (m, 3H), 7.49 (d, J=8.3 Hz, 2H), 7.10 (d, J=7.8 Hz, 1H), 7.06 (s, 1H), 4.95 (s, 1H), 2.91 (s, 3H), 2.80-2.71 (m, 4H), 2.48 (s, 3H), 1.82-1.72 (m, 4H), 0.88 (s, 9H). LCMS (M+H)=484.29.

Example 154

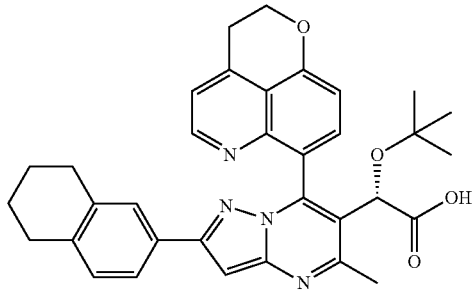 [SMILES: Cc1nc2cc(-c3ccc4c(c3)CCCC4)nn2c(-c2ccc3c4c(ccnc24)CCO3)c1[C@H](OC(C)(C)C)C(=O)O]

(2S)-2-(tert-Butoxy)-2-(7-(2,3-dihydropyrano[4,3,2-de]quinolin-7-yl)-5-methyl-2-(5,6,7,8-tetrahydronaphthalen-2-yl)pyrazolo[1,5-a]pyrimidin-6-yl) acetic acid ¹H NMR (500 MHz, DMSO-d₆) δ: 8.61 (d, J=4.3 Hz, 1H), 7.99-7.94 (m, 1H), 7.35-7.31 (m, 2H), 7.30-7.26 (m, 1H), 7.24 (d, J=7.9 Hz, 1H), 7.00-6.93 (m, 2H), 4.82 (s, 1H), 4.57 (t, J=5.8 Hz, 2H), 3.39-3.32 (m, 4H), 2.69-2.67 (m, 2H), 2.66 (s, 3H), 1.70 (t, J=2.9 Hz, 4H), 0.68 (s, 9H). LCMS (M+H)= 563.4.

Example 155

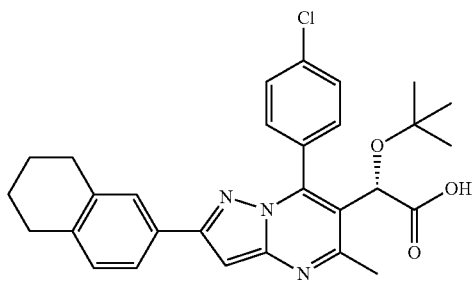 [SMILES: Cc1nc2cc(-c3ccc4c(c3)CCCC4)nn2c(-c2ccc(Cl)cc2)c1[C@H](OC(C)(C)C)C(=O)O]

(S)-2-(tert-Butoxy)-2-(7-(4-chlorophenyl)-5-methyl-2-(5,6,7,8-tetrahydronaphthalen-2-yl)pyrazolo[1,5-a] pyrimidin-6-yl)acetic acid ¹H NMR (400 MHz, DMSO-d₆) δ: 7.87-7.73 (m, 4H), 7.60-7.54 (m, 2H), 7.10 (d, J=7.8 Hz, 1H), 7.07 (s, 1H), 4.83 (s, 1H), 2.82-2.71 (m, 4H), 2.62 (s, 3H), 1.72-1.79 (m., 4H), 0.90 (s, 9H). LCMS (M+H)=504.4.

Example 156

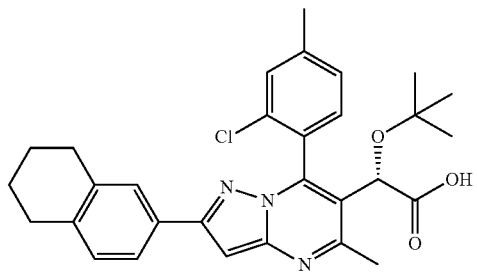 [SMILES: Cc1ccc(-c2c([C@H](OC(C)(C)C)C(=O)O)c(C)nc3cc(-c4ccc5c(c4)CCCC5)nn23)c(Cl)c1]

(2S)-2-(tert-Butoxy)-2-(7-(2-chloro-4-methylphenyl)-5-methyl-2-(5,6,7,8-tetrahydronaphthalen-2-yl)pyrazolo[1,5-a]pyrimidin-6-yl)acetic acid $^1$H NMR (500 MHz, DMSO-$d_6$) δ: 7.56-7.48 (m, 3H), 7.39 (d, J=7.6 Hz, 1H), 7.34 (d, J=7.6 Hz, 1H), 7.09 (d, J=7.6 Hz, 1H), 7.03 (s, 1H), 4.83 (br. s., 1H), 2.76-2.74 (m, 4H), 2.73 (br. s., 3H), 2.46 (s, 3H), 1.74 (t, J=3.1 Hz, 4H), 1.06 (s, 10H). LCMS (M+H)=520.16.

Example 157

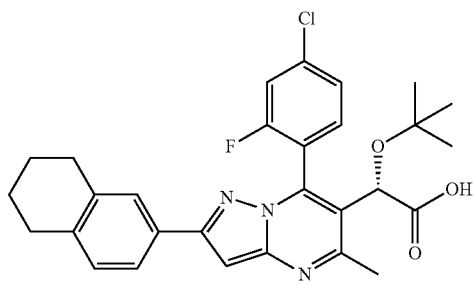 [SMILES: Cc1nc2cc(-c3ccc4c(c3)CCCC4)nn2c(-c2ccc(Cl)cc2F)c1[C@H](OC(C)(C)C)C(=O)O]

(2S)-2-(tert-Butoxy)-2-(7-(4-chloro-2-fluorophenyl)-5-methyl-2-(5,6,7,8-tetrahydronaphthalen-2-yl)pyrazolo[1,5-a]pyrimidin-6-yl)acetic acid $^1$H NMR (400 MHz, DMSO-$d_6$) δ: 7.85 (dd, J=9.7, 1.9 Hz, 1H), 7.65 (dd, J=8.3, 1.8 Hz, 1H), 7.61-7.52 (m, 3H), 7.15-7.06 (m, 2H), 4.78 (s, 1H), 2.82-2.70 (m, 4H), 2.64 (s, 3H), 1.72-1.78 (m, 4H), 0.94 (s, 9H). LCMS (M+H)=522.14. Examples 158-164 were prepared using the synthetic route similar to scheme 10.

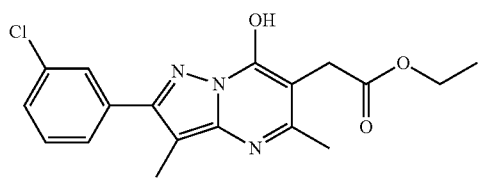 [SMILES: CCOC(=O)Cc1c(C)nc2c(C)c(-c3cccc(Cl)c3)nn2c1Cl]

Ethyl 2-(2-(3-chlorophenyl)-7-hydroxy-3,5-dimethylpyrazolo[1,5-a]pyrimidin-6-yl)acetate A mixture of 3-(3-chlorophenyl)-4-methyl-1H-pyrazol-5-amine (10 g, 48.2 mmol), diethyl 2-acetylsuccinate (28.9 ml, 144 mmol) and TsOH.H$_2$O (100 mg) in o-xylene (200 mL) was heated at 120 C for 2 h. After this, the resulting reaction slurry was cooled, filtered, washed with hexanes and dried to afford ethyl 24243-chlorophenyl)-7-hydroxy-3,5-dimethylpyrazolo[1,5-a]pyrimidin-6-yl)acetate (13.48 g, 37.5 mmol, 78% yield) as light brown solid which was used in the next step without purification. $^1$H NMR (500 MHz, DMSO-$d_6$) δ: 11.98 (s, 1H), 7.79 (t, J=1.7 Hz, 1H), 7.74 (dt, J=7.4, 1.5 Hz, 1H), 7.58-7.49 (m, 2H), 4.09 (q, J=7.0 Hz, 2H), 3.56 (s, 2H), 2.37 (s, 3H), 2.32 (s, 3H), 1.20 (t, J=7.2 Hz, 3H). LCMS (M+H) calcd for $C_{18}H_{19}ClN_3O_3$: 360.1. found: 360.3.

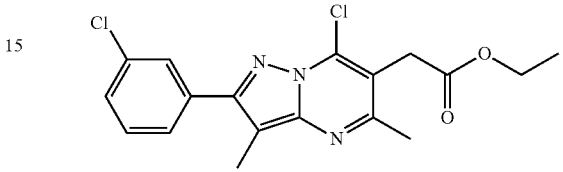

Ethyl 2-(7-chloro-2-(3-chlorophenyl)-3,5-dimethylpyrazolo[1,5-a]pyrimidin-6-yl)acetate A suspension of ethyl 2-(2-(3-chlorophenyl)-7-hydroxy-3,5-dimethylpyrazolo[1,5-a]pyrimidin-6-yl)acetate (11.5 g, 20.78 mmol), N,N-dimethylaniline (5.04 g, 41.6 mmol) and POCl$_3$ (40 ml, 429 mmol) was heated (120° C. oil bath) for 3 hrs. The reaction was then concentrated in-vacuo and the dark residue taken up in EtOAc (75 mL) and stirred with ice-water (75 mL) for 30 min. The organic layer was washed with water (2×50 mL). The combined aqueous layers were extracted with EtOAc (50 mL) and the combined organic layers washed with brine (50 mL), dried (Na$_2$SO$_4$), filtered and concentrated to give a brown solid. The crude product was purified by silica gel flash column chromatography, eluting with 10%-30% EtOAc in hexane. Product fractions were pooled and concentrated under reduced pressure, affording the purified product, ethyl 2-(7-chloro-2-(3-chlorophenyl)-3,5-dimethylpyrazolo[1,5-a]pyrimidin-6-yl)acetate (8.3 g, 20.45 mmol, 98% yield) as an off-white powdery solid. $^1$H NMR (500 MHz, CDCl$_3$) δ: 7.87 (t, J=1.7 Hz, 1H), 7.74 (dt, J=7.3, 1.5 Hz, 1H), 7.44-7.36 (m, 2H), 4.21 (q, J=7.1 Hz, 2H), 3.89 (s, 2H), 2.62 (s, 3H), 2.52 (s, 3H), 1.28 (t, J=7.2 Hz, 3H).

LC/MS (M+H)=378.2.

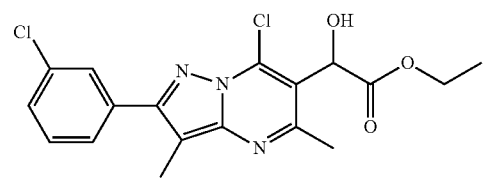 [SMILES: CCOC(=O)C(O)c1c(C)nc2c(C)c(-c3cccc(Cl)c3)nn2c1Cl]

Ethyl 2-(7-chloro-2-(3-chlorophenyl)-3,5-dimethylpyrazolo[1,5-a]pyrimidin-6-yl)-2-hydroxyacetate To a cold (−78° C. dry ice/acetone) stirred solution of 0.91 M KHMDS in THF (32 ml, 29.1 mmol) in additional THF (100 ml) was added ethyl 2-(7-chloro-2-(3-chlorophenyl)-3,5-dimethylpyrazolo[1,5-a]pyrimidin-6-yl)acetate (8.3 g, 21.94 mmol) in THF (100 ml), by dropwise addition over 30 min. The mixture was stirred for 20 min, and then a solution of 3-phenyl-2-(phenylsulfonyl)-1,2-oxaziridine (7.45 g, 28.5 mmol) in THF (50 ml) was added. The reaction was stirred for 2.5 hrs at −78° C. The orange reaction mixture was quenched with sat. NH$_4$Cl (100 mL), diluted with EtOAc (300 mL), washed with water (200 mL), brine (100 mL), dried (Na$_2$SO$_4$), filtered and concentrated to give a yellow solid. The crude residue was loaded onto a flash silica gel column and eluted with 10%-30% EtOAc in hexanes. Product fractions were pooled and concentrated under reduced pressure, affording ethyl 2-(7-chloro-2-(3-chlorophenyl)-3,5-dimethylpyrazolo[1,5-a]pyrimidin-6-yl)-2-hydroxyacetate (5.4 g, 11.40 mmol, 51.9% yield) as a yellow solid. $^1$H NMR (500 MHz, CDCl$_3$) δ: 7.89-7.84 (m, 1H), 7.74 (dt, J=7.2, 1.6 Hz, 1H), 7.44-7.36 (m, 2H), 5.73 (s, 1H), 4.32-4.26 (m, 2H), 3.65 (br. s., 1H), 2.63 (s, 3H), 2.51 (s, 3H), 1.24 (t, J=7.02 Hz, 3H). LCMS (M+H)=394.06.

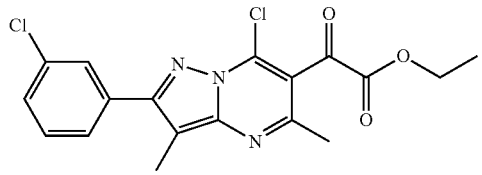 [SMILES: CCOC(=O)C(=O)c1c(C)nc2c(C)c(-c3cccc(Cl)c3)nn2c1Cl]

Ethyl 2-(7-chloro-2-(3-chlorophenyl)-3,5-dimethylpyrazolo[1,5-a]pyrimidin-6-yl)-2-oxoacetate To a solution of ethyl 2-(7-chloro-2-(3-chlorophenyl)-3,5-dimethylpyrazolo[1,5-a]pyrimidin-6-yl)-2-hydroxyacetate (5.4 g, 12.33 mmol) in CH$_2$Cl$_2$ (100 ml) was added Dess-Martin periodinane (5.75 g, 13.56 mmol). The reaction was stirred 1 hr, then diluted with EtOAc (600 mL) and washed with saturated aqueous NaHCO$_3$ (200 mL). The organic layer was then dried (NaHSO$_4$), filtered, and concentrated. The residue was triturate with Et$_2$O, stirring vigorously for 30 min, collecting solids by vacuum. The semi-pure product was purified by flash silica gel column and eluted with 10-20% EtOAc in hexanes, affording the product, ethyl 2-(7-chloro-2-(3-chlorophenyl)-3,5-dimethylpyrazolo[1,5-a]pyrimidin-6-yl)-2-oxoacetate (3.5 g, 8.92 mmol, 72.4% yield) as a pale yellow solid. $^1$H NMR (500 MHz, CDCl$_3$) δ: 7.89-7.86 (m, 1H), 7.78-7.73 (m, 1H), 7.45-7.41 (m, 2H), 4.45 (q, J=7.1 Hz, 2H), 2.63 (s, 3H), 2.53 (s, 3H), 1.42 (t, J=7.2 Hz, 3H). LCMS (M+H)=392.1.

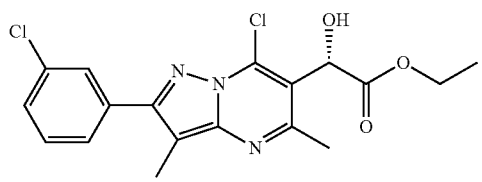

(S)-Ethyl 2-(7-chloro-2-(3-chlorophenyl)-3,5-dimethylpyrazolo[1,5-a]pyrimidin-6-yl)-2-hydroxyacetate To a stirred suspension of ethyl 2-(7-chloro-2-(3-chlorophenyl)-3,5-dimethylpyrazolo[1,5-a]pyrimidin-6-yl)-2-oxoacetate (3.45 g, 8.80 mmol) in anhydrous toluene (200 ml) was added 1.1 M (R)-1-methyl-3,3-diphenylhexahydropyrrolo[1,2-c][1,3,2]oxazaborole in toluene (3.20 ml, 3.52 mmol). The mixture was cooled (−40° C., dry ice/acetonitrile) and a solution of 1.0 M catecholborane in THF (17.59 ml, 17.59 mmol) was added over 1 min. The mixture was maintained at −40° C. for 2 hrs, and then warmed to room temperature with stirring for 16 hrs. The reaction was diluted with EtOAc (600 mL) and sat. Na$_2$CO$_3$ (200 mL). The mixture was stirred vigorously for 30 min, the layers were separated, and the organic layer washed with sat Na$_2$CO$_3$ (5×100 mL), dried (Na$_2$SO$_4$), filtered, and concentrated under reduced pressure. The crude product was purified by flash silica gel column chromatography, eluting with 10%-30% EtOAc in hexanes, affording the product, (S)-ethyl 2-(7-chloro-2-(3-chlorophenyl)-3,5-dimethylpyrazolo[1,5-a]pyrimidin-6-yl)-2-hydroxyacetate (3.08 g, 7.81 mmol, 84% yield) as a white solid. $^1$H NMR (500 MHz, CDCl$_3$) δ: 7.85-7.79 (m, 1H), 7.69 (dt, J=7.1, 1.6 Hz, 1H), 7.40-7.32 (m, 2H), 5.71 (s, 1H), 4.26 (q, J=7.1 Hz, 2H), 4.02 (br. s., 1H), 2.60 (s, 3H), 2.47 (s, 3H), 1.21 (t, J=7.2 Hz, 3H). LCMS (M+H)=394.2. Chiral column analysis indicated 98.1% chiral purity (ee: 96.2%).

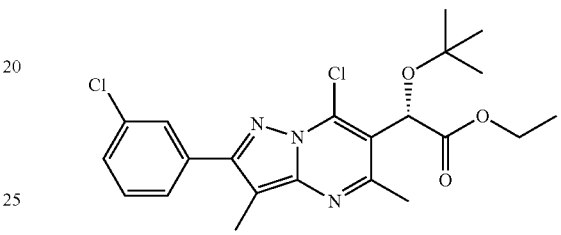

(S)-Ethyl 2-(tert-butoxy)-2-(7-chloro-2-(3-chlorophenyl)-3,5-dimethylpyrazolo[1,5-a]pyrimidin-6-yl)acetate A solution of (S)-ethyl 2-(7-chloro-2-(3-chlorophenyl)-3,5-dimethylpyrazolo[1,5-a]pyrimidin-6-yl)-2-hydroxyacetate (3.08 g, 7.81 mmol) in CH$_2$Cl$_2$ (130 ml) was treated with tert-butyl acetate (73.9 ml, 547 mmol) and perchloric acid (2.014 ml, 23.44 mmol), and the reaction was stoppered. The reaction was stirred for 2.5 hrs, then diluted with CH$_2$Cl$_2$ (130 ml) and carefully quenched with sat. NaHCO$_3$ (100 mL). The organic layer was separated and washed with brine (100 mL), dried (Na$_2$SO$_4$), filtered and concentrated to give a light amber mobile oil. The crude product was purified by flash silica gel column chromatography, eluting with 10%-30% EtOAc in hexanes, to afford the product, (S)-ethyl 2-(tert-butoxy)-2-(7-chloro-2-(3-chlorophenyl)-3,5-dimethylpyrazolo[1,5-a]pyrimidin-6-yl)acetate (2.05 g, 4.42 mmol, 56.5% yield) as a viscous oil, which began to crystallize upon standing. $^1$H NMR (500 MHz, CDCl$_3$) δ: 7.87 (t, J=1.5 Hz, 1H), 7.74 (dt, J=7.3, 1.5 Hz, 1H), 7.46-7.36 (m, 2H), 5.63 (s, 1H), 4.19 (q, J=7.0 Hz, 2H), 2.68 (s, 3H), 2.51 (s, 3H), 1.26 (s, 9H), 1.21 (t, J=7.0 Hz, 3H).

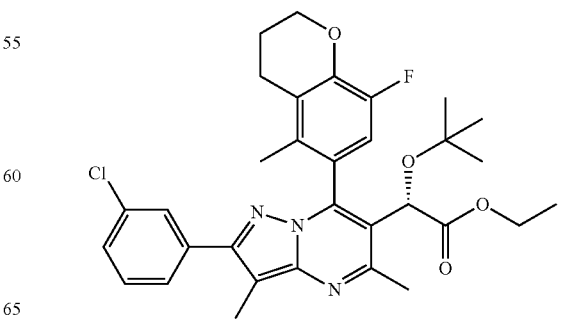

(2S)-Ethyl 2-(tert-butoxy)-2-(2-(3-chlorophenyl)-7-(8-fluoro-5-methylchroman-6-yl)-3,5-dimethylpyrazolo[1,5-a]pyrimidin-6-yl)acetate A solution of (S)-ethyl 2-(tert-butoxy)-2-(7-chloro-2-(3-chlorophenyl)-3,5-dimethylpyrazolo[1,5-a]pyrimidin-6-yl)acetate (0.207 g, 0.460 mmol), 2-(8-fluoro-5-methylchroman-6-yl)-4,4,5,5-tetramethyl-1,3,2-dioxaborolane (0.151 g, 0.517 mmol) and tetrakis(triphenylphosphine)palladium(0) (0.081 g, 0.070 mmol) in anhydrous DMF (4 mL) was treated with 2.0 M $K_2CO_3$ (0.55 mL, 1.100 mmol), degassed by nitrogen stream, then sealed and heated (110° C., microwave) for 60 min. The reaction slurry was filtered though a 0.45 micron syringe tip filter, and the filtrate was purified by biotage silica gel column, eluting with 0%-20% ethyl acetate in hexanes. Individual atropisomers eluted separately, and the early eluting isomer was concentrated under reduced pressure, affording the single isomer, (2S)-ethyl 2-(tert-butoxy)-2-(2-(3-chlorophenyl)-7-(8-fluoro-5-methylchroman-6-yl)-3,5-dimethylpyrazolo[1,5-a]pyrimidin-6-yl)acetate (0.095 g, 0.164 mmol, 35.7% yield) as a white glassy solid.

$^1$H NMR (500 MHz, $CDCl_3$) δ: 7.66 (t, J=1.5 Hz, 1H), 7.57 (dt, J=7.2, 1.6 Hz, 1H), 7.36-7.27 (m, 2H), 6.87 (d, J=10.7 Hz, 1H), 4.97 (s, 1H), 4.32 (dd, J=5.8, 4.3 Hz, 2H), 4.11 (q, J=7.3 Hz, 2H), 2.77 (s, 3H), 2.77-2.72 (m, 2H), 2.52-2.48 (m, 3H), 2.20-2.12 (m, 2H), 1.86 (s, 3H), 1.18 (t, J=7.3 Hz, 3H), 1.16 (s, 9H). LCMS (M+H)=580.4.

(2S)-Ethyl 2-(tert-butoxy)-2-(7-(8-fluoro-5-methylchroman-6-yl)-2-(3-(8-fluoro-5-methylchroman-6-yl)phenyl)-3,5-dimethylpyrazolo[1,5-a]pyrimidin-6-yl)acetate This intermediate was isolated as a by-product from the preceding reaction, (0.011 g, 0.015 mmol, 3.34% yield), as a clear viscous oil. $^1$H NMR (500 MHz, $CDCl_3$) δ: 7.64 (dt, J=7.8, 1.4 Hz, 1H), 7.55 (t, J=1.7 Hz, 1H), 7.42 (t, J=7.6 Hz, 1H), 7.22 (dt, J=7.8, 1.4 Hz, 1H), 6.86 (s, 1H), 6.88 (s, 1H), 4.97 (s, 1H), 4.34-4.27 (m, 2H), 4.27-4.21 (m, 2H), 4.10 (q, J=7.1 Hz, 2H), 2.77 (s, 3H), 2.76-2.67 (m, 4H), 2.51 (s, 3H), 2.18-2.09 (m, 4H), 2.07 (s, 3H), 1.87 (s, 3H), 1.18 (t, J=7.0 Hz, 3H), 1.16-1.12 (m, 9H). LCMS (M+H)=710.5.

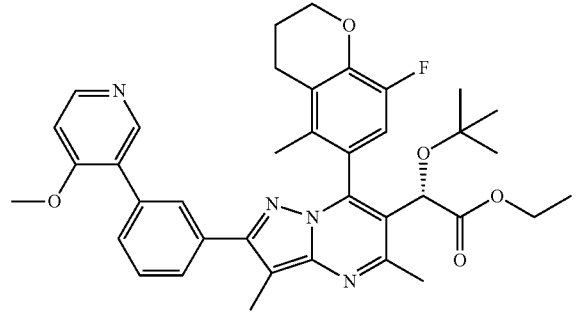 [SMILES: CCOC(=O)[C@@H](OC(C)(C)C)c1c(C)nc2c(C)c(-c3cccc(-c4cnccc4OC)c3)nn2c1-c1cc(F)c2c(c1C)CCCO2]

(2S)-Ethyl 2-(tert-butoxy)-2-(7-(8-fluoro-5-methylchroman-6-yl)-2-(3-(4-methoxypyridin-3-yl)phenyl)-3,5-dimethylpyrazolo[1,5-a]pyrimidin-6-yl)acetate.

To a 2-5 ml microwave tube was added dicyclohexyl (2',6'-dimethoxy-[1,1'-biphenyl]-2-yl)phosphine (0.061 g, 0.147 mmol), palladium(II) acetate (0.022 g, 0.098 mmol), and (2S)-ethyl 2-(tert-butoxy)-2-(2-(3-chlorophenyl)-7-(8-fluoro-5-methylchroman-6-yl)-3,5-dimethylpyrazolo[1,5-a]pyrimidin-6-yl)acetate (0.057 g, 0.098 mmol) in DMF (1 mL), followed by an aqueous solution of 2.0 M $K_3PO_4$ (0.098 mL, 0.197 mmol). The reaction was degassed using nitrogen stream and then heated (130° C., microwave) for 60 min. The reaction was filtered through a 0.45 micron syringe tip filter, and the residue was purified by preparative HPLC. Product fractions were pooled and concentrated under reduced pressure for afford the product, (2S)-ethyl 2-(tert-butoxy)-2-(7-(8-fluoro-5-methylchroman-6-yl)-2-(3-(4-methoxypyridin-3-yl)phenyl)-3,5-dimethylpyrazolo[1,5-a]pyrimidin-6-yl)acetate (0.022 g, 0.033 mmol, 33.8% yield), as an oily film. $^1$H NMR (500 MHz, $CDCl_3$) δ: 8.48 (d, J=5.8 Hz, 1H), 8.46-8.44 (m, 1H), 7.81 (s, 1H), 7.68 (dt, J=6.6, 1.9 Hz, 1H), 7.50-7.45 (m, 2H), 6.90 (d, J=5.8 Hz, 1H), 6.88 (d, J=11.0 Hz, 1H), 4.97 (s, 1H), 4.32-4.28 (m, 2H), 4.11 (q, J=7.1 Hz, 2H), 3.86 (s, 3H), 2.77 (s, 3H), 2.74 (t, J=6.6 Hz, 2H), 2.53 (s, 3H), 2.17-2.10 (m, 2H), 1.87 (s, 3H), 1.18 (t, J=7.2 Hz, 3H), 1.16 (s, 9H). LCMS (M+H)=653.6.

The following intermediates were prepared according to the above procedure.

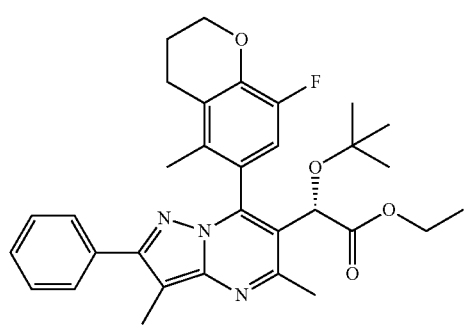 [SMILES: CCOC(=O)[C@@H](OC(C)(C)C)c1c(C)nc2c(C)c(-c3ccccc3)nn2c1-c1cc(F)c2c(c1C)CCCO2]

(2S)-Ethyl 2-(tert-butoxy)-2-(7-(8-fluoro-5-methyl-chroman-6-yl)-3,5-dimethyl-2-phenylpyrazolo[1,5-a]pyrimidin-6-yl)acetate $^1$H NMR (500 MHz, CDCl$_3$) δ: 7.71-7.66 (m, 2H), 7.42-7.36 (m, 2H), 7.36-7.30 (m, 1H), 6.88 (d, J=10.7 Hz, 1H), 4.97 (s, 1H), 4.34-4.28 (m, 2H), 4.10 (q, J=7.2 Hz, 2H), 2.77 (s, 3H), 2.76-2.72 (m, 2H), 2.51 (s, 3H), 2.19-2.11 (m, 2H), 1.87 (s, 3H), 1.17 (t, J=7.0 Hz, 3H), 1.16 (s, 9H). LCMS (M+H)=546.5.

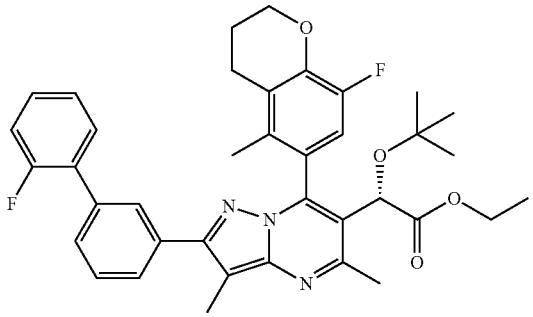 [SMILES: CCOC(=O)[C@@H](OC(C)(C)C)c1c(C)nc2c(C)c(-c3cccc(-c4ccccc4F)c3)nn2c1-c1cc(F)c2c(c1C)CCCO2]

(2S)-Ethyl 2-(tert-butoxy)-2-(7-(8-fluoro-5-methyl-chroman-6-yl)-2-(2'-fluoro-[1,1'-biphenyl]-3-yl)-3,5-dimethylpyrazolo[1,5-a]pyrimidin-6-yl)acetate

LCMS (M+H)=640.5.

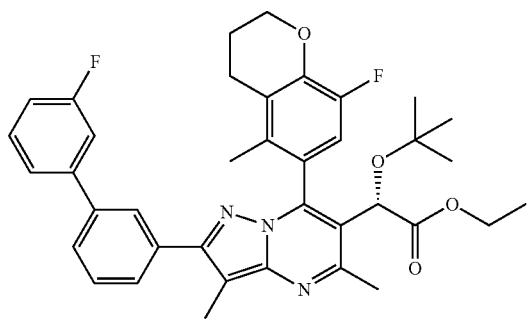 [SMILES: CCOC(=O)[C@@H](OC(C)(C)C)c1c(C)nc2c(C)c(-c3cccc(-c4cccc(F)c4)c3)nn2c1-c1cc(F)c2c(c1C)CCCO2]

(2S)-Ethyl 2-(tert-butoxy)-2-(7-(8-fluoro-5-methyl-chroman-6-yl)-2-(3'-fluoro-[1,1'-biphenyl]-3-yl)-3,5-dimethylpyrazolo[1,5-a]pyrimidin-6-yl)acetate

LCMS (M+H)=640.6.

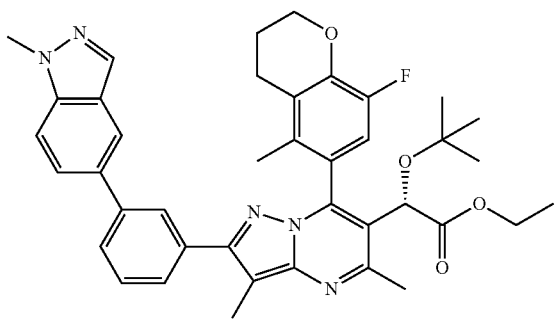 [SMILES: CCOC(=O)[C@@H](OC(C)(C)C)c1c(C)nc2c(C)c(-c3cccc(-c4ccc5c(cnn5C)c4)c3)nn2c1-c1cc(F)c2c(c1C)CCCO2]

(2S)-Ethyl 2-(tert-butoxy)-2-(7-(8-fluoro-5-methyl-chroman-6-yl)-3,5-dimethyl-2-(3-(1-methyl-1H-indazol-5-yl)phenyl)pyrazolo[1,5-a]pyrimidin-6-yl)acetate

LCMS (M+H)=676.6

Example 158

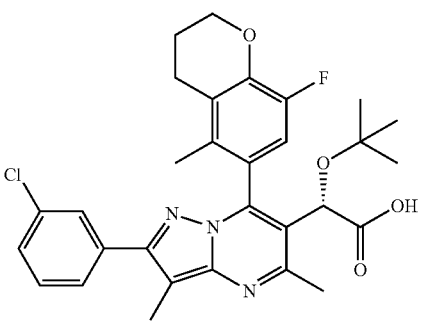 [SMILES: Cc1nc2c(C)c(-c3cccc(Cl)c3)nn2c(-c2cc(F)c3c(c2C)CCCO3)c1[C@H](OC(C)(C)C)C(=O)O]

(2S)-2-(tert-Butoxy)-2-(2-(3-chlorophenyl)-7-(8-fluoro-5-methylchroman-6-yl)-3,5-dimethylpyrazolo[1,5-a]pyrimidin-6-yl)acetic acid A solution of (2S)-ethyl 2-(tert-butoxy)-2-(2-(3-chlorophenyl)-7-(8-fluoro-5-methylchroman-6-yl)-3,5-dimethylpyrazolo[1,5-a]pyrimidin-6-yl)acetate (0.025 g, 0.043 mmol) in MeOH (2 mL) was treated with 1.0 M NaOH (0.215 mL, 0.215 mmol) and the reaction was stirred with heating (75° C. oil bath) for 16 hrs. The reaction was concentrated under reduced pressure to give a white paste. This was partitioned between 0.1N HCl (5 mL) and CH$_2$Cl$_2$ (5 mL). The layers were separated and the organic layer was dried (MgSO$_4$), filtered, and concentrated under reduced pressure, affording an off-white solid. The product was purified by preparative-HPLC. Product fractions were pooled and concentrated to 1/2 volume and the resulting solid was extracted with CH$_2$Cl$_2$ (2×10 mL). The combined organic extracts were dried (Na$_2$SO$_4$), filtered, and concentrated under reduced pressure, affording the product, (2S)-2-(tert-butoxy)-2-(2-(3-chlorophenyl)-7-(8-fluoro-5-methylchroman-6-yl)-3,5-dimethylpyrazolo[1,5-a]pyrimidin-6-yl)acetic acid (0.014 g, 0.024 mmol, 55.9% yield), as an off-white solid. $^1$H NMR (500 MHz, CDCl$_3$) d: 7.69-7.64 (m, 1H), 7.57 (dt, J=7.0, 1.7 Hz, 1H), 7.36-7.28 (m, 2H), 6.89 (d, J=10.7 Hz, 1H), 5.06 (s, 1H), 4.30 (t, J=5.2 Hz, 2H), 2.77-2.69 (m, 5H), 2.53-2.48 (m, 3H), 2.14 (m, 2H), 1.91 (s, 3H), 1.21-1.17 (m, 9H). LCMS (M+H)=552.4.

The following examples 159-164 were prepared according to the procedure for Example 158 using appropriate esters.

Example 159

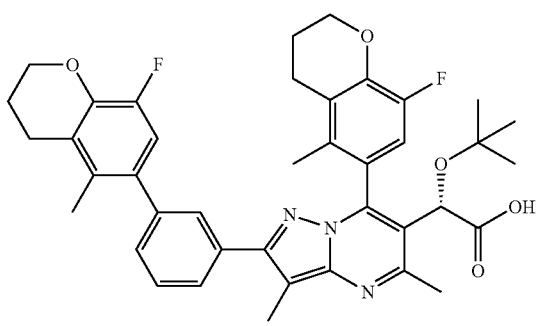 [SMILES: Cc1nc2c(C)c(-c3cccc(-c4cc(F)c5c(c4C)CCCO5)c3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(3-(8-fluoro-5-methylchroman-6-yl)phenyl)-3,5-dimethylpyrazolo[1,5-a]pyrimidin-6-yl)acetic acid ¹H NMR (500 MHz, CDCl₃-d) δ 7.62 (d, J=7.6 Hz, 1H), 7.55 (s, 1H), 7.40 (t, J=7.6 Hz, 1H), 7.20 (d, J=7.6 Hz, 1H), 6.94-6.81 (m, 2H), 4.91 (br. s., 1H), 4.25-4.22 (m, 2H), 4.18 (br. s., 1H), 2.69 (t, J=6.4 Hz, 2H), 2.62 (br. s., 4H), 2.51-2.46 (m, 3H), 2.13-2.07 (m, 2H), 2.05 (s, 3H), 2.00 (br. s., 2H), 1.89-1.82 (m, 3H), 1.25 (s, 3H), 1.05 (br. s., 9H). LCMS (M+H)=682.5.

Example 160

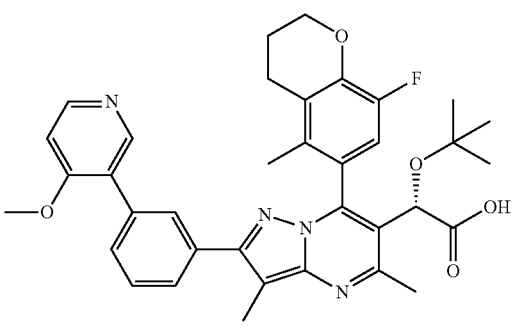 [SMILES: COc1ccncc1-c1cccc(-c2nn3c(-c4cc(F)c5c(c4C)CCCO5)c([C@H](OC(C)(C)C)C(=O)O)c(C)nc3c2C)c1]

(2S)-2-(tert-Butoxy)-2-(7-(8-fluoro-5-methylchroman-6-yl)-2-(3-(4-methoxypyridin-3-yl)phenyl)-3,5-dimethylpyrazolo[1,5-a]pyrimidin-6-yl)acetic acid ¹H NMR (500 MHz, CDCl₃) δ: 8.56 (d, J=6.1 Hz, 1H), 8.32 (s, 1H), 7.75-7.64 (m, 2H), 7.52-7.43 (m, 2H), 7.01 (d, J=6.1 Hz, 1H), 6.91 (d, J=10.7 Hz, 1H), 5.00 (s, 1H), 4.30-4.20 (m, 2H), 3.92 (s, 3H), 2.77 (s, 3H), 2.67 (t, J=6.4 Hz, 2H), 2.48 (s, 3H), 2.07 (br. s, 2H), 1.90 (s, 3H), 1.19 (s, 9H). LCMS (M+H)=625.5.

Example 161

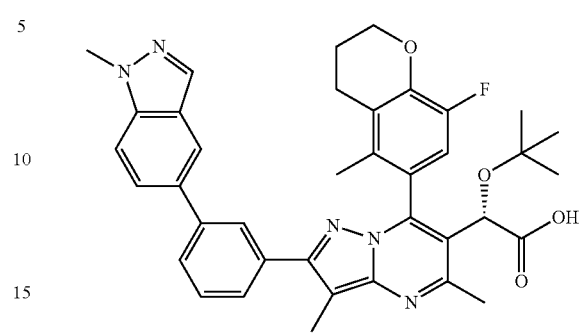

(2S)-2-(tert-Butoxy)-2-(7-(8-fluoro-5-methylchroman-6-yl)-3,5-dimethyl-2-(3-(1-methyl-1H-indazol-5-yl)phenyl)pyrazolo[1,5-a]pyrimidin-6-yl)acetic acid ¹H NMR (500 MHz, CDCl₃) δ: 8.04 (s, 1H), 7.92 (d, J=7.3 Hz, 2H), 7.72-7.64 (m, 2H), 7.61 (d, J=7.9 Hz, 1H), 7.53-7.43 (m, 2H), 6.94 (d, J=10.7 Hz, 1H), 5.09 (s, 1H), 4.35-4.24 (m, 2H), 4.12 (s, 3H), 2.80-2.67 (m, 5H), 2.57 (s, 3H), 2.19-2.09 (m, 2H), 1.95 (s, 3H), 1.22 (s, 9H). LCMS (M+H)=648.6.

Example 162

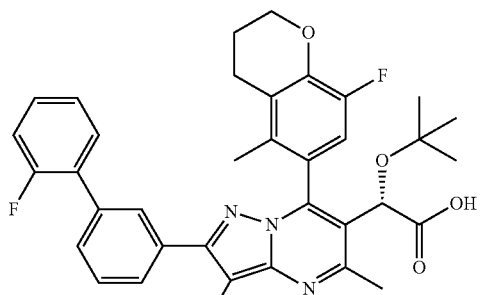

(2S)-2-(tert-Butoxy)-2-(7-(8-fluoro-5-methylchroman-6-yl)-2-(2'-fluoro-[1,1'-biphenyl]-3-yl)-3,5-dimethylpyrazolo[1,5-a]pyrimidin-6-yl)acetic acid ¹H NMR (500 MHz, CDCl₃) δ: 7.76 (d, J=1.2 Hz, 1H), 7.60 (d, J=7.6 Hz, 1H), 7.59-7.54 (m, 1H), 7.52-7.46 (m, 1H), 7.45-7.40 (m, 1H), 7.36-7.29 (m, 1H), 7.24-7.18 (m, 1H), 7.18-7.12 (m, 1H), 6.90 (d, J=10.7 Hz, 1H), 5.09 (s, 1H), 4.32-4.22 (m, 2H), 2.80 (s, 3H), 2.68 (t, J=6.6 Hz, 2H), 2.51 (s, 3H), 2.14-2.06 (m, 3H), 1.90 (s, 2H), 1.25 (s, 1H), 1.21 (s, 9H). LCMS (M+H)=612.5.

Example 163

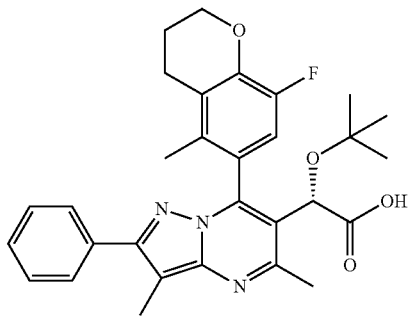 [SMILES: Cc1nc2c(C)c(-c3ccccc3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-3,5-dimethyl-2-phenylpyrazolo[1,5-a]pyrimidin-6-yl)acetic acid $^{1}$H NMR (500 MHz, CDCl$_3$) δ: 7.67 (d, J=7.3 Hz, 2H), 7.42-7.36 (m, 2H), 7.36-7.29 (m, 1H), 6.89 (d, J=10.7 Hz, 1H), 5.02 (s, 1H), 4.25 (br. s., 2H), 2.70 (br. s., 3H), 2.67 (br. s., 2H), 2.50 (s, 3H), 2.07 (br. s., 2H), 1.88 (s, 3H), 1.14 (s, 9H). LCMS (M+H)=518.5.

Example 164

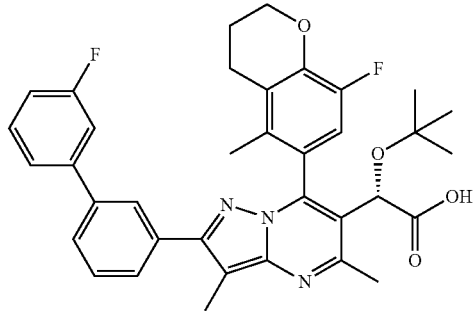 [SMILES: Cc1nc2c(C)c(-c3cccc(-c4cccc(F)c4)c3)nn2c(-c2cc(F)c3c(c2C)CCCO3)c1[C@H](OC(C)(C)C)C(=O)O]

(2S)-2-(tert-Butoxy)-2-(7-(8-fluoro-5-methylchroman-6-yl)-2-(3'-fluoro-[1,1'-biphenyl]-3-yl)-3,5-dimethylpyrazolo[1,5-a]pyrimidin-6-yl)acetic acid $^{1}$H NMR (500 MHz, CDCl$_3$) δ: 7.87-7.82 (m, 1H), 7.71-7.65 (m, 1H), 7.57-7.51 (m, 1H), 7.51-7.45 (m, 1H), 7.44-7.34 (m, 2H), 7.32-7.27 (m, 1H), 7.08-7.00 (m, 1H), 6.92 (d, J=10.7 Hz, 1H), 5.08 (s, 1H), 4.33-4.23 (m, 2H), 2.76-2.67 (m, 5H), 2.54 (s, 3H), 2.17-2.08 (m, 2H), 1.93 (s, 3H), 1.20 (s, 9H). LCMS (M+H)=612.5.

Examples 165-175 were synthesized using the procedure described above for example 115.

Example 165

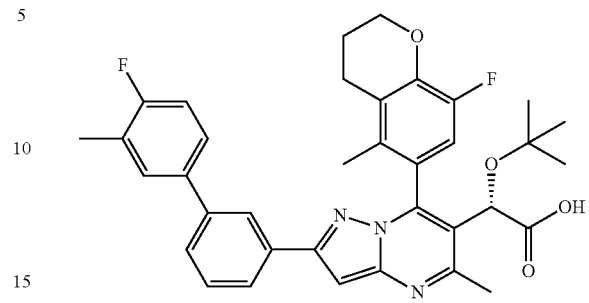

| (2S)-2-(tert-Butoxy)-2-(2-(4'-fluoro-3'-methyl-[1,1'-biphenyl]-3-yl)-7-(8-fluoro-5-methylchroman-6-yl)-5-methylpyrazolo[1,5-a]pyrimidin-6-yl)acetic acid | |
|---|---|
| MS (M + H)$^+$ Calcd. | 612 |
| MS (M + H)$^+$ Observ. | 612 |
| Retention Time | 3.22 min |
| LC Condition | |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^{1}$H NMR (500 MHz, DMSO-d$_6$) δ 8.06 (s, 1H), 7.78 (d, J=7.9 Hz, 1H), 7.69-7.61 (m, 2H), 7.56 (ddd, J=8.0, 5.1, 2.4 Hz, 1H), 7.50 (t, J=7.6 Hz, 1H), 7.31-7.21 (m, 2H), 7.11 (d, J=11.0 Hz, 1H), 4.84 (s, 1H), 4.36-4.23 (m, 2H), 2.79-2.72 (m, 2H), 2.71 (s, 3H), 2.33 (s, 3H), 2.10-2.06 (m, 2H), 1.83 (s, 3H), 1.10 (s, 9H).

Example 166

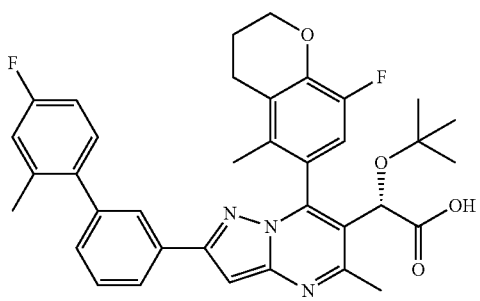

(2S)-2-(tert-Butoxy)-2-(2-(4'-fluoro-2'-methyl-[1,1'-biphenyl]-3-yl)-7-(8-fluoro-5-methylchroman-6-yl)-5-methylpyrazolo[1,5-a]pyrimidin-6-yl)acetic acid

| | |
|---|---|
| MS (M + H)⁺ Calcd. | 612 |
| MS (M + H)⁺ Observ. | 612 |
| Retention Time | 3.20 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-d$_6$) δ 7.82 (d, J=7.6 Hz, 1H), 7.76 (s, 1H), 7.50 (t, J=7.8 Hz, 1H), 7.39-7.24 (m, 2H), 7.23-7.16 (m, 2H), 7.14-7.04 (m, 2H), 4.82 (s, 1H), 4.33-4.20 (m, 2H), 2.77-2.66 (m, 5H), 2.24 (s, 3H), 2.12-2.00 (m, 2H), 1.82 (s, 3H), 1.09 (s, 9H).

Example 167

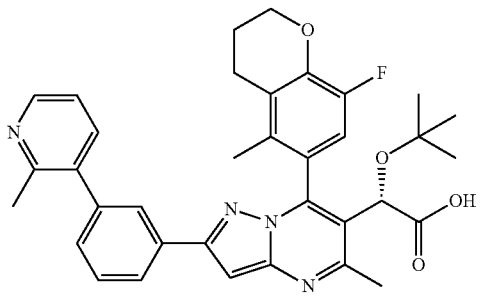

(2S)-2-(tert-Butoxy)-2-(7-(8-fluoro-5-methylchroman-6-yl)-5-methyl-2-(3-(2-methylpyridin-3-yl)phenyl)pyrazolo[1,5-a]pyrimidin-6-yl)acetic acid

| | |
|---|---|
| MS (M + H)⁺ Calcd. | 595 |
| MS (M + H)⁺ Observ. | 595 |
| Retention Time | 2.57 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-d$_6$) δ 8.50 (dd, J=4.7, 1.7 Hz, 1H), 7.90-7.81 (m, 2H), 7.67 (dd, J=7.6, 1.5 Hz, 1H), 7.53 (t, J=7.6 Hz, 1H), 7.41 (d, J=7.6 Hz, 1H), 7.33 (dd, J=7.6, 4.9 Hz, 1H), 7.22 (s, 1H), 7.10 (d, J=11.3 Hz, 1H), 4.83 (s, 1H), 4.37-4.20 (m, 2H), 2.78-2.71 (m, 2H), 2.69 (s, 3H), 2.44 (s, 3H), 2.13-2.02 (m, 2H), 1.82 (s, 3H), 1.09 (s, 9H).

Example 168

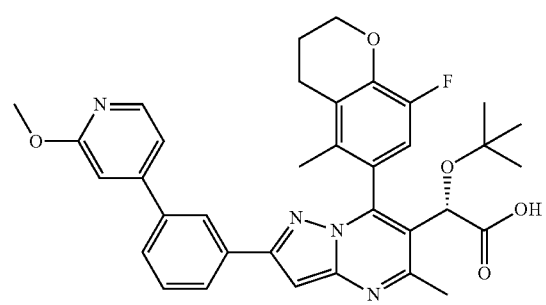

(2S)-2-(tert-Butoxy)-2-(7-(8-fluoro-5-methylchroman-6-yl)-2-(3-(2-methoxypyridin-4-yl)phenyl)-5-methylpyrazolo[1,5-a]pyrimidin-6-yl)acetic acid

| | |
|---|---|
| MS (M + H)⁺ Calcd. | 611 |
| MS (M + H)⁺ Observ. | 611 |
| Retention Time | 2.80 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-d$_6$) δ 8.27 (d, J=5.5 Hz, 1H), 8.19 (s, 1H), 7.89 (d, J=7.9 Hz, 1H), 7.79 (d, J=7.9 Hz, 1H), 7.56 (t, J=7.6 Hz, 1H), 7.38 (dd, J=5.5, 1.5 Hz, 1H), 7.33 (s, 1H), 7.19 (s, 1H), 7.11 (d, J=11.3 Hz, 1H), 4.84 (s, 1H), 4.36-4.22 (m, 2H), 3.93 (s, 3H), 2.79-2.73 (m, 2H), 2.71 (s, 3H), 2.08 (t, J=5.6 Hz, 2H), 1.83 (s, 3H), 1.10 (s, 9H).

Example 169

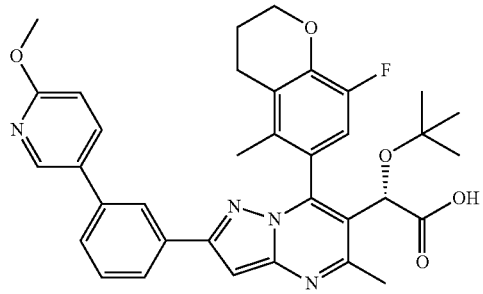 [SMILES: COc1ccc(-c2cccc(-c3cc4nc(C)c([C@H](OC(C)(C)C)C(=O)O)c(-c5cc(F)c6c(c5C)CCCO6)n4n3)c2)cn1]

Hz, 1H), 4.86 (s, 1H), 4.35-4.23 (m, 2H), 2.79-2.73 (m, 2H), 2.71 (s, 3H), 2.56 (s, 3H), 2.08 (t, J=5.5 Hz, 2H), 1.83 (s, 3H), 1.10 (s, 9H).

Example 171

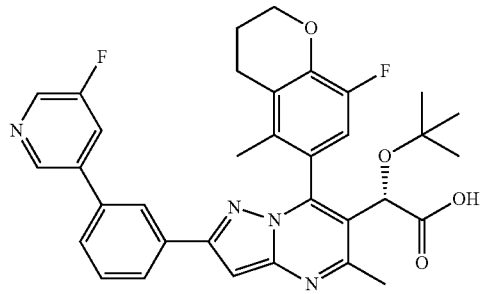

| (2S)-2-(tert-Butoxy)-2-(7-(8-fluoro-5-methylchroman-6-yl)-2-(3-(6-methoxypyridin-3-yl)phenyl)-5-methylpyrazolo[1,5-a]pyrimidin-6-yl)acetic acid | |
|---|---|
| MS (M + H)+ Calcd. | 611 |
| MS (M + H)+ Observ. | 611 |
| Retention Time | 2.85 min |
|  | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-$d_6$) δ 8.55 (d, J=2.4 Hz, 1H), 8.13-8.05 (m, 2H), 7.79 (d, J=7.9 Hz, 1H), 7.66 (d, J=7.9 Hz, 1H), 7.51 (t, J=7.6 Hz, 1H), 7.26 (s, 1H), 7.09 (d, J=11.3 Hz, 1H), 6.95 (d, J=8.5 Hz, 1H), 4.78 (s, 1H), 4.34-4.21 (m, 2H), 3.92 (s, 3H), 2.75-2.73 (m, 2H), 2.71 (s, 3H), 2.08 (t, J=5.6 Hz, 2H), 1.83 (s, 3H), 1.09 (s, 9H).

Example 170

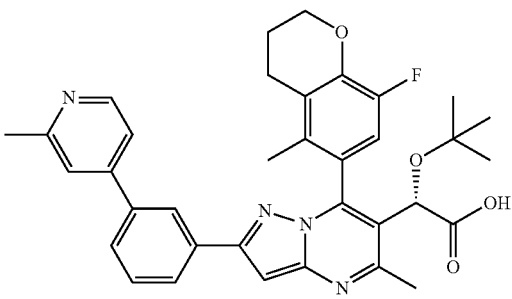 [SMILES: Cc1cc(-c2cccc(-c3cc4nc(C)c([C@H](OC(C)(C)C)C(=O)O)c(-c5cc(F)c6c(c5C)CCCO6)n4n3)c2)ccn1]

| (2S)-2-(tert-Butoxy)-2-(7-(8-fluoro-5-methylchroman-6-yl)-5-methyl-2-(3-(2-methylpyridin-4-yl)phenyl)pyrazolo[1,5-a]pyrimidin-6-yl)acetic acid | |
|---|---|
| MS (M + H)+ Calcd. | 595 |
| MS (M + H)+ Observ. | 595 |
| Retention Time | 2.58 min |
|  | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-$d_6$) δ 8.54 (d, J=5.2 Hz, 1H), 8.20 (s, 1H), 7.89 (d, J=7.9 Hz, 1H), 7.79 (d, J=7.9 Hz, 1H), 7.66 (s, 1H), 7.61-7.52 (m, 2H), 7.33 (s, 1H), 7.11 (d, J=11.3

| (2S)-2-(tert-Butoxy)-2-(7-(8-fluoro-5-methylchroman-6-yl)-2-(3-(5-fluoropyridin-3-yl)phenyl)-5-methylpyrazolo[1,5-a]pyrimidin-6-yl)acetic acid | |
|---|---|
| MS (M + H)+ Calcd. | 599 |
| MS (M + H)+ Observ. | 599 |
| Retention Time | 2.67 min |
|  | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-$d_6$) δ 8.89 (s, 1H), 8.63 (d, J=2.7 Hz, 1H), 8.28-8.11 (m, 2H), 7.88 (d, J=7.6 Hz, 1H), 7.81 (d, J=7.6 Hz, 1H), 7.57 (t, J=7.8 Hz, 1H), 7.33 (s, 1H), 7.10 (d, J=11.3 Hz, 1H), 4.81 (s, 1H), 4.35-4.19 (m, 2H), 2.79-2.67 (m, 5H), 2.08 (t, J=5.8 Hz, 2H), 1.83 (s, 3H), 1.09 (s, 9H).

Example 172

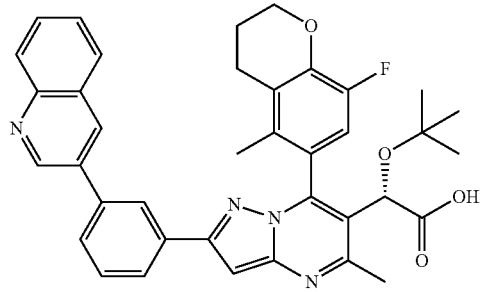 [SMILES: Cc1nc2cc(-c3cccc(-c4cnc5ccccc5c4)c3)nn2c(-c2cc(F)c3c(c2C)CCCO3)c1[C@H](OC(C)(C)C)C(=O)O]

| (2S)-2-(tert-Butoxy)-2-(7-(8-fluoro-5-methylchroman-6-yl)-5-methyl-2-(3-(quinolin-3-yl)phenyl)pyrazolo[1,5-a]pyrimidin-6-yl)acetic acid | |
|---|---|
| MS (M + H)+ Calcd. | 631 |
| MS (M + H)+ Observ. | 631 |
| Retention Time | 2.85 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-d$_6$) δ 9.32 (d, J=2.4 Hz, 1H), 8.74 (d, J=2.1 Hz, 1H), 8.33 (s, 1H), 8.10 (d, J=8.5 Hz, 2H), 7.90 (t, J=7.5 Hz, 2H), 7.84-7.78 (m, 1H), 7.73-7.65 (m, 1H), 7.62 (t, J=7.8 Hz, 1H), 7.35 (s, 1H), 7.12 (d, J=11.3 Hz, 1H), 4.84 (s, 1H), 4.37-4.20 (m, 2H), 2.78-2.68 (m, 5H), 2.14-2.02 (m, 2H), 1.84 (s, 3H), 1.10 (s, 9H).

Example 173

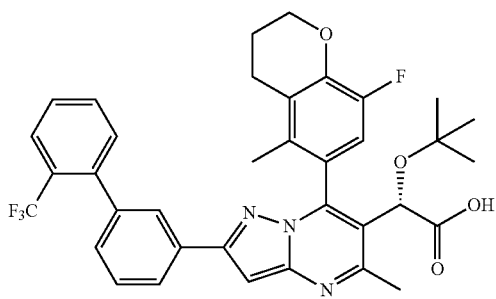 [SMILES: Cc1nc2cc(-c3cccc(-c4ccccc4C(F)(F)F)c3)nn2c(-c2cc(F)c3c(c2C)CCCO3)c1[C@H](OC(C)(C)C)C(=O)O]

| (2S)-2-(tert-Butoxy)-2-(7-(8-fluoro-5-methylchroman-6-yl)-5-methyl-2-(2'-(trifluoromethyl)-[1,1'-biphenyl]-3-yl)pyrazolo[1,5-a]pyrimidin-6-yl)acetic acid | |
|---|---|
| MS (M + H)+ Calcd. | 648 |
| MS (M + H)+ Observ. | 648 |
| Retention Time | 3.16 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-d$_6$) δ 7.88 (dd, J=11.9, 7.9 Hz, 2H), 7.79 (s, 1H), 7.78-7.72 (m, 1H), 7.69-7.62 (m, 1H), 7.56-7.44 (m, 2H), 7.33 (d, J=7.6 Hz, 1H), 7.17 (s, 1H), 7.09 (d, J=11.3 Hz, 1H), 4.81 (s, 1H), 4.33-4.20 (m, 2H), 2.74-2.66 (m, 5H), 2.06 (br. s., 2H), 1.82 (s, 3H), 1.08 (s, 9H).

Example 174

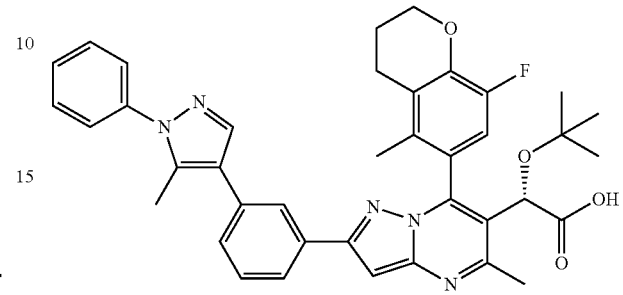

| (2S)-2-(tert-Butoxy)-2-(7-(8-fluoro-5-methylchroman-6-yl)-5-methyl-2-(3-(5-methyl-1-phenyl-1H-pyrazol-4-yl)phenyl)pyrazolo[1,5-a]pyrimidin-6-yl)acetic acid | |
|---|---|
| MS (M + H)+ Calcd. | 660 |
| MS (M + H)+ Observ. | 660 |
| Retention Time | 2.95 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-d$_6$) δ 8.02-7.92 (m, 3H), 7.78-7.70 (m, 1H), 7.63-7.56 (m, 3H), 7.54-7.45 (m, 3H), 7.20 (s, 1H), 7.10 (d, J=11.3 Hz, 1H), 4.85 (s, 1H), 4.34-4.21 (m, 2H), 2.79-2.67 (m, 5H), 2.42 (s, 3H), 2.09 (d, J=5.2 Hz, 2H), 1.83 (s, 3H), 1.10 (s, 9H).

Example 175

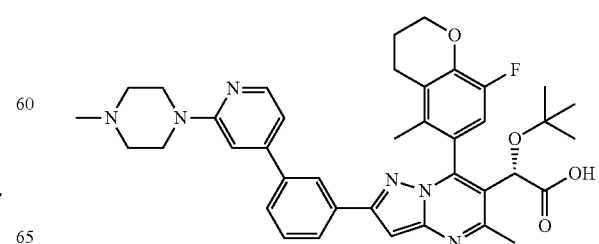

| (2S)-2-(tert-Butoxy)-2-(7-(8-fluoro-5-methylchroman-6-yl)-5-methyl-2-(3-(2-(4-methylpiperazin-1-yl)pyridin-4-yl)phenyl)pyrazolo[1,5-a]pyrimidin-6-yl)acetic acid | |
|---|---|
| MS (M + H)+ Calcd. | 679 |
| MS (M + H)+ Observ. | 679 |
| Retention Time | 2.45 min |
| | LC Condition |
| Solvent A | 5% acetonitrile:95% Water:10 mM Ammonium Acetate |
| Solvent B | 95% acetonitrile:5% Water:10 mM Ammonium Acetate |
| Start % B | 0 |
| Final % B | 100 |
| Gradient Time | 4 min |
| Flow Rate | 1 mL/min |
| Wavelength | 220 |
| Solvent Pair | acetonitrile:Water:Ammonium Acetate |
| Column | Waters BEH C18, 2.0 × 50 mm, 1.7-μm particles |

$^1$H NMR (500 MHz, DMSO-$d_6$) δ 8.52 (d, J=2.4 Hz, 1H), 8.04 (s, 1H), 7.92 (dd, J=8.9, 2.7 Hz, 1H), 7.73 (d, J=7.6 Hz, 1H), 7.63 (d, J=7.9 Hz, 1H), 7.48 (t, J=7.6 Hz, 1H), 7.27 (s, 1H), 7.11 (d, J=11.0 Hz, 1H), 6.96 (d, J=9.2 Hz, 1H), 4.84 (s, 1H), 4.35-4.22 (m, 2H), 3.58 (br. s., 4H), 2.78-2.66 (m, 5H), 2.48 (br. s., 4H), 2.28 (s, 3H), 2.08 (t, J=5.5 Hz, 2H), 1.82 (s, 3H), 1.10 (s, 9H).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

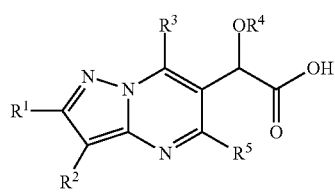

where:
$R^1$ is H, alkyl, cycloalkyl, or $Ar^1$;
$R^2$ is H, alkyl, cycloalkyl, or $Ar^1$;
$R^3$ is alkyl or $Ar^2$;
$R^4$ is alkyl or haloalkyl;
$R^5$ is alkyl;
$Ar^1$ is phenyl, pyridinyl, tetralinyl, indazolyl, or chromanyl, and is substituted with 0-3 substituents selected from halo, alkyl, haloalkyl, alkoxy, haloalkoxy, phenyl, benzyl, phenoxy, benzyloxy, halobenzyloxy, (alkoxy)benzyloxy, phenoxyalkyl, CONH(phenyl), CONH(benzyl), and $Ar^3$;
$Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;

or $Ar^2$ is

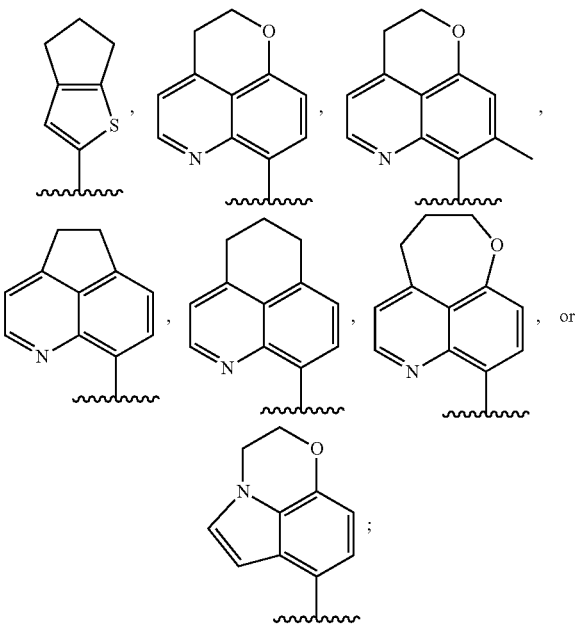

$Ar^3$ is phenyl, pyridinyl, pyrazolyl, quinolinyl, chromanyl, or indazolyl, and is substituted with 0-3 substituents selected from the group consisting of halo, alkyl, haloalkyl, alkoxy, haloalkoxy, phenyl, and methylpiperazinyl;

or a pharmaceutically acceptable salt thereof.

2. A compound of claim 1 where:
$R^1$ is H, alkyl, cycloalkyl, or $Ar^1$;
$R^2$ is H, alkyl, cycloalkyl, or $Ar^1$;
$R^3$ is alkyl or $Ar^2$;
$R^4$ is alkyl or haloalkyl;
$R^5$ is alkyl;
$Ar^1$ is phenyl, pyridinyl, or chromanyl, and is substituted with 0-3 substituents selected from halo, alkyl, haloalkyl, alkoxy, haloalkoxy, phenyl, benzyl, phenoxy, and phenoxyalkyl;
$Ar^2$ is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido;

or Ar² is

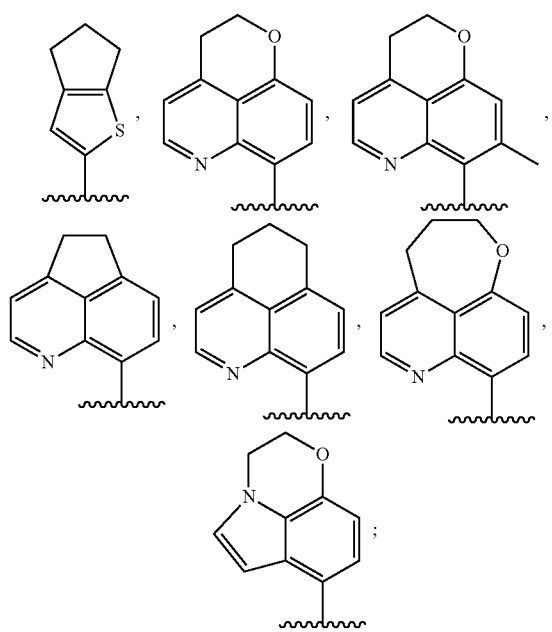

or a pharmaceutically acceptable salt thereof.

3. A compound of claim 1 where R¹ is Ar¹; R² is H; R³ is Ar²; R⁴ is alkyl; R⁵ is methyl; Ar¹ is phenyl, pyridinyl, or chromanyl, and is substituted with 0-3 substituents selected from halo, alkyl, haloalkyl, alkoxy, haloalkoxy, phenyl, benzyl, phenoxy, and phenoxyalkyl; and Ar² is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido; or a pharmaceutically acceptable salt thereof.

4. A compound of claim 1 where R¹ is Ar¹; R² is H; R³ is Ar²; R⁴ is alkyl; R⁵ is methyl; Ar¹ is phenyl or pyridinyl, and is substituted with 1 Ar³ substituent and 0-2 substituents selected from halo, alkyl, haloalkyl, alkoxy, and haloalkoxy; and Ar² is phenyl, pyridinyl, indanyl, naphthyl, tetrahydronaphthalenyl, benzofuranyl, dihydrobenzofuranyl, benzodioxyl, chromanyl, isochromanyl, benzodioxanyl, quinolinyl, tetrahydroquinolinyl, isoquinolinyl, tetrahydroisoquinolinyl, dihydrobenzoxazinyl, indolyl, dihydroindolyl, benzthiazolyl, or benzothiazolyl, and is substituted with 0-3 substituents selected from halo, cyano, alkyl, haloalkyl, cycloalkyl, halocycloalkyl, hydroxy, alkoxy, haloalkoxy, phenoxy, benzyloxy, thioalkyl, and acetamido; or a pharmaceutically acceptable salt thereof.

5. A compound of claim 1 where R¹ is Ar¹; R² is H; and Ar¹ is phenyl or pyridinyl, and is substituted with 1 Ar³ substituent and 0-2 substituents selected from halo, alkyl, haloalkyl, alkoxy, and haloalkoxy.

6. A compound of claim 5 where Ar² is phenyl, pyridinyl, indanyl, naphthyl, benzofuranyl, dihydrobenzofuranyl, benzodioxyl, chromanyl, benzodioxanyl, or indolyl, and is substituted with 0-3 substituents selected from halo, cyano, alkyl, haloalkyl, hydroxy, alkoxy, haloalkoxy, phenoxy, benzyloxy, and acetamido.

7. A compound of claim 1 where R⁴ is alkyl.

8. A compound of claim 1 where R⁵ is methyl.

9. A compound of claim 1 where Ar² is phenyl, pyridinyl, indanyl, naphthyl, benzofuranyl, dihydrobenzofuranyl, benzodioxyl, chromanyl, benzodioxanyl, or indolyl, and is substituted with 0-3 substituents selected from halo, cyano, alkyl, haloalkyl, hydroxy, alkoxy, haloalkoxy, phenoxy, benzyloxy, and acetamido.

10. A compound of claim 1 where Ar³ is phenyl, pyridinyl, or pyrazolyl, and is substituted with 1-3 substituents selected from the group consisting of halo, alkyl, haloalkyl, alkoxy, and haloalkoxy.

11. A composition useful for treating HIV infection comprising a therapeutic amount of a compound of claim 1 and a pharmaceutically acceptable carrier.

12. The composition of claim 11 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

13. A method for treating HIV infection comprising administering a therapeutically effective amount of a compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 8,633,200 B2
APPLICATION NO. : 13/224802
DATED : January 21, 2014
INVENTOR(S) : Annapurna Pendri et al.

It is certified that error appears in the above-identified patent and that said Letters Patent is hereby corrected as shown below:

In the Claims:

Claim 3:

Column 283, line 35, change "tetrahydronaphthalcnyl," to -- tetrahydronaphthalene, --.

Signed and Sealed this
Seventh Day of April, 2015

Michelle K. Lee
*Director of the United States Patent and Trademark Office*